United States Patent
Nakamura et al.

(10) Patent No.: US 9,221,865 B2
(45) Date of Patent: Dec. 29, 2015

(54) SYNTHETIC INTERMEDIATE OF 1-(2-DEOXY-2-FLUORO-4-THIO-β-D-ARABINOFURANOSYL)CYTOSINE, SYNTHETIC INTERMEDIATE OF THIONUCLEOSIDE, AND METHOD FOR PRODUCING THE SAME

(71) Applicant: FUJIFILM Corporation, Tokyo (JP)

(72) Inventors: Kouki Nakamura, Ashigarakami-gun (JP); Satoshi Shimamura, Ashigarakami-gun (JP); Junichi Imoto, Ashigarakami-gun (JP); Motomasa Takahashi, Ashigarakami-gun (JP); Katsuyuki Watanabe, Ashigarakami-gun (JP); Kenji Wada, Ashigarakami-gun (JP); Yuuta Fujino, Ashigarakami-gun (JP); Takuya Matsumoto, Ashigarakami-gun (JP); Makoto Takahashi, Ashigarakami-gun (JP); Hideki Okada, Ashigarakami-gun (JP); Takehiro Yamane, Ashigarakami-gun (JP); Takayuki Ito, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/621,119

(22) Filed: Feb. 12, 2015

(65) Prior Publication Data

US 2015/0152131 A1 Jun. 4, 2015

Related U.S. Application Data

(63) Continuation of application No. PCT/JP2013/071871, filed on Aug. 13, 2013.

(30) Foreign Application Priority Data

Aug. 13, 2012 (JP) .................................. 2012-179380
Jan. 25, 2013 (JP) .................................. 2013-012693

(51) Int. Cl.

| | |
|---|---|
| C07D 409/04 | (2006.01) |
| C07H 19/06 | (2006.01) |
| A61K 31/7068 | (2006.01) |
| C07C 303/28 | (2006.01) |
| C07C 45/00 | (2006.01) |
| C07B 53/00 | (2006.01) |
| C07C 309/73 | (2006.01) |
| C07C 249/04 | (2006.01) |
| C07C 251/38 | (2006.01) |
| C07H 13/04 | (2006.01) |
| C07H 13/08 | (2006.01) |

(Continued)

(52) U.S. Cl.

CPC ............ *C07H 19/06* (2013.01); *A61K 31/7068* (2013.01); *C07B 53/00* (2013.01); *C07C 45/00* (2013.01); *C07C 67/29* (2013.01); *C07C 68/06* (2013.01); *C07C 69/28* (2013.01); *C07C 69/618* (2013.01); *C07C 69/76* (2013.01); *C07C 69/78* (2013.01); *C07C 69/92* (2013.01); *C07C 69/96* (2013.01); *C07C 249/04* (2013.01); *C07C 251/38* (2013.01); *C07C 303/28* (2013.01); *C07C 309/73* (2013.01); *C07H 1/00* (2013.01); *C07H 7/04* (2013.01); *C07H 13/04* (2013.01); *C07H 13/08* (2013.01); *C07H 15/04* (2013.01); *C07H 15/18* (2013.01); *C07H 15/203* (2013.01); *C07H 17/02* (2013.01); *C07H 19/067* (2013.01); *C07H 19/073* (2013.01); *C07H 23/00* (2013.01)

(58) Field of Classification Search

CPC ........................................................ C07D 409/04
See application file for complete search history.

(56) References Cited

U.S. PATENT DOCUMENTS

6,103,707 A 8/2000 Yamada et al.
6,147,058 A 11/2000 Yoshimura et al.

FOREIGN PATENT DOCUMENTS

CN 101058557 A 10/2007
JP 10-282039 A 10/1998

(Continued)

OTHER PUBLICATIONS

Choo et al., "Synthesis, Anti-HIV Activity, and Molecular Mechanism of Drug Resistance of L-2',3'-Didehydro-2',3'-dideoxy-2'-fluoro-4'-thionucleosides," Journal of Medicinal Chemistry, 2003, vol. 46, No. 3, pp. 389-398.

Cottrell et al., "Reactions of Sugar Chlorosulfates VII. Some Conformational Aspects," Canadian Journal of Chemistry, Jul. 1, 1966, vol. 44, No. 13, pp. 1483-1491.

Fanton et al., "Enzymatic and Organocatalyzed Asymmetric Aldolization Reactions for the Synthesis of Thiosugar Scaffolds," European Journal of Organic Chemistry, 2012, pp. 203-210.

International Search Report issued in PCT/JP2013/071871, mailed on Nov. 26, 2013.

Jean-Baptiste et al., "Synthesis of 2',3'-Dideoxy-2'-Fluoro-4'-Thionucleosides from a Fluoroxanthate," Synlett, 2008, No. 6, pp. 817-820.

Kawana et al., "The Synthesis of 2',3'-Dideoxycytidine and Its 2'-Azido Analogue. Applications of the Deoxygenative [1,2]-Hydride Shift of Sulfonates with Mg(OMe) 2-NaBH4," The Chemical Society of Japan, Chemistry Letters, 1987, pp. 2419-2422.

(Continued)

*Primary Examiner* — Bruck Kifle

(74) *Attorney, Agent, or Firm* — Birch, Stewart, Kolasch & Birch, LLP

(57) ABSTRACT

A compound represented by a formula [1D] as shown below (wherein $R^{1A}$, $R^{1B}$, $R^{2A}$, $R^{2B}$, $R^{3A}$ and $R^{3B}$ represent a hydrogen atom, an optionally substituted $C_{1-6}$ alkyl group, and the like) is useful as an intermediate for producing a thionucleoside, and the production method of the present invention is useful as a method for producing a thionucleoside.

[1D]

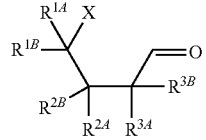

6 Claims, No Drawings

(51) Int. Cl.

| | |
|---|---|
| *C07H 15/04* | (2006.01) |
| *C07H 15/18* | (2006.01) |
| *C07H 15/203* | (2006.01) |
| *C07H 17/02* | (2006.01) |
| *C07H 19/067* | (2006.01) |
| *C07H 19/073* | (2006.01) |
| *C07H 23/00* | (2006.01) |
| *C07C 69/78* | (2006.01) |
| *C07H 1/00* | (2006.01) |
| *C07H 7/04* | (2006.01) |
| *C07C 67/29* | (2006.01) |
| *C07C 68/06* | (2006.01) |
| *C07C 69/28* | (2006.01) |
| *C07C 69/618* | (2006.01) |
| *C07C 69/76* | (2006.01) |
| *C07C 69/92* | (2006.01) |
| *C07C 69/96* | (2006.01) |

(56) References Cited

FOREIGN PATENT DOCUMENTS

| JP | 2006-335737 A | 12/2006 |
|---|---|---|
| WO | WO 97/38001 A1 | 10/1997 |
| WO | WO 2011/074484 A1 | 6/2011 |

OTHER PUBLICATIONS

Khare et al., "Synthesis of 4-deoxy-4-thioarabinofuranosyl disaccharides, analogs of Mycobacterial arabinogalactan," Indian Journal of Chemistry, vol. 47B. Nov. 2008, pp. 1748-1752.

Ototani et al., "Preparation and Antitumor Activity of 4'-Thic Analogs of 2,2'-Anhydro-1-β-D-arabinofuranosylcytosine," Journal of Medicinal Chemistry, 1974, vol. 17, No. 5, pp. 535-537.

PCT/ISA/237—Issued in PCT/JP2013/071871, mailed on Nov. 26, 2013.

Wang et al., "A Practical Synthesis of Sugar-Derived Cyclic Nitrones: Powerful Synthons for the Synthesis of Iminosugars," Synlett, 2010, No. 3, pp. 488-492.

Yoshimura et al., "An Alternative Synthesis of the Antineoplastic Nucleoside 4'-ThioFAC and Its Application to the Synthesis of 4'-ThioFAG and 4'-Thiocytarazid," J. Org. Chem., 1999, vol. 64, No. 21, pp. 7912-7920.

Zheng et al, "Synthesis of L•β-3'-Deoxy-3',3'-difluoro-4'-thionucleosides," Organic Letters, 2006, vol. 8, No. 26, pp. 6083-6086.

International Preliminary Report on Patentability and Written Opinion of the International Searching Authority (forms PCT/IB/338, PCT/IB/373, PCT/ISA/237 and PCT/IB/326), dated Feb. 26, 2015, for International Application No. PCT/JP2013/071871, along with English translations.

Canadian Office Action for Application No. 2,880,794, dated Nov. 2, 2015.

SYNTHETIC INTERMEDIATE OF 1-(2-DEOXY-2-FLUORO-4-THIO-β-D-ARABINOFURANOSYL)CYTOSINE, SYNTHETIC INTERMEDIATE OF THIONUCLEOSIDE, AND METHOD FOR PRODUCING THE SAME

The present application is a continuation of PCT/JP2013/071871 filed on Aug. 13, 2013 and claims priorities under 35 U.S.C. §119 of Japanese Patent Application No. 179380/2012 filed on Aug. 13, 2012 and Japanese Patent Application No. 12693/2013 filed on Jan. 25, 2013. Each of the above applications are hereby expressly incorporated by reference, in its entirety, into the present application.

TECHNICAL FIELD

The present invention relates to a compound useful for the production of a thionucleoside useful as a medicament, etc., and a method for producing the same.

Moreover, the present invention relates to a compound useful for the production of 1-(2-deoxy-2-fluoro-4-thio-β-D-arabinofuranosyl)cytosine useful as an antitutmor agent, etc., and a method for producing the same.

BACKGROUND ART

It has been known that a thionucleoside in which an oxygen atom is replaced with a sulfur atom shows antiviral activity and/or antitumor activity.

For instance, it has been known that 1-(2-deoxy-2-fluoro-4-thio-β-D-arabinofuranosyl)cytosine (hereinafter referred to as "Compound A" at times) has excellent antitumor activity, and that this compound is useful as a tumor therapeutic agent (Patent Literature 1). As a method for producing Compound A, a method using 1,2:5,6-di-O-isopropylidene-α-D-allofuranose has been known, for example (Patent Literature 1). In addition, a method using 5-O-benzyl-2,3-O-isopropylidene-L-lyxono-1,4-lactone has also been known (Patent Literature 2).

Moreover, as a method for producing a sulfur-containing 5-membered ring compound, a method of allowing a γ-halogenoester to react with potassium thioacetate (Non Patent Literature 1), a method of allowing a γ-halogenoketone to react with sodium hydrogen sulfide (Non Patent Literature 2), etc. have been known.

PRIOR ART LITERATURE

Patent Literature

Patent Literature 1: International Publication WO1997/038001
Patent Literature 2: International Publication WO 2011/074484

Non Patent Literature

Non Patent Literature 1: Journal of Medicinal Chemistry, 2003, Vol. 46, pp. 389-398
Non Patent Literature 2: European Journal of Organic Chemistry, 2012, pp. 203-210

SUMMARY OF INVENTION

Problem to be Solved by the Invention

However, the production method described in Non Patent Literature 1 has been problematic in that this method involves a reaction carried out under a cryogenic temperature (−78° C.), in that the method uses a reagent that should be handled with care, and in terms of low stereoselectivity. The production method described in Non Patent Literature 2 has been problematic in terms of limited structure of a thionucleoside and low reactivity.

Moreover, the production methods described in Patent Literature 1 and Patent Literature 2 have also been problematic in that the methods include a large number of steps, in that they require column chromatography, in that they have low yields, in that they use harmful reagents, etc.

Hence, it has been strongly desired to develop a method for industrially producing a thionucleoside and Compound A, which involves a short-term reaction performed at high reaction rate with high stereoselectivity, and does not require reaction conditions and reagents that are not preferable for industrial production of the compounds.

It is an object of the present invention to provide novel compounds useful for the production of a thionucleoside, etc., and a method for producing the same.

It is another object of the present invention to provide novel compounds useful for the production of Compound A that is useful as an antitumor agent, and a method for producing the same.

Means for Solution to Problem

The present inventors have conducted intensive studies directed towards achieving the aforementioned objects. As a result, the inventors have found that a compound represented by a formula [1E] shown below can be obtained in a short time, at a high reaction rate, and with high stereoselectivity, by allowing a compound represented by a formula [1D] shown below to react with a sulfur compound. Further, the inventors have found that a thionucleoside can be industrially produced through a compound represented by a formula [1Aa] from a compound represented by a formula [4Aa].

Moreover, the present inventors have also found that a compound represented by a formula [1] shown below is an intermediate useful for the production of Compound A. Furthermore, the inventors have also found that Compound A can be industrially produced from a compound represented by a formula [4] as shown below, through the compound represented by the formula [1], in a short time, at a high reaction rate, and with high stereoselectivity, without using reaction conditions and reagents that are not preferable for industrial production of the compound, thereby completing the present invention.

Specifically, according to the present invention, there is provided a production method of a compound represented by the following formula [1E]:

[Formula 1]

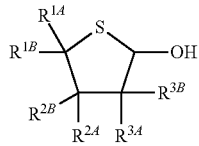

[1E]

(wherein $R^{1A}$, $R^{1B}$, $R^{2A}$, $R^{2B}$, $R^{3A}$ and $R^{3B}$ have the same meanings as those described below)
which comprises allowing a compound represented by the following formula [1D]:

[Formula 2]

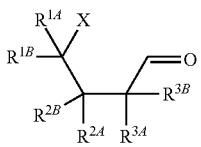

[1D]

(wherein $R^{1A}$ and $R^{1B}$, which are the same or different, each represent a hydrogen atom, an optionally protected carboxyl group, an optionally substituted $C_{1-6}$ alkyl group, an optionally substituted $C_{2-6}$ alkenyl group, an optionally substituted $C_{2-6}$ alkynyl group, an optionally substituted aryl group or an optionally substituted heterocyclic group; $R^{2A}$ and $R^{2B}$, which are the same or different, each represent a hydrogen atom, a hydroxyl group, a halogen atom, a cyano group, an azide group, an optionally protected amino group, an optionally protected carboxyl group, a group represented by the following formula [15]:

[Formula 3]

  [15]

(wherein $R^{2a}$ represents a hydroxyl-protecting group), an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{1-6}$ alkylthio group, an optionally substituted aryl group, an optionally substituted aryloxy group, an optionally substituted arylthio group, an optionally substituted heterocyclic group, an optionally substituted heterocyclic oxy group or an optionally substituted heterocyclic thio group; or $R^{2A}$ and $R^{2B}$ may together form an optionally substituted $C_{1-6}$ alkylidene group; $R^{3A}$ and $R^{3B}$, which are the same or different, each represent a hydrogen atom, a hydroxyl group, a halogen atom, a cyano group, an azide group, an optionally protected amino group, an optionally protected carboxyl group, a group represented by the following formula [16]:

[Formula 4]

  [16]

(wherein $R^{3a}$ represents a hydroxyl-protecting group), an optionally substituted $C_{1-6}$ alkyl group, an optionally substituted $C_{2-6}$ alkenyl group, an optionally substituted $C_{2-6}$ alkynyl group, an optionally substituted $C_{1-6}$ alkoxy group, an optionally substituted $C_{1-6}$ alkylthio group, an optionally substituted aryl group, an optionally substituted aryloxy group, an optionally substituted arylthio group, an optionally substituted heterocyclic group, an optionally substituted heterocyclic oxy group or an optionally substituted heterocyclic thio group; or $R^{3A}$ and $R^{3B}$ may together form an optionally substituted $C_{1-6}$ alkylidene group; or $R^{2A}$ and $R^{3A}$ may together form a group represented by the following formula [17]:

[Formula 5]

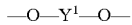  [17]

(wherein $Y^1$ represents an optionally substituted $C_{1-6}$ alkylene group or an optionally substituted siloxane group; and the bond on the left side binds to a carbon atom binding to $R^{2A}$), or a bond; or $R^{2A}$, $R^{2B}$, $R^{3A}$ and $R^{3B}$ may form an optionally substituted aromatic ring together with carbon atoms to which they bind; and X represents a leaving group), to react with a sulfur compound.

In addition, according to the present invention, there is provided a production method of a thionucleoside derivative represented by the following formula [11A]:

[Formula 6]

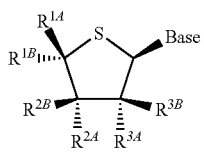

[11Aa]

(wherein Base represents an optionally protected nucleic acid base; and $R^{1A}$, $R^{1B}$, $R^{2A}$, $R^{2B}$, $R^{3A}$ and $R^{3B}$ have the same meanings as those described above)
which comprises
  allowing a compound represented by the following formula [4Aa]:

[Formula 7]

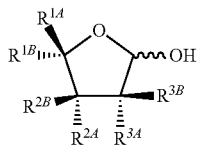

[4Aa]

(wherein $R^{1A}$, $R^{1B}$, $R^{2A}$, $R^{2B}$, $R^{3A}$ and $R^{3B}$ have the same meanings as those described above), to react with a compound represented by the following formula [5]:

[Formula 8]

 $H_2NOR^7$  [5]

(wherein $R^7$ represents a hydrogen atom, an optionally substituted $C_{1-6}$ alkyl group, an optionally substituted aryl group, an optionally substituted heterocyclic group or an optionally substituted silyl group), or a salt thereof, to obtain a compound represented by the following formula [1Aa]:

[Formula 9]

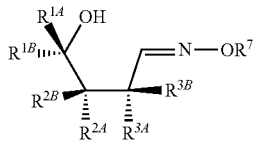

[1Aa]

(wherein $R^{1A}$, $R^{1B}$, $R^{2A}$, $R^{2B}$, $R^{3A}$, $R^{3B}$ and $R^7$ have the same meanings as those described above),
  then subjecting the compound represented by the formula [1Aa] to the following method (1), or (2):
  "(1) a method of allowing the compound represented by the formula [1Aa] to react with a halogenating agent in the presence of a base, or
  (2) a method of allowing the compound represented by the formula [1Aa] to react, in the presence of a base, with a compound represented by the following formula [6]:

[Formula 10]

 $R^8SO_2X^1$  [6]

(wherein $R^8$ represents an optionally substituted $C_{1-6}$ alkyl group or an optionally substituted aryl group; and $X^1$ represents a halogen atom), to obtain a compound represented by the following formula [1Ba]:

[Formula 11]

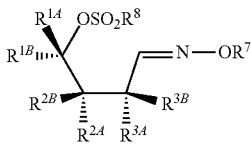

[1Ba]

(wherein $R^{1A}$, $R^{1B}$, $R^{2A}$, $R^{2B}$, $R^{3A}$, $R^{3B}$, $R^7$ and $R^8$ have the same meanings as those described above), and then allowing the compound represented by the formula [1Ba] to react with a halide of alkaline metal,"

so as to obtain a compound represented by the following formula [1Ca]:

[Formula 12]

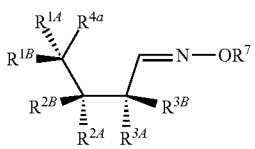

[1Ca]

(wherein $R^{4a}$ represents a halogen atom; and $R^{1A}$, $R^{1B}$, $R^{2A}$, $R^{2B}$, $R^{3A}$, $R^{3B}$ and $R^7$ have the same meanings as those described above), then hydrolyzing the compound represented by the formula [1Ca] to obtain a compound represented by the following formula [1Dd]:

[Formula 13]

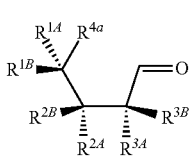

[1Dd]

(wherein $R^{1A}$, $R^{1B}$, $R^{2A}$, $R^{2B}$, $R^{3A}$, $R^{3B}$ and $R^{4a}$ have the same meanings as those described above), then allowing the compound represented by the formula [1Dd] to react with a sulfur compound to obtain a compound represented by the following formula [1Ea]:

[Formula 14]

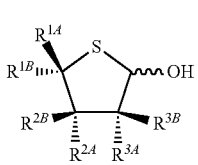

[1Ea]

(wherein $R^{1A}$, $R^{1B}$, $R^{2A}$, $R^{2B}$, $R^{3A}$ and $R^{3B}$ have the same meanings as those described above), then allowing the compound represented by the formula [1Ea] to react with a compound represented by the following formula [7]:

[Formula 15]

(wherein $R^9$ represents an optionally substituted acyl group, an optionally substituted $C_{1-6}$ alkylsulfonyl group or an optionally substituted arylsulfonyl group; and $X^2$ represents a halogen atom), or with a compound represented by the following formula [8]:

[Formula 16]

(wherein $R^9$ has the same meanings as those described above), to obtain a compound represented by the following formula [9Aa]:

[Formula 17]

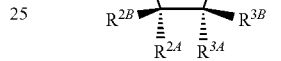

(wherein $R^{1A}$, $R^{1B}$, $R^{2A}$, $R^{2B}$, $R^{3A}$, $R^{3B}$ and $R^9$ have the same meanings as those described above), then allowing the compound represented by the formula [9Aa] to react with a protected nucleic acid base, and then deprotecting the resultant reaction product, as necessary.

Moreover, according to the present invention, there is provided a production method of a thionucleoside derivative represented by the following formula [11Ab]:

[Formula 18]

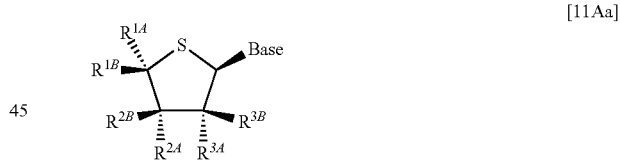

[11Aa]

(wherein $R^{1A}$, $R^{1B}$, $R^{2A}$, $R^{2B}$, $R^{3A}$, $R^{3B}$ and Base have the same meanings as those described above)

which comprises hydrolyzing a compound represented by the following formula [1Ba]:

[Formula 19]

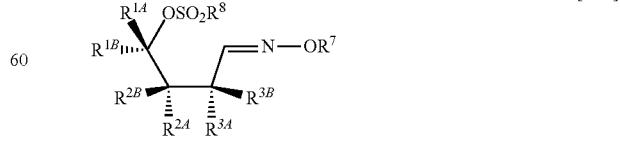

[1Ba]

(wherein $R^{1A}$, $R^{1B}$, $R^{2A}$, $R^{2B}$, $R^{3A}$, $R^{3B}$, $R^7$ and $R^8$ have the same meanings as those described above), to obtain a compound represented by the following formula [1De]:

[Formula 20]

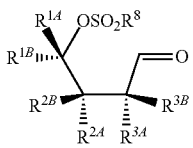

[1De]

(wherein $R^{1A}$, $R^{1B}$, $R^{2A}$, $R^{2B}$, $R^{3A}$, $R^{3B}$ and $R^8$ have the same meanings as those described above), then allowing the compound represented by the formula [1De] to react with a sulfur compound to obtain a compound represented by the following formula [1Eb]:

[Formula 21]

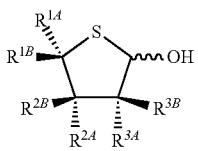

[1Eb]

(wherein $R^{1A}$, $R^{1B}$, $R^{2A}$, $R^{2B}$, $R^{3A}$ and $R^{3B}$ have the same meanings as those described above), then allowing the compound represented by the formula [1Eb] to react with a compound represented by the following formula [7]:

[Formula 22]

$R^9X^2$        [7]

(wherein $R^9$ and $X^2$ have the same meanings as those described above), or with a compound represented by the following formula [8]:

[Formula 23]

$R^9—O—R^9$        [8]

(wherein $R^9$ has the same meanings as those described above), to obtain a compound represented by the following formula [9Ab]:

[Formula 24]

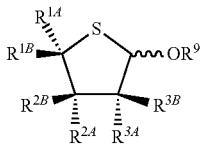

[9Ab]

(wherein $R^{1A}$, $R^{1B}$, $R^{2A}$, $R^{2B}$, $R^{3A}$, $R^{3B}$ and $R^9$ have the same meanings as those described above), then allowing the compound represented by the formula [9Ab] to react with a protected nucleic acid base, and then deprotecting the resultant reaction product, as necessary.

Furthermore, according to the present invention, there is provided a production method of 1-(2-deoxy-2-halogeno-4-thio-β-D-arabinofuranosyl)cytosine represented by the following formula [14]:

[Formula 25]

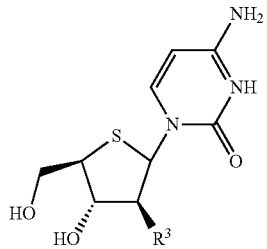

[14]

(wherein $R^3$ has the same meanings as those described below) which comprises allowing a compound represented by the following formula [4]:

[Formula 26]

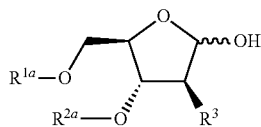

[4]

(wherein $R^{1a}$ represents a hydroxyl-protecting group; $R^{2a}$ represents a hydroxyl-protecting group; or $R^{1a}$ and $R^{2a}$ may together form an optionally substituted $C_{1-3}$ alkylene group; and $R^3$ represents a halogen atom) to react with a compound represented by the following formula [5]:

[Formula 27]

$H_2NOR^7$        [5]

(wherein $R^7$ has the same meanings as those described above), or a salt thereof, to obtain a compound represented by the following formula [1a]:

[Formula 28]

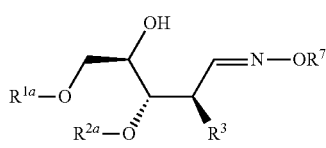

[1a]

(wherein $R^{1a}$, $R^{2a}$, $R^3$ and $R^7$ have the same meanings as those described above), then subjecting the compound represented by the formula [1a] to the following method (1), or (2):

"(1) a method of allowing the compound represented by the formula [1a] to react with a halogenating agent in the presence of a base, or (2) a method of allowing the compound represented by the formula [1a] to react, in the presence of a base, with a compound represented by the following formula [6]:

[Formula 29]

$R^8SO_2X^1$        [6]

(wherein $R^8$ represents an optionally substituted $C_{1-6}$ alkyl group or an optionally substituted aryl group; and $X^1$ represents a halogen atom), to obtain a compound represented by the following formula [1b]:

[Formula 30]

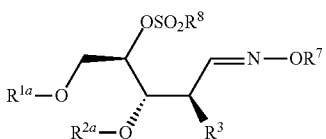
[1b]

(wherein $R^{1a}$, $R^{2a}$, $R^3$, $R^7$ and $R^8$ have the same meanings as those described above), and then allowing the compound represented by the formula [1b] to react with a halide of alkaline metal,"
so as to obtain a compound represented by the following formula [1c]:

[Formula 31]

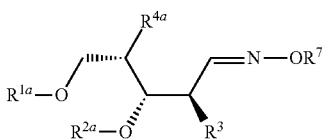
[1c]

(wherein $R^{4a}$ represents a halogen atom; and $R^{1a}$, $R^{2a}$, $R^3$ and $R^7$ have the same meanings as those described above),
then hydrolyzing the compound represented by the formula [1c] to obtain a compound represented by the following formula [1d]:

[Formula 32]

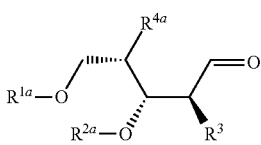
[1d]

(wherein $R^{1a}$, $R^{2a}$, $R^3$ and $R^{4a}$ have the same meanings as those described above),
then allowing the compound represented by the formula [1d] to react with a sulfur compound to obtain a compound represented by the following formula [1e]:

[Formula 33]

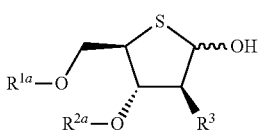
[1e]

(wherein $R^{1a}$, $R^{2a}$ and $R^3$ have the same meanings as those described above),
then allowing the compound represented by the formula [1e] to react with a compound represented by the following formula [7]:
[Formula 34]

$R^9X^2$ [7]

(wherein $R^9$ represents an optionally substituted acyl group, an optionally substituted $C_{1-6}$ alkylsulfonyl group or an optionally substituted arylsulfonyl group; and $X^2$ represents a halogen atom), or with a compound represented by the following formula [8]:
[Formula 35]

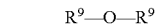
$R^9$—O—$R^9$ [8]

(wherein $R^9$ has the same meanings as those described above), to obtain a compound represented by the following formula [9]:

[Formula 36]

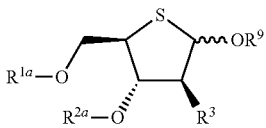
[9]

(wherein $R^{1a}$, $R^{2a}$, $R^3$ and $R^9$ have the same meanings as those described above),
then subjecting the compound represented by the formula [9] to any one of the following methods (1) to (4):
"(1) a method of allowing the compound represented by the formula [9] to react with protected cytosine or protected $N^4$-acylcytosine to obtain a compound represented by the following formula [11]:

[Formula 37]

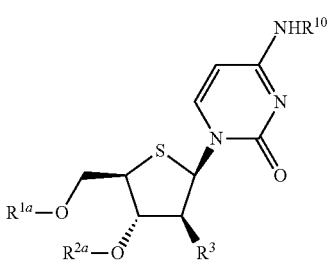
[11]

(wherein $R^{10}$ represents a hydrogen atom or an optionally substituted acyl group; and $R^{1a}$, $R^{2a}$ and $R^3$ have the same meanings as those described above), and then deprotecting the compound represented by the formula [11],
(2) a method of allowing the compound represented by the formula [9] to react with protected cytosine to obtain a compound represented by the following formula [11a]:

[Formula 38]

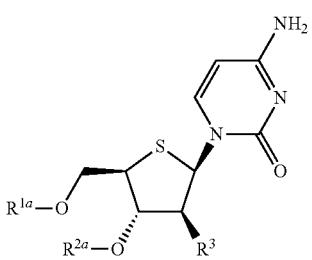
[11a]

(wherein $R^{1a}$, $R^{2a}$ and $R^3$ have the same meanings as those described above), then allowing the compound represented by the formula [11a] to react with a compound represented by the following formula [12]:

[Formula 39]

  [12]

(wherein $R^{10a}$ represents an optionally substituted acyl group; and $X^4$ represents a halogen atom), or with a compound represented by the following formula [13]:
[Formula 40]

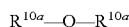  [13]

(wherein $R^{10a}$ has the same meanings as those described above), to obtain a compound represented by the following formula [11b]:

[Formula 41]

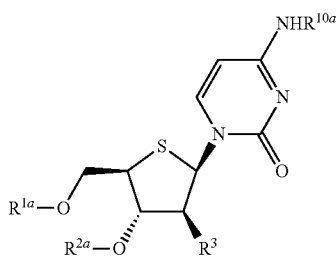  [11b]

(wherein $R^{1a}$, $R^{2a}$, $R^3$ and $R^{10a}$ have the same meanings as those described above), and then deprotecting the compound represented by the formula [11b], (3) a method of halogenating the compound represented by the formula [9] to obtain a compound represented by the following formula [10]:

[Formula 42]

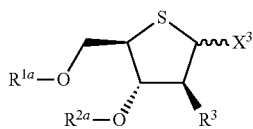  [10]

(wherein $X^3$ represents a halogen atom; and $R^{1a}$, $R^{2a}$ and $R^3$ have the same meanings as those described above), then allowing the compound represented by the formula [10] to react with protected cytosine or protected $N^4$-acylcytosine to obtain a compound represented by the following formula [11]:

[Formula 43]

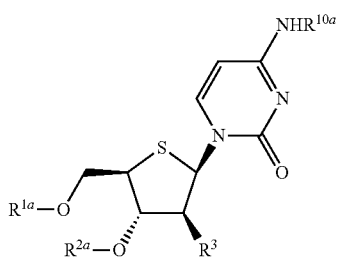  [11]

(wherein $R^{1a}$, $R^{2a}$, $R^3$ and $R^{10}$ have the same meanings as those described above), and then deprotecting the compound represented by the formula [11], and (4) a method of halogenating the compound represented by the formula [9] to obtain a compound represented by the following formula [10]:
[Formula 44]

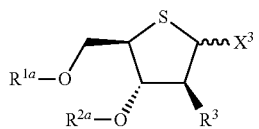  [10]

(wherein $R^{1a}$, $R^{2a}$, $R^3$ and $X^3$ have the same meanings as those described above), then allowing the compound represented by the formula [10] to react with protected cytosine to obtain a compound represented by the following formula [11a]:

[Formula 45]

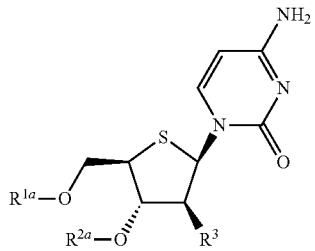  [11a]

(wherein $R^{1a}$, $R^{2a}$ and $R^3$ have the same meanings as those described above), then allowing the compound represented by the formula [11a] to react with a compound represented by the following formula [12]:
[Formula 46]

  [12]

(wherein $R^{10a}$ and $X^4$ have the same meanings as those described above)), or with a compound represented by the following formula [13]:
[Formula 47]

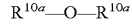  [13]

(wherein $R^{10a}$ has the same meanings as those described above), to obtain a compound represented by the following formula [11b]:

[Formula 48]

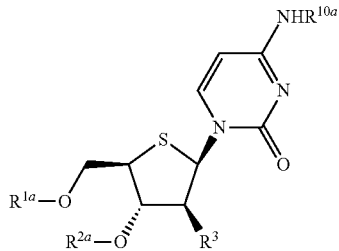  [11b]

(wherein $R^{1a}$, $R^{2a}$, $R^3$ and $R^{10a}$ have the same meanings as those described above), and then deprotecting the compound represented by the formula [11b]".

Further, according to the present invention, there is provided a compound represented by the following formula [1F]:

[Formula 49]

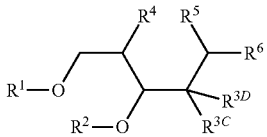

[1F]

(wherein $R^1$ represents a hydrogen atom or a hydroxyl-protecting group; $R^2$ represents a hydrogen atom or a hydroxyl-protecting group; or $R^1$ and $R^2$ may together form an optionally substituted $C_{1-3}$ alkylene group; $R^{3C}$ represents a hydrogen atom, a halogen atom, a group represented by the following formula [16]:
[Formula 50]

$$—OR^{3a} \quad [16]$$

(wherein $R^{3a}$ represents a hydroxyl-protecting group), or an optionally substituted $C_{1-6}$ alkyl group; $R^{3D}$ represents a hydrogen atom, a halogen atom, a group represented by the following formula [16]:
[Formula 51]

$$—OR^{3a} \quad [16]$$

(wherein $R^{3a}$ has the same meanings as those described above), or an optionally substituted $C_{1-6}$ alkyl group; $R^4$ represents a halogen atom, a hydroxyl group, an optionally substituted $C_{1-6}$ alkylsulfonyloxy group or an optionally substituted arylsulfonyloxy group; $R^5$ and $R^6$ together represent a group represented by the following form formula [2]:
[Formula 52]

$$=Y \quad [2]$$

(wherein Y represents an oxygen atom or a group represented by the following formula [3]:
[Formula 53]

$$=N—OR^7 \quad [3]$$

(wherein $R^7$ has the same meanings as those described above)); or $R^4$ and $R^5$ together represent a sulfur atom; and $R^6$ represents a hydroxyl group, provided that, when $R^5$ and $R^6$ together represent a group represented by the following formula [2a]:
[Formula 54]

$$=O \quad [2a]$$

, one of $R^{3C}$ and $R^{3D}$ represents a halogen atom, the other represents a hydrogen atom, and $R^4$ represents a halogen atom, an optionally substituted $C_{1-6}$ alkylsulfonyloxy group or an optionally substituted arylsulfonyloxy group;

when $R^4$ and $R^5$ together represent a sulfur atom, and one of $R^{3C}$ and $R^{3D}$ represents a hydrogen atom, the other represents a halogen atom, a group represented by the following formula [16]:
[Formula 55]

$$—OR^{3a} \quad [16]$$

(wherein $R^{3a}$ has the same meanings as those described above), or an optionally substituted $C_{1-6}$ alkyl group;

when $R^4$ and $R^5$ together represent a sulfur atom, one of $R^{3C}$ and $R^{3D}$ represents a hydrogen atom, and the other represents a group represented by the following formula [16]:
[Formula 56]

$$—OR^{3a} \quad [16]$$

(wherein $R^{3a}$ represents a hydroxyl-protecting group), $R^2$ represents a hydroxyl-protecting group;

when $R^5$ and $R^6$ together represent a group represented by the following formula [3]:
[Formula 57]

$$=N—OR^7 \quad [3]$$

(wherein $R^7$ has the same meanings as those described above), one of $R^{3C}$ and $R^{3D}$ represents a group represented by the following formula [16]:
[Formula 58]

$$—OR^{3a} \quad [16]$$

(wherein $R^{3a}$ has the same meanings as those described above), the other represents a hydrogen atom, and $R^4$ represents an iodine atom, a hydroxyl group, an optionally substituted $C_{1-6}$ alkylsulfonyloxy group or an optionally substituted arylsulfonyloxy group, $R^1$ represents an optionally substituted acyl group, and $R^2$ represents an optionally substituted acyl group; and when $R^5$ and $R^6$ together represent a group represented by the following formula [3]:
[Formula 59]

$$=N—OR^7 \quad [3]$$

(wherein $R^7$ has the same meanings as those described above), $R^{3C}$ represents a hydrogen atom, $R^{3D}$ represents a hydrogen atom, and $R^4$ represents a hydroxyl group, $R^1$ represents an optionally substituted aroyl group, and $R^2$ represents an optionally substituted aroyl group.)

Still further, according to the present invention, there is provided a compound represented by the following formula [1]:

[Formula 60]

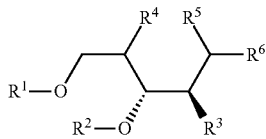

[1]

(wherein $R^1$ represents a hydrogen atom or a hydroxyl-protecting group; $R^2$ represents a hydrogen atom or a hydroxyl-protecting group; or $R^1$ and $R^2$ may together form an optionally substituted $C_{1-3}$ alkylene group; $R^3$ represents a halogen atom; $R^4$ represents a halogen atom, a hydroxyl group, an optionally substituted $C_{1-6}$ alkylsulfonyloxy group or an optionally substituted arylsulfonyloxy group; $R^5$ and $R^6$ together represent a group represented by the following formula [2]:

[Formula 61]

$$=Y \quad [2]$$

(wherein Y represents an oxygen atom or a group represented by the following formula [3]:
[Formula 62]

=N—OR$^7$ [3]

(wherein R$^7$ represents a hydrogen atom, an optionally substituted C$_{1-6}$ alkyl group, an optionally substituted aryl group, an optionally substituted heterocyclic group or an optionally substituted silyl group)); or R$^4$ and R$^5$ together represent a sulfur atom; and R$^6$ represents a hydroxyl group, provided that,
when R$^5$ and R$^6$ together represent a group represented by the following formula [2a]:
[Formula 63]

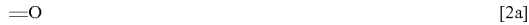
=O [2a]

R$^4$ represents a halogen atom, an optionally substituted C$_{1-6}$ alkylsulfonyloxy group or an optionally substituted arylsulfonyloxy group).

Still further, according to the present invention, there is provided a compound represented by the following formula [1G]:

[Formula 64]

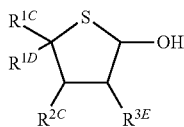
[1G]

(wherein R$^{1C}$ represents a methyl group or an optionally substituted aryl group, R$^{1D}$ represents a hydrogen atom, R$^{2C}$ represents hydrogen atom or an optionally substituted aryl group, R$^{3E}$ represents a hydrogen atom, an optionally substituted C$_{1-6}$ alkylthio group, an optionally substituted aryloxy group, an optionally substituted arylthio group or an optionally substituted heterocyclic thio group, or R$^{2C}$ and R$^{3E}$ together represent a group represented by the following formula [17]:
[Formula 65]

—O—Y$^1$—O— [17]

(wherein Y$^1$ represents an optionally substituted C$_{1-6}$ alkylene group or an optionally substituted siloxane group, and the bond on the left side binds to a carbon atom binding to R$^{2C}$), or a bond, provided that, when one of R$^{1C}$ and R$^{1D}$ represents a methyl group, the other represents a hydrogen atom, and R$^{2C}$ represents a hydrogen atom, R$^{3E}$ represents an optionally substituted C$_{1-6}$ alkylthio group, an optionally substituted aryloxy group, an optionally substituted arylthio group or an optionally substituted heterocyclic thio group; or R$^{1C}$ represents a hydrogen atom, R$^{1D}$ represents a hydrogen atom, R$^{2C}$ represents a hydrogen atom, and R$^{3E}$ represents an optionally substituted aroylamino group; or R$^{1C}$ represents a hydrogen atom, R$^{1D}$ represents a hydrogen atom, R$^{2C}$ and R$^{3E}$ together form a benzene ring substituted with a protected hydroxyl group, together with carbon atoms to which they bind; or R$^{1C}$ represents an optionally protected carboxyl group, R$^{1D}$ represents an optionally protected carboxyl group, R$^{2C}$ represents a hydrogen atom, and R$^{3E}$ represents a hydrogen atom).

Advantageous Effects of Invention

The compound of the present invention is useful as an intermediate for producing a thionucleoside, and the production method of the present invention is useful as a method for producing a thionucleoside.

Moreover, the compound of the present invention is useful as an intermediate for producing Compound A. The production method of the present invention is useful as a method for producing Compound A.

EMBODIMENTS FOR CARRYING OUT THE INVENTION

Hereinafter, the present invention will be described in detail.

In the present invention, individual terms have the following meanings, unless otherwise specified.

The term "halogen atom" is used herein to mean a fluorine atom, a chlorine atom, a bromine atom or an iodine atom.

The term "C$_{1-6}$ alkyl group" is used herein to mean linear or branched C$_{1-6}$ alkyl groups, such as methyl, ethyl, propyl, isopropyl, butyl, sec-butyl, isobutyl, tert-butyl, pentyl and hexyl groups.

The term "C$_{2-6}$ alkenyl group" is used herein to mean linear or branched C$_{2-6}$ alkenyl groups, such as vinyl, allyl, propenyl, isopropenyl, butenyl, isobutenyl, 1,3-butadienyl, pentenyl and hexenyl groups.

The term "C$_{2-6}$ alkynyl group" is used herein to mean linear or branched C$_{2-6}$ alkynyl groups, such as ethynyl, propynyl, butynyl, pentynyl and hexynyl groups.

The term "C$_{3-8}$ cycloalkyl group" is used herein to mean C$_{3-8}$ cycloalkyl groups, such as cyclopropyl, cyclobutyl, cyclopentyl and cyclohexyl groups.

The term "aryl group" is used herein to mean a phenyl or naphthyl group, etc.

The term "ar-C$_{1-6}$ alkyl group" is used herein to mean ar-C$_{1-6}$ alkyl groups, such as benzyl, diphenylmethyl, trityl, phenethyl and naphthylmethyl groups.

The term "C$_{1-3}$ alkylene group" is used herein to mean a methylene, ethylene or propylene group, etc.

The term "C$_{1-6}$ alkylidene group" is used herein to mean linear or branched C$_{1-6}$ alkylidene groups, such as methylidene, ethylidene, propylidene, butylidene, pentylidene and hexylidene.

The term "C$_{1-6}$ alkoxy group" is used herein to mean linear or branched C$_{1-6}$ alkyloxy groups, such as methoxy, ethoxy, propoxy, isopropoxy, butoxy, isobutoxy, sec-butoxy, tert-butoxy, pentyloxy and hexyloxy groups.

The term "aryloxy group" is used herein to mean a phenoxy or naphthyloxy group, etc.

The term "C$_{1-6}$ alkoxy C$_{1-6}$ alkyl group" is used herein to mean C$_{1-6}$ alkyloxy C$_{1-6}$ alkyl groups, such as methoxymethyl and 1-ethoxyethyl groups.

The term "C$_{2-6}$ alkanoyl group" is used herein to mean linear or branched C$_{2-6}$ alkanoyl groups, such as acetyl, propionyl, valeryl, isovaleryl and pivaloyl groups.

The term "aroyl group" is used herein to mean a benzoyl or naphthoyl group, etc.

The term "heterocyclic carbonyl group" is used herein to mean a nicotinoyl, thenoyl, pyrrolidinocarbonyl or furoyl group, etc.

The term "(α-substituted) aminoacetyl group" is used herein to mean (α-substituted) aminoacetyl groups having an optionally protected N-terminus, which are derived from amino acids (such as glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline and hydroxyproline).

The term "acyl group" is used herein to mean a formyl group, succinyl group, glutaryl group, maleoyl group, phthaloyl group, $C_{2-6}$ alkanoyl group, aroyl group, heterocyclic carbonyl group or (α-substituted) aminoacetyl group, etc.

The term "$C_{2-6}$ alkanoyloxy group" is used herein to mean linear or branched $C_{2-6}$ alkanoyloxy groups, such as acetyloxy and propionyloxy groups.

The term "aroyloxy group" is used herein to mean a benzoyloxy or naphthoyloxy group, etc.

The term "acyloxy group" is used herein to mean a $C_{2-6}$ alkanoyloxy group or aroyloxy group.

The term "$C_{1-6}$ alkoxycarbonyl group" is used herein to mean linear or branched $C_{1-6}$ alkyloxycarbonyl groups, such as methoxycarbonyl, ethoxycarbonyl, isopropoxycarbonyl, tert-butoxycarbonyl and 1,1-dimethylpropoxycarbonyl groups.

The term "aryloxycarbonyl group" is used herein to mean a phenyloxycarbonyl or naphthyloxycarbonyl group, etc.

The term "ar-$C_{1-6}$ alkoxycarbonyl group" is used herein to mean ar-$C_{1-6}$ alkyloxycarbonyl groups, such as benzyloxycarbonyl, phenethyloxycarbonyl and naphthylmethyloxycarbonyl groups.

The term "$C_{1-6}$ alkoxycarbonyloxy group" is used herein to mean linear or branched $C_{1-6}$ alkyloxycarbonyloxy groups, such as methoxycarbonyloxy, ethoxycarbonyloxy, isopropoxycarbonyloxy, tert-butoxycarbonyloxy and 1,1-dimethylpropoxycarbonyloxy groups.

The term "$C_{1-6}$ alkylamino group" is used herein to mean linear or branched $C_{1-6}$ alkylamino groups, such as methylamino, ethylamino, propylamino, isopropylamino, butylamino, sec-butylamino, tert-butylamino, pentylamino and hexylamino groups.

The term "di($C_{1-6}$ alkyl)amino group" is used herein to mean linear or branched di($C_{1-6}$ alkyl)amino groups, such as dimethylamino, diethylamino, dipropylamino, diisopropylamino, dibutylamino, di(tert-butyl)amino, dipentylamino, dihexylamino, (ethyl)(methyl)amino and (methyl)(propyl) amino groups.

The term "aroylamino group" is used herein to mean amino groups substituted with aroyl groups, such as a benzoylamino group.

The term "$C_{1-6}$ alkylthio group" is used herein to mean $C_{1-6}$ alkylthio groups, such as methylthio, ethylthio and propylthio groups.

The term "$C_{1-6}$ alkylsulfonyl group" is used herein to mean $C_{1-6}$ alkylsulfonyl groups, such as methylsulfonyl, ethylsulfonyl and propylsulfonyl groups.

The term "arylsulfonyl group" is used herein to mean a benzenesulfonyl, p-toluenesulfonyl or naphthalenesulfonyl group, etc.

The term "$C_{1-6}$ alkylsulfonyloxy group" is used herein to mean $C_{1-6}$ alkylsulfonyloxy groups, such as methylsulfonyloxy, ethylsulfonyloxy and propylsulfonyloxy groups.

The term "arylsulfonyloxy group" is used herein to mean a phenylsulfonyloxy or naphthylsulfonyloxy group, etc.

The term "aromatic ring" is used herein to mean a benzene ring or naphthalene ring, etc.

The term "siloxane group" is used herein to mean a disiloxane group or trisiloxane group, etc.

The term "monocyclic nitrogen-containing heterocyclic group" is used herein to mean monocyclic nitrogen-containing heterocyclic groups that contain only a nitrogen atom as a heteroatom forming the ring, such as azetidinyl, pyrrolidinyl, pyrrolinyl, pyrrolyl, piperidyl, tetrahydropyridyl, pyridyl, homopiperidinyl, octahydroazocinyl, imidazolidinyl, imidazolinyl, imidazolyl, pyrazolidinyl, pyrazolinyl, pyrazolyl, piperazinyl, pyrazinyl, pyridazinyl, pyrimidinyl, homopiperazinyl, triazolyl and tetrazolyl groups.

The term "monocyclic oxygen-containing heterocyclic group" is used herein to mean tetrahydrofuranyl, furanyl, tetrahydropyranyl or pyranyl group, etc.

The term "monocyclic sulfur-containing heterocyclic group" is used herein to mean a thienyl group, etc.

The term "monocyclic nitrogen-oxygen-containing heterocyclic group" is used herein to mean monocyclic nitrogen-oxygen-containing heterocyclic groups containing only a nitrogen atom and an oxygen atom as heteroatoms forming the ring, such as oxazolyl, isooxazolyl, oxadiazolyl and morpholinyl groups.

The term "monocyclic nitrogen-sulfur-containing heterocyclic group" is used herein to mean monocyclic nitrogen-sulfur-containing heterocyclic groups containing only a nitrogen atom and a sulfur atom as heteroatoms forming the ring, such as thiazolyl, isothiazolyl, thiadiazolyl, thiomorpholinyl, 1-oxidothiomorpholinyl and 1,1-dioxidothiomorpholinyl groups.

The term "monocyclic heterocyclic group" is used herein to mean a monocyclic nitrogen-containing heterocyclic group, monocyclic oxygen-containing heterocyclic group, monocyclic sulfur-containing heterocyclic group, monocyclic nitrogen-oxygen-containing heterocyclic group or monocyclic nitrogen-sulfur-containing heterocyclic group, etc.

The term "bicyclic nitrogen-containing heterocyclic group" is used herein to mean bicyclic nitrogen-containing heterocyclic groups containing only a nitrogen atom as a heteroatom forming the ring, such as indolinyl, indolyl, isoindolinyl, isoindolyl, benzimidazolyl, indazolyl, benzotriazolyl, quinolyl, tetrahydroquinolinyl, quinolyl, tetrahydroisoquinolinyl, isoquinolinyl, quinolizinyl, cinnolinyl, phthalazinyl, quinazolinyl, dihydroquinoxalinyl, quinoxalinyl, naphthyridinyl, purinyl, pteridinyl and quinuclidinyl groups.

The term "bicyclic oxygen-containing heterocyclic group" is used herein to mean bicyclic oxygen-containing heterocyclic groups containing only an oxygen atom as a heteroatom forming the ring, such as 2,3-dihydrobenzofuranyl, benzofuranyl, isobenzofuranyl, chromanyl, chromenyl, isochromanyl, 1,3-benzodioxolyl, 1,3-benzodioxanyl and 1,4-benzodioxanyl groups.

The term "bicyclic sulfur-containing heterocyclic group" is used herein to mean bicyclic sulfur-containing heterocyclic groups containing only a sulfur atom as a heteroatom forming the ring, such as 2,3-dihydrobenzothienyl and benzothienyl groups.

The term "bicyclic nitrogen-oxygen-containing heterocyclic group" is used herein to mean bicyclic nitrogen-oxygen-containing heterocyclic groups containing only a nitrogen atom and an oxygen atom as heteroatoms forming the ring, such as benzoxazolyl, benzisooxazolyl, benzoxadiazolyl, benzomorpholinyl, dihydropyranopyridyl, dihydrodioxinopyridyl and dihydropyridoxazinyl groups.

The term "bicyclic nitrogen-sulfur-containing heterocyclic group" is used herein to mean bicyclic nitrogen-sulfur-containing heterocyclic groups containing a nitrogen atom and a sulfur atom as heteroatoms forming the ring, such as benzothiazolyl, benzisothiazolyl and benzothiadiazolyl groups.

The term "bicyclic heterocyclic group" is used herein to mean a bicyclic nitrogen-containing heterocyclic group, bicyclic oxygen-containing heterocyclic group, bicyclic sulfur-containing heterocyclic group, bicyclic nitrogen-oxygen-containing heterocyclic group or bicyclic nitrogen-sulfur-containing heterocyclic group, etc.

The term "heterocyclic group" is used herein to mean a monocyclic heterocyclic group or a bicyclic heterocyclic group.

The term "heterocyclic oxy group" is used herein to mean a group, in which a hydrogen atom (—H) binding to a carbon atom forming the ring of a heterocyclic group is substituted with an oxygen atom (—O).

The term "heterocyclic thio group" is used herein to mean a group, in which a hydrogen atom (—H) binding to a carbon atom forming the ring of a heterocyclic group is substituted with a sulfur atom (—S—).

The term "silyl group" is used herein to mean a trimethylsilyl, triethylsilyl, triisopropylsilyl, tributylsilyl, tert-butyldimethylsilyl or tert-butyldiphenylsilyl group, etc.

The term "silylation" is used herein to mean substitution of a hydrogen atom of a hydroxyl group, amino group, carboxyl group, amide group or mercapto group with a silyl group.

The term "$N^4$-acylcytosine" is used herein to mean cytosines, in which an amino group is protected by an optionally substituted acyl group, such as $N^4$-formylcytosine, $N^4$-acetylcytosine, $N^4$-propionylcytosine, $N^4$-pivaloylcytosine, $N^4$-benzoylcytosine, $N^4$-(4-methylbenzoyl)cytosine, $N^4$-(4-bromobenzoyl)cytosine, $N^4$-(4-nitrobenzoyl)cytosine and $N^4$-(4-methoxybenzoyl)cytosine.

The term "protected cytosine" is used herein to mean cytosines protected by a silyl group, such as $N^4$,O-bis(trimethylsilyl)-4-amino-2-hydroxypyrimidine and $N^4$,O-bis(triethylsilyl)-4-amino-2-hydroxypyrimidine.

The term "protected $N^4$-acylcytosine" is used herein to mean $N^4$-acylcytosines protected by a silyl group, such as 2-trimethylsilyloxy-4-acetylaminopyrimidine, $N^4$,O-bis(trimethylsilyl)-4-acetylamino-2-hydroxypyrimidine, 2-triethylsilyloxy-4-acetylaminopyrimidine, $N^4$,O-bis(triethylsilyl)-4-acetylamino-2-hydroxypyrimidine, 2-trimethylsilyloxy-4-benzoylaminopyrimidine and $N^4$,O-bis(trimethylsilyl)-4-benzoylamino-2-hydroxypyrimidine.

The term "nucleic acid base" is used herein to mean an optionally substituted adenine, an optionally substituted guanine, an optionally substituted cytosine, an optionally substituted thymine or an optionally substituted uracil.

The term "protected nucleic acid base" is used herein to mean nucleic acid bases, in which an amino group and/or a hydroxyl group are protected by silyl groups.

The term "leaving group" is used herein to mean a halogen atom, a $C_{1-6}$ alkylsulfonyloxy group or an arylsulfonyloxy group. The $C_{1-6}$ alkylsulfonyloxy group and the arylsulfonyloxy group may be optionally substituted with one or more groups selected from Substituent Group A.

The hydroxyl-protecting group includes all groups that can be generally used as protecting groups for hydroxyl groups. Examples of the hydroxyl-protecting group include those described in W. Greene et al., Protective Groups in Organic Synthesis, 4th edition, pp. 16-366, 2007, John Wiley & Sons, INC.

Specific examples of the hydroxyl-protecting group include a $C_{1-6}$ alkyl group, a $C_{2-6}$ alkenyl group, an ar-$C_{1-6}$ alkyl group, a $C_{1-6}$ alkoxy $C_{1-6}$ alkyl group, an acyl group, a $C_{1-6}$ alkoxycarbonyl group, a $C_{1-6}$ alkylsulfonyl group, an arylsulfonyl group, a tetrahydrofuranyl group, a tetrahydropyranyl group and a silyl group. These groups may be optionally substituted with one or more groups selected from Substituent Group A.

The amino-protecting group includes all groups that can be generally used as protecting groups for amino groups. Examples of the amino-protecting group include those described in W. Greene et al., Protective Groups in Organic Synthesis, 4th edition, pp. 696-926, 2007, John Wiley & Sons, INC.

Specific examples of the amino-protecting group include an ar-$C_{1-6}$ alkyl group, a $C_{1-6}$ alkoxy $C_{1-6}$ alkyl group, an acyl group, a $C_{1-6}$ alkoxycarbonyl group, an aryloxycarbonyl group, a $C_{1-6}$ alkylsulfonyl group, an arylsulfonyl group and a silyl group. These groups may be optionally substituted with one or more groups selected from Substituent Group A.

The carboxyl-protecting group includes all groups that can be generally used as protecting groups for carboxyl groups. Examples of the carboxyl-protecting group include those described in W. Greene et al., Protective Groups in Organic Synthesis, 4th edition, pp. 533-646, 2007, John Wiley & Sons, INC.

Specific examples of the carboxyl-protecting group include a $C_{1-6}$ alkyl group, a $C_{2-6}$ alkenyl group, an aryl group, an ar-$C_{1-6}$ alkyl group, a $C_{1-6}$ alkoxy $C_{1-6}$ alkyl group and a silyl group. These groups may be optionally substituted with one or more groups selected from Substituent Group A.

Substituent Group A: a halogen atom, a cyano group, a nitro group, an optionally protected amino group, an optionally protected hydroxyl group, an optionally protected carboxyl group, a carbamoyl group optionally substituted with one or more groups selected from Substituent Group B, a sulfamoyl group optionally substituted with one or more groups selected from Substituent Group B, a $C_{1-6}$ alkyl group optionally substituted with one or more groups selected from Substituent Group B, a $C_{2-6}$ alkenyl group optionally substituted with one or more groups selected from Substituent Group B, a $C_{2-6}$ alkynyl group optionally substituted with one or more groups selected from Substituent Group B, a $C_{3-8}$ cycloalkyl group optionally substituted with one or more groups selected from Substituent Group B, an aryl group optionally substituted with one or more groups selected from Substituent Group B, a $C_{1-6}$ alkoxy group optionally substituted with one or more groups selected from Substituent Group B, an aryloxy group optionally substituted with one or more groups selected from Substituent Group B, an acyl group optionally substituted with one or more groups selected from Substituent Group B, a $C_{1-6}$ acyloxy group optionally substituted with one or more groups selected from Substituent Group B, a $C_{1-6}$ alkoxycarbonyl group optionally substituted with one or more groups selected from Substituent Group B, an aryloxycarbonyl group optionally substituted with one or more groups selected from Substituent Group B, a $C_{1-6}$ alkoxycarbonyloxy group optionally substituted with one or more groups selected from Substituent Group B, a $C_{1-6}$ alkylamino group optionally substituted with one or more groups selected from Substituent Group B, a di($C_{1-6}$ alkyl) amino group optionally substituted with one or more groups selected from Substituent Group B, a $C_{1-6}$ alkylthio group optionally substituted with one or more groups selected from Substituent Group B, a $C_{1-6}$ alkylsulfonyl group optionally substituted with one or more groups selected from Substituent Group B, a $C_{1-6}$ alkylsulfonyloxy group optionally substituted with one or more groups selected from Substituent Group B, a $C_{1-12}$ silyl group optionally substituted with one or more groups selected from Substituent Group B, a heterocyclic group optionally substituted with one or more groups selected from Substituent Group B, and an oxo group.

Substituent Group B: a halogen atom, a cyano group, a nitro group, an optionally protected amino group, an optionally protected hydroxyl group, an optionally protected carboxyl group, a $C_{1-6}$ alkyl group, aryl group, a $C_{1-6}$ alkoxy group, a heterocyclic group, and an oxo group.

The aliphatic hydrocarbons include pentane, hexane or cyclohexane, etc.

The halogenated hydrocarbons include methylene chloride, chloroform or 1,2-dichloroethane, etc.

The alcohols include methanol, ethanol, propanol, 2-propanol, butanol or 2-methyl-2-propanol, etc.

The ethers include diethyl ether, diisopropyl ether, dioxane, tetrahydrofuran, anisole, ethylene glycol dimethyl ether, diethylene glycol dimethyl ether or diethylene glycol diethyl ether, etc.

The esters include methyl acetate, ethyl acetate, propyl acetate, isopropyl acetate or butyl acetate, etc.

The ketones include acetone, 2-butanone or 4-methyl-2-pentanone, etc.

The nitriles include acetonitrile, etc.

The amides include N,N-dimethylformamide, N,N-dimethylacetamide or N-methylpyrrolidone, etc.

The sulfoxides include dimethyl sulfoxide, etc.

The carboxylic acid includes acetic acid, etc.

The aromatic hydrocarbons include benzene, chlorobenzene, dichlorobenzene, nitrobenzene, toluene or xylene, etc.

Theureas include 1,3-dimethyl-2-imidazolidinone, etc.

The base includes an organic base and an inorganic base.

The organic base includes triethylamine, pyridine or N-methylimidazole, etc.

The inorganic base includes sodium hydroxide, potassium hydroxide, sodium carbonate, potassium carbonate, sodium hydrogen carbonate or sodium phosphate, etc.

The $C_{1-6}$ alkyl group, $C_{2-6}$ alkenyl group, $C_{2-6}$ alkynyl group, aryl group and heterocyclic group, which are represented by $R^{1A}$ and $R^{1B}$, may be optionally substituted with one or more groups selected from Substituent Group A.

The aryl group represented by $R^{1C}$ may be optionally substituted with one or more groups selected from Substituent Group A.

The $C_{1-6}$ alkyl group, $C_{1-6}$ alkenyl group, $C_{2-6}$ alkynyl group, $C_{1-6}$ alkoxy group, $C_{1-6}$ alkylthio group, aryl group, aryloxy group, arylthio group, heterocyclic group, heterocyclic oxy group and heterocyclic thio group, which are represented by $R^{2A}$ and $R^{2B}$, may be optionally substituted with one or more groups selected from Substituent Group A.

The aryl group, which is represented by $R^{2C}$, may be optionally substituted with one or more groups selected from Substituent Group A.

The $C_{1-6}$ alkylidene group, which is formed together by $R^{2A}$ and $R^{2B}$, may be optionally substituted with one or more groups selected from Substituent Group A.

The $C_{1-6}$ alkyl group, $C_{2-6}$ alkenyl group, $C_{2-6}$ alkynyl group, $C_{1-6}$ alkoxy group, $C_{1-6}$ alkylthio group, aryl group, aryloxy group, arylthio group, heterocyclic group, heterocyclic oxy group and heterocyclic thio group, which are represented by $R^{3A}$ and $R^{3B}$, may be optionally substituted with one or more groups selected from Substituent Group A.

The $C_{1-6}$ alkylidene group, which is formed together by $R^{3A}$ and $R^{3B}$, may be optionally substituted with one or more groups selected from Substituent Group A.

The $C_{1-6}$ alkyl group, which is represented by $R^{3C}$ and $R^{3D}$, may be optionally substituted with one or more groups selected from Substituent Group A.

The $C_{1-6}$ alkylthio group, aryloxy group, arylthio group, heterocyclic thio group and aroylamino group, which are represented by $R^{3E}$, may be optionally substituted with one or more groups selected from Substituent Group A.

The aromatic ring, which is formed by $R^{2A}$, $R^{2B}$, $R^{3A}$ and $R^{3B}$ together with carbon atoms to which they bind, may be optionally substituted with one or more groups selected from Substituent Group A.

The benzene ring, which is formed by $R^{2A}$, $R^{2B}$, $R^{3A}$ and $R^{3B}$ together with carbon atoms to which they bind, may be optionally substituted with one or more groups selected from Substituent Group A.

The $C_{1-6}$ alkylene group or optionally substituted siloxane group, which is represented by $Y^1$ may be optionally substituted with one or more groups selected from Substituent Group A.

The nucleic acid base and the protected nucleic acid base may be optionally substituted with one or more groups selected from Substituent Group A.

The acyl group and aroyl group, which are represented by $R^1$ and $R^2$, may be optionally substituted with one or more groups selected from Substituent Group A.

The $C_{1-3}$ alkylene group, which is formed together by $R^1$ and $R^2$, may be optionally substituted with one or more groups selected from Substituent Group A.

The $C_{1-3}$ alkylene group, which is formed together by $R^{1a}$ and $R^{2a}$, may be optionally substituted with one or more groups selected from Substituent Group A.

The benzoyl group, which is represented by $R^{1a}$, may be optionally substituted with one or more groups selected from Substituent Group A.

The benzoyl group, which is represented by $R^{2a}$, may be optionally substituted with one or more groups selected from Substituent Group A.

The $C_{1-6}$ alkylsulfonyloxy group, which is represented by $R^4$, may be optionally substituted with one or more groups selected from Substituent Group A.

The arylsulfonyloxy group, which is represented by $R^4$, may be optionally substituted with one or more groups selected from Substituent Group A The $C_{1-6}$ alkyl group, which is represented by $R^7$, may be optionally substituted with one or more groups selected from Substituent Group A.

The aryl group, which is represented by $R^7$, may be optionally substituted with one or more groups selected from Substituent Group A.

The heterocyclic group, which is represented by $R^7$, may be optionally substituted with one or more groups selected from Substituent Group A.

The silyl group, which is represented by $R^7$, may be optionally substituted with one or more groups selected from Substituent Group A.

The $C_{1-6}$ alkyl group, which is represented by $R^8$, may be optionally substituted with one or more groups selected from Substituent Group A.

The aryl group, which is represented by $R^8$, may be optionally substituted with one or more groups selected from Substituent Group A.

The acyl group, which is represented by $R^9$, may be optionally substituted with one or more groups selected from Substituent Group A.

The $C_{1-6}$ alkylsulfonyl group, which is represented by $R^9$, may be optionally substituted with one or more groups selected from Substituent Group A.

The arylsulfonyl group, which is represented by $R^9$, may be optionally substituted with one or more groups selected from Substituent Group A.

The acyl group, which is represented by $R^{10}$ and $R^{10a}$, may be optionally substituted with one or more groups selected from Substituent Group A.

Preferred examples of the compound represented by the formula [1F] include the following compounds.

A compound, in which $R^1$ represents a hydroxyl-protecting group, is preferable.

A compound, in which $R^2$ represents a hydroxyl-protecting group, is preferable.

A compound, in which $R^1$ and $R^2$ each represent a hydroxyl-protecting group, is preferable.

As such a hydroxyl-protecting group represented by $R^1$ or $R^2$, a $C_{1-6}$ alkyl group optionally substituted with one or more groups selected from Substituent Group A, an ar-$C_{1-6}$ alkyl group optionally substituted with one or more groups selected from Substituent Group A, an acyl group optionally substituted with one or more groups selected from Substituent Group A, a $C_{1-6}$ alkoxycarbonyl group optionally substituted with one or more groups selected from Substituent Group A, an ar-$C_{1-6}$ alkoxycarbonyl group optionally substituted with one or more groups selected from Substituent Group A, a silyl group optionally substituted with one or more groups selected from Substituent Group A, a cinnamoyl group optionally substituted with one or more groups selected from Substituent Group A, a tetrahydrofuranyl group or a tetrahydropyranyl group is preferable; an ar-$C_{1-6}$ alkyl group optionally substituted with one or more groups selected from Substituent Group A, an acyl group optionally substituted with one or more groups selected from Substituent Group A, a $C_{1-6}$ alkoxycarbonyl group optionally substituted with one or more groups selected from Substituent Group A, an ar-$C_{1-6}$ alkoxycarbonyl group optionally substituted with one or more groups selected from Substituent Group A, a silyl group optionally substituted with one or more groups selected from Substituent Group A, or a cinnamoyl group optionally substituted with one or more groups selected from Substituent Group A is more preferable; a $C_{2-6}$ alkanoyl group optionally substituted with one or more groups selected from Substituent Group A, or an aroyl group optionally substituted with one or more groups selected from Substituent Group A, is further preferable; an acetyl group, a pivaloyl group, or a benzoyl group optionally substituted with one or more groups selected from Substituent Group A is even further preferable; a benzoyl group optionally substituted with one or more groups selected from Substituent Group A is still further preferable; a benzoyl group, a 4-chlorobenzoyl group, a 2,4-dichlorobenzoyl group, a 4-nitrobenzoyl group, a 4-methoxybenzoyl group, a 4-(trifluoromethyl)benzoyl group, a 4-phenylbenzoyl group, a 3,5-dimethylbenzoyl group or a 4-methylbenzoyl group is particularly preferable; and a benzoyl group is most preferable.

A compound, in which $R^{3C}$ represents a hydrogen atom or a halogen atom, is preferable; a compound, in which $R^{3C}$ represents a hydrogen atom, a fluorine atom or a chlorine atom, is more preferable; and a compound, in which $R^{3C}$ represents a hydrogen atom or a fluorine atom, is further preferable.

A compound, in which $R^{3D}$ represents a hydrogen atom or a halogen atom, is preferable; a compound, in which $R^{3D}$ represents a hydrogen atom, a fluorine atom or a chlorine atom, is more preferable; and a compound, in which $R^{3D}$ represents a hydrogen atom or a fluorine atom, is further preferable.

A compound, in which $R^4$ represents a halogen atom, a hydroxyl group, a $C_{1-6}$ alkylsulfonyloxy group optionally substituted with one or more groups selected from Substituent Group A, or an arylsulfonyloxy group optionally substituted with one or more groups selected from Substituent Group A, is preferable; a compound, in which $R^4$ represents a chlorine atom, a bromine atom, a hydroxyl group, a methylsulfonyl group, a 2-nitrobenzenesulfonyloxy group, a 3-nitrobenzenesulfonyloxy group, a 4-nitrobenzenesulfonyloxy group, a 2,4,5-trichlorobenzenesulfonyloxy group or a pentafluorobenzenesulfonyloxy group, is more preferable; and a compound, in which $R^4$ represents a hydroxyl group, a chlorine atom, a bromine atom, a methylsulfonyl group or a 2,4,5-trichlorobenzenesulfonyloxy group, is further preferable.

Preferable is a compound, in which when $R^5$ and $R^6$ together represent a group represented by the following formula [2a]:

[Formula 66]

 [2a]

one of $R^{3C}$ and $R^{3D}$ represents a halogen atom, and the other represents a hydrogen atom; and more preferable is a compound, in which one of $R^{3C}$ and $R^{3D}$ represents a fluorine atom, and the other represents a hydrogen atom. A compound, in which $R^4$ represents a halogen atom, an optionally substituted $C_{1-6}$ alkylsulfonyloxy group or an optionally substituted arylsulfonyloxy group, is preferable.

Preferable is a compound, in which when $R^4$ and $R^5$ together represent a sulfur atom and one of $R^{3C}$ and $R^{3D}$ represents a hydrogen atom, the other represents a halogen atom; and more preferable is a compound in which the other represents a fluorine atom.

Preferable is a compound, in which when $R^4$ and $R^5$ together represent a sulfur atom, one of $R^{3C}$ and $R^{3D}$ represents a hydrogen atom, and the other represents a group represented by the following formula [16]:

[Formula 67]

 [16]

(wherein $R^{3a}$ represents a hydroxyl-protecting group), $R^2$ represents a hydroxyl-protecting group.

Preferable is a compound, in which $R^5$ and $R^6$ together represent a group represented by the following formula [3]:

[Formula 68]

 [3]

(wherein $R^7$ has the same meanings as those described above), one of $R^{3C}$ and $R^{3D}$ represents a group represented by the following formula [16]:

[Formula 69]

 [16]

(wherein $R^{3a}$ has the same meanings as those described above), the other represents a hydrogen atom, and $R^4$ represents an iodine atom, a hydroxyl group, an optionally substituted $C_{1-6}$ alkylsulfonyloxy group or an optionally substituted arylsulfonyloxy group, $R^1$ represents an optionally substituted acyl group and $R^2$ represents an optionally substituted acyl group.

Preferable is a compound, in which when $R^5$ and $R^6$ together represent a group represented by the following formula [3]:

[Formula 70]

 [3]

(wherein $R^7$ has the same meanings as those described above), one of $R^{3C}$ and $R^{3D}$ represents a hydrogen atom, the other represents a hydrogen atom, and $R^4$ represents a hydroxyl group, $R^1$ represents an optionally substituted aroyl group and $R^2$ represents an optionally substituted aroyl group.

Preferable is a compound, in which when Y is a group represented by the following formula [3]:
[Formula 71]

$$=N-OR^7 \quad [3]$$

(wherein $R^7$ has the same meanings as those described above), $R^7$ represents a hydrogen atom, an optionally substituted $C_{1-6}$ alkyl group or an optionally substituted aryl group; more preferable is a compound, in which $R^7$ represents a hydrogen atom, a methyl group, a benzyl group or a phenyl group; and further preferable is a compound in which $R^7$ represents a methyl group or a benzyl group.

Preferable is a compound, in which when $R^4$ and $R^5$ together represent a sulfur atom, $R^6$ represents a hydroxyl group.

Preferred examples of the compound represented by the formula [1] include the following compounds.

A compound, in which $R^1$ represents a hydroxyl-protecting group, is preferable.

A compound, in which $R^2$ represents a hydroxyl-protecting group, is preferable.

A compound, in which $R^1$ and $R^2$ each represent a hydroxyl-protecting group, is preferable.

$R^1$ and $R^2$ may be identical to or different from each other.

As such a hydroxyl-protecting group represented by $R^1$ or $R^2$, a $C_{1-6}$ alkyl group optionally substituted with one or more groups selected from Substituent Group A, an ar-$C_{1-6}$ alkyl group optionally substituted with one or more groups selected from Substituent Group A, an acyl group optionally substituted with one or more groups selected from Substituent Group A, a $C_{1-6}$ alkoxycarbonyl group optionally substituted with one or more groups selected from Substituent Group A, an ar-$C_{1-6}$ alkoxycarbonyl group optionally substituted with one or more groups selected from Substituent Group A, a silyl group optionally substituted with one or more groups selected from Substituent Group A, a cinnamoyl group optionally substituted with one or more groups selected from Substituent Group A, a tetrahydrofuranyl group or a tetrahydropyranyl group is preferable; an ar-$C_{1-6}$ alkyl group optionally substituted with one or more groups selected from Substituent Group A, an acyl group optionally substituted with one or more groups selected from Substituent Group A, a $C_{1-6}$ alkoxycarbonyl group optionally substituted with one or more groups selected from Substituent Group A, an ar-$C_{1-6}$ alkoxycarbonyl group optionally substituted with one or more groups selected from Substituent Group A, a silyl group optionally substituted with one or more groups selected from Substituent Group A, or a cinnamoyl group optionally substituted with one or more groups selected from Substituent Group A is more preferable; a $C_{2-6}$ alkanoyl group optionally substituted with one or more groups selected from Substituent Group A, or an aroyl group optionally substituted with one or more groups selected from Substituent Group A, is further preferable; an acetyl group, a pivaloyl group, or a benzoyl group optionally substituted with one or more groups selected from Substituent Group A is even further preferable; a benzoyl group optionally substituted with one or more groups selected from Substituent Group A is still further preferable; a benzoyl group, a 4-chlorobenzoyl group, a 2,4-dichlorobenzoyl group, a 4-nitrobenzoyl group, a 4-methoxybenzoyl group, a 4-(trifluoromethyl)benzoyl group, a 4-phenylbenzoyl group, a 3,5-dimethylbenzoyl group or a 4-methylbenzoyl group is particularly preferable; and a benzoyl group is most preferable.

The benzoyl group used as a protecting group is advantageous in that it is easily removed during deprotection, and in that it withstands reaction conditions for the production method of the present invention. In addition, a compound protected by a benzoyl group, which is obtained by the production method of the present invention, has excellent crystallinity, and it is easily purified.

A compound, in which $R^3$ represents a fluorine atom or a chlorine atom, is preferable; and a compound, in which $R^3$ represents a fluorine atom, is more preferable.

A compound, in which $R^4$ represents a halogen atom, a hydroxyl group or an arylsulfonyloxy group optionally substituted with one or more groups selected from Substituent Group A, is preferable; a compound, in which $R^4$ represents a chlorine atom, a bromine atom, a hydroxyl group, a 2-nitrobenzenesulfonyloxy group, a 3-nitrobenzenesulfonyloxy group, a 4-nitrobenzenesulfonyloxy group, a 2,4,5-trichlorobenzenesulfonyloxy group or a pentafluorobenzenesulfonyloxy group, is more preferable; and a compound, in which $R^4$ represents a hydroxyl group, a chlorine atom, a bromine atom or a 2,4,5-trichlorobenzenesulfonyloxy group, is further preferable.

Preferable is a compound, in which when $R^4$ represents a halogen atom, a hydroxyl group, an optionally substituted $C_{1-6}$ alkylsulfonyloxy group or an optionally substituted arylsulfonyloxy group, $R^5$ and $R^6$ together represent a group represented by the following formula [2]:
[Formula 72]

$$=Y \quad [2]$$

(wherein Y has the same meanings as those described above).

The aforementioned compound, in which Y represents an oxygen atom, is more preferable.

Preferable is a compound, in which when Y represents a group represented by the following formula [3]:
[Formula 73]

$$=N-OR^7 \quad [3]$$

(wherein $R^7$ has the same meanings as those described above), $R^7$ represents a hydrogen atom, an optionally substituted $C_{1-6}$ alkyl group or an optionally substituted aryl group; the aforementioned compound, in which $R^7$ represents a hydrogen atom, a methyl group, a benzyl group or a phenyl group, is more preferable; and the aforementioned compound, in which $R^7$ represents a methyl group or a benzyl group, is further preferable.

A compound, in which when $R^4$ and $R^5$ together represent a sulfur atom, $R^6$ represents a hydroxyl group, is preferable.

Preferred examples of the compound represented by the formula [1G] include the following compounds.

A compound, in which $R^{1C}$ represents a methyl group and $R^{1D}$ represents a hydrogen atom, is preferable.

A compound in which $R^{2C}$ and $R^{3E}$ together represent a group represented by the following formula [17]:
[Formula 74]

$$-O-Y^1-O- \quad [17]$$

(wherein $Y^1$ has the same meanings as those described above), or a bond, is preferable.

A compound, in which $Y^1$ represents an optionally substituted $C_{1-6}$ alkylene group, is preferable.

Preferred examples of the production method of the present invention include the following production methods.

Preferable is a production method using a compound, in which $R^{1A}$ and $R^{1B}$, which are the same or different, each represent a hydrogen atom, an optionally protected carboxyl group, an optionally substituted $C_{1-6}$ alkyl group or an optionally substituted aryl group; more preferable is a production method using a compound, in which $R^{1A}$ and $R^{1B}$, which are the same or different, each represent a hydrogen atom or a $C_{1-6}$ alkyl group optionally substituted with one or more groups selected from Substituent Group A; and further preferable is a production method using a compound, in which $R^{1A}$ and $R^{1B}$, which are the same or different, each represent a hydrogen atom, a methyl group or a group represented by the following formula [18]:
[Formula 75]

 [18]

(wherein $R^{1a}$ has the same meanings as those described above).

Since the ring-closure reaction of the present invention has high reactivity and high stereoselectivity, it provides particularly great effects when at least one of $R^{1A}$ and $R^{1B}$ is a substituent.

Particularly preferable is a production method using a compound, in which one of $R^{1A}$ and $R^{1B}$ represents a hydrogen atom, and the other represents a methyl group or a group represented by the following formula [18]:
[Formula 76]

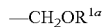 [18]

(wherein $R^{1a}$ has the same meanings as those described above).

Preferable is a production method using a compound, in which $R^{1a}$ represents a $C_{1-6}$ alkyl group optionally substituted with one or more groups selected from Substituent Group A, an ar-$C_{1-6}$ alkyl group optionally substituted with one or more groups selected from Substituent Group A, an acyl group optionally substituted with one or more groups selected from Substituent Group A, a $C_{1-6}$ alkoxycarbonyl group optionally substituted with one or more groups selected from Substituent Group A, an ar-$C_{1-6}$ alkoxycarbonyl group optionally substituted with one or more groups selected from Substituent Group A, a silyl group optionally substituted with one or more groups selected from Substituent Group A, a cinnamoyl group optionally substituted with one or more groups selected from Substituent Group A, a tetrahydrofuranyl group or a tetrahydropyranyl group; more preferable is a production method using a compound, in which $R^{1a}$ represents an ar-$C_{1-6}$ alkyl group optionally substituted with one or more groups selected from Substituent Group A, an acyl group optionally substituted with one or more groups selected from Substituent Group A, a $C_{1-6}$ alkoxycarbonyl group optionally substituted with one or more groups selected from Substituent Group A, an ar-$C_{1-6}$ alkoxycarbonyl group optionally substituted with one or more groups selected from Substituent Group A, a silyl group optionally substituted with one or more groups selected from Substituent Group A, or a cinnamoyl group optionally substituted with one or more groups selected from Substituent Group A; further preferable is a production method using a compound, in which $R^{1a}$ represents a $C_{2-6}$ alkanoyl group optionally substituted with one or more groups selected from Substituent Group A, or an aroyl group optionally substituted with one or more groups selected from Substituent Group A; further preferable is a production method using a compound, in which $R^{1a}$ represents an acetyl group, a pivaloyl group, or a benzoyl group optionally substituted with one or more groups selected from Substituent Group A; even further preferable is a production method using a compound, in which Ria represents a benzoyl group optionally substituted with one or more groups selected from Substituent Group A; still further preferable is a production method using a compound, in which $R^{1a}$ represents a benzoyl group optionally substituted with one or more groups selected from Substituent Group A; particularly preferable is a production method using a compound, in which Ria represents a benzoyl group, a 4-chlorobenzoyl group, a 2,4-dichlorobenzoyl group, a 4-nitrobenzoyl group, a 4-methoxybenzoyl group, a 4-(trifluoromethyl)benzoyl group, a 4-phenylbenzoyl group, a 3,5-dimethylbenzoyl group or a 4-methylbenzoyl group; and most preferable is a production method using a compound, in which $R^{1a}$ represents a benzoyl group.

The benzoyl group used as a protecting group is advantageous in that it is easily removed during deprotection, and in that it withstands reaction conditions for the production method of the present invention. In addition, a compound protected by a benzoyl group, which is obtained by the production method of the present invention, has excellent crystallinity, and it is easily purified.

Preferable is a production method using a compound, in which $R^{2A}$ and $R^{2B}$, which are the same or different, each represent a hydrogen atom, a halogen atom, a cyano group, a group represented by the following formula [15]:
[Formula 77]

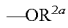 [15]

(wherein $R^{2a}$ has the same meanings as those described above), or an optionally substituted aryl group; more preferable is a production method using a compound in which $R^{2A}$ and $R^{2B}$, which are the same or different, each represent a hydrogen atom, a group represented by the following formula [15]:
[Formula 78]

 [15]

(wherein $R^{2a}$ has the same meanings as those described above), or an optionally substituted aryl group; and further preferable is a production method using a compound, in which $R^{2A}$ and $R^{2B}$, which are the same or different, each represent a hydrogen atom or a group represented by the following formula [15]:
[Formula 79]

 [15]

(wherein $R^{2a}$ has the same meanings as those described above).

Particularly preferable is a production method using a compound, in which one of $R^{2A}$ and $R^{2B}$ represents a hydrogen atom, and the other represents a group represented by the following formula [15]:
[Formula 80]

 [15]

(wherein $R^{2a}$ has the same meanings as those described above).

Preferable is a production method using a compound, in which $R^{2a}$ represents a $C_{1-6}$ alkyl group optionally substituted with one or more groups selected from Substituent Group A, an ar-$C_{1-6}$ alkyl group optionally substituted with one or more groups selected from Substituent Group A, an acyl group optionally substituted with one or more groups selected from Substituent Group A, a $C_{1-6}$ alkoxycarbonyl group optionally substituted with one or more groups selected from Substituent Group A, an ar-$C_{1-6}$ alkoxycarbonyl group optionally substituted with one or more groups selected from Substituent Group A, a silyl group optionally substituted with one or more groups selected from Substituent Group A, a cinnamoyl group optionally substituted with one or more groups selected from Substituent Group A, a tetrahydrofuranyl group or a tetrahydropyranyl group; more preferable is a production method using a compound, in which $R^{2a}$ represents an ar-$C_{1-6}$ alkyl group optionally substituted with one or more groups selected from Substituent Group A, an acyl group optionally substituted with one or more groups selected from Substituent Group A, a $C_{1-6}$ alkoxycarbonyl group optionally substituted with one or more groups selected from Substituent Group A, an ar-$C_{1-6}$ alkoxycarbonyl group optionally substituted with one or more groups selected from Substituent Group A, a silyl group optionally substituted with one or more groups selected from Substituent Group A, or a cinnamoyl group optionally substituted with one or more groups selected from Substituent Group A; further preferable is a production method using a compound, in which $R^{2a}$ represents a $C_{2-6}$ alkanoyl group optionally substituted with one or more groups selected from Substituent Group A, or an aroyl group optionally substituted with one or more groups selected from Substituent Group A; further preferable is a production method using a compound, in which $R^{2a}$ represents an acetyl group, a pivaloyl group, or a benzoyl group optionally substituted with one or more groups selected from Substituent Group A; even further preferable is a production method using a compound, in which $R^{2a}$ represents a benzoyl group optionally substituted with one or more groups selected from Substituent Group A; still further preferable is a production method using a compound, in which $R^{2a}$ represents a benzoyl group optionally substituted with one or more groups selected from Substituent Group A; particularly preferable is a production method using a compound, in which $R^{2a}$ represents a benzoyl group, a 4-chlorobenzoyl group, a 2,4-dichlorobenzoyl group, a 4-nitrobenzoyl group, a 4-methoxybenzoyl group, a 4-(trifluoromethyl)benzoyl group, a 4-phenylbenzoyl group, a 3,5-dimethylbenzoyl group or a 4-methylbenzoyl group; and most preferable is a production method using a compound, in which $R^{2a}$ represents a benzoyl group.

The benzoyl group used as a protecting group is advantageous in that it is easily removed during deprotection, and in that it withstands reaction conditions for the production method of the present invention. In addition, a compound protected by a benzoyl group, which is obtained by the production method of the present invention, has excellent crystallinity, and it is easily purified.

$R^{1a}$ and $R^{2a}$ may be identical to or different from each other.

Preferable is a production method using a compound, in which $R^{3A}$ and $R^{3B}$, which are the same or different, each represent a hydrogen atom, a halogen atom, an optionally protected amino group, a group represented by the following formula [16]:
[Formula 81]

$$-OR^{3a} \quad [16]$$

(wherein $R^{3a}$ has the same meanings as those described above), an optionally substituted $C_{1-6}$ alkyl group, an optionally substituted $C_{1-6}$ alkylthio group, an optionally substituted aryloxy group, an optionally substituted arylthio group or an optionally substituted heterocyclic thio group; and more preferable is a production method using a compound, in which $R^{3A}$ and $R^{3B}$, which are the same or different, each represent a hydrogen atom, a halogen atom, a group represented by the following formula [16]:
[Formula 82]

$$-OR^{3a} \quad [16]$$

(wherein $R^{3a}$ has the same meanings as those described above), or an aryloxy group optionally substituted with one or more groups selected from Substituent Group A.

Preferable is a production method using a compound, in which one of $R^{3A}$ and $R^{3B}$ represents a hydrogen atom, and the other represents a halogen atom, a group represented by the following formula [16]:
[Formula 83]

$$-OR^{3a} \quad [16]$$

(wherein $R^{3a}$ has the same meanings as those described above), or an aryloxy group optionally substituted with one or more groups selected from Substituent Group A; and more preferable is a production method using a compound, in which one of $R^{3A}$ and $R^{3B}$ represents a hydrogen atom, and the other represents a halogen atom or a group represented by the following formula [16]:
[Formula 84]

$$-OR^{3a} \quad [16]$$

(wherein $R^{3a}$ has the same meanings as those described above).

Preferable is a production method using a compound, in which $R^{2A}$ and $R^{3A}$ together represent a group represented by the following formula [17]:
[Formula 85]

$$-O-Y^1-O- \quad [17]$$

(wherein $Y^1$ has the same meanings as those described above), or a bond.

Preferable is a production method using a compound, in which $Y^1$ represents an optionally substituted $C_{1-6}$ alkylene group.

Preferable is a production method using a compound, in which $R^3$ represents a fluorine atom or a chlorine atom; and more preferable is a production method using a compound, in which $R^3$ represents a fluorine atom.

Preferable is a production method using a compound, in which $R^4$ represents a halogen atom, a hydroxyl group, or an arylsulfonyloxy group optionally substituted with one or more groups selected from Substituent Group A; more preferable is a production method using a compound, in which $R^4$ represents a chlorine atom, a bromine atom, a hydroxyl group, a 2-nitrobenzenesulfonyloxy group, a 3-nitrobenzenesulfonyloxy group, a 4-nitrobenzenesulfonyloxy group, a 2,4,5-trichlorobenzenesulfonyloxy group or a pentafluorobenzenesulfonyloxy group; and further preferable is a production method using a compound, in which $R^4$ represents a hydroxyl group, a chlorine atom, a bromine atom or a 2,4,5-trichlorobenzenesulfonyloxy group.

Preferable is a production method using a compound, in which $R^4$ represents a halogen atom, a hydroxyl group, an optionally substituted $C_{1-6}$ alkylsulfonyloxy group or an optionally substituted arylsulfonyloxy group, and $R^5$ and $R^6$ together represent a group represented by the following formula [2]:
[Formula 86]

$$=Y \quad [2]$$

(wherein Y has the same meanings as those described above).

More preferable is a production method using the aforementioned compound, in which Y represents an oxygen atom.

Preferable is a production method using a compound, in which when Y represents a group represented by the following formula [3]:
[Formula 87]

$$=N-OR^7 \quad [3]$$

(wherein $R^7$ has the same meanings as those described above), $R^7$ represents a hydrogen atom, an optionally substituted $C_{1-6}$ alkyl group or an optionally substituted aryl group; and more preferable is a production method using a compound, in which $R^7$ represents a hydrogen atom, a methyl group, a benzyl group or a phenyl group; and further preferable is a production method using a compound, in which $R^7$ represents a methyl group or a benzyl group.

Preferable is a production method using a compound, in which when $R^4$ and $R^5$ together represent a sulfur atom, $R^6$ represents a hydroxyl group.

Preferable is a production method using a compound, in which $R^9$ represents an optionally substituted acyl group; more preferable is a production method using a compound, in which $R^9$ represents an acyl group; and further preferable is a production method using a compound, in which $R^9$ represents an acetyl group.

Preferable is a production method using a compound, in which $X^3$ represents a bromine atom.

Preferable is a production method using a compound, in which the nucleic acid base represents adenine optionally substituted with one or more groups selected from Substituent Group A, guanine optionally substituted with one or more groups selected from Substituent Group A, cytosine optionally substituted with one or more groups selected from Substituent Group A, thymine optionally substituted with one or more groups selected from Substituent Group A, or uracil optionally substituted with one or more groups selected from Substituent Group A; and more preferable is a production method using a compound, in which the nucleic acid base represents cytosine optionally substituted with one or more groups selected from Substituent Group A.

Preferable is a production method using a compound, in which the protected cytosine is $N^4$,O-bis(trimethylsilyl)-4-amino-2-hydroxypyrimidine.

Preferable is a production method using a compound, in which the protected $N^4$-acylcytosine is 2-trimethylsilyloxy-4-acetylaminopyrimidine or $N^4$,O-bis(trimethylsilyl)-4-acetylamino-2-hydroxypyrimidine; and more preferable is a production method using a compound, in which the protected $N^4$-acylcytosine is $N^4$,O-bis(trimethylsilyl)-4-acetylamino-2-hydroxypyrimidine.

Preferable is a production method using a compound, in which $R^{10a}$ represents a formyl group, an optionally substituted $C_{2-6}$ alkanoyl group or an optionally substituted aroyl group; more preferable is a production method using a compound, in which $R^{10a}$ represents a $C_{2-6}$ alkanoyl group; and further preferable is a production method using a compound, in which $R^{10a}$ represents an acetyl group.

In a step of producing the compound represented by the formula [11b] from the compound represented by the formula [11a], it is preferable to use the compound represented by the formula [13].

The method for producing 1-(2-deoxy-2-halogeno-4-thio-β-D-arabinofuranosyl)cytosine from the compound represented by the formula [9] is preferably the method (3) or (4), and more preferably the method (4).

In the case of using the method (3), it is preferable to use protected $N^4$-acylcytosine.

It is preferable to isolate the compound represented by the formula [11b] as a solid. By isolating the compound, the purity of Compound A is improved.

Next, the production method of the present invention will be described.

Production Method 1

[Formula 88]

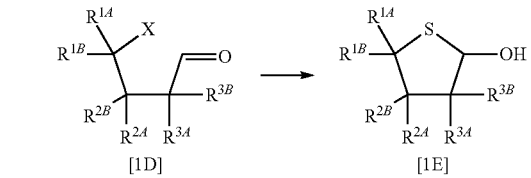

wherein $R^{1A}$, $R^{1B}$, $R^{2A}$, $R^{2B}$, $R^{3A}$, $R^{3B}$ and X have the same meanings as those described above.

The compound represented by the formula [1E] can be produced by allowing the compound represented by the formula [1D] to react with a sulfur compound.

The solvent used in this reaction is not particularly limited, as long as it does not affect the reaction. Examples of the solvent include aliphatic hydrocarbons, halogenated hydrocarbons, alcohols, ethers, esters, ketones, nitriles, amides, sulfoxides, aromatic hydrocarbons, ureas and water. These solvents may be used in combination.

Preferred examples of the solvent include ethers, esters, nitriles, amides and ureas. Among these, amides are more preferable.

The amount of the solvent used is not particularly limited. The solvent may be used at a ratio (v/w) of 1:1 to 50:1, and preferably at a ratio (v/w) of 1:1 to 15:1, with respect to the compound represented by the formula [1D].

Examples of the sulfur compound used in this reaction include hydrogen sulfide and a salt thereof.

Examples of the salt of hydrogen sulfide include sodium hydrogen sulfide, sodium sulfide, potassium hydrogen sulfide, calcium hydrogen sulfide and magnesium sulfide. Among these, sodium hydrogen sulfide is preferable.

The sulfur compound may be used at a molar ratio of 0.2:1 to 10:1, preferably at a molar ratio of 0.5:1 to 2.0:1, and more preferably at a molar ratio of 0.7:1 to 1.5:1, with respect to the compound represented by the formula [1D].

The reaction temperature may be −20° C. to 100° C. It is preferably −10° C. to 80° C., and more preferably −5° C. to 60° C.

The reaction time may be 5 minutes to 50 hours. It is preferably 5 minutes to 24 hours, and more preferably 5 minutes to 6 hours.

In the present production method, a sulfur compound is added to a formyl group of the compound represented by the formula [1D], and a nucleophilic substitution reaction then progresses, and the ring is then closed. Thus, it can be assumed that the reaction can be carried out in a short time, with high reactivity and with high stereoselectivity. However, the present invention is not limited to this reaction mechanism.

It is to be noted that the compound represented by the formula [1D] may be produced by subjecting sugars to a ring-opening reaction, or by another method.

Production Method 2

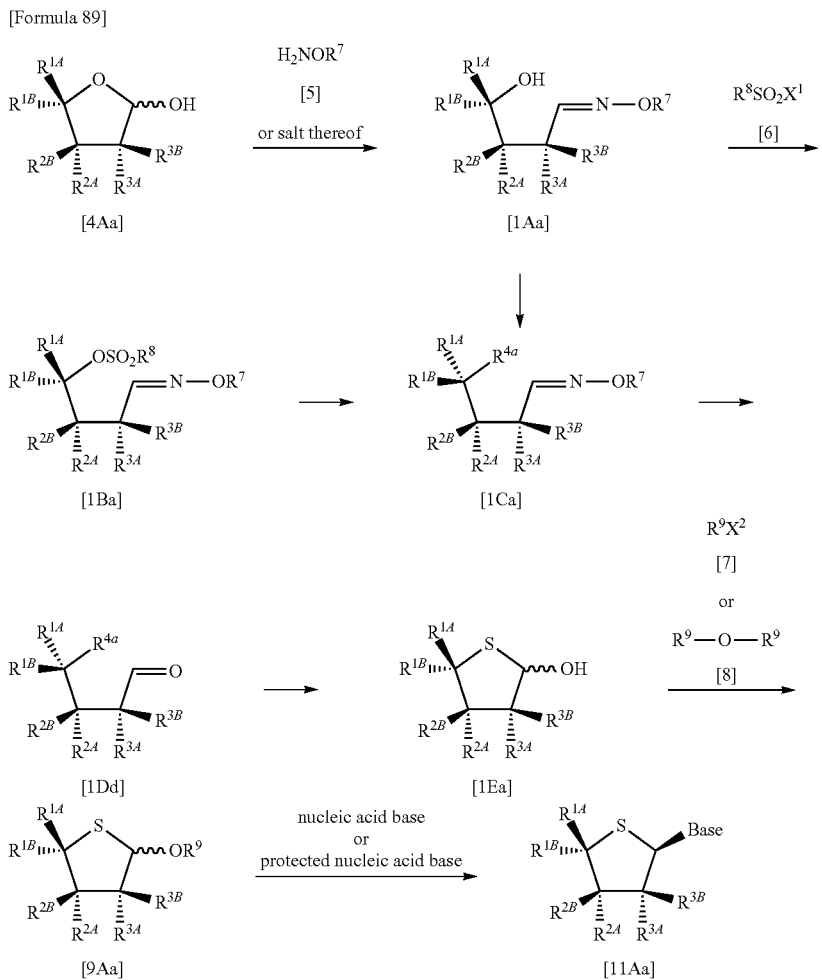

[Formula 89]

wherein $R^{1A}$, $R^{1B}$, $R^{2A}$, $R^{2B}$, $R^{3A}$, $R^{3B}$, $R^{4a}$, $R^7$, $R^8$, $R^9$, $X^1$, $X^2$ and Base have the same meanings as those described above.

(First Step)

For example, ((2R,3R,4S)-3-benzoyloxy-4-fluoro-5-hydroxyoxolan-2-yl) methyl=benzoate has been known as a compound represented by the formula [4Aa].

For example, O-methylhydroxylamine and O-benzylhydroxylamine have been known as compounds represented by the formula [5] or salts thereof.

The compound represented by the formula [1Aa] can be produced by allowing the compound represented by the formula [4Aa] to react with the compound represented by the formula [5] or a salt thereof.

The solvent used in this reaction is not particularly limited, as long as it does not affect the reaction. Examples of the solvent include aliphatic hydrocarbons, halogenated hydrocarbons, alcohols, ethers, esters, nitriles, amides, sulfoxides, aromatic hydrocarbons and water. These solvents may be used in combination.

Preferred examples of the solvent include halogenated hydrocarbons, alcohols, nitriles, aromatic hydrocarbons and water.

The amount of the solvent used is not particularly limited. The solvent may be used at a ratio (v/w) of 1:1 to 50:1, and preferably at a ratio (v/w) of 1:1 to 15:1, with respect to the compound represented by the formula [4Aa].

The compound represented by the formula [5] used in this reaction or a salt thereof may be used at a molar ratio of 0.5:1 to 10:1, preferably at a molar ratio of 0.8:1 to 5.0:1, and more preferably at a molar ratio of 1.0:1 to 2.0:1, with respect to the compound represented by the formula [4Aa].

When a salt of the compound represented by the formula [5] is used, it is preferable to add a base thereto.

Examples of the base include organic bases and inorganic bases. Among others, triethylamine and sodium hydrogen carbonate are preferable.

The base may be used at a molar ratio of 0.1:1 to 10:1, preferably at a molar ratio of 0.2:1 to 2.0:1, and more preferably at a molar ratio of 0.5:1 to 1.5:1, with respect to the compound represented by the formula [5].

The reaction temperature may be −10° C. to 100° C. It is preferably −5° C. to 80° C., and more preferably 0° C. to 60° C.

The reaction time may be 5 minutes to 50 hours. It is preferably 5 minutes to 24 hours, and more preferably 5 minutes to 6 hours.

(Second Step)

As compounds represented by the formula [6], 4-nitrobenzenesulfonyl chloride, 2,4,5-trichlorobenzenesulfonyl chloride and pentafluorobenzenesulfonyl chloride have been known, for example.

The compound represented by the formula [1Ba] can be produced by allowing the compound represented by the formula [1Aa] to react with the compound represented by the formula [6] in the presence of a base.

The solvent used in this reaction is not particularly limited, as long as it does not affect the reaction. Examples of the solvent include aliphatic hydrocarbons, halogenated hydrocarbons, ethers, esters, ketones, nitriles, amides, sulfoxides and aromatic hydrocarbons. These solvents may be used in combination.

Preferred examples of the solvent include esters, nitriles and aromatic hydrocarbons.

The amount of the solvent used is not particularly limited. The solvent may be used at a ratio (v/w) of 1:1 to 50:1, and preferably at a ratio (v/w) of 1:1 to 15:1, with respect to the compound represented by the formula [1Aa].

Examples of the base used in this reaction include organic bases and inorganic bases. Among others, triethylamine and N-methylimidazole are preferable.

The base may be used at a molar ratio of 0.5:1 to 10:1, preferably at a molar ratio of 0.8:1 to 4.0:1, and more preferably at a molar ratio of 1.0:1 to 3.0:1, with respect to the compound represented by the formula [1Aa].

The compound represented by the formula [6] used in this reaction may be used at a molar ratio of 0.5:1 to 10:1, preferably at a molar ratio of 0.8:1 to 4.0:1, and more preferably at a molar ratio of 1.0:1 to 2.0:1, with respect to the compound represented by the formula [1Aa].

The reaction temperature may be $-10°$ C. to $100°$ C. It is preferably $-5°$ C. to $80°$ C., and more preferably $0°$ C. to $60°$ C.

The reaction time may be 5 minutes to 50 hours. It is preferably 5 minutes to 24 hours, and more preferably 5 minutes to 6 hours.

(Third Step)

The compound represented by the formula [1Ca] can be produced by allowing the compound represented by the formula [1Ba] to react with a halide of alkaline metal.

The solvent used in this reaction is not particularly limited, as long as it does not affect the reaction. Examples of the solvent include aliphatic hydrocarbons, halogenated hydrocarbons, ethers, esters, ketones, nitriles, amides, sulfoxides, aromatic hydrocarbons and ureas. These solvents may be used in combination.

Preferred examples of the solvent include ethers, esters, nitriles, amides and ureas. Among these, amides and ureas are more preferable.

The amount of the solvent used is not particularly limited. The solvent may be used at a ratio (v/w) of 1:1 to 50:1, and preferably at a ratio (v/w) of 1:1 to 15:1, with respect to the compound represented by the formula [1Ba].

Examples of the halide of alkaline metal used in this reaction include lithium fluoride, sodium fluoride, potassium fluoride, lithium bromide, sodium bromide, potassium bromide, lithium chloride, sodium chloride, potassium chloride, lithium iodide, sodium iodide and potassium iodide. Among these, lithium bromide is preferable.

The halide of alkaline metal may be used at a molar ratio of 0.5:1 to 20:1, preferably at a molar ratio of 0.8:1 to 8.0:1, and more preferably at a molar ratio of 1.0:1 to 5.0:1, with respect to the compound represented by the formula [1Ba].

The reaction temperature may be $-50°$ C. to $150°$ C. It is preferably $-10°$ C. to $120°$ C., more preferably $0°$ C. to $100°$ C., and further preferably $20°$ C. to $80°$ C.

The reaction time may be 5 minutes to 50 hours. It is preferably 5 minutes to 24 hours, and more preferably 5 minutes to 6 hours.

(Alternative Method)

The compound represented by the formula [1Ca] can be produced by allowing the compound represented by the formula [1Aa] to react with a halogenating agent in the presence of a base.

The solvent used in this reaction is not particularly limited, as long as it does not affect the reaction. Examples of the solvent include aliphatic hydrocarbons, halogenated hydrocarbons, ethers, esters, ketones, nitriles, amides, sulfoxides, aromatic hydrocarbons, ureas and water. These solvents may be used in combination.

Preferred examples of the solvent include ethers, esters, nitriles, amides, aromatic hydrocarbons and ureas. Among these, amides are more preferable.

The amount of the solvent used is not particularly limited. The solvent may be used at a ratio (v/w) of 1:1 to 50:1, and preferably at a ratio (v/w) of 1:1 to 15:1, with respect to the compound represented by the formula [1Aa].

Examples of the halogenating agent used in this reaction include a chlorinating agent and a brominating agent.

Examples of the chlorinating agent include phosphoryl chloride, phosphorus trichloride, phosphorus pentachloride, Vilsmeier reagent (N,N-dimethylformamide-phosphorus pentachloride, N,N-dimethylformamide-phosphorus oxychloride, etc.), Rydon reagent ($Ph_3PCl_2$, triphenylphosphine-carbon tetrachloride), thionyl chloride and sulfuryl chloride. Among others, sulfuryl chloride is preferable.

Examples of the brominating agent include phosphorus tribromide, N,N-dimethylformamide-phosphorus tribromide, triphenylphosphine-carbon tetrabromide and triphenylphosphine dibromide.

The halogenating agent may be used at a molar ratio of 0.1:1 to 10:1, preferably at a molar ratio of 0.8:1 to 5.0:1, and more preferably at a molar ratio of 1.0:1 to 2.0:1, with respect to the compound represented by the formula [1Aa].

Examples of the base used in this reaction include organic bases and inorganic bases. Among others, triethylamine and pyridine are preferable.

The base may be used at a molar ratio of 0.5:1 to 50:1, preferably at a molar ratio of 0.8:1 to 20:1, and more preferably at a molar ratio of 1.0:1 to 10:1, with respect to the compound represented by the formula [1Aa].

In this reaction, it is preferable to add a salt to the reaction system.

Examples of the salt include lithium chloride, lithium bromide, sodium bromide, calcium bromide and pyridine hydrochloride.

In this halogenation reaction, in general, an epimeric mixture is obtained. In order to improve the optical purity of the compound of the formula [1Ca], it is preferable to use sulfuryl chloride and lithium chloride in combination.

The salt may be used at a molar ratio of 0.5:1 to 20:1, preferably at a molar ratio of 0.8:1 to 5.0:1, and more preferably at a molar ratio of 1.0:1 to 3.0:1, with respect to the compound represented by the formula [1Aa].

The reaction temperature may be $-50°$ C. to $80°$ C. It is preferably $-40°$ C. to $60°$ C., and more preferably $-30°$ C. to $40°$ C.

The reaction time may be 5 minutes to 50 hours. It is preferably 5 minutes to 24 hours, and more preferably 5 minutes to 6 hours.

(Fourth Step)

The compound represented by the formula [1Dd] can be produced by hydrolyzing the compound represented by the formula [1Ca] in the presence of an acid.

The solvent used in this reaction is not particularly limited, as long as it does not affect the reaction. Examples of the solvent include aliphatic hydrocarbons, halogenated hydrocarbons, alcohols, ethers, esters, ketones, nitriles, amides, sulfoxides, aromatic hydrocarbons, ureas and water. These solvents may be used in combination.

Preferred examples of the solvent include ethers, esters, nitriles, amides and water. Among these, ethers and water are more preferable.

The amount of the solvent used is not particularly limited. The solvent may be used at a ratio (v/w) of 1:1 to 50:1, and preferably at a ratio (v/w) of 1:1 to 15:1, with respect to the compound represented by the formula [1Ca].

Examples of the acid used in this reaction include hydrochloric acid, sulfuric acid, toluenesulfonic acid, acetic acid, glyoxylic acid and phosphoric acid. Among others, glyoxylic acid is preferable.

The acid may be used at a molar ratio of 0.5:1 to 100:1, preferably at a molar ratio of 1.0:1 to 60:1, and more preferably at a molar ratio of 1.5:1 to 40:1, with respect to the compound represented by the formula [1Ca].

In this reaction, it is preferable to add a carbonyl compound to the reaction system.

Examples of the carbonyl compound include: ketones such as acetone and 2-butanone; and aldehydes such as formaldehyde, benzaldehyde, glyoxal and glyoxylic acid. Among these, aldehydes are preferable, and glyoxylic acid is more preferable.

The carbonyl compound may be used at a molar ratio of 0.5:1 to 100:1, preferably at a molar ratio of 1.0:1 to 60:1, and more preferably at a molar ratio of 1.5:1 to 40:1, with respect to the compound represented by the formula [1Ca].

The reaction temperature may be −10° C. to 120° C. It is preferably 0° C. to 100° C., and more preferably 20° C. to 80° C.

The reaction time may be 5 minutes to 50 hours. It is preferably 5 minutes to 24 hours, and more preferably 5 minutes to 6 hours.

(Fifth Step)

The compound represented by the formula [1Ea] can be produced by allowing the compound represented by the formula [1Dd] to react with a sulfur compound.

This reaction may be carried out in accordance with the method described in Production Method 1.

(Sixth Step)

For example, acetyl chloride, benzoyl chloride, benzenesulfonyl chloride and methanesulfonyl chloride have been known as compounds represented by the formula [7].

For example, acetic anhydride and propionic anhydride have been known as compounds represented by the formula [8].

The compound represented by the formula [9Aa] can be produced by allowing the compound represented by the formula [Ea] to react with the compound represented by the formula [7] or the compound represented by the formula [8].

The solvent used in this reaction is not particularly limited, as long as it does not affect the reaction. Examples of the solvent include aliphatic hydrocarbons, halogenated hydrocarbons, ethers, esters, ketones, nitriles, amides, sulfoxides and aromatic hydrocarbons. These solvents may be used in combination.

Preferred examples of the solvent include ethers, esters, nitriles and amides. Among these, ethers, nitriles and amides are more preferable.

The amount of the solvent used is not particularly limited. The solvent may be used at a ratio (v/w) of 1:1 to 50:1, and preferably at a ratio (v/w) of 1:1 to 15:1, with respect to the compound represented by the formula [1Ea].

The compound represented by the formula [7] or the compound represented by the formula [8] may be used in this reaction at a molar ratio of 0.5:1 to 50:1, preferably at a molar ratio of 0.8:1 to 20:1, and more preferably at a molar ratio of 1.0:1 to 10:1, with respect to the compound represented by the formula [1Ea].

In this reaction, it is preferable to add a base to the reaction system. Examples of the base include organic bases and inorganic bases. Among others, triethylamine is preferable.

The base may be used at a molar ratio of 0.5:1 to 50:1, preferably at a molar ratio of 0.8:1 to 20:1, and more preferably at a molar ratio of 1.0:1 to 15:1, with respect to the compound represented by the formula [1Ea].

The reaction temperature may be −10° C. to 100° C. It is preferably −5° C. to 80° C., and more preferably 0° C. to 60° C.

The reaction time may be 5 minutes to 50 hours. It is preferably 5 minutes to 24 hours, and more preferably 5 minutes to 6 hours.

(Seventh Step)

The nucleic acid base or the protected nucleic acid base used herein is not particularly limited, as long as it is known to be used in a glycosylation reaction.

The compound represented by the formula [11Aa] can be produced by allowing the compound represented by the formula [9Aa] to react with a nucleic acid base or a protected nucleic acid base in the presence of an acid.

The solvent used in this reaction is not particularly limited, as long as it does not affect the reaction. Examples of the solvent include aliphatic hydrocarbons, halogenated hydrocarbons, ethers, esters, ketones, nitriles, amides, sulfoxides and aromatic hydrocarbons. These solvents may be used in combination.

Preferred examples of the solvent include aliphatic hydrocarbons, halogenated hydrocarbons, nitriles and aromatic hydrocarbons. Among these, halogenated hydrocarbons and aromatic hydrocarbons are more preferable.

The amount of the solvent used is not particularly limited. The solvent may be used at a ratio (v/w) of 1.0:1 to 50:1, and preferably at a ratio (v/w) of 1.0:1 to 15:1, with respect to the compound represented by the formula [9Aa].

Examples of the acid used in this reaction include Lewis acids such as aluminum chloride, aluminum bromide, tin tetrachloride, titanium tetrachloride, titanium(IV) isopropoxide, zinc chloride and trimethylsilyl=trifluoromethanesulfonate.

Preferred acids include aluminum chloride, tin tetrachloride and trimethylsilyl=trifluoromethanesulfonate, and among these, trimethylsilyl=trifluoromethanesulfonate is more preferable.

The amount of the acid used is not particularly limited. The acid may be used at a molar ratio of 0.0001:1 to 10:1, and preferably at a molar ratio of 0.001:1 to 1.0:1, with respect to the compound represented by the formula [9Aa].

The nucleic acid base or the protected nucleic acid base may be used in this reaction at a molar ratio of 1.0:1 to 50:1, preferably at a molar ratio of 1.0:1 to 10:1, and more preferably at a molar ratio of 1.0:1 to 5:1, with respect to the compound represented by the formula [9Aa].

The reaction temperature may be 20° C. to 150° C., and preferably 20° C. to 100° C.

The reaction time may be 5 minutes to 50 hours. It is preferably 30 minutes to 24 hours, and more preferably 1 hour to 10 hours.

When the compound represented by the formula [1Aa] has a protecting group, a thionucleoside can be produced by performing deprotection.

This method may be carried out according to the method described in Protective Groups in Organic Synthesis, 4th edition, pp. 696-926, 2007, John Wiley & Sons, INC., etc.

Production Method 3

[Formula 90]

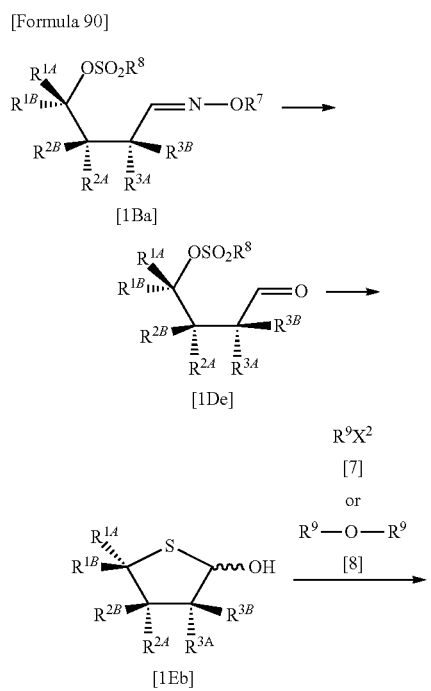

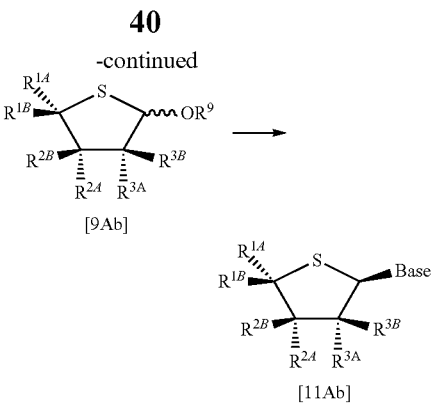

wherein $R^{1A}$, $R^{1B}$, $R^{2A}$, $R^{2B}$, $R^{3A}$, $R^{3B}$, $R^7$, $R^8$, $R^9$, $X^2$ and Base have the same meanings as those described above.

(First Step)

The compound represented by the formula [1De] can be produced by hydrolyzing the compound represented by the formula [1Ba] in the presence of an acid.

This method may be carried out in accordance with the method described in Production Method 2 (Fourth Step).

(Second Step)

The compound represented by the formula [1Eb] can be produced by allowing the compound represented by the formula [1De] to react with a sulfur compound.

This reaction may be carried out in accordance with the method described in Production Method 1.

(Third Step)

The compound represented by the formula [9Ab] can be produced by allowing the compound represented by the formula [1Eb] to react with the compound represented by the formula [7] or the compound represented by the formula [8].

This method may be carried out in accordance with the method described in Production Method 2 (Sixth Step).

(Fourth Step)

The compound represented by the formula [11Ab] can be produced by allowing the compound represented by the formula [9Ab] to react with a nucleic acid base or a protected nucleic acid base in the presence of an acid.

This method may be carried out in accordance with the method described in Production Method 2 (Seventh Step).

Production Method 4

[Formula 91]

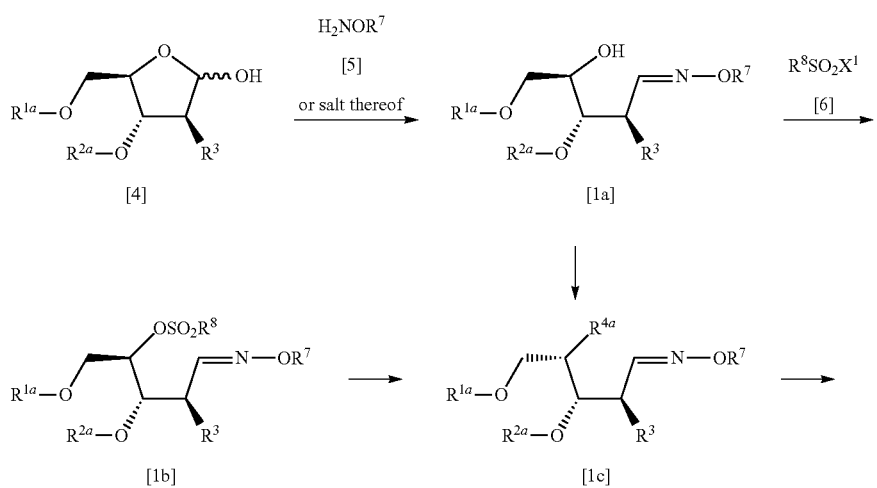

-continued

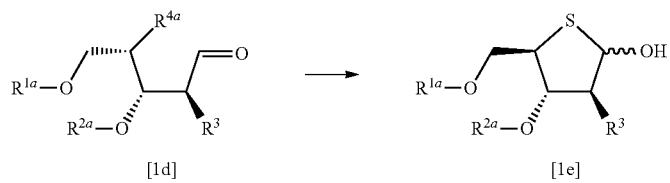

[1d] → [1e]

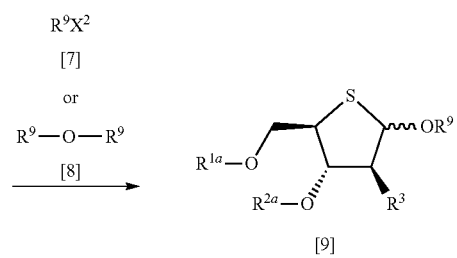

[9]

wherein $R^{1a}$, $R^{2a}$, $R^3$, $R^{4a}$, $R^7$, $R^8$, $R^9$, $X^1$ and $X^2$ have the same meanings as those described above.

(First Step)

For example, ((2R,3R,4S)-3-benzoyloxy-4-fluoro-5-hydroxyoxolan-2-yl)methyl=benzoate has been known as a compound represented by the formula [4].

O-methylhydroxylamine, O-benzylhydroxylamine and the like have been known as compounds represented by the formula [5] or salts thereof.

The compound represented by the formula [1a] can be produced by allowing the compound represented by the formula [4] to react with the compound represented by the formula [5] or a salt thereof.

The solvent used in this reaction is not particularly limited, as long as it does not affect the reaction. Examples of the solvent include aliphatic hydrocarbons, halogenated hydrocarbons, alcohols, ethers, esters, nitriles, amides, sulfoxides, aromatic hydrocarbons and water. These solvents may be used in combination.

Preferred examples of the solvent include halogenated hydrocarbons, alcohols, nitriles, aromatic hydrocarbons and water.

The amount of the solvent used is not particularly limited. The solvent may be used at a ratio (v/w) of 1:1 to 50:1, and preferably at a ratio (v/w) of 1:1 to 15:1, with respect to the compound represented by the formula [4].

The compound represented by the formula [5] or a salt thereof may be used in this reaction at a molar ratio of 0.5:1 to 10:1, preferably at a molar ratio of 0.8:1 to 5.0:1, and more preferably at a molar ratio of 1.0:1 to 2.0:1, with respect to the compound represented by the formula [4].

When a salt of the compound represented by the formula [5] is used, it is preferable to add a base thereto.

Examples of the base include organic bases and inorganic bases. Among others, triethylamine and sodium hydrogen carbonate are preferable.

The base may be used at a molar ratio of 0.1:1 to 10:1, preferably at a molar ratio of 0.2:1 to 2.0:1, and more preferably at a molar ratio of 0.5:1 to 1.5:1, with respect to the salt of the compound represented by the formula [5].

The reaction temperature may be −10° C. to 100° C. It is preferably −5° C. to 80° C., and more preferably 0° C. to 60° C.

The reaction time may be 5 minutes to 50 hours. It is preferably 5 minutes to 24 hours, and more preferably 5 minutes to 6 hours.

(Second Step)

As compounds represented by the formula [6], 4-nitrobenzenesulfonyl chloride, 2,4,5-trichlorobenzenesulfonyl chloride and pentafluorobenzenesulfonyl chloride have been known, for example.

The compound represented by the formula [1b] can, be produced by allowing the compound represented by the formula [1a] to react with the compound represented by the formula [6] in the presence of a base.

The solvent used in this reaction is not particularly limited, as long as it does not affect the reaction. Examples of the solvent include aliphatic hydrocarbons, halogenated hydrocarbons, ethers, esters, ketones, nitriles, amides, sulfoxides and aromatic hydrocarbons. These solvents may be used in combination.

Preferred examples of the solvent include esters, nitriles and aromatic hydrocarbons.

The amount of the solvent used is not particularly limited. The solvent may be used at a ratio (v/w) of 1:1 to 50:1, and preferably at a ratio (v/w) of 1:1 to 15:1, with respect to the compound represented by the formula [1a].

Examples of the base used in this reaction include organic bases and inorganic bases. Among others, triethylamine and N-methylimidazole are preferable.

The base may be used at a molar ratio of 0.5:1 to 10:1, preferably at a molar ratio of 0.8:1 to 4.0:1, and more preferably at a molar ratio of 1.0:1 to 3.0:1, with respect to the compound represented by the formula [1a].

The compound represented by the formula [6] may be used in this reaction at a molar ratio of 0.5:1 to 10:1, preferably at a molar ratio of 0.8:1 to 4.0:1, and more preferably at a molar ratio of 1.0:1 to 2.0:1, with respect to the compound represented by the formula [1a].

The reaction temperature may be −10° C. to 100° C. It is preferably −5° C. to 80° C., and more preferably 0° C. to 60° C.

The reaction time may be 5 minutes to 50 hours. It is preferably 5 minutes to 24 hours, and more preferably 5 minutes to 6 hours.

(Third Step)

The compound represented by the formula [1c] can be produced by allowing the compound represented by the formula [1b] to react with a halide of alkaline metal.

The solvent used in this reaction is not particularly limited, as long as it does not affect the reaction. Examples of the solvent include aliphatic hydrocarbons, halogenated hydrocarbons, ethers, esters, ketones, nitriles, amides, sulfoxides, aromatic hydrocarbons and ureas. These solvents may be used in combination.

Preferred examples of the solvent include ethers, esters, nitriles, amides and ureas. Among these, amides and ureas are more preferable.

The amount of the solvent used is not particularly limited. The solvent may be used at a ratio (v/w) of 1:1 to 50:1, and preferably at a ratio (v/w) of 1:1 to 15:1, with respect to the compound represented by the formula [1b].

Examples of the halide of alkaline metal used in this reaction include lithium fluoride, sodium fluoride, potassium fluoride, lithium bromide, sodium bromide, potassium bromide, lithium chloride, sodium chloride, potassium chloride, lithium iodide, sodium iodide and potassium iodide. Among these, lithium bromide is preferable.

The halide of alkaline metal may be used at a molar ratio of 0.5:1 to 20:1, preferably at a molar ratio of 0.8:1 to 8.0:1, and more preferably at a molar ratio of 1.0:1 to 5.0:1, with respect to the compound represented by the formula [1b].

The reaction temperature may be −50° C. to 150° C. It is preferably −10° C. to 120° C., more preferably 0° C. to 100° C., and further preferably 20° C. to 80° C.

The reaction time may be 5 minutes to 50 hours. It is preferably 5 minutes to 24 hours, and more preferably 5 minutes to 6 hours.

(Alternative Method)

The compound represented by the formula [1c] can be produced by allowing the compound represented by the formula [1a] to react with a halogenating agent in the presence of a base.

The solvent used in this reaction is not particularly limited, as long as it does not affect the reaction. Examples of the solvent include aliphatic hydrocarbons, halogenated hydrocarbons, ethers, esters, ketones, nitriles, amides, sulfoxides, aromatic hydrocarbons, ureas and water. These solvents may be used in combination.

Preferred examples of the solvent include ethers, esters, nitriles, amides, aromatic hydrocarbons and ureas. Among these, amides are more preferable.

The amount of the solvent used is not particularly limited. The solvent may be used at a ratio (v/w) of 1:1 to 50:1, and preferably at a ratio (v/w) of 1:1 to 15:1, with respect to the compound represented by the formula [1a].

Examples of the halogenating agent used in this reaction include a chlorinating agent and a brominating agent.

Examples of the chlorinating agent include phosphoryl chloride, phosphorus trichloride, phosphorus pentachloride, Vilsmeier reagent (N,N-dimethylformamide-phosphorus pentachloride, N,N-dimethylformamide-phosphorus oxychloride, etc.), Rydon reagent ($Ph_3PCl_2$, triphenylphosphine-carbon tetrachloride), thionyl chloride and sulfuryl chloride. Among others, sulfuryl chloride is preferable.

Examples of the brominating agent include phosphorus tribromide, N,N-dimethylformamide-phosphorus tribromide, triphenylphosphine-carbon tetrabromide and triphenylphosphine dibromide.

The halogenating agent may be used at a molar ratio of 0.1:1 to 10:1, preferably at a molar ratio of 0.8:1 to 5.0:1, and more preferably at a molar ratio of 1.0:1 to 2.0:1, with respect to the compound represented by the formula [1a].

Examples of the base used in this reaction include organic bases and inorganic bases. Among others, triethylamine and pyridine are preferable.

The base may be used at a molar ratio of 0.5:1 to 50:1, preferably at a molar ratio of 0.8:1 to 20:1, and more preferably at a molar ratio of 1.0:1 to 10:1, with respect to the compound represented by the formula [1a].

In this reaction, it is preferable to add a salt to the reaction system.

Examples of the salt include lithium chloride, lithium bromide, sodium bromide, calcium bromide and pyridine hydrochloride.

In this halogenation reaction, in general, an epimeric mixture is obtained. In order to improve the optical purity of the compound of the formula [1c], it is preferable to use sulfuryl chloride and lithium chloride in combination.

The salt may be used at a molar ratio of 0.5:1 to 20:1, preferably at a molar ratio of 0.8:1 to 5.0:1, and more preferably at a molar ratio of 1.0:1 to 3.0:1, with respect to the compound represented by the formula [1a].

The reaction temperature may be −50° C. to 80° C. It is preferably −40° C. to 60° C., and more preferably −30° C. to 40° C.

The reaction time may be 5 minutes to 50 hours. It is preferably 5 minutes to 24 hours, and more preferably 5 minutes to 6 hours.

(Fourth Step)

The compound represented by the formula [1d] can be produced by hydrolyzing the compound represented by the formula [1c] in the presence of an acid.

The solvent used in this reaction is not particularly limited, as long as it does not affect the reaction. Examples of the solvent include aliphatic hydrocarbons, halogenated hydrocarbons, alcohols, ethers, esters, ketones, nitriles, amides, sulfoxides, aromatic hydrocarbons, ureas and water. These solvents may be used in combination.

Preferred examples of the solvent include ethers, esters, nitriles, amides and water. Among these, ethers and water are more preferable.

The amount of the solvent used is not particularly limited. The solvent may be used at a ratio (v/w) of 1:1 to 50:1, and preferably at a ratio (v/w) of 1:1 to 15:1, with respect to the compound represented by the formula [1c].

Examples of the acid used in this reaction include hydrochloric acid, sulfuric acid, toluenesulfonic acid, acetic acid, glyoxylic acid and phosphoric acid. Among others, glyoxylic acid is preferable.

The acid may be used at a molar ratio of 0.5:1 to 100:1, preferably at a molar ratio of 1.0:1 to 60:1, and more preferably at a molar ratio of 1.5:1 to 40:1, with respect to the compound represented by the formula [1c].

In this reaction, it is preferable to add a carbonyl compound to the reaction system.

Examples of the carbonyl compound include: ketones such as acetone and 2-butanone; and aldehydes such as formaldehyde, benzaldehyde, glyoxal and glyoxylic acid; Among these, aldehydes are preferable, and glyoxylic acid is more preferable.

The carbonyl compound may be used at a molar ratio of 0.5:1 to 100:1, preferably at a molar ratio of 1.0:1 to 60:1, and more preferably at a molar ratio of 1.5:1 to 40:1, with respect to the compound represented by the formula [1c].

The reaction temperature may be −10° C. to 120° C. It is preferably 0° C. to 100° C., and more preferably 20° C. to 80° C.

The reaction time may be 5 minutes to 50 hours. It is preferably 5 minutes to 24 hours, and more preferably 5 minutes to 6 hours.

(Fifth Step)

The compound represented by the formula [1e] can be produced by allowing the compound represented by the formula [1d] to react with a sulfur compound.

The solvent used in this reaction is not particularly limited, as long as it does not affect the reaction. Examples of the solvent include aliphatic hydrocarbons, halogenated hydrocarbons, alcohols, ethers, esters, ketones, nitriles, amides, sulfoxides, aromatic hydrocarbons, ureas and water. These solvents may be used in combination.

Preferred examples of the solvent include ethers, esters, nitriles, amides and ureas. Among these, amides are more preferable.

The amount of the solvent used is not particularly limited. The solvent may be used at a ratio (v/w) of 1:1 to 50:1, and preferably at a ratio (v/w) of 1:1 to 15:1, with respect to the compound represented by the formula [1d].

Examples of the sulfur compound used in this reaction include hydrogen sulfide and a salt thereof.

Examples of the salt of hydrogen sulfide include sodium hydrogen sulfide, sodium sulfide, potassium hydrogen sulfide, calcium hydrogen sulfide and magnesium sulfide. Among these, sodium hydrogen sulfide is preferable.

The hydrogen sulfide or a salt thereof may be used at a molar ratio of 0.2:1 to 10:1, preferably at a molar ratio of 0.5:1 to 2.0:1, and more preferably at a molar ratio of 0.7:1 to 1.5:1, with respect to the compound represented by the formula [1d].

The reaction temperature may be −20° C. to 100° C. It is preferably −10° C. to 80° C., and more preferably −5° C. to 60° C.

The reaction time may be 5 minutes to 50 hours. It is preferably 5 minutes to 24 hours, and more preferably 5 minutes to 6 hours.

(Sixth Step)

As compounds represented by the formula [7], acetyl chloride, benzoyl chloride, benzenesulfonyl chloride and methanesulfonyl chloride have been known, for example.

As compounds represented by the formula [8], acetic anhydride and propionic anhydride have been known, for example.

The compound represented by the formula [9] can be produced by allowing the compound represented by the formula [1e] to react with the compound represented by the formula [7] or the compound represented by the formula [8].

The solvent used in this reaction is not particularly limited, as long as it does not affect the reaction. Examples of the solvent include aliphatic hydrocarbons, halogenated hydrocarbons, ethers, esters, ketones, nitriles, amides, sulfoxides and aromatic hydrocarbons. These solvents may be used in combination.

Preferred examples of the solvent include ethers, esters, nitriles and amides. Among these, ethers, nitriles and amides are more preferable.

The amount of the solvent used is not particularly limited. The solvent may be used at a ratio (v/w) of 1:1 to 50:1, and preferably at a ratio (v/w) of 1:1 to 15:1, with respect to the compound represented by the formula [1e].

The compound represented by the formula [7] or the compound represented by the formula [8] may be used in this reaction at a molar ratio of 0.5:1 to 50:1, preferably at a molar ratio of 0.8:1 to 20:1, and more preferably at a molar ratio of 1.0:1 to 10:1, with respect to the compound represented by the formula [1e].

In this reaction, it is preferable to add a base to the reaction system. Examples of the base include organic bases and inorganic bases. Among others, triethylamine is preferable.

The base may be used at a molar ratio of 0.5:1 to 50:1, preferably at a molar ratio of 0.8:1 to 20:1, and more preferably at a molar ratio of 1.0:1 to 15:1, with respect to the compound represented by the formula [1e].

The reaction temperature may be −10° C. to 100° C. It is preferably −5° C. to 80° C., and more preferably 0° C. to 60° C.

The reaction time may be 5 minutes to 50 hours. It is preferably 5 minutes to 24 hours, and more preferably 5 minutes to 6 hours.

Method (1)

[Formula 92]

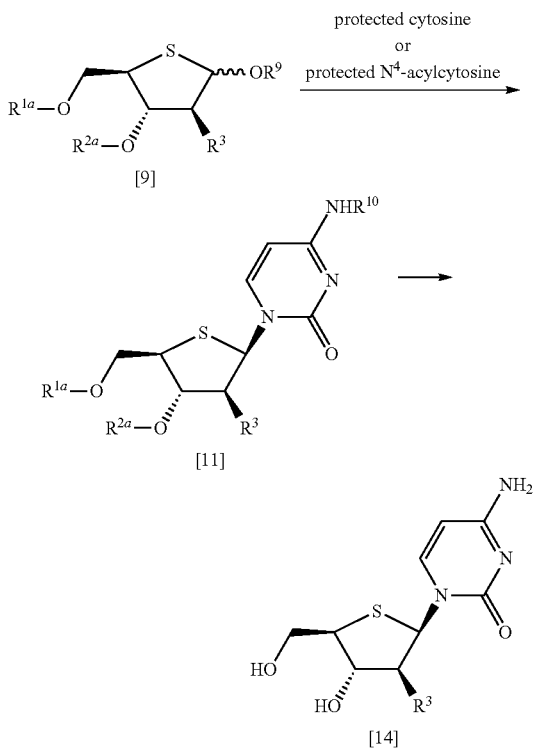

wherein $R^{1a}$, $R^{2a}$, $R^3$, $R^9$ and $R^{10}$ have the same meanings as those described above.

(First Step)

Protected cytosine or protected $N^4$-acylcytosine can be produced by allowing cytosine or $N^4$-acylcytosine to react with a silylating agent in the presence of a catalyst.

The solvent used in this reaction is not particularly limited, as long as it does not affect the reaction. Examples of the solvent include aliphatic hydrocarbons, halogenated hydrocarbons, ethers, nitriles and aromatic hydrocarbons. These solvents may be used in combination.

Preferred examples of the solvent include aliphatic hydrocarbons, halogenated hydrocarbons and aromatic hydrocarbons. Among these, aromatic hydrocarbons are more preferable, and chlorobenzene and toluene are further preferable.

The amount of the solvent used is not particularly limited. The solvent may be used at a ratio (v/w) of 1.0:1 to 50:1, and preferably at a ratio (v/w) of 1.0:1 to 15:1, with respect to cytosine or $N^4$-acylcytosine.

An example of the silylating agent used in this reaction is 1,1,1,3,3,3-hexamethyldisilazane.

The amount of the silylating agent used is not particularly limited. The silylating agent may be used at a molar ratio of 1.0:1 to 50:1, and preferably at a molar ratio of 1.0:1 to 10:1, with respect to the cytosine or $N^4$-acylcytosine.

Examples of the catalyst used in this reaction include ammonium salts such as ammonium hydrogen sulfate.

The catalyst may be used at a molar ratio of 0.001:1 to 1:1, and preferably at a molar ratio of 0.01:1 to 0.1:1, with respect to the cytosine or $N^4$-acylcytosine.

The reaction temperature may be 20° C. to 150° C., and preferably 50° C. to 150° C.

The reaction time may be 5 minutes to 50 hours. It is preferably 5 minutes to 10 hours, and more preferably 5 minutes to 6 hours.

This reaction is preferably carried out in an inert gas (e.g. nitrogen or argon) atmosphere.

Preferably, the protected cytosine or the protected N⁴-acylcytosine is directly used in the subsequent reaction without being subjected to isolation.

The compound represented by the formula [11] can be produced by allowing the compound represented by the formula [9] to react with the protected cytosine or the protected N⁴-acylcytosine in the presence of an acid.

The solvent used in this reaction is not particularly limited, as long as it does not affect the reaction. Examples of the solvent include aliphatic hydrocarbons, halogenated hydrocarbons, ethers, esters, ketones, nitriles, amides, sulfoxides and aromatic hydrocarbons. These solvents may be used in combination.

Preferred examples of the solvent include aliphatic hydrocarbons, halogenated hydrocarbons, nitriles and aromatic hydrocarbons. Among these, halogenated hydrocarbons and aromatic hydrocarbons are more preferable.

The amount of the solvent used is not particularly limited. The solvent may be used at a ratio (v/w) of 1.0:1 to 50:1, and preferably at a ratio (v/w) of 1.0:1 to 15:1, with respect to the compound represented by the formula [9].

Examples of the acid used in this reaction include Lewis acids such as aluminum chloride, aluminum bromide, tin tetrachloride, titanium tetrachloride, titanium(IV) isopropoxide, zinc chloride and trimethylsilyl=trifluoromethanesulfonate.

Preferred acids include aluminum chloride, tin tetrachloride and trimethylsilyl=trifluoromethanesulfonate, and among these, trimethylsilyl=trifluoromethanesulfonate is more preferable.

The amount of the acid used is not particularly limited. The acid may be used at a molar ratio of 0.0001:1 to 10:1, and preferably at a molar ratio of 0.001:1 to 1.0:1, with respect to the compound represented by the formula [9].

The protected cytosine or the protected N⁴-acylcytosine may be used in this reaction at a molar ratio of 1.0:1 to 50:1, preferably at a molar ratio of 1.0:1 to 10:1, and more preferably at a molar ratio of 1.0:1 to 5:1, with respect to the compound represented by the formula [9].

The reaction temperature may be 20° C. to 150° C., and preferably 20° C. to 100° C.

The reaction time may be 5 minutes to 50 hours. It is preferably 30 minutes to 24 hours, and more preferably 1 hour to 10 hours.

(Second Step)

The compound represented by the formula [14] can be produced by deprotecting the compound represented by the formula [11].

This method may be carried out in accordance with the method described in Patent Literature 1 or Protective Groups in Organic Synthesis, 4th edition, pp. 696-926, 2007, John Wiley & Sons, INC.

A preferred example of deprotection is a method using a base.

The solvent used in this reaction is not particularly limited, as long as it does not affect the reaction. Examples of the solvent include aliphatic hydrocarbons, halogenated hydrocarbons, alcohols, ethers and water. These solvents may be used in combination.

Preferred examples of the solvent include alcohols and water. Among these, alcohols are more preferable.

The amount of the solvent used is not particularly limited. The solvent may be used at a ratio (v/w) of 1.0:1 to 50:1, and preferably at a ratio (v/w) of 1.0:1 to 15:1, with respect to the compound represented by the formula [11].

Examples of the base used in this reaction include: inorganic bases such as sodium hydroxide and potassium hydroxide; ammonia; and metal alkoxides such as sodium methoxide and sodium ethoxide.

Preferred examples of the base include ammonia and metal alkoxides. Among others, ammonia and sodium methoxide are more preferable.

The amount of the base used is not particularly limited. The base may be used at a molar ratio of 0.001:1 to 10:1, and preferably at a molar ratio of 0.01:1 to 1.0:1.

The reaction temperature may be 0° C. to 100° C., and preferably 10° C. to 70° C.

The reaction time may be 5 minutes to 7 days, and preferably 1 hour to 24 hours.

Method (2)

[Formula 93]

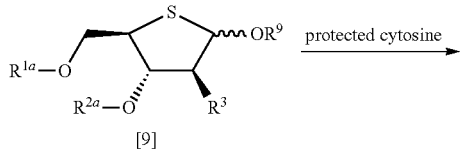

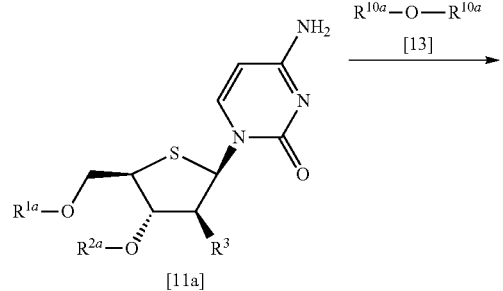

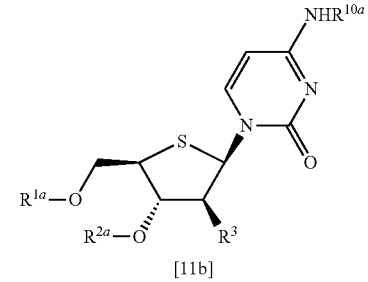

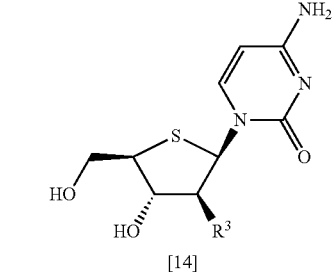

wherein R¹ᵃ, R²ᵃ, R³, R⁹, R¹⁰ᵃ and X⁴ have the same meanings as those described above.

49

(First Step)

The compound represented by the formula [11a] can be produced by allowing the compound represented by the formula [9] to react with protected cytosine.

This method may be carried out in accordance with the method described in Method 1 (First Step).

Preferably, the compound represented by the formula [11a] is directly used in the subsequent reaction, without being subjected to isolation.

(Second Step)

As compounds represented by the formula [12], acetyl chloride, propionyl chloride, pivaloyl chloride and benzoyl chloride have been known, for example.

As a compound represented by the formula [13], acetic anhydride has been known, for example.

The compound represented by the formula [11b] can be produced by allowing the compound represented by the formula [11a] to react with the compound represented by the formula [12] or the compound represented by the formula [13] in the presence or absence of a base and in the presence or absence of a catalyst.

The solvent used in this reaction is not particularly limited, as long as it does not affect the reaction. Examples of the solvent include aliphatic hydrocarbons, halogenated hydrocarbons, ethers, esters, ketones, nitriles and aromatic hydrocarbons. These solvents may be used in combination.

Preferred examples of the solvent include aliphatic hydrocarbons, halogenated hydrocarbons and aromatic hydrocarbons. Among these, halogenated hydrocarbons and aromatic hydrocarbons are more preferable.

The amount of the solvent used is not particularly limited. The solvent may be used at a ratio (v/w) of 1:1 to 50:1, and preferably at a ratio (v/w) of 1:1 to 15:1, with respect to the compound represented by the formula [11a].

When the compound represented by the formula [12] is used, it is preferable to add a base thereto.

Examples of the base include organic bases and inorganic bases, and among these, organic bases are preferable.

The base may be used at a molar ratio of 0.5:1 to 10:1, and preferably at a molar ratio of 1.0:1 to 5:1, with respect to the compound represented by the formula [11a].

When the compound represented by the formula [13] is used, it is preferable to add a catalyst thereto.

Examples of the catalyst include organic bases. Among others, dimethylaminopyridine is preferable.

The catalyst may be used at a molar ratio of 0.001:1 to 1.0:1, and preferably at a molar ratio of 0.01:1 to 1.0:1, with respect to the compound represented by the formula [11a].

The compound represented by the formula [12] or the compound represented by the formula [13] may be used at a molar ratio of 1.0:1 to 20:1, and preferably at a molar ratio of 1.0:1 to 10:1, with respect to the compound represented by the formula [11a].

The reaction temperature may be −20° C. to 100° C., and preferably −10° C. to 80° C.

The reaction time may be 5 minutes to 50 hours. It is preferably 5 minutes to 24 hours, and more preferably 5 minutes to 6 hours.

In this reaction, it is preferable to isolate the compound represented by the formula [11b] as a solid. By isolating the compound represented by the formula [11b], the purity of the compound represented by the formula [14] is improved.

(Third Step)

The compound represented by the formula [14] can be produced by deprotecting the compound represented by the formula [11b].

50

This method may be carried out in accordance with the method described in Production Method 1 (Second Step).

Method (3)

[Formula 94]

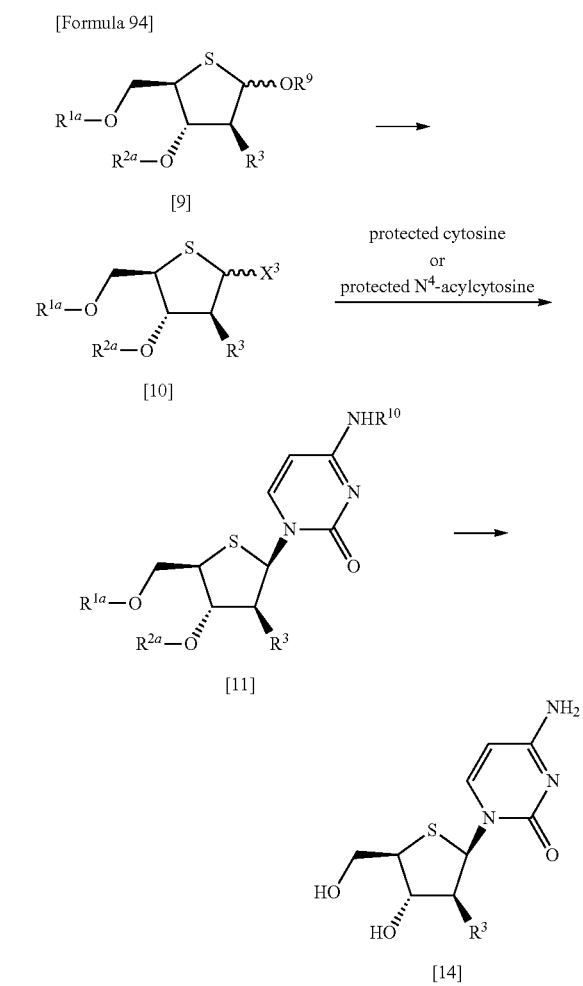

wherein $R^{1a}$, $R^{2a}$, $R^3$, $R^9$, $R^{10}$ and $X^3$ have the same meanings as those described above.

(First Step)

The compound represented by the formula [10] can be produced by halogenating the compound represented by the formula [9].

The solvent used in this reaction is not particularly limited, as long as it does not affect the reaction. Examples of the solvent include aliphatic hydrocarbons, halogenated hydrocarbons, ethers, esters, carboxylic acids, ketones, nitriles, amides and sulfoxides. These solvents may be used in combination.

Preferred examples of the solvent include halogenated hydrocarbons, ethers, carboxylic acids and nitriles. Among these, halogenated hydrocarbons are more preferable.

The amount of the solvent used is not particularly limited. The solvent may be used at a ratio (v/w) of 1:1 to 100:1, and preferably at a ratio (v/w) of 1:1 to 10:1, with respect to the compound represented by the formula [9].

Examples of a reagent used in the halogenation include hydrogen halide, a halide of alkaline metal and a halogenating agent.

Examples of the hydrogen halide include hydrogen chloride, hydrogen bromide and hydrogen iodide. Among these, hydrogen bromide is preferable.

Examples of the halide of alkaline metal include lithium bromide, sodium bromide, potassium bromide, lithium chloride, sodium chloride, potassium chloride, lithium iodide, sodium iodide and potassium iodide.

Examples of the halogenating agent used in this reaction include phosphoryl chloride, phosphorus trichloride, phosphorus pentachloride, thionyl chloride, sulfuryl chloride and phosphorus tribromide.

A preferred reagent is hydrogen halide, and among others, hydrogen bromide is more preferable.

The reagent may be used at a molar ratio of 1:1 to 100:1, preferably at a molar ratio of 1:1 to 10:1, and more preferably at a molar ratio of 1:1 to 5:1, with respect to the compound represented by the formula [9].

The reaction temperature may be −30° C. to 40° C., and preferably −5° C. to 10° C.

The reaction time may be 5 minutes to 10 hours. It is preferably 5 minutes to 3 hours, and more preferably 5 minutes to 1 hour.

(Second Step)

The compound represented by the formula [11] can be produced by allowing the compound represented by the formula [10] to react with protected cytosine or protected $N^4$-acylcytosine.

This method may be carried out in accordance with the method described in Patent Literature 1 or Method (1) (First Step).

(Third Step)

The compound represented by the formula [14] can be produced by deprotecting the compound represented by the formula [11].

This method may be carried out in accordance with the method described in Method 1 (Second Step).

Method (4)

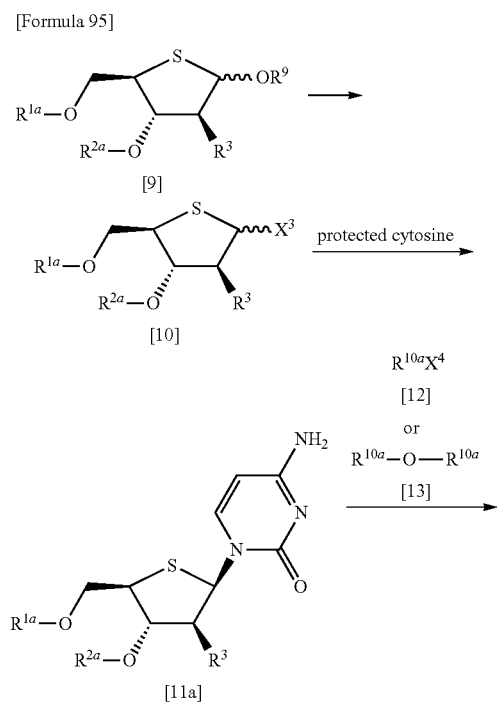

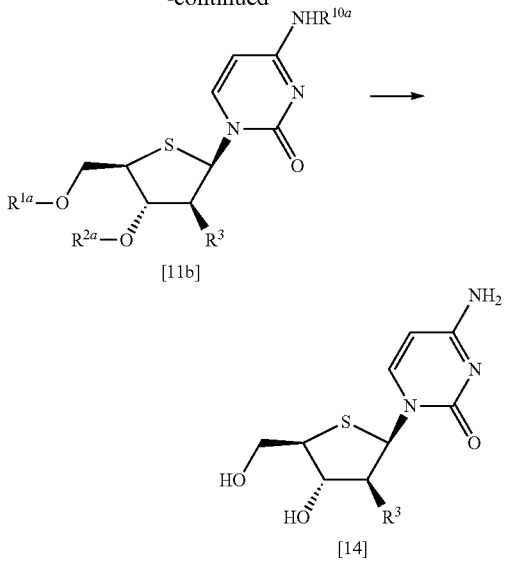

wherein $R^{1a}$, $R^{2a}$, $R^3$, $R^9$, $R^{10a}$, $X^3$ and $X^4$ have the same meanings as those described above.

(First Step)

The compound represented by the formula [10] can be produced by halogenating the compound represented by the formula [9].

This method may be carried out in accordance with the method described in Method (3) (First Step).

(Second Step)

The compound represented by the formula [11a] can be produced by allowing the compound represented by the formula [10] to react with protected cytosine.

This method may be carried out in accordance with the method described in Method (3) (Second Step).

(Third Step)

As compounds represented by the formula [12], acetyl chloride, propionyl chloride, pivaloyl chloride and benzoyl chloride have been known, for example.

As a compound represented by the formula [13], acetic anhydride is known, for example.

The compound represented by the formula [11b] can be produced by allowing the compound represented by the formula [11a] to react with the compound represented by the formula [12] or the compound represented by the formula [13].

This method may be carried out in accordance with the method described in Method (2) (Second Step).

(Fourth Step)

The compound represented by the formula [14] can be produced by deprotecting the compound represented by the formula [11b].

This method may be carried out in accordance with the method described in Method (1) (Second Step).

In the above-described production methods, protecting groups for the hydroxyl group, amino group or carboxyl group can be rearranged, as appropriate.

The compounds obtained by the above-described production methods can be isolated and purified by common methods such as extraction, crystallization, distillation or column chromatography. In addition, the compounds obtained by the above-described production methods may be directly used in the subsequent reaction without being isolated.

A compound having a formyl group, which is obtained by the above described production method, may include water adducts and alcohol adducts in some cases. The present invention includes all of them.

The compounds obtained by the above-described production methods may include tautomers and enantiomers in some cases. The present invention includes these isomers.

Moreover, when crystalline polymorphisms, salts, hydrates or solvates are present, the present invention includes all of the crystalline forms, salts, hydrates or solvates.

Hereinafter, the present invention will be described in the following examples. However, these examples are not intended to limit the scope of the present invention.

EXAMPLES

Unless otherwise specified, SNAP KP-Sil Cartridge (Biotage Japan Ltd.), FR-260 Hi-Flash™ Column (YAMAZEN), or Wakogel C-200 were used for silica gel column chromatography.

The mixing ratio used regarding eluent indicates a volume ratio.

For instance, the phrase "hexane/ethyl acetate=90/10 to 50/50" means that an eluent consisting of "hexane:ethyl acetate=90:10" was changed to an eluent consisting of "hexane:ethyl acetate=50:50."

The $^1$H-NMR spectra were measured employing Bruker AV400N (Bruker) or Bruker AV300 (Bruker), using tetramethylsilane as an internal standard. The total δ value was indicated with ppm.

The $^{19}$F-NMR spectra were measured employing Bruker AV400N (Bruker), and the total δ value was indicated with ppm.

The LC/MS analysis was carried out under the following conditions.
Measurement apparatus: Waters SQD
Column: Waters BEHC 18, 1.7 μm, 2.1×30 mm
Solvent: Liquid A: 0.1% formic acid/water
  Liquid B: 0.1% formic acid/acetonitrile
Gradient cycle: 0.00 min (liquid A/liquid B=95/5), 2.00 min (liquid A/liquid B=5/95), 3.00 min (liquid A/liquid B=5/95), 3.01 min (liquid A/liquid B=100/0), 3.80 min (liquid A/liquid B=100/0)
Flow rate: 0.5 mL/min
Column temperature: room temperature
Ionization method: electron spray ionization (ESI) method (in which positive and negative ion peaks are detected)
Detection wavelength: 254 nm Individual abbreviations used in the Examples have the following meanings.
Ac: acetyl
Bn: benzyl
Bz: benzoyl
Cbz: benzyloxycarbonyl
Et: ethyl
Me: methyl
Ms: methylsulfonyl
Ph: phenyl
PMB: 4-methoxybenzyl
$^i$Pr: isopropyl
TBDPS: tert-butyl(diphenyl)silyl
THP: tetrahydropyranyl
TIPS: tris(propan-2-yl)silyl
Tol: (4-methylphenyl)carbonyl
DMSO-d$_6$: deuterated dimethyl sulfoxide
RT (min): retention time (min)

Example 1

(1)

[Formula 96]

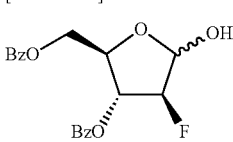

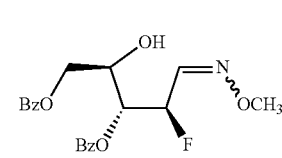

474 mL of methanol and 21.4 g of O-methylhydroxylamine hydrochloride were added to 119 g of ((2R,3R,4S)-3-(benzoyloxy)-4-fluoro-5-hydroxyoxolan-2-yl)methyl=benzoate. Thereafter, 35.7 mL of triethylamine was added dropwise to the mixture at a temperature of 0° C. to 10° C., and the thus obtained mixture was then stirred at room temperature for 5 hours. Thereafter, 400 mL of ethyl acetate and 400 mL of a saturated sodium hydrogen carbonate aqueous solution were added to the reaction mixture, and the water layer was then removed. The organic layer was dried over anhydrous magnesium sulfate, and the solvent was then distilled away under reduced pressure, so as to obtain 92.6 g of (2R,3R,4R)-1-(benzoyloxy)-4-fluoro-2-hydroxy-5-(methoxyimino)pentan-3-yl=benzoate in the form of a colorless oily product. $^1$H-NMR was measured. As a result, the syn-anti ratio was found to be 78:22.

$^1$H-NMR (CDCl$_3$) δ value:
3.05 (0.22H, d, J=5.6 Hz), 3.11 (0.78H, d, J=6.0 Hz), 3.83 (2.34H, s), 3.92 (0.66H, s), 4.35-4.49 (m, 2H), 4.55-4.68 (m, 1H), 5.42-5.54 (m, 0.78H), 5.48-5.67 (m, 0.78H), 5.74 (0.22H, ddd, J=28.0, 8.0, 1.6 Hz), 6.06 (0.22H, ddd, J=46.4, 4.8, 1.6 Hz), 6.84 (0.22H, dd, J=11.2, 4.8 Hz), 7.38-7.48 (4.78H, m), 7.54-7.63 (2H, m), 8.00-8.10 (4H, m)

(2)

[Formula 97]

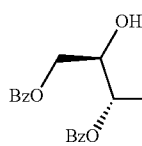

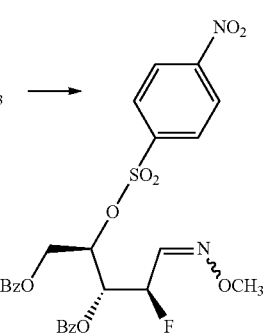

64.4 g of 4-nitrobenzenesulfonyl chloride was added to a solution of 87.0 g of (2R,3R,4R)-1-(benzoyloxy)-4-fluoro-2-hydroxy-5-(methoxyimino)pentan-3-yl=benzoate in 300 mL of an ethyl acetate at a temperature of 0° C. to 10° C. Thereafter, 40.5 mL of triethylamine was added dropwise to the mixture at 15° C. or lower over 30 minutes, and the thus obtained mixture was then stirred at 26° C. for 5 hours. Thereafter, 300 mL of a 5% sodium hydrogen carbonate aqueous solution was added to the reaction mixture, and the obtained mixture was then stirred at the same temperature as described above for 2 hours, Thereafter, the water layer was removed, and the organic layer was successively washed with a mixed solution of 100 mL of 1 mol/L hydrochloric acid and 100 mL of a 10% sodium chloride aqueous solution, and with a mixed solution of 100 mL of a 5% sodium hydrogen carbonate aqueous solution and 100 mL of a 10% sodium chloride aqueous solution. The resultant was dried over anhydrous sodium sulfate, and the solvent was then distilled away under reduced pressure, so as to obtain 126 g of (2R,3R,4R)-1-(benzoyloxy)-4-fluoro-5-(methoxyimino)-2-(((4-nitrobenzene)sulfonyl)oxy)pentan-3-yl=benzoate in the form of a light yellow solid. Thereafter, $^1$H-NMR was measured. As a result, the syn-anti ratio was found to be 1:2.

$^1$H-NMR (CDCl$_3$) δ value:

8.20-8.15 (2H, m), 8.10-8.05 (2H, m), 8.03-7.96 (2H, m), 7.92-7.86 (2H, m), 7.64-7.54 (2H, m), 7.48-7.38 (4.23H, m), 6.82 (0.77H, dd, J=11.2, 4.4 Hz), 5.94 (0.77H, ddd, J=26.4, 6.0, 2.4 Hz), 5.84 (0.77H, ddd, J=46.8, 4.4, 2.4 Hz), 5.77 (0.23H, ddd, J=23.2, 5.6, 2.8 Hz), 5.43 (0.23H, ddd, J=6.8, 5.6, 2.8 Hz), 5.40 (0.77H, ddd, J=7.2, 6.0, 2.8 Hz), 5.34 (0.23H, ddd, J=46.0, 6.8, 2.8 Hz), 4.76 (0.23H, dd, J=12.4, 2.8 Hz), 4.75 (0.77H, dd, J=12.4, 2.8 Hz), 4.52 (0.77H, dd, J=12.4, 7.2 Hz), 4.51 (0.23H, dd, J=12.4, 6.8 Hz), 3.89 (2.31H, s), 3.85 (0.69H, s)

$^{19}$F-NMR(CDCl$_3$) δ value:

−204.4-204.7 (0.77F, m), −196.4-196.6 (0.23F, m)

(3)

successively washed with 250 mL of 1 mol/L hydrochloric acid and 250 mL of a 10% sodium chloride aqueous solution, and was then dried over anhydrous sodium sulfate. The solvent was distilled away under reduced pressure, so as to obtain 79.9 g of a brown oily product.

As a result of the measurement of $^1$H-NMR, it was found that the brown oily product was a mixture of (2S,3S,4R)-1-(benzoyloxy)-2-bromo-4-fluoro-5-(methoxyimino)pentan-3-yl=benzoate and (2R,3S,4R)-1-(benzoyloxy)-2-bromo-4-fluoro-5-(methoxyimino)pentan-3-yl=benzoate (87:13), and that the syn-anti ratio of (2S,3S,4R)-1-(benzoyloxy)-2-bromo-4-fluoro-5-(methoxyimino)pentan-3-yl=benzoate was 82:18. (2S,3S,4R)-1-(benzoyloxy)-2-bromo-4-fluoro-5-(methoxyimino)pentan-3-yl=benzoate $^1$H-NMR (CDCl$_3$) δ value:

8.15-8.00 (4H, m), 7.65-7.55 (2H, m), 7.51-7.40 (4.82H, m), 6.87 (0.18H, dd, J=11.2, 4.8 Hz), 6.07 (0.18H, ddd, J=46.8, 4.4, 3.2 Hz), 5.94 (0.18H, ddd, J=24.4, 6.0, 3.2 Hz), 5.82 (0.82H, ddd, J=16.4, 6.0, 2.8 Hz), 5.52 (0.82H, dt, J=46.8, 6.0 Hz), 4.84-4.71 (1H, m), 4.64-4.55 (2H, m), 3.89 (2.46H, s), 3.85 (0.54H, s)

$^{19}$F-NMR(CDCl$_3$) δ value:

−193.3-193.5 (0.82F, m), −203.1-203.4 (0.18F, m)

(4)

[Formula 99]

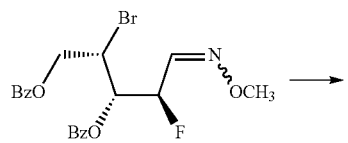

→

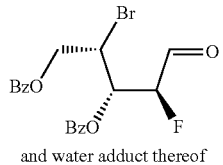

and water adduct thereof

[Formula 98]

153.4 g of anhydrous lithium bromide was added to a solution of 101.5 g of (2R,3R,4R)-1-(benzoyloxy)-4-fluoro-5-(methoxyimino)-2-(((4-nitrobenzene)sulfonyl)oxy)pentan-3-yl=benzoate in 350 mL of an N,N-dimethylformamide dividedly over six times at a temperature of 50° C. to 60° C. The obtained mixture was stirred at 57° C. for 4 hours 30 minutes. Thereafter, 400 mL of ethyl acetate and 250 mL of 1 mol/L hydrochloric acid were added to the reaction mixture, and the water layer was then removed. The organic layer was 170 mL of a 50% glyoxylic acid aqueous solution was added to a solution of 79.9 g of the brown oily product obtained in Example 1(3) in 255 mL of tetrahydrofuran, and the obtained mixture was then stirred at 56° C. for 12 hours. Thereafter, the reaction mixture was cooled to room temperature, and 255 mL of ethyl acetate and 170 mL of a 10% sodium chloride aqueous solution were added to the mixture, and the water layer was then removed. The organic layer was successively washed with 170 mL of a 10% sodium chloride aqueous solution, and with a mixed solution of 170 mL of a 5% sodium hydrogen carbonate aqueous solution and 170 mL of a 10% sodium chloride aqueous solution, and it was then dried over anhydrous sodium sulfate. The solvent was distilled away under reduced pressure, so as to obtain 70.4 g of a brown oily product.

The obtained oily product was a mixture of (2S,3S,4S)-1-(benzoyloxy)-2-bromo-4-fluoro-5-oxopentan-3-yl=benzoate and a water adduct thereof.

(5)

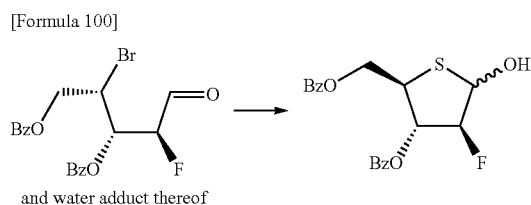

and water adduct thereof 26.7 g of a sodium hydrogen sulfide x-hydrate (Wako Pure Chemical Industries, Ltd.) was added to a solution of 70.4 g of the brown oily product obtained in Example 1(4) in 700 mL of N-methylpyrrolidone at a temperature of 0° C. to 10° C., and the obtained mixture was then stirred at the same temperature as described above for 2 hours. Thereafter, 13.4 g of a sodium hydrogen sulfide x-hydrate was added to the reaction mixture, and the thus obtained mixture was then stirred at 0° C. to 10° C. for 3 hours. Thereafter, 1050 mL of ethyl acetate and 700 mL of a 10% sodium chloride aqueous solution were added to the reaction mixture, and the water layer was then removed. The organic layer was successively washed with a mixed solution of 700 mL of 1 mol/L hydrochloric acid and 350 mL of a 10% sodium chloride aqueous solution, and with a mixed solution of 350 mL of a 5% sodium hydrogen carbonate aqueous solution and 350 mL of a 10% sodium chloride aqueous solution, and it was then dried over anhydrous sodium sulfate. The solvent was distilled away under reduced pressure, so as to obtain 52.1 g of ((2R,3S,4S)-3-(benzoyloxy)-4-fluoro-5-hydroxythiolan-2-yl)methyl=benzoate in the form of a light brown oily product.

$^1$H-NMR (CDCl$_3$) δ value:
8.08-7.97 (4H, m), 7.63-7.3 (6H, m), 6.05 (0.61H, ddd, J=12.0, 7.2, 5.6 Hz), 5.83 (0.39H, ddd, J=12.4, 2.8, 2.0 Hz), 5.64 (0.39H, ddd, J=9.6, 8.4, 2.0 Hz), 5.49 (0.61H, m), 5.31 (0.39H, dt, J=47.6, 2.0 Hz), 5.20 (0.61H, ddd, J=51.2, 7.2, 4.0 Hz), 4.67 (0.61H, dd, J=11.6, 6.8 Hz), 4.60 (0.6H, dd, J=11.6, 6.8 Hz), 4.53-4.47 (0.78H, m), 4.21 (0.39H, tdd, J=8.0, 2.8, 1.2 Hz), 3.75 (0.61H, td, J=6.8, 5.6 Hz), 3.01 (0.61H, d, J=4.8 Hz, —OH), 2.64 (0.39H, d, J=8.4 Hz, —OH)

$^{19}$F-NMR(CDCl$_3$) δ value:
−183.6-183.9 (0.61F, m), −192.3-192.6 (0.39F, m)

(6)

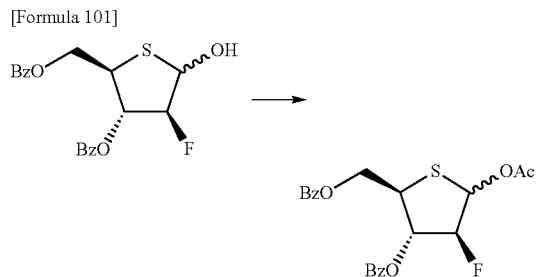

26.0 mL of acetic anhydride was added to a solution of 52.1 g of ((2R,3S,4S)-3-(benzoyloxy)-4-fluoro-5-hydroxythiolan-2-yl)methyl=benzoate in 210 mL of tetrahydrofuran, and 58.0 mL of triethylamine was then added dropwise to the mixture at 10° C. or lower. The obtained mixture was stirred at room temperature for 1 hour. Thereafter, 100 mL of ethyl acetate, 210 mL of a 5% sodium hydrogen carbonate aqueous solution and 100 mL of a 10% sodium chloride aqueous solution were added to the reaction mixture, and the obtained mixture was then stirred for 1 hour. Thereafter, the water layer was removed, and the organic layer was successively washed with a mixed solution of 150 mL of 1 mol/L hydrochloric acid and 100 mL of a 10% sodium chloride aqueous solution, and with a mixed solution of 50 mL of a 5% sodium hydrogen carbonate aqueous solution and 100 mL of a 10% sodium chloride aqueous solution, and it was then dried over anhydrous sodium sulfate. The solvent was distilled away under reduced pressure. The obtained residue was recrystallized from methanol, so as to obtain 29.3 g of ((2R,3S,4S)-5-(acetyloxy)-3-(benzoyloxy)-4-fluorothiolan-2-yl)methyl=benzoate in the form of a white solid.

(7)

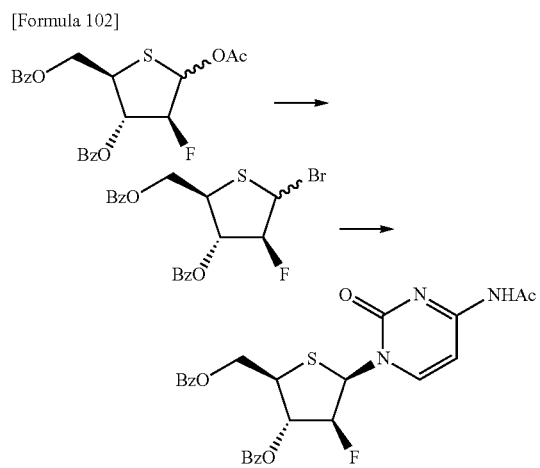

9.2 mL of a 30% hydrogen bromide/acetic acid solution was added to a solution of 5.0 g of ((2R,3S,4S)-5-(acetyloxy)-3-(benzoyloxy)-4-fluorothiolan-2-yl)methyl=benzoate in 20 mL of methylene chloride in a nitrogen atmosphere under cooling on ice, and the obtained mixture was then stirred at a temperature of 5° C. to 7° C. for 3 hours. Thereafter, 10 mL of a 30% sodium acetate aqueous solution was added dropwise to the reaction mixture. The organic layer was fractionated, and the water layer was extracted with methylene chloride. The organic layer was combined with the extract, and the obtained mixture was then washed with a 25% sodium hydrogen carbonate aqueous solution. The water layer was extracted with methylene chloride twice. The organic layer was combined with the extract, and the obtained mixture was then washed with a 3% sodium hydrogen carbonate aqueous solution. The water layer was extracted with methylene chloride. The organic layer was combined with the extract, and the obtained mixture was then dried over anhydrous sodium sulfate. The solvent was concentrated under reduced pressure, so as to obtain 15 mL of a methylene chloride solution of ((2R, 3S,4S)-3-(benzoyloxy)-5-bromo-4-fluorothiolan-2-yl)methyl=benzoate.

Separately, in a nitrogen atmosphere, 7.7 g of 1,1,1,3,3,3-hexamethyldisilazane and 15.8 mg of ammonium sulfate were added to a suspension of 3.66 g of acetylcytosine in 15 mL of ethylbenzene, and the obtained mixture was then stirred at a temperature of 110° C. to 115° C. for 2 hours. Thereafter, the reaction mixture was cooled to room temperature, and the solvent was then distilled away under reduced pressure, so as to obtain 7.5 g of a white solid.

1.25 mL of N-ethylpyrrolidone was added to the obtained white solid, and 15 mL of the above-described methylene chloride solution was then added dropwise to the mixture at a temperature of 70° C. to 75° C. The thus obtained mixture was stirred at the same temperature as described above for 1 hour. Thereafter, the reaction mixture was cooled to room temperature, and 75 mL of methylene chloride, 4 mL of water and 5 g of Celite were then added to the mixture, followed by stirring at a temperature of 27° C. to 28° C. for 2 hours. Thereafter, insoluble matters were removed by filtration, and the residue was then washed with methylene chloride. The filtrate was combined with the wash liquid, and the mixture was then washed with a solution of 2.85 g of dipotassium hydrogen phosphate and 0.38 g of potassium dihydrogen phosphate in 14.3 mL of water. The water layer was extracted with methylene chloride. The organic layer was combined with the extract, and insoluble matters were then removed by filtration. The solvent was replaced with propyl acetate. The precipitated solid was collected by filtration, and was then washed with propyl acetate, so as to obtain 1.53 g of ((2R,3S,4S,5R)-3-(benzoyloxy)-5-(4-acetamido-2-oxo-1,2-dihydropyrimidin-1-yl)-4-fl uorothiolan-2-yl)methyl=4-benzoate in the form of a white solid.

(8)

[Formula 103]

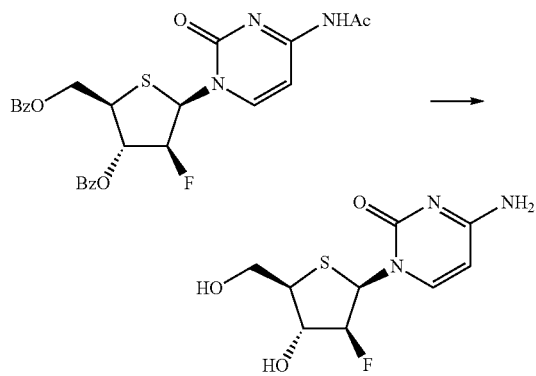

20 mL of 25% ammonia water was added to a solution of 2.03 g of ((2R,3S,4S,5R)-3-(benzoyloxy)-5-(4-acetamido-2-oxo-1,2-dihydropyrimidin-1-yl)-4-fl uorothiolan-2-yl)methyl=4-benzoate in 40 mL of methanol, and the obtained mixture was then stirred at room temperature for 12 hours. Thereafter, the solvent was concentrated under reduced pressure, and the precipitated solid was then washed with methanol, so as to obtain 374 mg of (2R,3S,4S,5R)-3-hydroxy-2-hydroxymethyl-5-(4-amino-2-oxo-1,2-dihydropyrimidin-1-yl)-4-fluorothiolane in the form of a white solid.

The wash liquid was concentrated under reduced pressure, and the precipitated solid was then dissolved in 150 mL of ethyl acetate. 80 mL of the solvent was distilled away under reduced pressure. The precipitated solid was collected by filtration, and was then washed with ethyl acetate, so as to obtain 491 mg of (2R,3S,4S,5R)-3-hydroxy-2-hydroxymethyl-5-(4-amino-2-oxo-1,2-dihydropyrimidin-1-yl)-4-fluorothiolane in the form of a white solid.

$^1$H-NMR (DMSO-$d_6$) δ value:
7.99 (1H, d, J=7.9 Hz), 7.28-7.20 (2H, brs), 6.46 (1H, dd, J=14.5, 5.3 Hz), 5.88 (1H, d, J=4.6 Hz), 5.77 (1H, d, J=7.9 Hz), 5.25 (1H, t, J=5.3 Hz), 4.92 (1H, dt, J=50.9, 5.3 Hz), 4.30-4.19 (1H, m), 3.78-3.54 (2H, m), 3.23 (1H, q, J=5.9 Hz)

Example 2

(1)

[Formula 104]

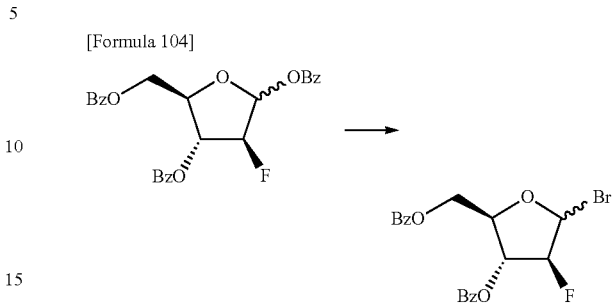

In a nitrogen atmosphere, 76 mL of 30% hydrogen bromide/acetic acid was added dropwise to a suspension of 150 g of (3S,4R,5R)-4-(benzoyloxy)-5-((benzoyloxy)methyl)-3-fluorooxolan-2-yl=benzoate in 105 mL of acetic acid at room temperature, and the obtained mixture was then stirred at 25° C. for 8 hours. Thereafter, 450 mL of toluene and 450 mL of water were added to the reaction mixture, and the thus obtained mixture was then stirred for 5 minutes. After that, the water layer was removed. The obtained organic layer was successively washed with 450 mL of water and 450 mL of a 5% sodium hydrogen carbonate aqueous solution, and was then dried over anhydrous sodium sulfate. The solvent was distilled away under reduced pressure, so as to obtain 136 g of ((2R,3R,4S)-3-(benzoyloxy)-5-bromo-4-fluorooxolan-2-yl)methyl=benzoate in the form of a colorless oily product.

As a result of the measurement of $^1$H-NMR, it was found that the obtained compounds were all α forms.

$^1$H-NMR (CDCl$_3$) δ value:
8.11 (2H, dd, J=8.0, 0.8 Hz), 8.07 (2H, dd, J=8.0, 0.8 Hz), 7.63 (1H, tt, J=8.0, 0.8 Hz), 7.56 (1H, tt, J=8.0, 0.8 Hz), 7.49 (2H, t, J=8.0 Hz), 7.43 (2H, t, J=8.0 Hz), 6.64 (1H, d, J=12.4 Hz), 5.60 (1H, d, J=50.0 Hz), 5.54 (1H, dd, J=22.0, 3.0 Hz), 4.68-4.86 (3H, m)

$^{19}$F-NMR(CDCl$_3$) δ value:
−165.8-166.1 (1F, m)

(2)

[Formula 105]

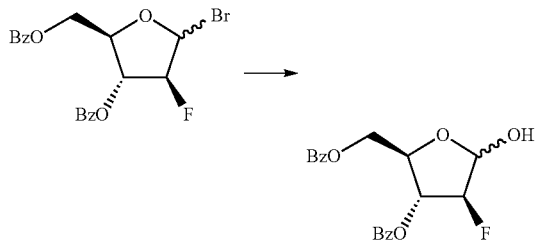

270 mL of acetonitrile and 300 mL of a 10% sodium hydrogen carbonate aqueous solution were added to 136 g of ((2R,3R,4S)-3-(benzoyloxy)-5-bromo-4-fluorooxolan-2-yl)methyl=benzoate, and the obtained mixture was then stirred at 50° C. for 4 hours. Thereafter, 150 mL of toluene was added to the reaction mixture, and the water layer was then removed. Thereafter, the residue was cooled to 25° C. to obtain a toluene/acetonitrile solution of ((2R,3R,4S)-3-(benzoyloxy)-4-fluoro-5-hydroxyoxolan-2-yl)methyl=benzoate.

The obtained ((2R,3R,4S)-3-(benzoyloxy)-4-fluoro-5-hydroxyoxolan-2-yl)methyl=benzoate was used in the form of a solution for the subsequent reaction, without being isolated.

(3)

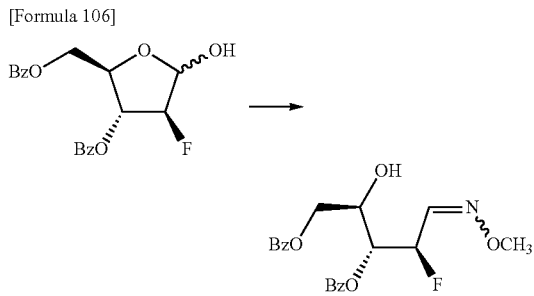

[Formula 106]

135 mL of water and 40.2 g of O-methylhydroxylamine hydrochloride were added to a toluene/acetonitrile solution of ((2R,3R,4S)-3-(benzoyloxy)-4-fluoro-5-hydroxyoxolan-2-yl)methyl=benzoate. Subsequently, 58.2 mL of triethylamine was added dropwise to the mixture at a temperature of 25° C. to 30° C., and the obtained mixture was then stirred for 6 hours.

Thereafter, 150 mL of toluene and 300 mL of a 10% sodium chloride aqueous solution were added to the reaction mixture, and the water layer was then removed. The organic layer was dried over anhydrous sodium sulfate, and the solvent was then distilled away under reduced pressure, so as to obtain 122 g of (2R,3R,4R)-1-(benzoyloxy)-4-fluoro-2-hydroxy-5-(methoxyimino)pentan-3-yl=benzoate in the form of a colorless oily product.

$^1$H-NMR was measured. As a result, the syn-anti ratio was found to be 3:1.

$^1$H-NMR (CDCl$_3$) δ value:
8.10-8.00 (4H, m), 7.63-7.54 (2H, m), 7.48-7.38 (4.75H, m), 6.84 (0.25H, dd, J=11.2, 4.8 Hz), 60.06 (0.25H, ddd, J=46.4, 4.8, 1.6 Hz), 5.74 (0.25H, ddd, J=28.0, 8.0, 1.6 Hz), 5.75 (0.75H, ddd, J=45.6, 6.8, 2.4 Hz), 5.49 (0.75H, ddd, J=26.0, 8.4, 2.4 Hz), 4.64 (0.75H, dd, J=12.0, 2.4 Hz), 4.60 (0.25H, dd, J=11.2, 2.4 Hz), 4.50-4.35 (2H, m), 3.91 (0.75H, s), 3.82 (2.25H, s), 3.11 (0.75H, d, J=6.0 Hz), 3.05 (0.25H, d, J=5.6 Hz)

$^{19}$F-NMR(CDCl$_3$) δ value:
−199.9-200.2 (0.75F, m), −207.3-207.5 (0.25F, m)

Example 3

(1)

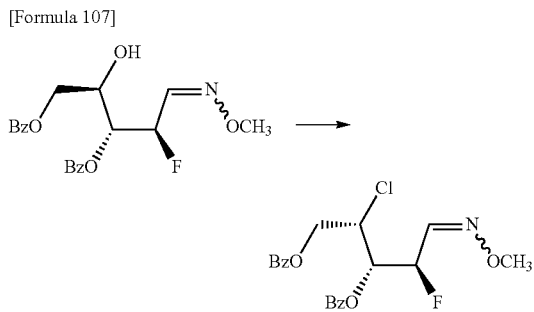

[Formula 107]

In a nitrogen atmosphere, 6.50 g of lithium chloride was added to a mixed solution of 30.0 g of (2R,3R,4R)-1-(benzoyloxy)-4-fluoro-2-hydroxy-5-(methoxyimino)pentan-3-yl=benzoate in 150 mL of N,N-dimethylacetamide and 30 mL of pyridine. Subsequently, 6.40 mL of sulfuryl chloride was added dropwise to the mixture at a temperature of −20° C. to 0° C. over 20 minutes, and the thus obtained mixture was then stirred at room temperature for 3 hours. Thereafter, 300 mL of ethyl acetate, 150 mL of a 20% sodium chloride aqueous solution and 100 mL of water were added to the reaction mixture, and the water layer was then removed. The organic layer was washed with 150 mL of 1 mol/L hydrochloric acid twice, and then with 150 mL of a saturated sodium hydrogen carbonate aqueous solution, and it was then dried over anhydrous magnesium sulfate. The solvent was distilled away under reduced pressure, so as to obtain 34.2 g of (2S,3S,4R)-1-(benzoyloxy)-2-chloro-4-fluoro-5-(methoxyimino)pentan-3-yl=benzoate in the form of a colorless oily product.

The obtained (2S,3S,4R)-1-(benzoyloxy)-2-chloro-4-fluoro-5-(methoxyimino)pentan-3-yl=benzoate was directly used in the subsequent reaction without being isolated.

A small amount of reaction solution was diluted with deuterated chloroform, and $^1$H-NMR was then measured. As a result, the syn/anti ratio was found to be 85:15.

$^1$H-NMR (CDCl$_3$) δ value:
3.84 (0.45H, s), 3.88 (2.55H, s), 4.54-4.74 (3H, m), 5.52 (0.85H, dt, J=46.4, 6.4 Hz), 5.85 (0.85H, ddd, J=17.2, 5.9, 3.2 Hz), 5.88-6.00 (0.15H, m), 5.95-6.12 (0.15H, m), 6.88 (0.15H, dd, J=1.2, 4.8 Hz), 7.40-7.53 (4.85H, m), 7.55-7.66 (2H, m), 8.01-8.15 (4H, m)

(2)

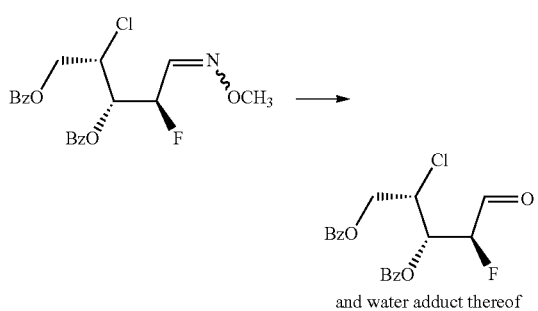

[Formula 108]

and water adduct thereof

In a nitrogen atmosphere, a mixture of 30.6 g of the (2S, 3S,4R)-1-(benzoyloxy)-2-chloro-4-fluoro-5-(methoxyimino)pentan-3-yl=benzoate obtained in Example 3(1), 183 mL of tetrahydrofuran and 133 mL of glyoxylic acid was stirred at 60° C. for 10 hours. Thereafter, 300 mL of ethyl acetate, 200 mL of a 20% sodium chloride aqueous solution, 300 mL of water and 65.1 g of sodium hydrogen carbonate were added to the reaction mixture, and the water layer was then removed. The organic layer was dried over anhydrous magnesium sulfate, and the solvent was then distilled away under reduced pressure, so as to obtain 27.3 g of a colorless oily product.

The obtained oily product was a mixture of (2S,3S,4S)-1-(benzoyloxy)-2-chloro-4-fluoro-5-oxopentan-3-yl=benzoate and a water adduct thereof.

$^1$H-NMR (CDCl$_3$) δ value:
4.69-4.78 (3H, m), 5.37 (1H, dd, J=46.8, 4.0 Hz), 5.85 (1H, dt, J=20.8, 3.6 Hz), 7.39-7.53 (4H, m), 7.54-7.66 (2H, m), 8.01-8.12 (4H, m), 9.83 (1H, d, J=6.4 Hz)

(3)

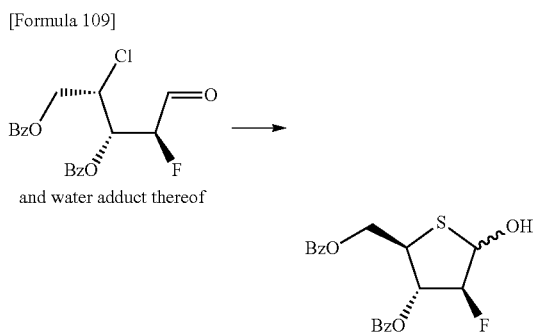

[Formula 109]

and water adduct thereof

In a nitrogen atmosphere, 96.2 mg of a sodium monohydrogen sulfide n-hydrate was added to a solution of 350 mg of the colorless oily product obtained in Example 3(2) in 5.25 mL of N-methylpyrrolidone, and the obtained mixture was then stirred at room temperature for 5 hours. Thereafter, 7.90 mL of ethyl acetate, 5.25 mL of a 20% sodium chloride aqueous solution and 5.25 mL of a saturated sodium hydrogen carbonate aqueous solution were added to the reaction mixture, and the water layer was then removed. The organic layer was dried over anhydrous magnesium sulfate, and the solvent was then distilled away under reduced pressure. The obtained residue was purified by silica gel column chromatography (hexane:ethyl acetate=3:1), so as to obtain 80.0 mg of ((2R,3S,4S)-3-(benzoyloxy)-4-fluoro-5-hydroxythiolan-2-yl)methyl=benzoate in the form of a colorless oily product.

$^1$H-NMR (CDCl$_3$) δ value:
3.74 (0.55H, q, J=6.8 Hz), 4.17-4.23 (0.45H, m), 4.44-4.55 (0.90H, m), 4.56-4.64 (0.55H, m), 4.64-4.72 (0.55H, m), 5.20 (0.55H, ddd, J=51.5, 7.6, 4.0 Hz), 5.32 (0.45H, dt, J=47.6, 2.4 Hz), 5.48 (0.55H, t, J=4.4 Hz), 5.64 (0.45H, dd, J=8.4 11.2, 1.6 Hz), 5.82 (0.45H, dt, J=12.8, 3.2 Hz), 6.04-6.12 (0.55H, m), 7.28-7.65 (6H, m), 7.94-8.16 (4H, m)

(4)

[Formula 110]

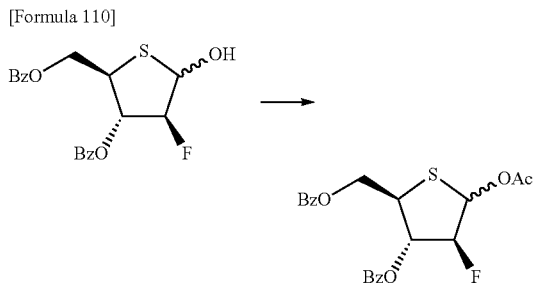

In a nitrogen atmosphere, 39.5 mL of triethylamine and 17.9 mL of acetic anhydride were added dropwise to a solution of 10.3 g of ((2R,3S,4S)-3-(benzoyloxy)-4-fluoro-5-hydroxythiolan-2-yl)methyl=benzoate in 20 mL of ethyl acetate, and the obtained mixture was then stirred at room temperature for 4 hours. Thereafter, 50 mL of ethyl acetate, 20 mL of a 20% sodium chloride aqueous solution and 30 mL of a saturated sodium hydrogen carbonate aqueous solution were added to the reaction mixture, and the water layer was then removed. Thereafter, 30 mL of saturated ammonium chloride water was added to the organic layer, and the water layer was then removed. The organic layer was dried over anhydrous magnesium sulfate, and the solvent was then distilled away under reduced pressure. The obtained residue was purified by silica gel column chromatography (hexane/ethyl acetate=3/1), so as to obtain 8.35 g of ((2R,3S,4S)-5-(acetyloxy)-3-(benzoyloxy)-4-fluorothiolan-2-yl) methyl=benzoate in the form of a brown oily product.

$^1$H-NMR (CDCl$_3$) δ value:
2.12 (1.29H, s), 2.13 (1.71H, s), 3.74 (0.57H, q, J=6.8 Hz), 4.11 (0.43H, q, J=6.8 Hz), 4.43-4.59 (1.43H, m), 4.69 (0.57H, dd, J=11.1, 6.0 Hz), 5.31 (0.57H, ddd, J=50.8, 9.1, 4.8 Hz), 5.39 (0.43H, dt, J=47.6, 3.2 Hz), 5.85 (0.43H, dt, J=12.0, 4.0 Hz), 6.08 (0.57H, dt, J=11.6, 8.4 Hz), 6.18 (0.57H, d, J=4.8 Hz), 6.24 (0.43H, dd, J=13.6, 2.0 Hz), 7.28-7.36 (1.14H, m), 7.37-7.65 (4.86H, m), 7.92-7.98 (1.14H, m), 8.00-8.09 (2.86H, m)

Example 4

(1)

[Formula 111]

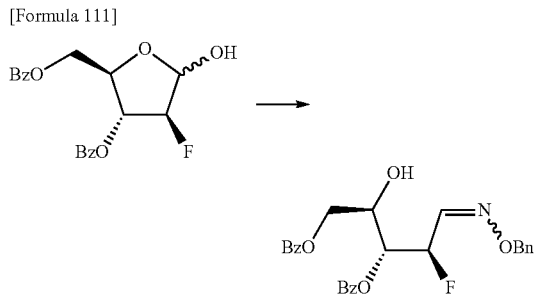

200 mL of a 5% sodium hydrogen carbonate aqueous solution was added to a suspension of 17.2 g of O-benzylhydroxylamine hydrochloride in 86 mL of ethyl acetate, and the water layer was then removed. Thereafter, the solvent was concentrated under reduced pressure. To the obtained residue, 130 mL of methylene chloride, 19.4 g of ((2R,3R,4S)-3-(benzoyloxy)-4-fluoro-5-hydroxyoxolan-2-yl)methyl=benzoate, 13.6 g of sodium hydrogen carbonate and 1.36 g of pyridinium p-toluenesulfonate were added, and the obtained mixture was then stirred at 50° C. for 1 hour. Thereafter, the reaction mixture was cooled to room temperature. Subsequently, 100 mL of ethyl acetate, 100 mL of a 20% sodium chloride aqueous solution and 50 mL of a saturated sodium hydrogen carbonate aqueous solution were added to the mixture, and the water layer was then removed. The organic layer was dried over anhydrous magnesium sulfate, and the solvent was then distilled away under reduced pressure. The obtained residue was purified by silica gel column chromatography (hexane/ethyl acetate=3/1), so as to obtain 36.4 g of (2R,3R, 4R)-3-(benzoyloxy)-5-((benzyloxy)imino)-4-fluoro-2-hydroxypentyl=benzoate in the form of a colorless oily product.

$^1$H-NMR (CDCl$_3$) δ value:
2.88 (0.31H, s), 2.91 (0.69H, s), 4.33-4.46 (2H, m), 4.55-4.64 (1H, m), 5.06 (1.38H, s), 5.16 (0.62H, dd, J=6.8, 5.5 Hz), 5.49 (0.69H, ddd, J=25.9, 7.6, 1.6 Hz), 5.58 (0.69H, ddd, J=46.7, 6.4, 2.4 Hz), 5.79 (0.31H, dd, J=27.5, 7.9 Hz), 6.10 (0.31H, ddd, J=46.7, 4.8, 2.0 Hz), 6.90 (0.31H, dd, J=11.2, 4.8 Hz), 7.24 (5H, m), 7.38-7.53 (4.69H, m), 7.54-7.64 (2H, m), 7.99-8.10 (4H, m)

(2)

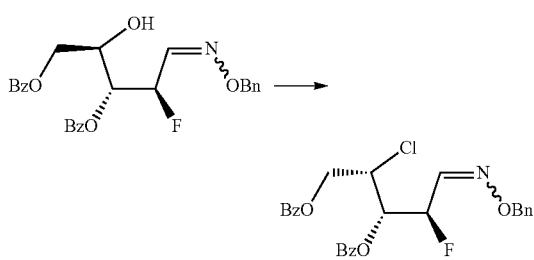
[Formula 112]

In a nitrogen atmosphere, a mixture of 1.00 g of (2R,3R,4R)-3-(benzoyloxy)-5-((benzyloxy)imino)-4-fluoro-2-hydroxypentyl=benzoate, 5.00 mL of N,N-dimethylformamide and 1.00 mL of pyridine was cooled to −20° C. While the internal temperature was kept at 0° C. or lower, 0.210 mL of sulfuryl chloride was added dropwise to the reaction mixture over 20 minutes, and the thus obtained mixture was then stirred at room temperature for 3 hours. Thereafter, 10 mL of ethyl acetate, 5 mL of a 20% sodium chloride aqueous solution and 5 mL of water were added to the reaction mixture, and the water layer was then removed. 5 mL of 1 mol/L hydrochloric acid was added to the organic layer, and the water layer was then removed. This operation was repeated twice. Subsequently, 5 mL of a saturated sodium hydrogen carbonate aqueous solution was added to the organic layer, and the water layer was then removed. The organic layer was dried over anhydrous magnesium sulfate, and the solvent was then distilled away under reduced pressure. The obtained residue was purified by silica gel column chromatography (hexane/ethyl acetate=3/1), so as to obtain 1.01 g of (2S,3S,4R)-3-(benzoyloxy)-5-((benzyloxy)imino)-2-chloro-4-fluoropentyl=benzoate in the form of a colorless oily product.

$^1$H-NMR (CDCl$_3$) δ value:
4.48-4.75 (3H, m), 5.07 (0.4H, s), 5.11 (1.6H, s), 5.52 (0.8H, dt, J=46.8, 6.0 Hz), 5.84 (0.8H, ddd, J=16.4, 6.0, 3.2 Hz), 5.89-6.00 (0.2H, m), 6.01-6.18 (0.2H, m), 6.92 (0.2H, dd, J=8.1, 3.6 Hz), 7.25-7.34 (5H, m), 7.39-7.51 (4.8H, m), 7.53-7.64 (2H, m), 8.00-8.12 (4H, m)

(3)

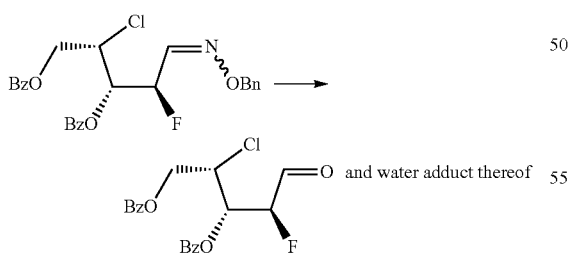
[Formula 113]

In a nitrogen atmosphere, a mixture of 0.610 g of (2S,3S,4R)-3-(benzoyloxy)-5-((benzyloxy)imino)-2-chloro-4-fluoropentyl=benzoate, 3.00 mL of benzaldehyde and 0.300 mL of concentrated sulfuric acid was stirred at room temperature for 1 hour. Thereafter, 5 mL of ethyl acetate, 5 mL of a 20% sodium chloride aqueous solution and 5 mL of a saturated sodium hydrogen carbonate aqueous solution were added to the reaction mixture, and the water layer was then removed. The organic layer was dried over anhydrous magnesium sulfate, and the solvent was then distilled away under reduced pressure. The obtained residue was purified by silica gel column chromatography (hexane/ethyl acetate=3/1), so as to obtain 0.260 g of a colorless oily product.

The obtained oily product was a mixture of (2S,3S,4S)-1-(benzoyloxy)-2-chloro-4-fluoro-5-oxopentan-3-yl=benzoate and a water adduct thereof.

$^1$H-NMR (CDCl$_3$) δ value:
4.69-4.78 (3H, m), 5.37 (1H, dd, J=46.8, 4.0 Hz), 5.85 (1H, dt, J=20.8, 3.6 Hz), 7.39-7.53 (4H, m), 7.54-7.66 (2H, m), 8.01-8.12 (4H, m), 9.83 (1H, d, J=6.4 Hz)

Example 5

(1)

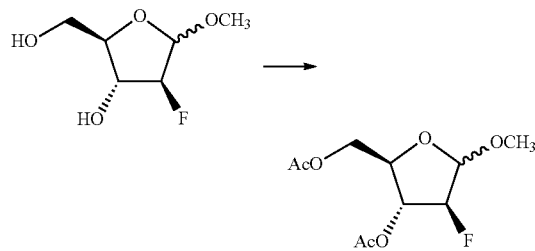
[Formula 114]

A mixture of 1.70 g of (2R,3R,4S)-4-fluoro-2-(hydroxymethyl)-5-methoxyoxolan-3-ol, 30 mL of tetrahydrofuran, 4.24 mL of triethylamine, 2.8 mL of acetic anhydride and 0.01 g of 4-dimethylaminopyridine was stirred at 25° C. for 2 hours. Thereafter, ethyl acetate and water were added to the reaction mixture. The organic layer was fractionated, was then washed with a sodium hydrogen carbonate aqueous solution, and was then dried over anhydrous magnesium sulfate. The solvent was distilled away under reduced pressure, so as to obtain 2.2 g of ((2R,3R,4S)-3-(acetyloxy)-4-fluoro-5-methoxyoxolan-2-yl)methyl=acetate in the form of a colorless oily product.

$^1$H-NMR (DMSO-d$_6$) δ value:
5.28-5.12 (2H, m), 5.01 (1H, d, J=4.0 Hz), 4.31 (1H, dd, J=3.6, 11.2 Hz), 4.10-4.02 (2H, m), 3.34 (3H, s), 2.09 (3H, s), 2.23 (3H, s)

(2)

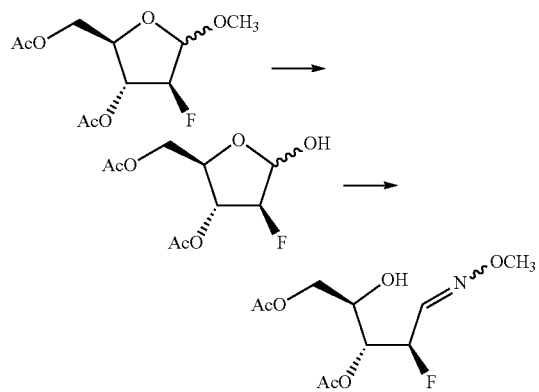
[Formula 115]

A mixture of 2.1 g of ((2R,3R,4S)-3-(acetyloxy)-4-fluoro-5-methoxyoxolan-2-yl)methyl=acetate, 9 mL of trifluoroacetic acid and 1 mL of water was stirred at 50° C. for 8 hours. Thereafter, ethyl acetate and a sodium hydrogen carbonate aqueous solution were added to the reaction mixture. The organic layer was fractionated, and was then dried over anhydrous magnesium sulfate. The solvent was distilled away under reduced pressure, so as to obtain ((2R,3R,4S)-3-(acetyloxy)-4-fluoro-5-hydroxyoxolan-2-yl)methyl=acetate in the form of a colorless oily product.

A mixture of the obtained ((2R,3R,4S)-3-(acetyloxy)-4-fluoro-5-hydroxyoxolan-2-yl)methyl=acetate, 10 mL of methanol, 0.85 g of O-methylhydroxylamine hydrochloride and 0.7 mL of triethylamine was stirred at 25° C. for 0.5 hours. Thereafter, ethyl acetate and water were added to the reaction mixture. The organic layer was fractionated, and was then dried over anhydrous sodium sulfate. The solvent was distilled away under reduced pressure. The obtained residue was purified by silica gel column chromatography (hexane/ethyl acetate=1/1), so as to obtain 0.35 g of (2R,3R,4R)-1-(acetyloxy)-4-fluoro-2-hydroxy-5-(methoxyimino)pentan-3-yl=acetate in the form of a colorless oily product.

$^1$H-NMR (DMSO-$d_6$) δ value:
7.51 (0.75H, dd, J=6.8, 7.2 Hz), 7.02 (0.25H, dd, J=4.8, 10.4 Hz), 5.93-5.73 (1.25H, m), 5.36 (0.75H, ddd, J=2.8, 6.8, 45.6 Hz), 5.12 (0.25H, ddd, J=1.6, 9.2, 29.6 Hz), 4.97 (0.75H, ddd, J=2.4, 80.4, 26.4 Hz), 4.05-3.85 (3H, m), 3.83 (0.75H, s), 3.80 (2.25H, s), 2.06 (2.25H, s), 2.04 (0.75H, s), 1.99 (3H. m)

(3)

[Formula 116]

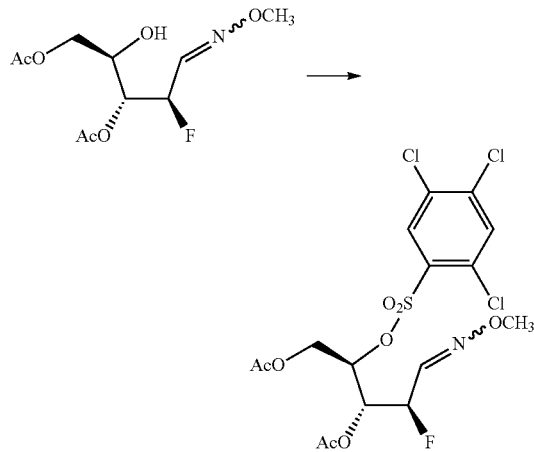

A mixture of 0.35 g of the (2R,3R,4R)-1-(acetyloxy)-4-fluoro-2-hydroxy-5-(methoxyimino)pentan-3-yl=acetate, 5 mL of acetonitrile, 0.15 mL of N-methylimidazole and 0.41 g of 2,4,5-trichlorobenzenesulfonyl chloride was stirred at 25° C. for 5 hours. Further, 0.10 g of 2,4,5-trichlorobenzenesulfonyl chloride was added to the reaction mixture, and the thus obtained mixture was then left at 25° C. for 3 days. Subsequently, 1.0 mL of N-methylimidazole was added to the reaction mixture, and the thus obtained mixture was then left at 25° C. for 1 day. Thereafter, ethyl acetate and water were added to the reaction mixture. The organic layer was fractionated, and it was washed with diluted hydrochloric acid twice, and then with a sodium hydrogen carbonate aqueous solution. The resultant was dried over anhydrous magnesium sulfate, and the solvent was then distilled away under reduced pressure. The obtained residue was purified by silica gel column chromatography (hexane/ethyl acetate=3/1), so as to obtain 0.44 g of a colorless solid. The obtained solid was recrystallized from methanol, so as to obtain 0.29 g of (2R,3R,4R)-1-(acetyloxy)-4-fluoro-5-(methoxyimino)-2-(((2,4,5-trichlorobenzene)sulfonyl)oxy)pentan-3-yl=acetate in the form of a colorless solid.

$^1$H-NMR (DMSO-$d_6$) δ value:
8.33 (1.0H, m), 8.23 (1.0H, m), 7.55 (0.75H, dd, J=6.0, 7.2 Hz), 7.05 (0.25H, dd, J=4.8, 11.2 Hz), 5.81 (0.25H, ddd, J=2.0, 4.8, 46.4 Hz), 5.53 (0.25H, ddd, J=2.4, 5.2, 28.4 Hz), 5.49-5.33 (1.5H, m), 5.18-5.11 (1H, m), 4.35-4.12 (2H, m), 3.81 (3H, m), 2.07 (3H, m), 1.86-1.85 (3H, m)

Example 6

(1)

[Formula 117]

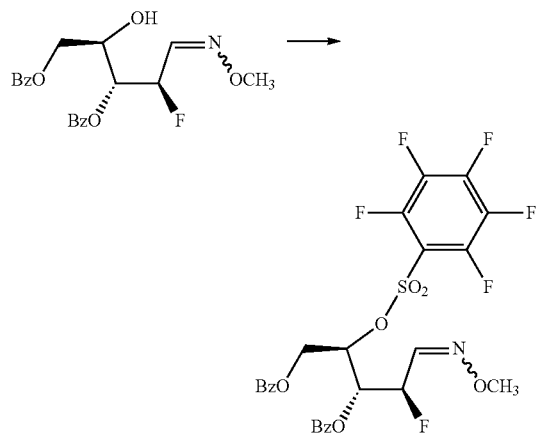

In a nitrogen atmosphere, 0.53 mL of pentafluorobenzenesulfonyl chloride was added dropwise to a solution of 1.3 g of (2R,3R,4R)-1-(benzoyloxy)-4-fluoro-2-hydroxy-5-(methoxyimino)pentan-3-yl=benzoatein 4 mL of an ethyl acetate and 4.0 mL of triethylamine at a temperature of 0° C. to 4° C., and the obtained mixture was then stirred at 0° C. for 2 hours 40 minutes. Thereafter, 0.27 mL of triethylamine and 0.26 mL of pentafluorobenzenesulfonyl chloride were added dropwise to the reaction mixture, and the thus obtained mixture was then stirred for 1 hour. Thereafter, 5.4 mL of a saturated sodium hydrogen carbonate aqueous solution and dimethylaminopyridine were added to the reaction mixture. The obtained mixture was stirred at room temperature for 30 minutes, and the water layer was then removed. The organic layer was dried over anhydrous magnesium sulfate, and the solvent was then distilled away under reduced pressure.

The obtained residue was purified by silica gel column chromatography, so as to obtain 1.8 g of (2R,3R,4R)-3-(benzoyloxy)-4-fluoro-5-(methoxyimino)-2-(((pentafluorobenzene)sulfo nyl)oxy)pentyl=benzoate in the form of a colorless oily product.

$^1$H-NMR (CDCl$_3$) δ value:
3.86 (2.16H, s), 3.92 (0.84H, s), 4.57 (1H, dd, J=13.2, 7.2 Hz), 4.80 (0.72H, dd, J=12.8, 2.8 Hz), 4.81 (0.28H, dd, J=12.8, 2.8 Hz), 5.42 (0.72H, ddd, J=45.6, 6.4, 3.2 Hz), 5.51-5.60 (1H, m), 5.83 (0.72H, ddd, J=22.8, 5.6, 3.2 Hz), 5.90 (0.28H, ddd, J=46.8, 4.4, 2.4 Hz), 6.0 (0.28H, ddd, J=26.0, 5.6, 2.4 Hz), 6.84 (0.28H, dd, J=11.2, 4.4 Hz), 7.38-8.07 (10.72H, m)

$^{19}$F-NMR(CDCl$_3$) δ value:

−133.79 (2F, m), −142.45 (1F, m), −157.66 (2F, m), −196.43 (0.72F, ddd, J=45.6, 22.8, 6.8 Hz), −204.90 (0.28F, ddd, J=46.8, 26.0, 11.2 Hz)

(2)

[Formula 118]

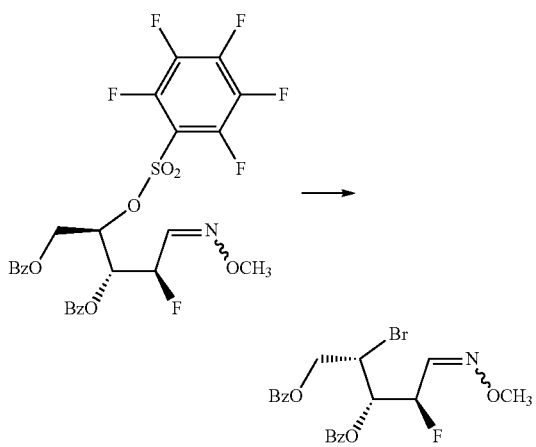

In a nitrogen atmosphere, 430 mg of anhydrous lithium bromide was added to a solution of 615 mg of (2R,3R,4R)-3-(benzoyloxy)-4-fluoro-5-(methoxyimino)-2-(((pentafluorobenzene)sulfonyl)oxy)pentyl=benzoate in 2.2 mL of dimethylimidazolidinone, and the obtained mixture was then stirred at room temperature for 2 hours. Thereafter, 3 mL of water and 3 mL of ethyl acetate were added to the reaction mixture, and the water layer was then removed. The organic layer was dried over anhydrous magnesium sulfate, and the solvent was then distilled away under reduced pressure. The obtained residue was purified by silica gel column chromatography, so as to obtain 379 mg of (2S,3S,4R)-1-(benzoyloxy)-2-bromo-4-fluoro-5-(methoxyimino)pentan-3-yl=benzoate in the form of a colorless oily product.

$^1$H-NMR (CDCl$_3$) δ value:

3.85 (0.51H, s), 3.88 (2.49H, s), 4.52-4.65 (2H, m), 4.70-4.85 (1H, m), 5.52 (0.83H, ddd, J=46.8, 6.4, 6.4 Hz), 5.82 (0.83H, ddd, J=16.4, 6.4, 2.8 Hz), 5.94 (0.17H, ddd, J=24.4, 6.0, 2.8 Hz), 6.07 (0.17H, ddd, J=47.2, 4.4, 2.8 Hz), 6.87 (0.17H, dd, J=10.8, 4.4 Hz), 7.41-8.16 (10.83H, m)

$^{19}$F-NMR(CDCl$_3$) δ value:

−193.45 (0.83F, ddd, J=46.8, 16.4, 6.4 Hz), −203.28 (0.17F, ddd, J=47.2, 24.4, 10.8 Hz)

Example 7

(1)

[Formula 119]

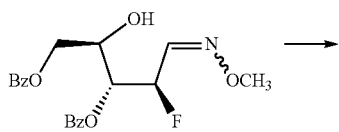

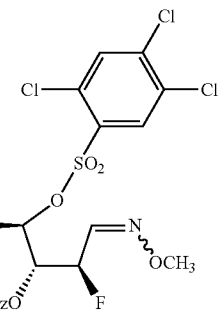

In a nitrogen atmosphere, 5.1 mL of 1-methylimidazole was added dropwise to a solution of 20.0 g of (2R,3R,4R)-1-(benzoyloxy)-4-fluoro-2-hydroxy-5-(methoxyimino)pentan-3-yl=benzoate and 17.3 g of 2,4,5-trichlorobenzenesulfonyl chloride in 50 mL of acetonitrile at a temperature of 0° C. to 4° C., and the obtained mixture was then stirred at room temperature for 22 hours. Thereafter, 50 mL of a saturated sodium hydrogen carbonate aqueous solution and 50 mL of water were added to the reaction mixture, and the thus obtained mixture was then stirred at room temperature for 1 hour. A solid was collected by filtration, and it was washed with 50 mL of water twice, and then with 25 mL of methanol twice, so as to obtain 28.3 g of (2R,3R,4R)-3-(benzoyloxy)-4-fluoro-5-(methoxyimino)-2-(((2,4,5-trichlorobenzene)sulfonyl)oxy)pentyl=benzoate in the form of a white solid.

$^1$H-NMR (CDCl$_3$) δ value:

3.85 (2.22H, s), 3.91 (0.78H, s), 4.54 (1H, dd, J=12.8, 6.4 Hz), 4.73 (0.74H, dd, J=12.8, 3.2 Hz), 4.75 (0.26H, dd, J=12.8, 2.8 Hz), 5.37-5.52 (1.74H, m), 5.82 (0.74H, ddd, J=22.8, 5.6, 2.8 Hz), 5.90 (0.26H, brs, J=48.0 Hz), 6.00 (0.26H, ddd, J=26.0, 5.6, 2.0 Hz), 6.83 (0.26H, dd, J=1.2, 4.4 Hz), 7.38-8.11 (12.74H, m)

$^{19}$F-NMR(CDCl$_3$) δ value:

−196.70 (0.74F, ddd, J=45.6, 22.8, 6.8 Hz), −204.90 (0.26F, ddd, J=48.0, 26.0, 11.2 Hz)

(2)

[Formula 120]

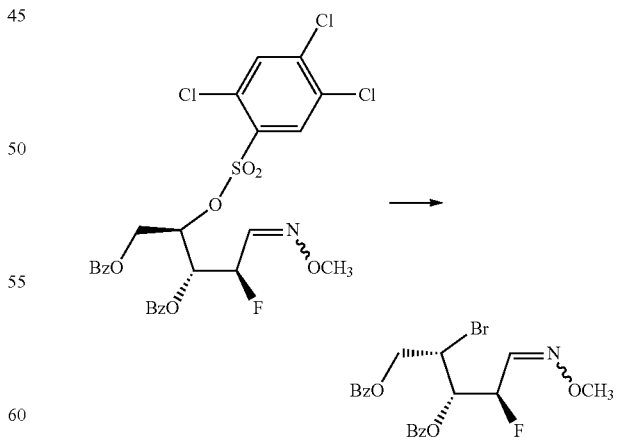

In a nitrogen atmosphere, 291 mg of anhydrous lithium bromide was added to a solution of 421 mg of (2R,3R,4R)-3-(benzoyloxy)-4-fluoro-5-(methoxyimino)-2-(((2,4,5-trichlorobenzene)sulfonyl)oxy)pentyl=benzoate in 1.34 mL of dimethylimidazolidinone, and the obtained mixture was then stirred at 40° C. for 4 hours. Thereafter, the reaction mixture was analyzed by high performance liquid chromatography. As a result, the reaction percentage was found to be 98%, and (2S,3S,4R)-1-(benzoyloxy)-2-bromo-4-fluoro-5-(methoxyimino)pentan-3-yl=benzoate was generated.

Example 8

(1)

[Formula 121]

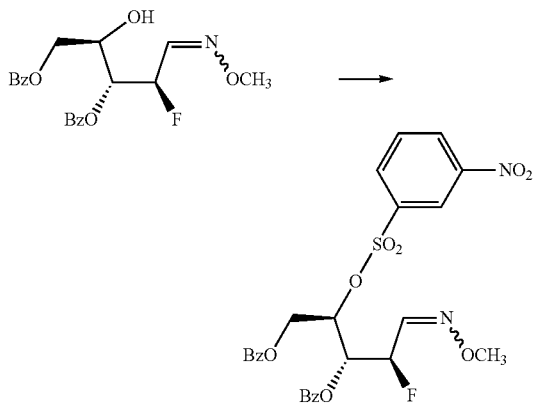

In a nitrogen atmosphere, 0.30 mL of 1-methylimidazole was added dropwise to a solution of 1.0 g of (2R,3R,4R)-1-(benzoyloxy)-4-fluoro-2-hydroxy-5-(methoxyimino)pentan-3-yl=benzoate and 857 mg of 3-nitrobenzenesulfonyl chloride in 5.0 mL of acetonitrile at a temperature of 0° C. to 4° C., and the obtained mixture was then stirred at room temperature for 15 hours 30 minutes. Thereafter, 5 mL of a saturated sodium hydrogen carbonate aqueous solution was added to the reaction mixture, and the thus obtained mixture was then stirred at room temperature for 30 minutes. Thereafter, 5.0 mL of ethyl acetate was added to the reaction mixture, and the water layer was then removed. The organic layer was dried over anhydrous magnesium sulfate, and the solvent was then distilled away under reduced pressure. The obtained residue was purified by silica gel column chromatography, so as to obtain 1.59 g of (2R,3R,4R)-3-(benzoyloxy)-4-fluoro-5-(methoxyimino)-2-(((3-nitrobenzene)sulfonyl)oxy)pentyl=benzoate in the form of a colorless oily product.

$^1$H-NMR (CDCl$_3$) δ value:

3.84 (2.01H, s), 3.89 (0.99H, s), 4.50 (1H, dd, J=12.8, 6.4 Hz), 4.73-4.80 (1H, m), 5.33 (0.67H, ddd, J=45.6, 6.8, 3.2 Hz), 5.39-5.48 (1H, m), 5.73-5.87 (1H, m), 5.95 (0.33H, ddd, J=26.4, 6.0, 2.4 Hz), 6.80 (0.33H, dd, J=110.2, 4.4 Hz), 7.30-8.75 (14.67H, m)

$^{19}$F-NMR(CDCl$_3$) δ value:

−196.64 (0.67F, ddd, J=45.6, 23.3, 6.8 Hz), −204.77 (0.33F, ddd, J=46.7, 26.4, 11.2 Hz)

(2)

[Formula 122]

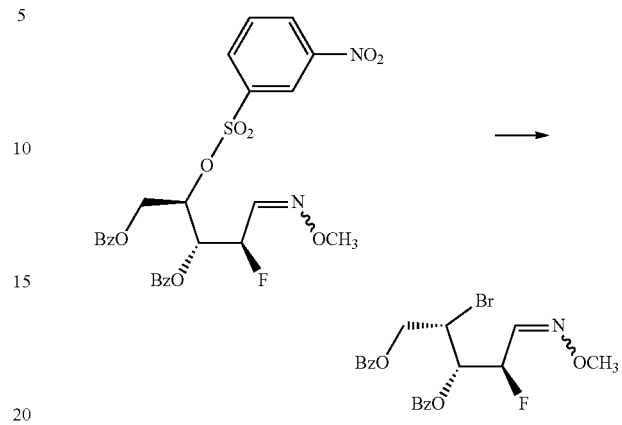

In a nitrogen atmosphere, 73.6 mg of anhydrous lithium bromide was added to a solution of 103 mg of (2R,3R,4R)-3-(benzoyloxy)-4-fluoro-5-(methoxyimino)-2-(((3-nitrobenzene)sulfonyl)oxy)pentyl=benzoate in 0.34 mL of N,N-dimethylformamide, and the obtained mixture was then stirred at 60° C. for 5 hours 30 minute. Thereafter, the reaction mixture was analyzed by high performance liquid chromatography. As a result, the reaction percentage was found to be 98%, and (2S,3S,4R)-1-(benzoyloxy)-2-bromo-4-fluoro-5-(methoxyimino)pentan-3-yl=benzoate was generated.

Example 9

(1)

[Formula 123]

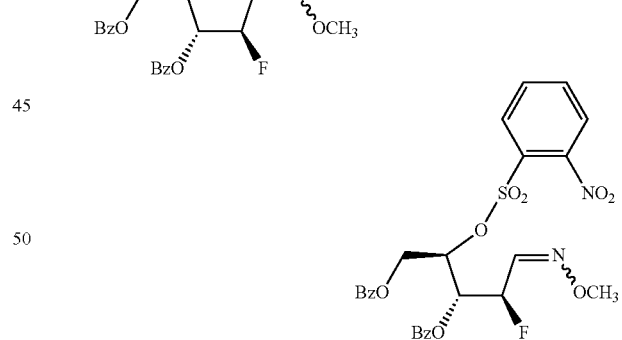

In a nitrogen atmosphere, 0.30 mL of 1-methylimidazole was added dropwise to a solution of 1.0 g of (2R,3R,4R)-1-(benzoyloxy)-4-fluoro-2-hydroxy-5-(methoxyimino)pentan-3-yl=benzoate and 857 mg of 2-nitrobenzenesulfonyl chloride in 5.0 mL of acetonitrile at a temperature of 0° C. to 4° C., and the obtained mixture was then stirred at room temperature for 15 hours 30 minutes. Thereafter, 5 mL of a saturated sodium hydrogen carbonate aqueous solution was added to the reaction mixture, and the thus obtained mixture was then stirred at room temperature for 30 minutes. Thereafter, 5.0 mL of ethyl acetate was added to the reaction mixture, and the water layer was then removed. The organic layer was dried over anhydrous magnesium sulfate, and the solvent was then distilled away under reduced pressure. The obtained residue was purified by silica gel column chromatography, so as to obtain 1.44 g of (2R,3R,4R)-3-(benzoyloxy)-4-fluoro-5-(methoxyimino)-2-(((2-nitrobenzene)sulfonyl)oxy) pentyl=benzoate in the form of a colorless oily product.

$^1$H-NMR (CDCl$_3$) δ value:

3.83 (2.13H, s), 3.90 (0.87H, s), 4.56 (1H, dd, J=12.8, 6.0 Hz), 4.84 (1H, dd, J=12.8, 2.8 Hz), 5.42 (0.71H, ddd, J=45.6, 6.4, 3.2 Hz), 5.39-5.55 (1.71H, m), 5.87 (0.71H, ddd, J=23.6, 6.0, 2.8 Hz), 5.93 (0.29H, ddd, J=49.2, 4.4, 2.4 Hz), 6.80 (0.29H, dd, J=11.2, 4.4 Hz), 7.35-8.15 (14.71H, m)

$^{19}$F-NMR(CDCl$_3$) δ value:

−197.12 (0.71F, ddd, J=45.6, 23.6, 6.8 Hz), −205.10 (0.29F, ddd, J=49.2, 26.4, 11.2 Hz)

(2)

[Formula 124]

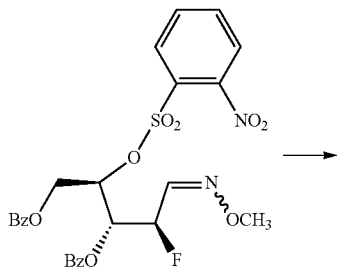

In a nitrogen atmosphere, 875 mg of anhydrous lithium bromide was added to a solution of 1.15 g of (2R,3R,4R)-3-(benzoyloxy)-4-fluoro-5-(methoxyimino)-2-(((2-nitrobenzene)sulfonyl)oxy)pentyl=benzoate in 4 mL of N,N-dimethylformamide, and the obtained mixture was then stirred at 60° C. for 3 hours. Thereafter, the reaction mixture was analyzed by high performance liquid chromatography. As a result, the reaction percentage was found to be 98%, and (2S,3S,4R)-1-(benzoyloxy)-2-bromo-4-fluoro-5-(methoxyimino)pentan-3-yl=benzoate was generated.

Example 10

(1)

[Formula 125]

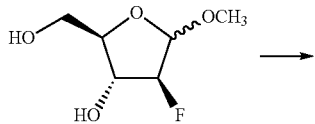

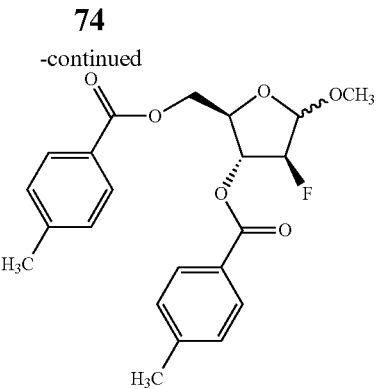

A mixture of 800 mg of (2R,3R,4S)-4-fluoro-2-(hydroxymethyl)-5-methoxyoxolan-3-ol, 67 mg of tetrabutylammonium chloride, 4 mL of toluene, 481 mg of sodium hydroxide, 4 mL of water and 1.56 g of 4-methylbenzoyl chloride was stirred at 5° C. for 1 hour, and then at room temperature for 2.5 hours. Thereafter, the organic layer was fractionated, it was then washed with a saturated sodium chloride aqueous solution twice, and it was then dried over anhydrous magnesium sulfate. After that, the solvent was distilled away under reduced pressure. The obtained residue was purified by column chromatography (ethyl acetate/hexane=1/10 to 1/2), so as to obtain 1.61 g of ((2R,3R,4S)-4-fluoro-5-methoxy-3-((4-methylphenyl)carbonyloxy)oxolan-2-yl)methyl=4-methylbenzoate in the form of a white solid.

$^1$H-NMR (CDCl$_3$) δ value:

7.98-7.93 (4H, m), 7.25-7.20 (4H, m), 5.79 (1H, ddd, J=17.2, 6.0, 6.0 Hz), 5.25 (1H, ddd, J=52.4, 6.4, 4.4 Hz), 5.07 (1H, d, J=4.4 Hz), 4.72 (1H, dd, J=1.6, 6.4 Hz), 4.56 (1H, dd, J=11.6, 6.4 Hz), 4.38-4.34 (1H, m), 3.48 (3H, s), 2.43 (3H, s)

19F-NMR(CDCl$_3$) δ value:

−206.73 (1F, dd, J=52.1, 17.5 Hz)

(2)

[Formula 126]

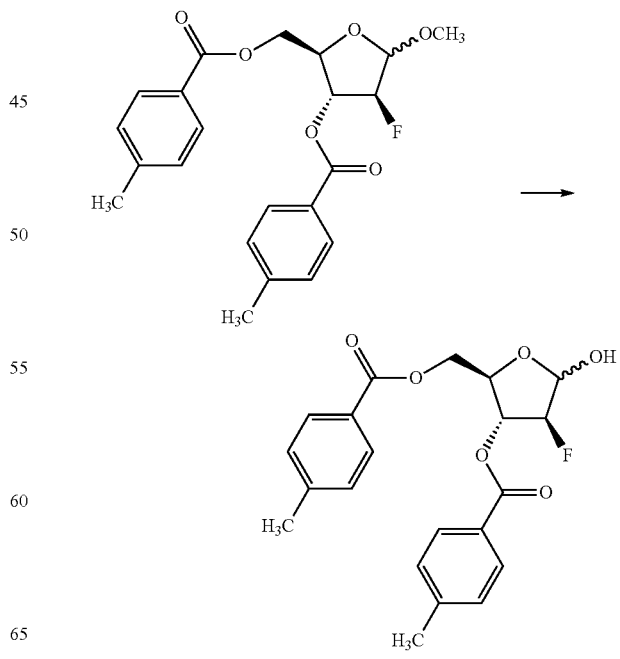

A mixture of 800 mg of ((2R,3R,4S)-4-fluoro-5-methoxy-3-((4-methylphenyl)carbonyloxy)oxolan-2-yl)methyl=4-methylbenzoate, 2.2 mL of trifluoroacetic acid and 268 mg of water was stirred at 50° C. for 7 hours. Thereafter, 50 mL of ethyl acetate was added to the reaction mixture, and the thus obtained mixture was washed with a saturated sodium hydrogen carbonate aqueous solution three times, and then with a saturated sodium chloride aqueous solution once. The organic layer was fractionated, and was then dried over anhydrous magnesium sulfate. After that, the solvent was distilled away under reduced pressure. The obtained residue was purified by column chromatography (ethyl acetate/hexane=1/10 to 1/2), so as to obtain 720 mg of ((2R,3R,4S)-4-fluoro-5-hydroxy-3-((4-methylphenyl)carbonyloxy)oxolan-2-yl)methyl=4-methylbenzoate in the form of a colorless oily product.

$^1$H-NMR (CDCl$_3$) δ value:

7.97-7.93 (4H, m), 7.24-7.21 (4H, m), 5.68 (1H, dd, J=10.0, 3.6 Hz), 5.47 (1H, dd, J=22.0, 4.4 Hz), 5.16 (1H, d, J=49.2 Hz), 4.74-4.67 (2H, m), 4.60-4.56 (1H, m), 2.93 (1H, dd, J=3.4, 3.4 Hz), 2.42 (3H, s), 2.40 (3H, s)

$^{19}$F-NMR(CDCl$_3$) δ value: −190.09 (1F, ddd, J=49.3, 22.4, 10.4 Hz)

(3)

[Formula 127]

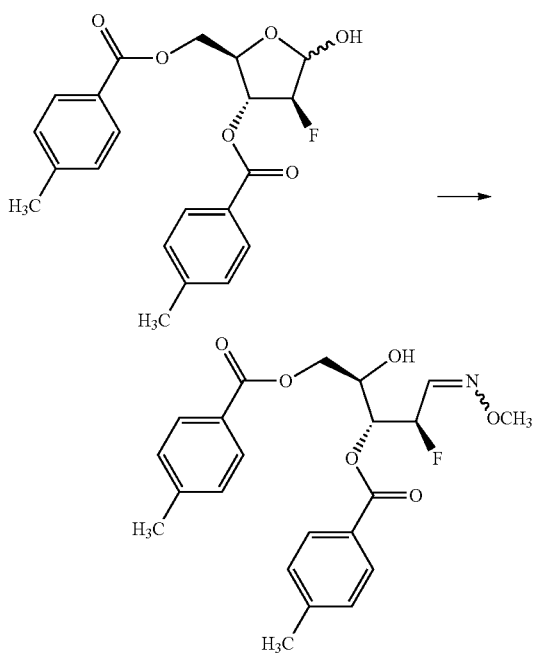

(2R,3R,4R)-4-fluoro-2-hydroxy-5-(methoxyimino)-3-((4-methylphenyl)carbonyloxy)pentyl=4-methylbenzoate was obtained in the form of a colorless oily product in the same manner as that of Example 1(1).

$^1$H-NMR (CDCl$_3$) δ value:

7.97-7.89 (4H, m), 7.39 (0.80H, dd, J=6.8, 6.8 Hz), 7.26-7.21 (4H, m), 6.83 (0.20H, dd, J=11.1, 4.7 Hz), 6.05 (0.20H, ddd, J=46.4, 4.2, 1.5 Hz), 5.70 (0.20H, dd, J=28.2, 1.9 Hz), 5.56 (0.80H, ddd, J=45.4, 6.9, 2.3 Hz), 5.44 (0.80H, ddd, J=26.0, 8.4, 2.4 Hz), 4.61 (0.80H, dd, J=12.4, 3.2 Hz), 4.57 (0.20H, dd, J=1.1, 10.9 Hz), 4.45-4.34 (2H, m), 3.91 (0.60H, s), 3.83 (2.40H, s), 3.03 (0.80H, d, J=5.8 Hz), 2.98 (0.20H, d, J=2.4 Hz), 2.42-2.41 (6H, m)

$^{19}$F-NMR(CDCl$_3$) δ value:

−200.06 (0.8F, ddd, J=45.2, 25.7, 6.9 Hz), −207.4 (0.2F, ddd, J=46.5, 28.2, 11.1 Hz)

(4)

[Formula 128]

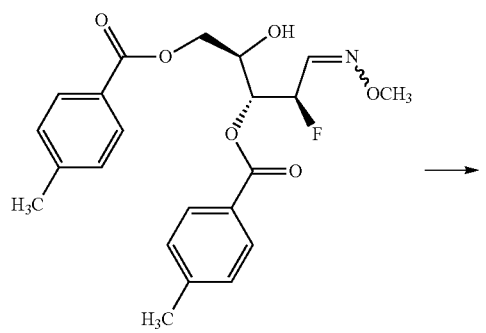

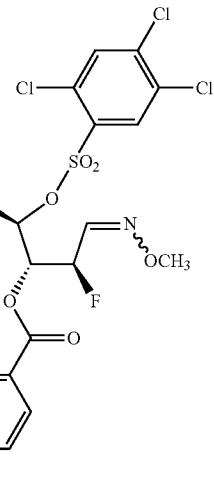

(2R,3R,4R)-2-fluoro-1-(methoxyimino)-5-((4-methylphenyl)carbonyloxy)-4-(((2,4,5-trichlorobenzene)sulfonyl)oxy)pentan-3-yl=4-methylbenzoate was obtained in the form of a white solid in the same manner as that of Example 7(1).

$^1$H-NMR (CDCl$_3$) δ value:

8.06 (1H, s), 7.83 (4H, dd, J=45.8, 8.2 Hz), 7.41-7.39 (1.18H, m), 7.26-7.20 (4H, m), 6.83 (0.82H, dd, J=11.0, 4.6 Hz), 6.00-5.91 (1.41H, m), 5.85-5.83 (0.41H, m), 5.77 (0.18H, ddd, 22.8, 5.9, 3.1 Hz), 5.46 (0.09H, ddd, J=28.5, 6.5, 2.9 Hz), 5.41-5.36 (0.91H, m), 4.72-4.65 (1H, m), 4.56-4.51 (1H, m), 3.90 (2.46H, s), 3.86 (0.54H, s), 2.42 (6H, s)

$^{19}$F-NMR(CDCl$_3$) δ value:

−196.58 (0.18F, ddd, J=45.6, 22.6, 6.7 Hz), −204.85 (0.82F, ddd, J=46.5, 26.3, 11.0 Hz)

(5)

[Formula 129]

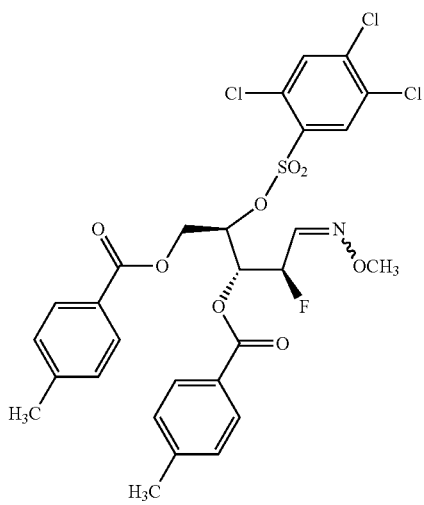

(2S,3S,4R)-2-bromo-4-fluoro-5-(methoxyimino)-3-((4-methylphenyl)carbonyl oxy)pentyl=4-methylbenzoate was obtained in the form of a colorless oily product in the same manner as that of Example 7(2).

¹H-NMR (CDCl₃) δ value:
8.02-7.88 (4H, m), 7.47 (0.86H, dd, J=6.4, 6.4 Hz), 7.28-7.19 (4H, m), 6.86 (0.14H, dd, J=11.2, 4.8 Hz), 6.05 (0.14H, ddd, J=47.0, 4.7, 3.0 Hz), 5.91 (0.14H, ddd, J=24.8, 5.7, 3.1 Hz), 5.79 (0.86H, ddd, J=17.2, 5.7, 3.1 Hz), 5.51 (0.86H, ddd, J=46.8, 5.2, 5.3 Hz), 4.79-4.70 (1.14H, m), 4.62-4.54 (1.86H, m), 3.88 (2.58H, m), 3.85 (0.42H, m), 2.43-2.40 (6H, m)

¹⁹F-NMR(CDCl₃) δ value:
−193.52 (0.86F, ddd, J=46.7, 16.8, 6.3 Hz), −203.30 (0.14F, ddd, J=46.9, 24.6, 10.8 Hz)

(6)

[Formula 130]

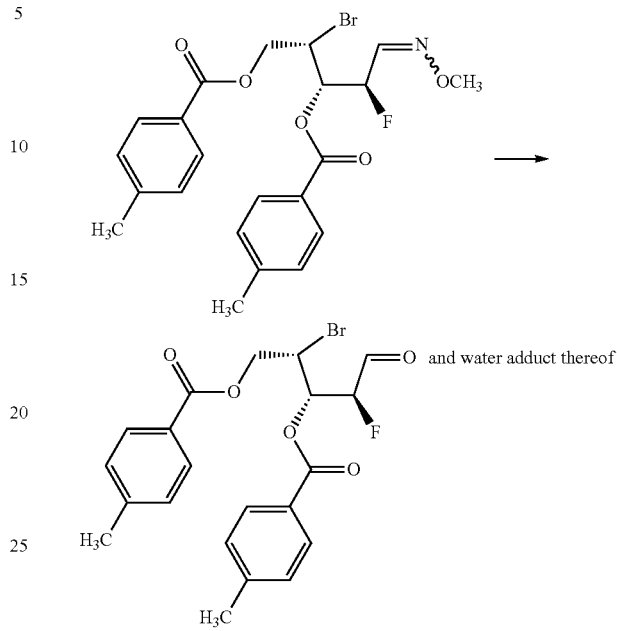

and water adduct thereof

A mixture of (2S,3S,4S)-2-bromo-4-fluoro-3-((4-methylphenyl)carbonyloxy)-5-oxopentyl=4-methylbenzoate and a water adduct thereof was obtained in the form of a colorless oily product in the same manner as that of Example 1(4).

¹H-NMR (CDCl₃) δ value:
9.81 (1H, d, J=6.0 Hz), 8.01-7.88 (4H, m), 7.26-7.18 (4H, m), 5.80-4.61 (5H, m), 2.42-2.34 (6H, m)

¹⁹F-NMR(CDCl₃) δ value:
−210.08 (1F, ddd, J=47.1, 20.8, 6.5 Hz)

(7)

[Formula 131]

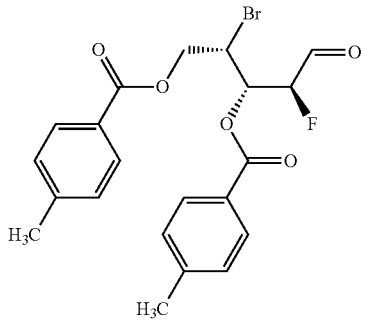

and water adduct thereof

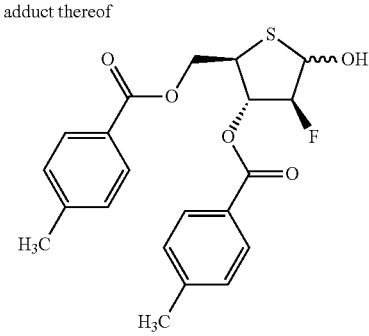

((2R,3S,4S)-4-fluoro-5-hydroxy-3-((4-methylphenyl)carbonyloxy)thiolan-2-yl)methyl=4-methylbenzoate was obtained in the form of a white solid in the same manner as that of Example 1(5).

$^1$H-NMR (CDCl$_3$) δ value:
8.01-7.87 (4H, m), 7.26-7.14 (4H, m), 6.03-5.97 (0.54H, m), 5.81 (0.46H, dt, J=12.1, 4.6 Hz), 5.62 (0.46H, dd, J=9.6 Hz), 5.49 (0.54H, dd, J=9.6, 5.2 Hz), 5.37 (0.23H, m), 5.25 (0.50H, m), 5.12 (0.27H, m), 4.68-4.56 (1.1H, m), 4.48-4.46 (0.92H, m), 4.19-4.15 (0.46H, m), 3.74 (0.54H, dd, J=12.0, 6.8 Hz), 2.81 (0.54H, dd, J=5.8, 1.4 Hz), 2.45-2.37 (6.46H, m)

$^{19}$F-NMR(CDCl$_3$) δ value:
−183.63 (0.54F, dd, J=47.4, 11.4 Hz), −192.74 (0.46F, ddd, J=51.2, 11.5, 5.1 Hz)

(8)

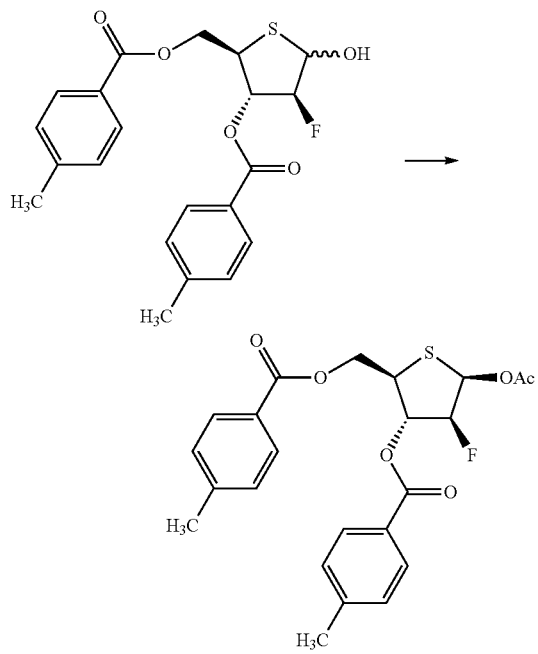

[Formula 132]

12 mg of dimethylaminopyridine and 622 mg of 2-picoline were added to a solution of 1.35 g of ((2R,3S,4S)-4-fluoro-5-hydroxy-3-((4-methylphenyl)carbonyloxy)thiolan-2-yl)methyl=4-methylbenzoate in 8.1 mL of tetrahydrofuran, and 511 mg of acetic anhydride was then added to the mixture at a temperature of 10° C. or lower. The obtained mixture was stirred at room temperature for 1 hour. Thereafter, ethyl acetate was added to the reaction mixture. The thus obtained mixture was washed with a saturated sodium chloride aqueous solution three times, and was then dried over anhydrous sodium sulfate. After that, the solvent was distilled away under reduced pressure. Methanol was added to the obtained residue, and a solid was collected by filtration, so as to obtain 546 mg of ((2R,3S,4S,5R)-5-acetyloxy-4-fluoro-3-((4-methylphenyl)carbonyloxy)thiolan-2-yl)methyl=4-methylbenzoate in the form of a white solid.

$^1$H-NMR (CDCl$_3$) δ value:
7.88 (4H, dd, J=28.0, 8.0 Hz), 7.16 (4H, dd, J=32.0, 8.0 Hz), 6.17 (1H, d, J=4.4 Hz), 6.08-6.01 (1H, m), 5.30 (1H, ddd, J=50.8, 9.6, 4.5 Hz), 4.66 (1H, dd, J=11.2, 6.0 Hz), 4.47 (1H, dd, J=11.4, 6.6 Hz), 3.72 (1H, dd, J=13.4, 6.6 Hz), 2.42 (3H, s), 2.36 (3H, s), 2.12 (3H, s)

$^{19}$F-NMR(CDCl$_3$) δ value: −191.83 (1F, dd, J=50.8, 11.7 Hz)

(9)

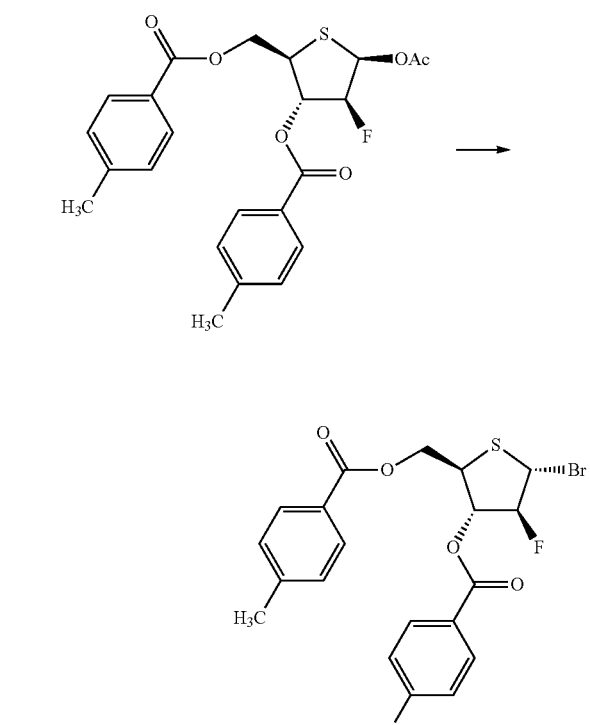

[Formula 133]

((2R,3S,4S,5R)-5-bromo-4-fluoro-3-((4-methylphenyl)carbonyloxy)thiolan-2-yl)methyl=4-methylbenzoate was obtained in the form of a colorless oily product in the same manner as that of Example 1(7).

$^1$H-NMR (CDCl$_3$) δ value:
8.01-7.86 (4H, m), 7.27-7.20 (4H, m), 5.82-5.80 (0.5H, m), 5.77-5.75 (0.5H, m), 5.73-5.71 (1H, m), 5.68-5.67 (0.5H, m), 5.58-5.56 (0.5H, m), 4.66-4.60 (1H, m), 4.57-4.49 (1H, m), 4.34-4.28 (1H, m), 2.42 (3H, s), 2.40 (3H, s)

$^{19}$F-NMR(CDCl$_3$) δ value: −163.52 (1F, dd, J=46.9, 14.4 Hz)

(10)

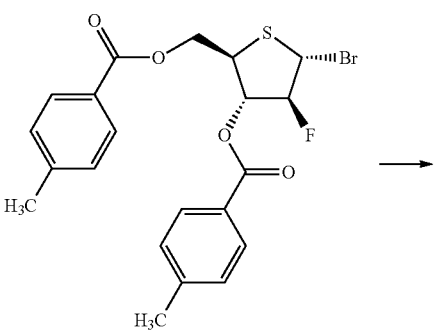

[Formula 134]

-continued

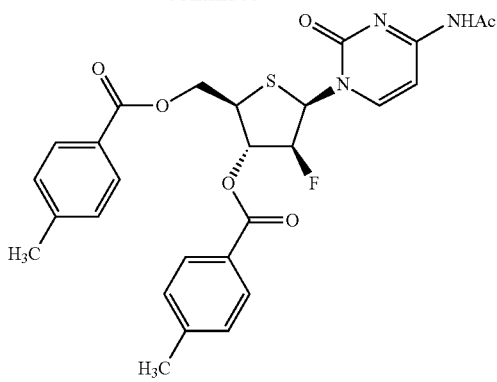

Using a methylene chloride solution of (((2R,3S,4S,5R)-5-bromo-4-fluoro-3-((4-methylphenyl)carbonyloxy)thiolan-2-yl)methyl=4-methylbenzoate, ((2R,3S,4S,5R)-5-(4-acetamido-2-oxo-1,2-dihydropyrimidin-1-yl)-4-fluoro-3-((4-methylphenyl)carbonyloxy)thiolan-2-yl)methyl=4-methylbenzoate was obtained in the form of a yellow-brown solid in the same manner as that of Example 22(2).

m/z (ESI-positive): 540.5 [M+H]$^+$ $^{19}$F-NMR(CDCl$_3$) δ value: −195.82 (1F, ddd, J=49.0, 23.5, 9.2 Hz)

(11)

[Formula 135]

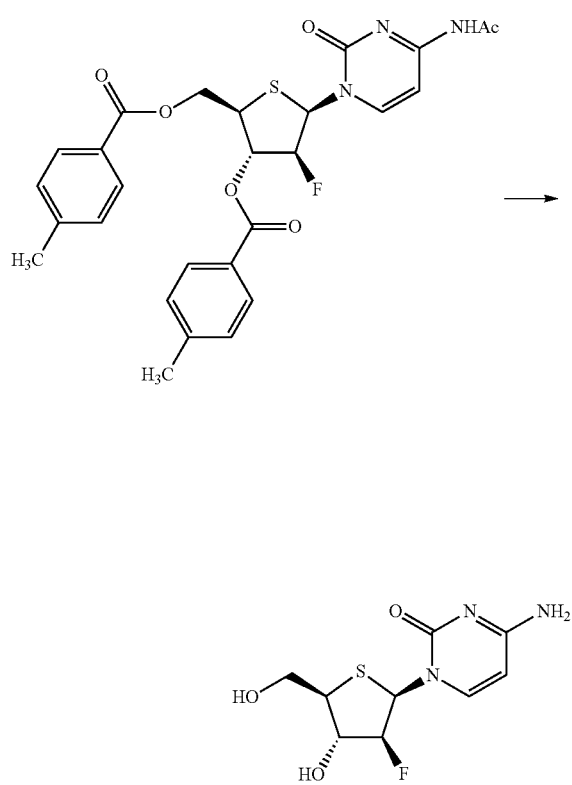

(2R,3S,4S,5R)-3-hydroxy-2-hydroxymethyl-5-(4-amino-2-oxo-1,2-dihydropyrimidin-1-yl)-4-fluorothiolane was obtained in the same manner as that of Example 1(8).

Example 11

(1)

[Formula 136]

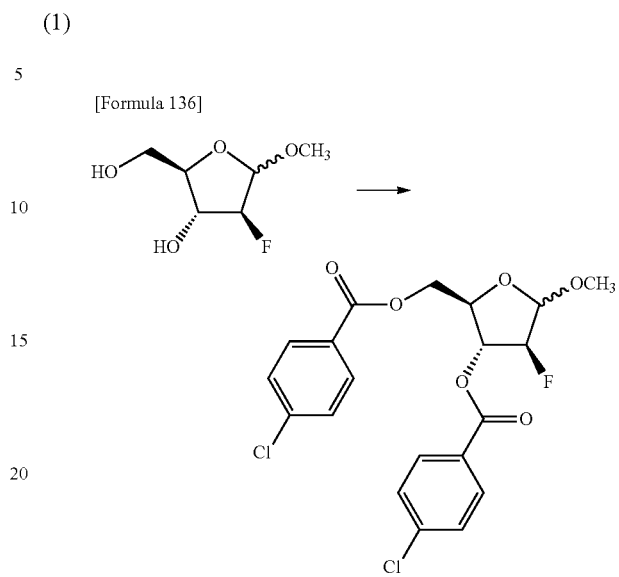

((2R,3R,4S)-3-((4-chlorophenyl)carbonyloxy)-4-fluoro-5-methoxyoxolan-2-yl)methyl=4-chlorobenzoate was obtained in the form of a white solid in the same manner as that of Example 10(1), with the exception that the reaction time was set at 8 hours.

$^1$H-NMR (CDCl$_3$) δ value:
8.02-7.96 (4H, m), 7.45-7.26 (4H, m), 5.83 (1H, ddd, J=17.2, 6.0, 6.0 Hz), 5.25 (1H, ddd, J=52.0, 6.4, 4.4 Hz), 5.07 (1H, d, J=4.4 Hz), 4.73 (1H, dd, J=11.6, 4.0 Hz), 4.56 (1H, dd, J=11.6, 6.4 Hz), 4.37-4.33 (1H, m), 3.48 (3H, s)

$^{19}$F-NMR(CDCl$_3$) δ value: −191.75 (1F, dd, J=50.6, 11.9 Hz)

(2)

[Formula 137]

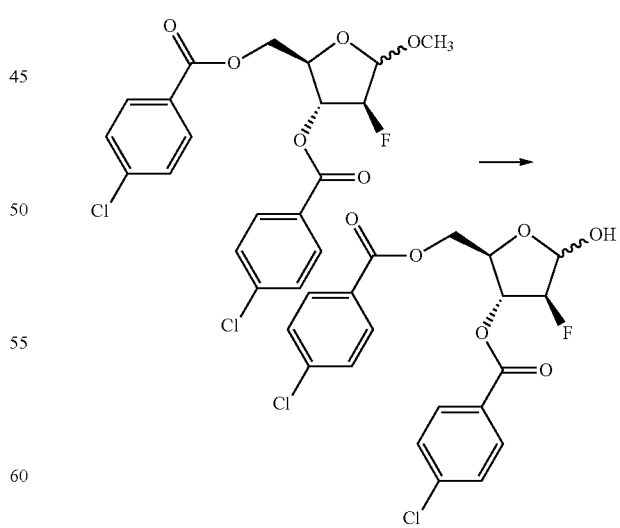

((2R,3R,4S)-3-((4-chlorophenyl)carbonyloxy)-4-fluoro-5-hydroxyoxolan-2-yl)methyl=4-chlorobenzoate was obtained in the form of a white solid in the same manner as that of Example 10(2).

¹H-NMR (CDCl₃) δ value:
8.01-7.97 (4H, m), 7.45-7.39 (4H, m), 5.69 (1H, d, J=10.0 Hz), 5.46 (1H, dd, J=21.8, 4.2 Hz), 5.16 (1H, d, J=49.2 Hz), 4.76-4.59 (3H, m), 2.92 (1H, brs)
¹⁹F-NMR(CDCl₃) δ value: −190.45 (1F, ddd, J=49.1, 21.9, 10.1 Hz)

(3)

[Formula 138]

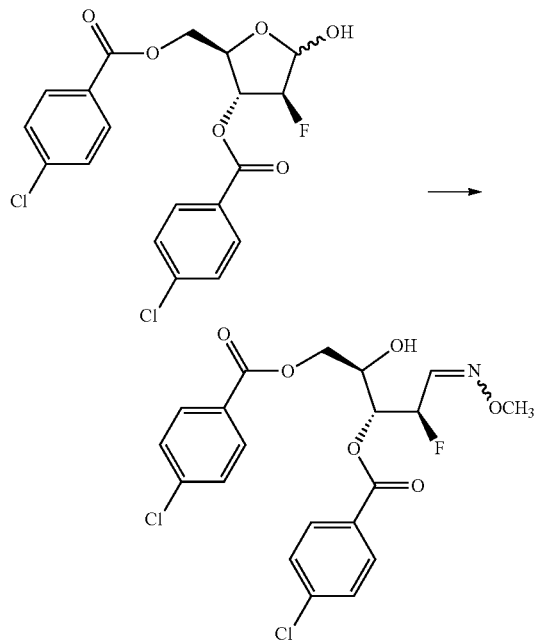

(2R,3R,4R)-3-((4-chlorophenyl)carbonyloxy)-4-fluoro-2-hydroxy-5-(methoxylmino)pentyl=4-chlorobenzoate was obtained in the form of a colorless oily product in the same manner as that of Example 1(1).

¹H-NMR (CDCl₃) δ value:
7.98-7.92 (4H, m), 7.58 (0.86H, dd, J=6.0, 6.0 Hz), 7.45-7.39 (4H, m), 6.82 (0.14H, dd, J=11.2, 4.6 Hz), 6.04 (0.14H, ddd, J=46.4, 4.6, 2.0 Hz), 5.75 (0.14H, dd, J=8.2, 2.0 Hz), 5.55-5.50 (1.72H, m), 4.63-4.54 (1H, m), 4.46-4.35 (2H, m), 3.91 (0.42H, s), 3.85 (2.58H, s), 3.08 (0.86H, d, J=60.6, 1.1 Hz), 2.91 (0.25H, d, J=6.0 Hz)
¹⁹F-NMR(CDCl₃) δ value:
−200.31 (0.86F, ddd, J=46.5, 23.6, 5.7 Hz), −207.35 (0.14F, ddd, J=45.2, 29.2, 10.4 Hz)

[Formula 139]

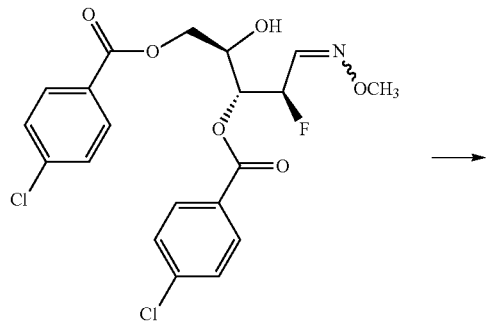

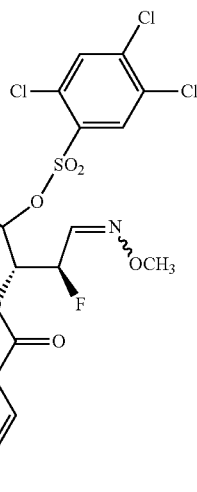

(4)
(2R,3R,4R)-1-((4-chlorophenyl)carbonyloxy)-4-fluoro-5-(methoxyimino)-2-(((2,4,5-trichlorobenzene)sulfonyl)oxy)pentan-3-yl=4-chlorobenzoate was obtained in the form of a white solid in the same manner as that of Example 7(1).
1H-NMR (CDCl₃) δ value:
7.99 (1H, s), 7.96-7.89 (4H, m), 7.65 (1H, s), 7.44-7.40 (4H, m), 7.35 (1H, m), 5.62-5.58 (1H, m), 5.37-5.22 (2H, m), 4.84-4.79 (1H, m), 4.68-4.63 (1H, m), 3.83 (3H, s)
¹⁹F-NMR(CDCl₃) δ value: −190.52 (1F, ddd, J=47.4, 17.4, 6.5 Hz)

(5)

[Formula 140]

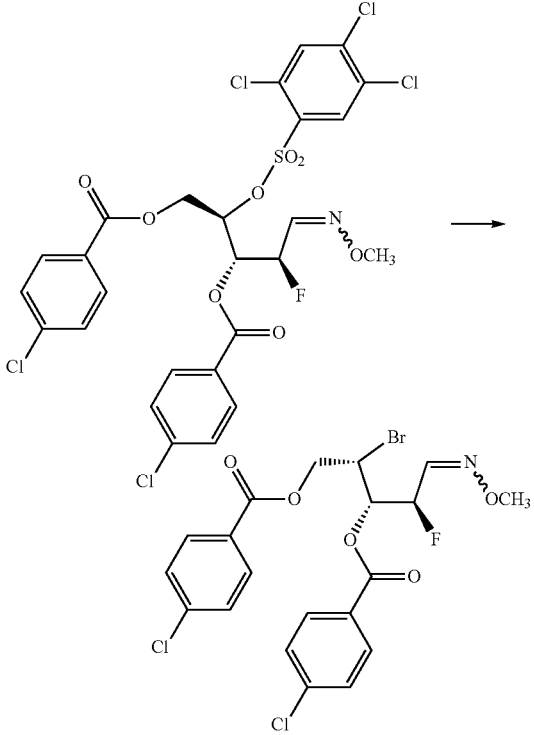

(2S,3S,4R)-2-bromo-3-((4-chlorophenyl)carbonyloxy)-4-fluoro-5-(methoxyimino)pentyl=4-chlorobenzoate was obtained in the form of a colorless oily product in the same manner as that of Example 7(2).

¹H-NMR (CDCl₃) δ value:
8.02-7.91 (4H, m), 7.46-7.40 (5H, m), 5.87 (1H, ddd, J=6.1, 6.1, 10.7 Hz), 5.14 (1H, ddd, J=46.8, 27.2, 110.7 Hz), 4.65-4.64 (2H, m), 4.53-4.48 (1H, m), 3.81 (3H, s)
¹⁹F-NMR(CDCl₃) δ value: −171.64 (1F, ddd, J=46.6, 8.7, 5.2 Hz)
(6)

[Formula 141]

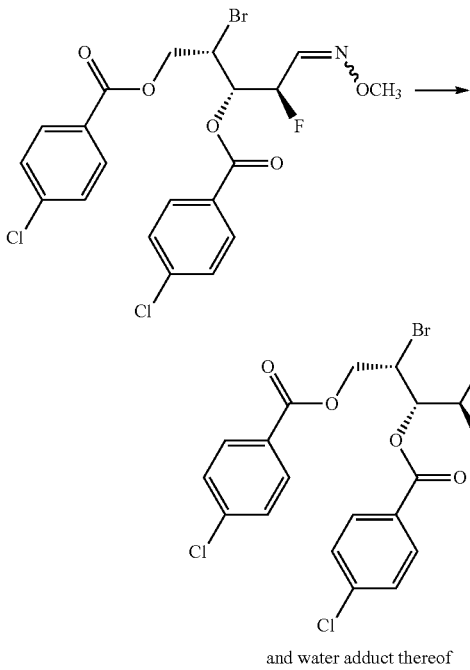

and water adduct thereof

A mixture of (2S,3S,4S)-2-bromo-3-((4-chlorophenyl)carbonyloxy)-4-fluoro-5-oxopentyl=4-chlorobenzoate and a water adduct thereof was obtained in the form of a colorless oily product in the same manner as that of Example 1(4), with the exception that the reaction was carried out at 60° C. for 7 hours and then at room temperature for 3 days.
¹H-NMR (CDCl₃) δ value:
9.80-9.78 (1H, m), 8.02-7.90 (4H, m), 7.48-7.39 (4H, m), 5.80-4.54 (5H, m)
¹⁹F-NMR(CDCl₃) δ value: −194.14 (1F, ddd, J=47.3, 18.5, 4.4 Hz)
(7)

[Formula 142]

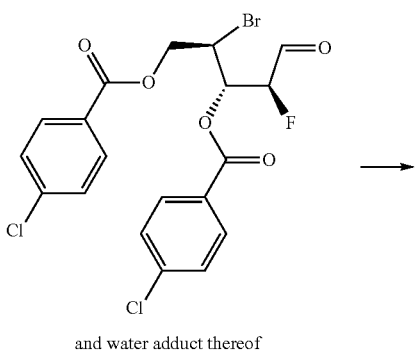

and water adduct thereof

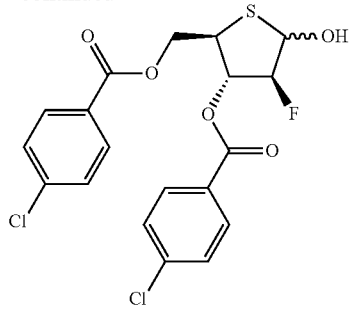

((2R,3S,4S)-3-((4-chlorophenyl)carbonyloxy)-4-fluoro-5-hydroxythiolan-2-yl)methyl=4-chlorobenzoate was obtained in the form of a yellow-brown solid in the same manner as that of Example 1(5), with the exception that the reaction was carried out at room temperature for 24 hours.
¹H-NMR (CDCl₃) δ value:
8.00-7.90 (4H, m), 7.44-7.31 (4H, m), 6.04-6.01 (0.56H, m), 5.79 (0.44H, dt, J=12.6, 5.3 Hz), 5.68-5.62 (0.44H, m), 5.48 (0.54H, dd, J=8.8, 4.4 Hz), 5.37-5.36 (0.22H, m), 5.27-5.24 (0.50H, m), 5.12-5.11 (0.28H, m), 4.65-4.59 (1.3H, m), 4.49-4.47 (0.7H, m), 4.20-4.15 (0.44H, m), 2.79 (0.54H, d, J=4.0 Hz), 2.37 (0.54H, d, J=8.0 Hz)
¹⁹F-NMR(CDCl₃) δ value:
−183.81 (0.54F, dd, J=46.7, 11.8 Hz), −192.29 (0.46F, ddd, J=51.6, 11.8, 4.2 Hz)
(8)

[Formula 143]

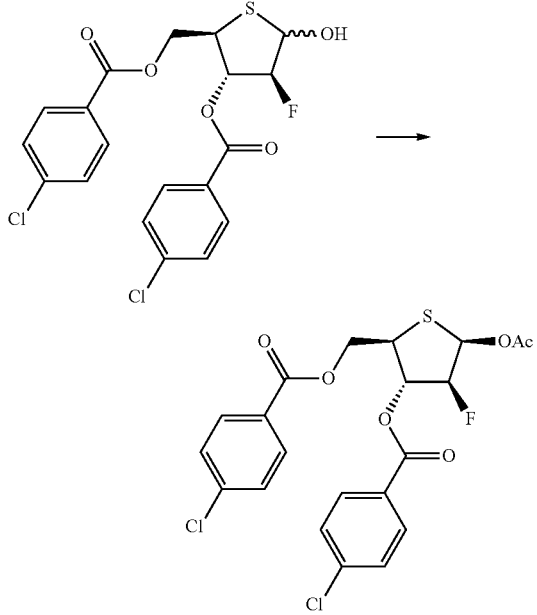

((2R,3S,4S,5R)-5-acetyloxy-3-((4-chlorophenyl)carbonyloxy)-4-fluorothiolan-2-yl)methyl=4-chlorobenzoate was obtained in the form of a white solid in the same manner as that of Example 10(8).
¹H-NMR (CDCl₃) δ value:
7.96 (4H, dd, J=14.0, 2.4 Hz), 7.41 (4H, dd, J=18.8, 8.4 Hz), 6.23 (1H, dd, J=14.0, 2.0 Hz), 5.82 (1H, ddd, J=12.0, 8.0, 3.0 Hz), 5.38 (1H, ddd, J=44.8, 3.4, 2.3 Hz), 4.55-4.43 (2H, m), 4.10-4.07 (1H, m), 2.12 (3H, s)

19F-NMR(CDCl$_3$) δ value: −191.76 (1F, dd, J=50.8, 11.7 Hz)

(9)

[Formula 144]

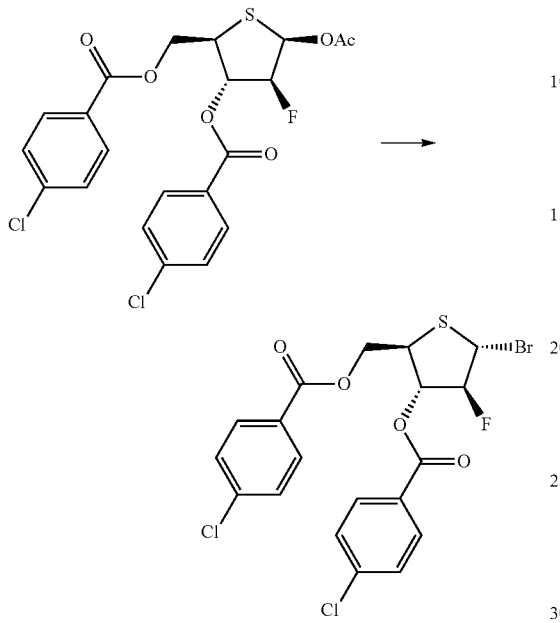

((2R,3S,4S,5R)-5-bromo-3-((4-chlorophenyl)carbonyloxy)-4-fluorothiolan-2-yl)methyl=4-chlorobenzoate was obtained in the form of a yellow-brown oily product in the same manner as that of Example 1(7).

$^1$H-NMR (CDCl$_3$) δ value:
8.01 (4H, dd, J=16.8, 8.4 Hz), 7.42 (4H, dd, J=10.8, 8.4 Hz), 5.82-5.80 (0.5H, m), 5.77-5.76 (0.5H, m), 5.74-5.73 (1H, m), 5.69 (0.5H, brs), 5.58-5.56 (0.5H, m), 4.65-4.50 (1H, m), 4.32-4.26 (H, m)

$^{19}$F-NMR(CDCl$_3$) δ value: −163.51 (1F, dd, J=47.2, 14.5 Hz)

(10)

[Formula 145]

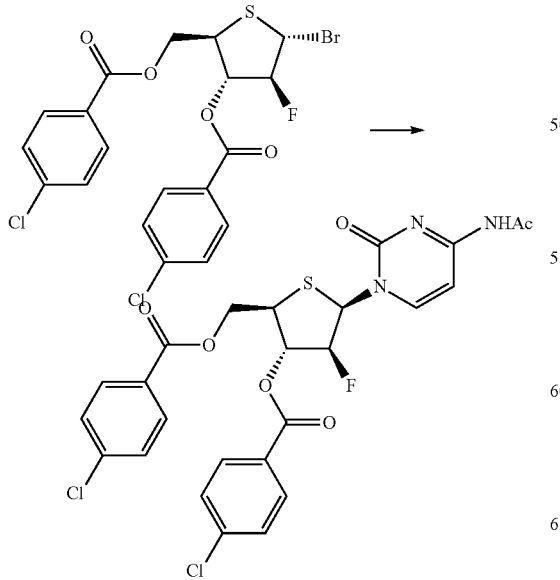

((2R,3S,4S,5R)-3-((4-chlorophenyl)carbonyloxy)-5-(4-acetamido-2-oxo-1,2-dihydropyrimidin-1-yl)-4-fluorothiolan-2-yl)methyl=4-chlorobenzoate was obtained in the form of a light yellow solid in the same manner as that of Example 22(2).

m/z (ESI-positive): 580.4[M+H]$^+$ $^{19}$F-NMR(CDCl$_3$) δ value: −196.19 (1F, ddd, J=49.1, 23.9, 8.7 Hz)

(11)

[Formula 146]

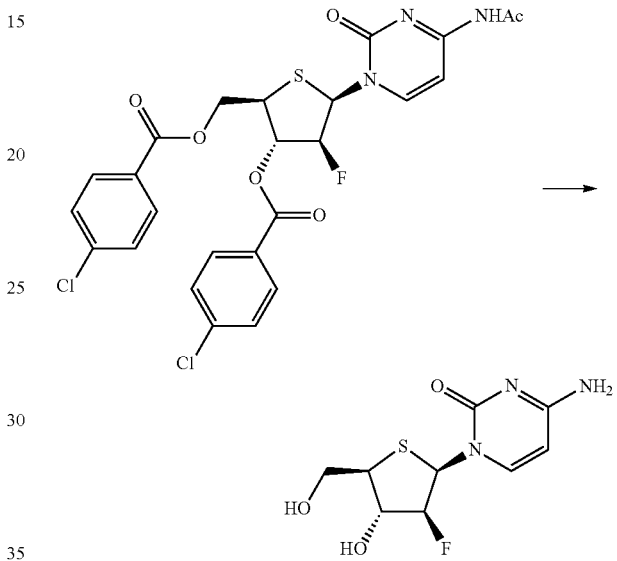

(2R,3S,4S,5R)-3-hydroxy-2-hydroxymethyl-5-(4-amino-2-oxo-1,2-dihydropyrimidin-1-yl)-4-fluorothiolane was obtained in the same manner as that of Example 1(8).

Example 12

(1)

[Formula 147]

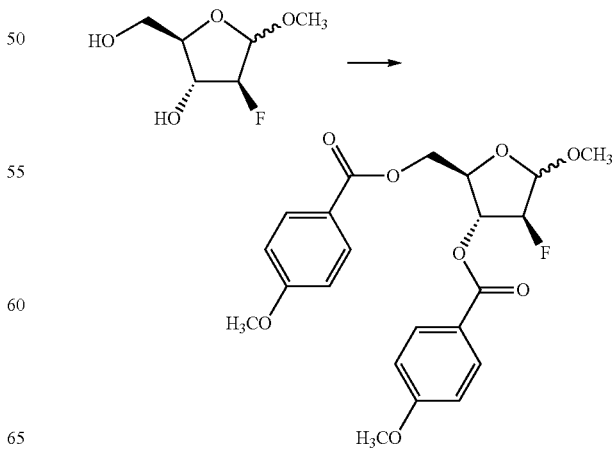

((2R,3R,4S)-4-fluoro-5-methoxy-3-((4-methoxyphenyl) carbonyloxy)oxolan-2-yl)methyl=4-methoxybenzoate was obtained in the form of a colorless oily product in the same manner as that of Example 10(1).

$^1$H-NMR (CDCl$_3$) δ value:

8.03-7.98 (4H, m), 6.93-6.88 (4H, m), 5.45 (1H, dd, J=23.2, 4.8 Hz), 5.21-5.03 (2H, m), 4.71 (1H, dd, J=12.0, 3.6 Hz), 4.60 (1H, dd, J=12.0, 4.4 Hz), 4.47-4.50 (1H, m), 3.87 (3H, s), 3.85 (3H, s), 3.45 (3H, s)

$^{19}$F-NMR(CDCl$_3$) δ value: −190.34 (1F, ddd, J=49.3, 23.1, 10.5 Hz)

(2)

[Formula 148]

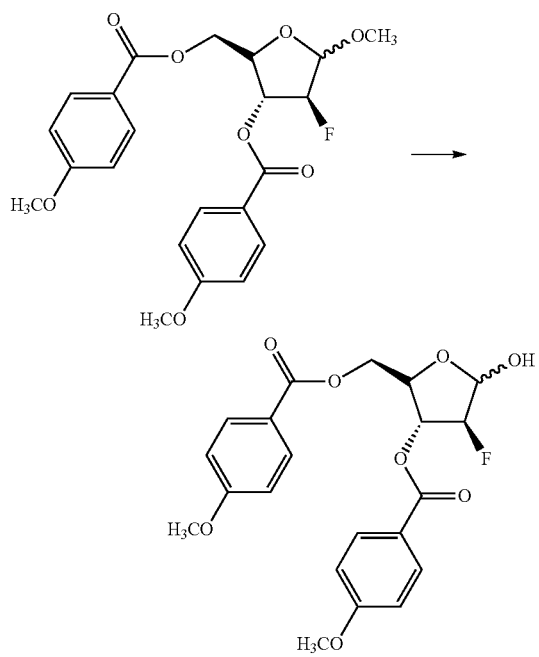

((2R,3R,4S)-4-fluoro-5-hydroxy-3-((4-methoxyphenyl) carbonyloxy)oxolan-2-yl)methyl=4-methoxybenzoate was obtained in the form of a colorless oily product in the same manner as that of Example 10(2).

1H-NMR (CDCl$_3$) δ value:

8.03-7.97 (4H, m), 6.94-6.88 (4H, m), 5.68 (1H, dd, J=10.4, 3.6 Hz), 5.45 (1H, dd, J=22.2, 4.2 Hz), 5.15 (1H, d, J=49.2 Hz), 4.72-4.55 (3H, m), 3.34 (1H, dd, J=3.4 Hz)

$^{19}$F-NMR(CDCl$_3$) δ value: −189.89-190.10 (1F, m)

(3)

[Formula 149]

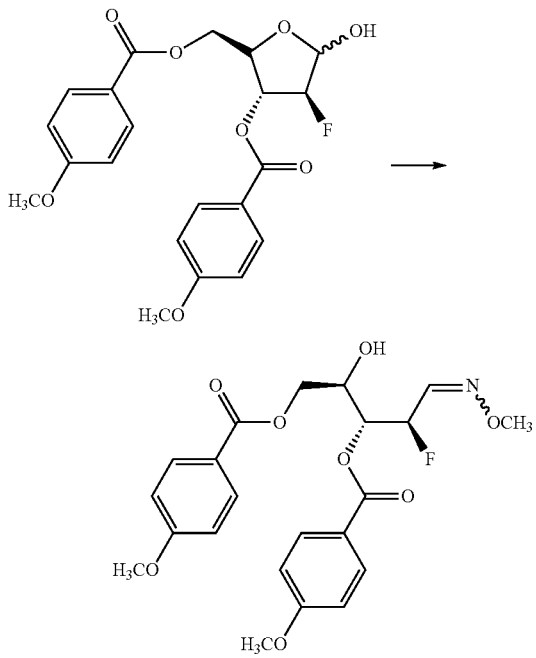

(2R,3R,4R)-4-fluoro-2-hydroxy-5-(methoxyimino)-3-((4-methoxyphenyl)carbonyloxy)pentyl=4-methoxybenzoate was obtained in the form of a colorless oily product in the same manner as that of Example 1(1).

1H-NMR (CDCl$_3$) δ value:

8.04-7.96 (4H, m), 7.39 (0.70H, dd, J=6.0, 6.0 Hz), 6.94-6.89 (4H, m), 6.83 (0.30H, dd, J=11.0, 4.8 Hz), 6.05 (0.30H, ddd, J=46.5, 4.8, 1.9 Hz), 5.71-5.62 (0.30H, m), 5.56 (0.70H, ddd, J=45.4, 6.9, 2.3 Hz), 5.42 (0.70H, ddd, J=26.0, 8.4, 2.3 Hz), 4.62-4.54 (1H, m), 4.42-4.32 (2H, m), 3.91 (0.9H, s), 3.87-3.85 (6H, m), 3.83 (2.1H, s), 3.06 (0.7H, d, J=2.4 Hz), 3.01 (0.3H, d, J=2.4 Hz)

$^{19}$F-NMR(CDCl$_3$) δ value:

−200.11 (0.7F, ddd, J=45.2, 26.0, 6.8 Hz), −207.36 (0.3F, ddd, J=46.5, 28.4, 10.9 Hz)

(4)

[Formula 150]

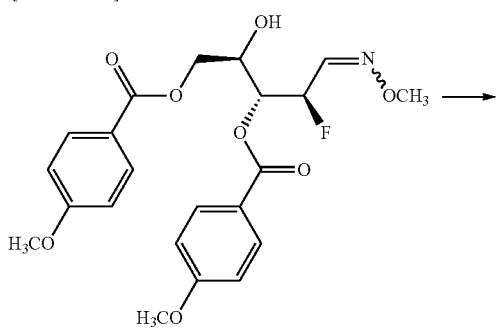

-continued

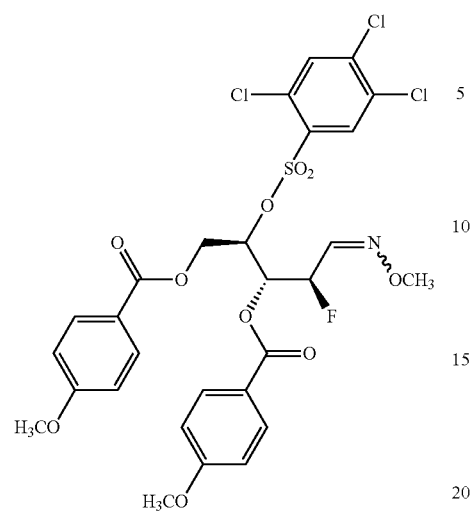

(2R,3R,4R)-2-fluoro-1-(methoxyimino)-5-((4-methoxyphenyl)carbonyloxy)-4-(((2,4,5-trichlorobenzene)sulfonyl)oxy)pentan-3-yl=4-methoxybenzoate was obtained in the form of a colorless oily product in the same manner as that of Example 7(1).

$^1$H-NMR (CDCl$_3$) δ value:

8.07-8.06 (1H, s), 7.98-7.82 (4H, m), 7.43-7.39 (1.73H, m), 6.93-6.88 (4H, m), 6.82 (0.27H, dd, J=11.0, 4.5 Hz), 5.96-5.95 (0.27H, m), 5.87 (0.27H, ddd, 22.7, 5.3, 2.3 Hz), 5.75 (0.73H, ddd, 22.9, 5.9, 3.1 Hz), 5.50-5.47 (0.36H, m), 5.42-5.36 (1.36H, m), 4.70-4.64 (1H, m), 4.53-4.48 (1H, m), 3.90-3.83 (9H, m)

$^{19}$F-NMR(CDCl$_3$) δ value:

−196.63 (0.73F, ddd, J=45.6, 23.0, 6.8 Hz), −204.89 (0.27F, ddd, J=46.5, 26.3, 11.0 Hz)

(5)

[Formula 151]

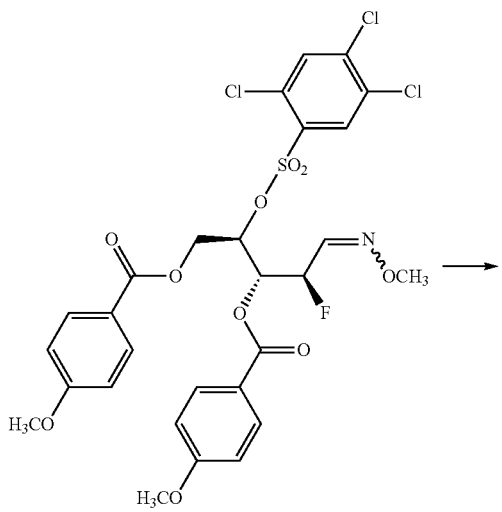

-continued

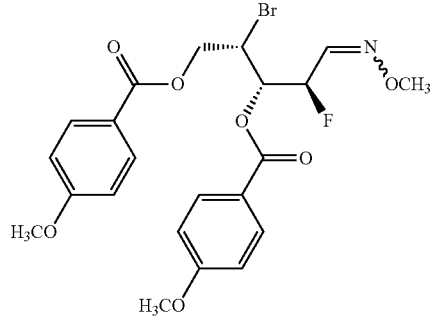

(2S,3S,4R)-2-bromo-4-fluoro-5-(methoxyimino)-3-((4-methoxyphenyl)carbon yloxy)pentyl=4-methoxybenzoate was obtained in the form of a colorless oily product in the same manner as that of Example 7(2).

$^1$H-NMR (CDCl$_3$) δ value:

8.08-7.94 (4H, m), 7.46 (1H, dd, J=6.5, 6.5 Hz), 6.96-6.89 (4H, m), 5.77 (1H, ddd, J=16.8, 6.0, 3.2 Hz), 5.50 (1H, ddd, J=46.8, 6.3, 6.3 Hz), 4.75-4.69 (1H, m), 4.57-4.53 (2H, m), 3.88-3.84 (9H, m)

$^{19}$F-NMR(CDCl$_3$) δ value: −193.50 (1F, ddd, J=46.1, 16.9, 6.2 Hz)

(6)

[Formula 152]

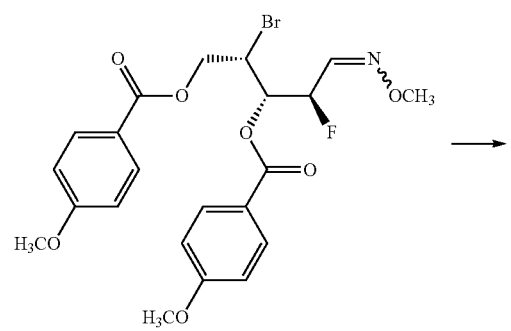

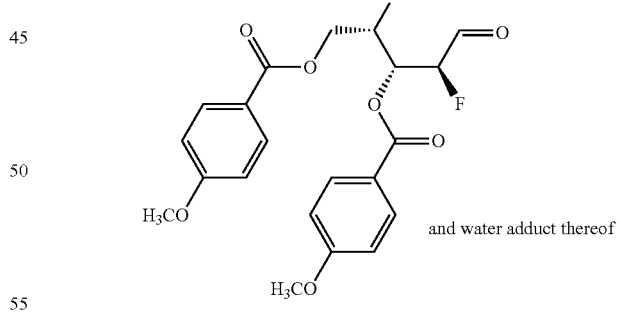

and water adduct thereof

A mixture of (2S,3S,4S)-2-bromo-4-fluoro-3-((4-methoxyphenyl)carbonyloxy)-5-oxopentyl=4-methoxybenzoate and a water adduct thereof was obtained in the form of a colorless oily product in the same manner as that of Example 1(4), with the exception that the reaction was carried out at 60° C. for 14 hours.

$^1$H-NMR (CDCl$_3$) δ value:

9.85-9.70 (1H, m), 8.02-7.9 (4H, m), 6.94-6.86 (4H, m), 6.07-4.38 (5H, m), 3.87-3.84 (6H, m)

$^{19}$F-NMR(CDCl$_3$) δ value: −210.07 (1F, ddd, J=47.3, 20.9, 6.4 Hz)

(7)

[Formula 153]

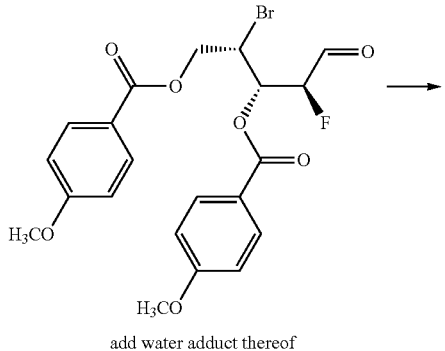

add water adduct thereof

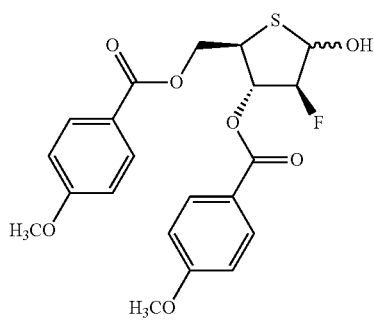

((2R,3S,4S)-4-fluoro-5-hydroxy-3-((4-methoxyphenyl)carbonyloxy)thiolan-2-yl)methyl=4-methoxybenzoate was obtained in the form of a colorless oily product in the same manner as that of Example 1(5), with the exception that the reaction was carried out at room temperature for 5 hours.

¹H-NMR (CDCl₃) δ value:

8.02-7.93 (4H, m), 6.93-6.82 (4H, m), 6.32-5.97 (0.54H, m), 5.80 (0.46H, dt, J=12.2, 4.9 Hz), 5.61 (0.46H, dt, J=9.7, 9.7 Hz), 5.48 (0.54H, dd, J=9.5, 5.0 Hz), 5.36-5.35 (0.23H, m), 5.25-5.23 (0.50H, m), 5.14-5.09 (0.27H, m), 4.65-4.54 (1.3H, m), 4.47-4.45 (0.7H, m), 4.25-4.17 (0.46H, m), 3.87-3.83 (6H, m), 3.73 (0.54H, d, J=12.3, 6.7 Hz), 2.78 (0.54H, d, J=5.3 Hz), 2.69 (0.46H, d, J=8.6 Hz)

¹⁹F-NMR(CDCl₃) δ value:

−183.54 (0.54F, dd, J=47.1, 11.4 Hz), −192.82 (0.46F, ddd, J=51.4, 11.7, 5.1 Hz)

(8)

[Formula 154]

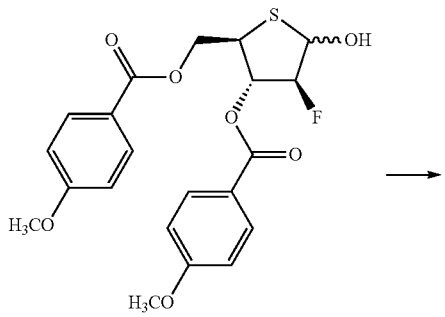

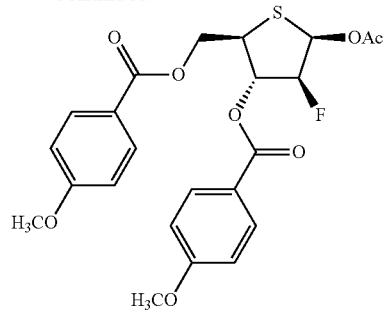

((2R,3S,4S,5R)-5-acetyloxy-4-fluoro-3-((4-methoxyphenyl)carbonyloxy)thiolan-2-yl)methyl=4-methoxybenzoate was obtained in the form of a white solid in the same manner as that of Example 10(8).

¹H-NMR (CDCl₃) δ value:

7.98 (4H, dd, J=9.8, 9.8 Hz), 6.89 (4H, dd, J=16.4, 8.8 Hz), 6.22 (1H, dd, J=13.6, 1.8 Hz), 5.81 (1H, ddd, J=12.3, 8.2, 3.0 Hz), 5.37 (1H, ddd, J=45.0, 3.5, 2.2 Hz), 4.54-4.40 (2H, m), 4.15-4.03 (1H, m), 3.87 (3H, s), 3.85 (3H, s), 2.11 (3H, s)

¹⁹F-NMR(CDCl₃) δ value: −191.95 (1F, dd, J=50.8, 11.7 Hz)

(9)

[Formula 155]

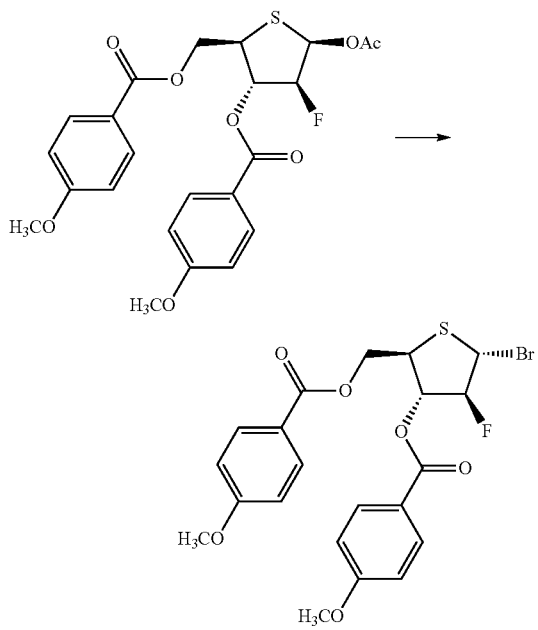

((2R,3S,4S,5R)-5-bromo-4-fluoro-3-((4-methoxyphenyl)carbonyloxy)thiolan-2-yl)methyl=4-methoxybenzoate was obtained in the form of a white solid in the same manner as that of Example 1(7).

¹H-NMR (CDCl₃) δ value:

8.03 (4H, dd, J=20.9, 8.9 Hz), 6.91 (4H, dd, J=11.3, 8.9 Hz), 5.81-5.79 (0.5H, m), 5.76-5.74 (0.5H, m), 5.72-5.71 (1H, m), 5.68 (0.5H, brs), 5.58-5.56 (0.5H, m), 4.64-4.47 (1H, m), 4.33-4.27 (1H, m), 3.87 (3H, s), 3.85 (3H, s)

¹⁹F-NMR(CDCl₃) δ value: −163.56 (1F, dd, J=47.2, 14.8 Hz)

(10)

[Formula 156]

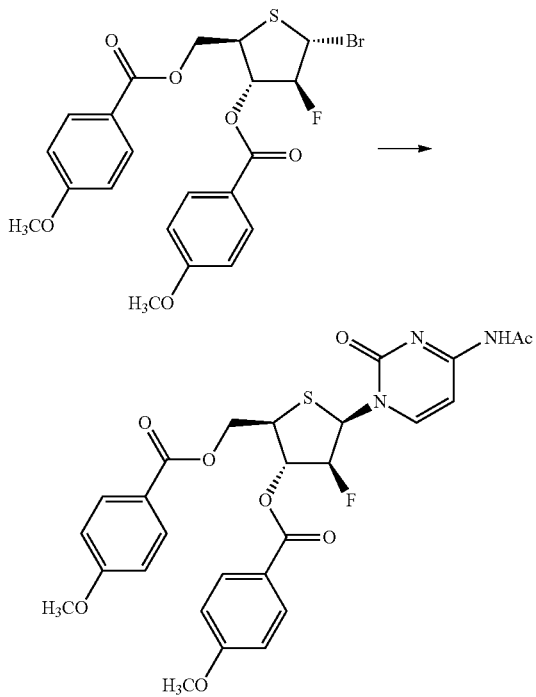

Using a methylene chloride solution of ((2R,3S,4S,5R)-5-bromo-4-fluoro-3-((4-methoxyphenyl)carbonyloxy)thiolan-2-yl)methyl=4-methoxybenzoate, ((2R,3S,4S,5R)-5-(4-acetamido-2-oxo-1,2-dihydropyrimidin-1-yl)-4-fluoro-3-((4-meth oxyphenyl)carbonyloxy)thiolan-2-yl)methyl=4-methoxybenzoate was obtained in the form of a light yellow solid in the same manner as that of Example 22(2).

m/z (ESI-positive): 572.5[M+H]$^+$ $^{19}$F-NMR(CDCl$_3$) δ value: −196.14 (1F, ddd, J=49.6, 23.7, 8.9 Hz)

(11)

[Formula 157]

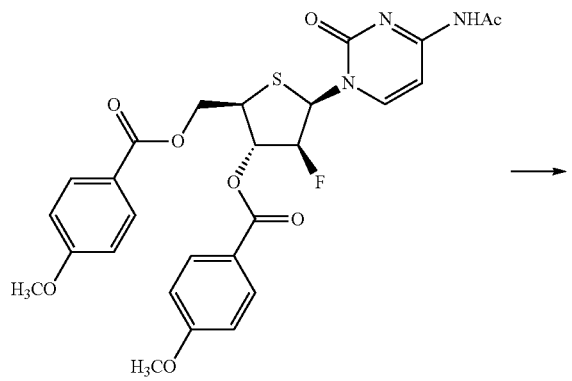

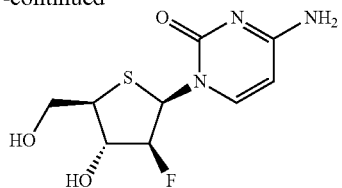

(2R,3S,4S,5R)-3-hydroxy-2-hydroxymethyl-5-(4-amino-2-oxo-1,2-dihydropyrimidin-1-yl)-4-fluorothiolane was obtained in the same manner as that of Example 1(8).

Example 13

(1) I

[Formula 158]

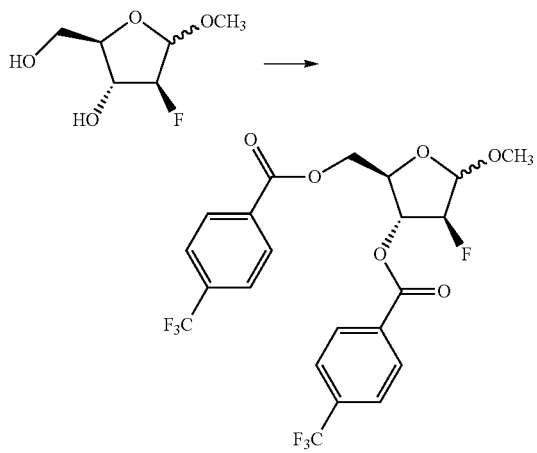

((2R,3R,4S)-4-fluoro-5-methoxy-3-((4-(trifluoromethyl)phenyl)carbonyloxy)oxolan-2-yl)methyl=4-(trifluoromethyl)benzoate was obtained in the form of a white solid in the same manner as that of Example 10(1).

$^1$H-NMR (CDCl$_3$) δ value:
8.21-8.15 (4H, m), 7.68-7.75 (4H, m), 5.83 (1H, ddd, J=17.2, 6.0, 6.0 Hz), 5.28 (1H, ddd, J=52.0, 6.4, 4.4 Hz), 5.09 (1H, d, J=4.4 Hz), 4.78 (1H, dd, J=12.0, 4.0 Hz), 4.62 (1H, dd, J=12.0, 6.4 Hz), 4.41-4.37 (1H, m), 3.49 (3H, s)

$^{19}$F-NMR(CDCl$_3$) δ value: −63.16 (3F, s), −63.23 (3F, s), −206.61 (1F, dd, J=52.3, 16.9 Hz)

(2)

[Formula 159]

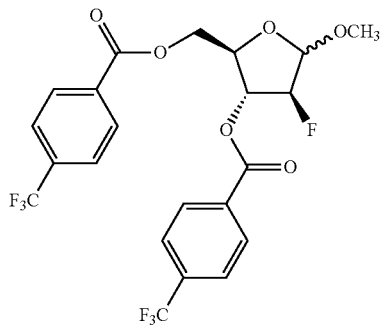

-continued

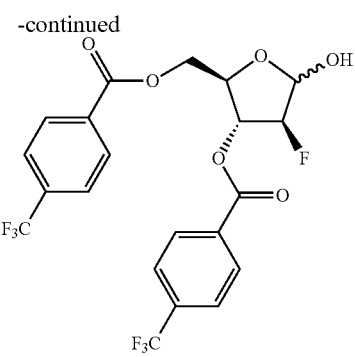

((2R,3R,4S)-4-fluoro-5-hydroxy-3-((4-(trifluoromethyl)phenyl)carbonyloxy)oxolan-2-yl)methyl=4-(trifluoromethyl)benzoate was obtained in the form of a colorless oily product in the same manner as that of Example 10(2).

$^{1}$H-NMR (CDCl$_3$) δ value:
8.18 (4H, dd, J=7.8, 7.8 Hz), 7.73 (4H, dd, J=12.4, 4.4 Hz), 5.72 (1H, dd, J=9.8, 2.6 Hz), 5.51 (1H, dd, J=21.6, 4.0 Hz), 5.19 (1H, d, J=49.2 Hz), 4.82-4.78 (1H, m), 4.72-4.64 (2H, m), 2.85 (1H, dd, J=3.2, 3.2 Hz)

$^{19}$F-NMR(CDCl$_3$) δ value:
−63.16 (3F, s), −63.24 (3F, s), −190.66 (1F, dddd, J=49.0, 21.7, 9.6, 2.4 Hz)

(3)

[Formula 160]

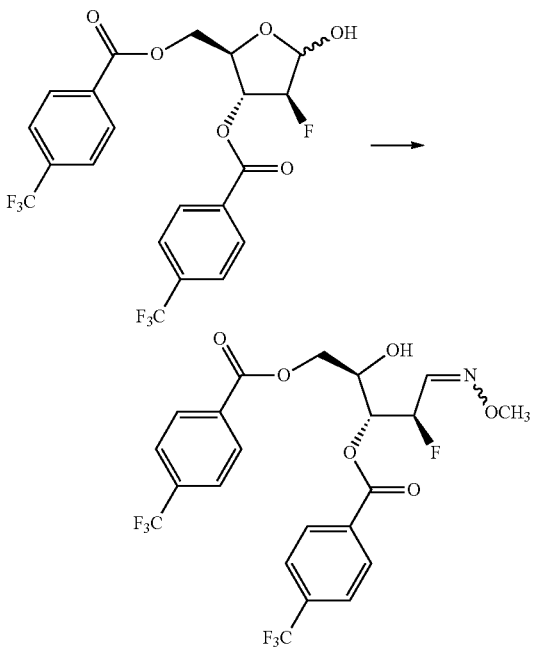

(2R,3R,4R)-4-fluoro-2-hydroxy-5-(methoxyimino)-3-((4-(trifluoromethyl)phenyl)carbonyloxy)pentyl=4-(trifluoromethyl)benzoate was obtained in the form of a colorless oily product in the same manner as that of Example 1(1).

$^{1}$H-NMR (CDCl$_3$) δ value:
8.19-8.11 (4H, m), 7.74-7.69 (4H, m), 7.40 (0.64H, dd, J=6.4, 6.4 Hz), 6.83 (0.36H, dd, J=11.2, 40.4 Hz), 6.10 (0.36H, ddd, J=46.4, 4.5, 2.0 Hz), 5.82 (0.36H, dd, J=8.1, 1.9 Hz), 5.65 (0.32H, dd, J=6.4, 2.4 Hz), 5.57-5.48 (0.96H, m), 4.67-4.60 (1H, m), 4.51-4.41 (2H, m), 3.93 (1.08H, s), 3.82 (1.92H, s), 2.88 (0.64H, d, J=5.8 Hz), 2.83 (0.36H, d, J=5.9 Hz), $^{19}$F-NMR(CDCl$_3$) δ value:
−63.23 (3F, s), −63.28 (3F, s), −200.2 (0.64F, ddd, J=45.2, 25.3, 7.2 Hz), −207.4 (0.36F, ddd, J=46.3, 27.5, 11.3 Hz)

(4)

[Formula 161]

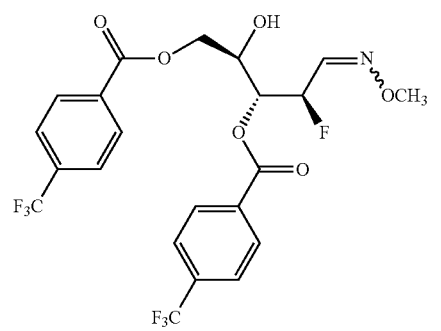

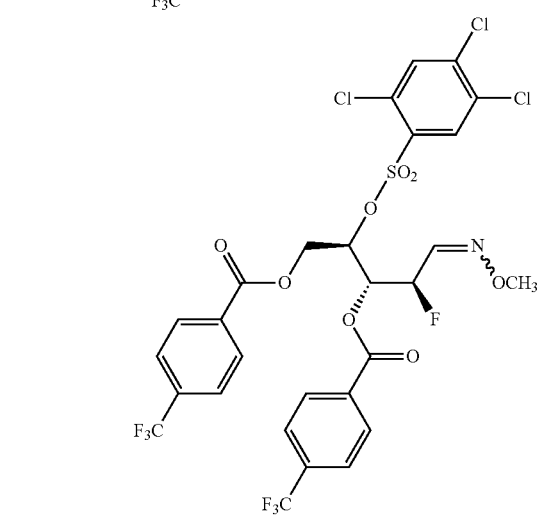

(2R,3R,4R)-2-fluoro-1-(methoxyimino)-4-(((2,4,5-trichlorobenzene)sulfonyl)oxy)-5-((4-(trifluoromethyl)phenyl)carbonyloxy)pentan-3-yl=4-(trifluoromethyl)benzoate was obtained in the form of a colorless oily product in the same manner as that of Example 7(1).

$^{1}$H-NMR (CDCl$_3$) δ value:
8.15-8.05 (5H, m), 7.75-7.70 (4H, m), 7.50 (1H, s), 7.41 (0.65H, dd, J=6.6, 6.6 Hz), 6.81 (0.35H, dd, J=1.3, 4.4 Hz), 6.02 (0.35H, ddd, J=25.7, 5.9, 2.5, 5.95-5.93 (0.17H, m), 5.86-5.78 (0.82H, m), 5.51-5.38 (1.65H, m), 4.81-4.74 (1H, m), 4.63-4.57 (1H, m), 3.92 (1.95H, s), 3.83 (1.05H, s)

$^{19}$F-NMR(CDCl$_3$) δ value:
−63.23 (3F, s), −63.30 (3F, s), −196.6 (0.65F, ddd, J=45.6, 21.9, 6.9 Hz), −204.9 (0.35F, ddd, J=46.9, 25.9, 11.4 Hz)

(5)

[Formula 162]

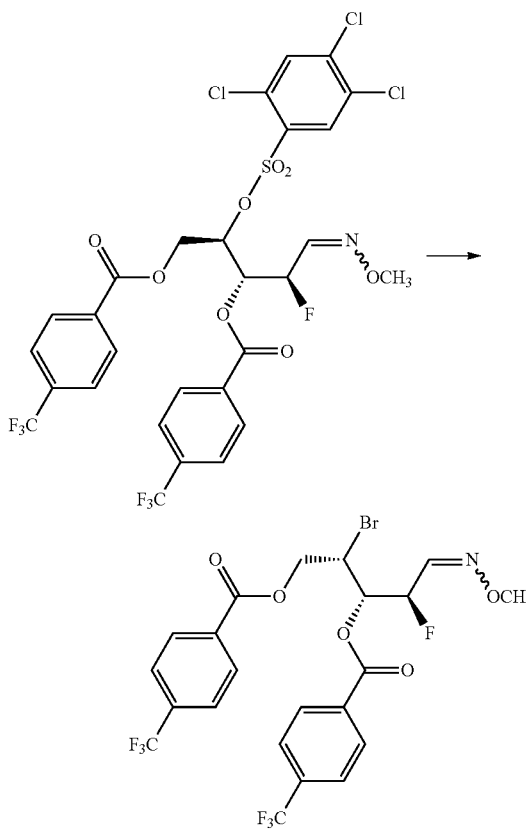

(2S,3S,4R)-2-bromo-4-fluoro-5-(methoxyimino)-3-((4-(trifluoromethyl)phenyl)carbonyloxy)pentyl=4-(trifluoromethyl)benzoate was obtained in the form of a colorless oily product in the same manner as that of Example 7(2).

$^1$H-NMR (CDCl$_3$) δ value:
8.23-8.08 (4H, m), 7.76-7.66 (4H, m), 7.49 (0.82H, dd, J=6.4, 6.4 Hz), 6.87 (0.18H, dd, J=11.2, 4.8 Hz), 6.07 (0.18H, ddd, 47.0, 4.6, 3.3 Hz), 5.93 (0.18H, ddd, 23.8, 5.7, 3.2 Hz), 5.83 (0.82H, ddd, 15.6, 6.2, 3.0 Hz), 5.53 (0.82H, ddd, 46.8, 6.3, 6.3 Hz), 4.81-4.70 (1H, m), 4.81-4.74 (1H, m), 40.65-4.58 (1H, m), 3.90 (2.46H, s), 3.88 (0.54H, s)

$^{19}$F-NMR(CDCl$_3$) δ value:
−63.24 (3F, s), −63.27 (3F, s), −193.37 (0.82F, ddd, J=46.7, 15.4, 6.4 Hz), −202.98 (0.18F, ddd, J=47.1, 23.5, 10.7 Hz)

(6)

[Formula 163]

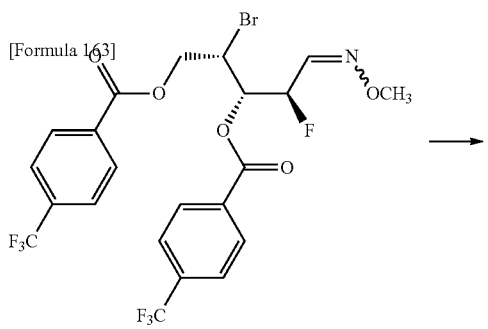

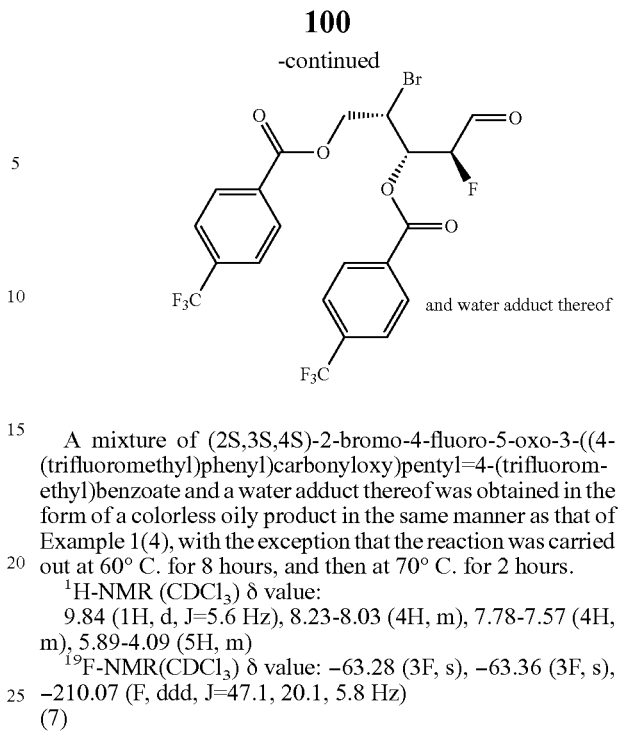

A mixture of (2S,3S,4S)-2-bromo-4-fluoro-5-oxo-3-((4-(trifluoromethyl)phenyl)carbonyloxy)pentyl=4-(trifluoromethyl)benzoate and a water adduct thereof was obtained in the form of a colorless oily product in the same manner as that of Example 1(4), with the exception that the reaction was carried out at 60° C. for 8 hours, and then at 70° C. for 2 hours.

$^1$H-NMR (CDCl$_3$) δ value:
9.84 (1H, d, J=5.6 Hz), 8.23-8.03 (4H, m), 7.78-7.57 (4H, m), 5.89-4.09 (5H, m)

$^{19}$F-NMR(CDCl$_3$) δ value: −63.28 (3F, s), −63.36 (3F, s), −210.07 (F, ddd, J=47.1, 20.1, 5.8 Hz)

(7)

[Formula 164]

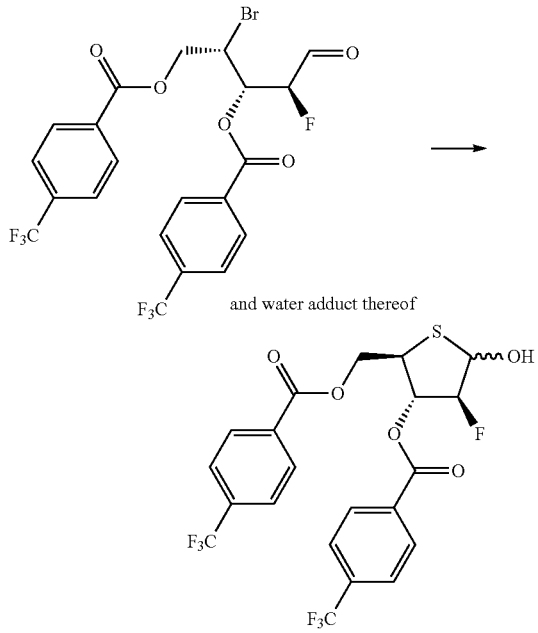

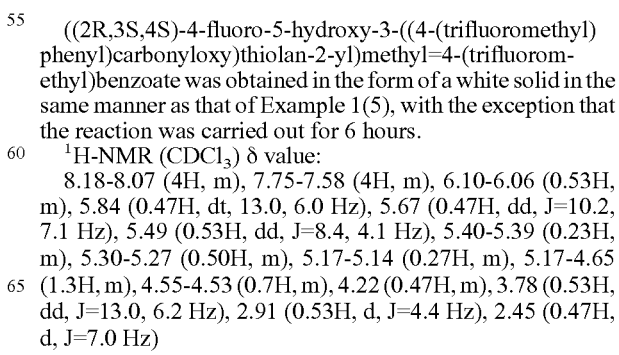

((2R,3S,4S)-4-fluoro-5-hydroxy-3-((4-(trifluoromethyl)phenyl)carbonyloxy)thiolan-2-yl)methyl=4-(trifluoromethyl)benzoate was obtained in the form of a white solid in the same manner as that of Example 1(5), with the exception that the reaction was carried out for 6 hours.

$^1$H-NMR (CDCl$_3$) δ value:
8.18-8.07 (4H, m), 7.75-7.58 (4H, m), 6.10-6.06 (0.53H, m), 5.84 (0.47H, dt, 13.0, 6.0 Hz), 5.67 (0.47H, dd, J=10.2, 7.1 Hz), 5.49 (0.53H, dd, J=8.4, 4.1 Hz), 5.40-5.39 (0.23H, m), 5.30-5.27 (0.50H, m), 5.17-5.14 (0.27H, m), 5.17-4.65 (1.3H, m), 4.55-4.53 (0.7H, m), 4.22 (0.47H, m), 3.78 (0.53H, dd, J=13.0, 6.2 Hz), 2.91 (0.53H, d, J=4.4 Hz), 2.45 (0.47H, d, J=7.0 Hz)

$^{19}$F-NMR(CDCl$_3$) δ value:

−63.28 (3F, s), −63.30 (3F, s), −184.00 (0.47F, dd, J=47.4, 11.9 Hz), −192.00 (0.53F, ddd, J=51.4, 11.8, 3.7 Hz)

(8)

[Formula 165]

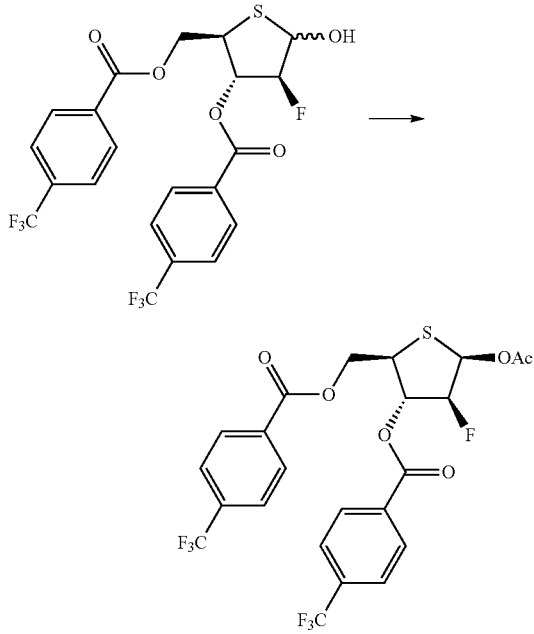

((2R,3S,4S,5R)-5-acetyloxy-4-fluoro-3-((4-(trifluoromethyl)phenyl)carbonyloxy)thiolan-2-yl)methyl=4-(trifluoromethyl)benzoate was obtained in the form of a white solid in the same manner as that of Example 10(8), with the exception that hexane was used instead of methanol as a solvent to be added to the obtained residue.

$^1$H-NMR (CDCl$_3$) δ value:

8.05 (4H, dd, J=22.0, 8.0 Hz), 7.62 (4H, dd, J=48.2, 8.2 Hz), 6.19 (1H, d, J=4.4 Hz), 6.11-6.04 (1H, m), 5.32 (1H, ddd, J=50.6, 9.1, 4.5 Hz), 4.62 (1H, ddd, J=55.6, 1.4, 6.6 Hz), 3.78 (1H, dd, J=13.6, 6.8 Hz), 2.16 (3H, s)

$^{19}$F-NMR(CDCl$_3$) δ value: −63.32 (3F, s), −63.33 (3F, s), −191.78 (1F, dd, J=50.6, 11.9 Hz)

(9)

[Formula 166]

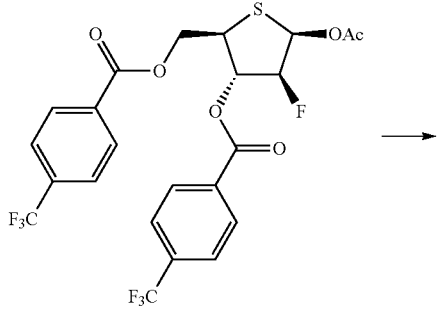

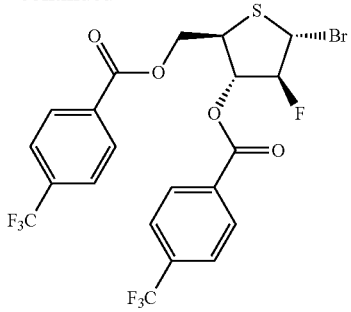

((2R,3S,4S,5R)-5-bromo-4-fluoro-3-((4-(trifluoromethyl)phenyl)carbonyloxy)thiolan-2-yl)methyl=4-(trifluoromethyl)benzoate was obtained in the form of a colorless oily product in the same manner as that of Example 1(7).

$^1$H-NMR (CDCl$_3$) δ value:

8.19 (4H, dd, J=15.8, 8.0 Hz), 7.72 (4H, dd, J=9.0, 9.0 Hz), 5.87-5.85 (0.5H, m), 5.82-5.80 (0.5H, m), 5.76 (1H, brs), 5.71 (0.5H, brs), 5.61 (0.5H, brs), 4.68-4.59 (2H, m), 4.36-4.30 (1H, m)

$^{19}$F-NMR(CDCl$_3$) δ value: −63.20 (3F, s), −63.28 (3F, s), −163.52 (1F, dd, J=46.9, 14.4 Hz)

(10)

[Formula 167]

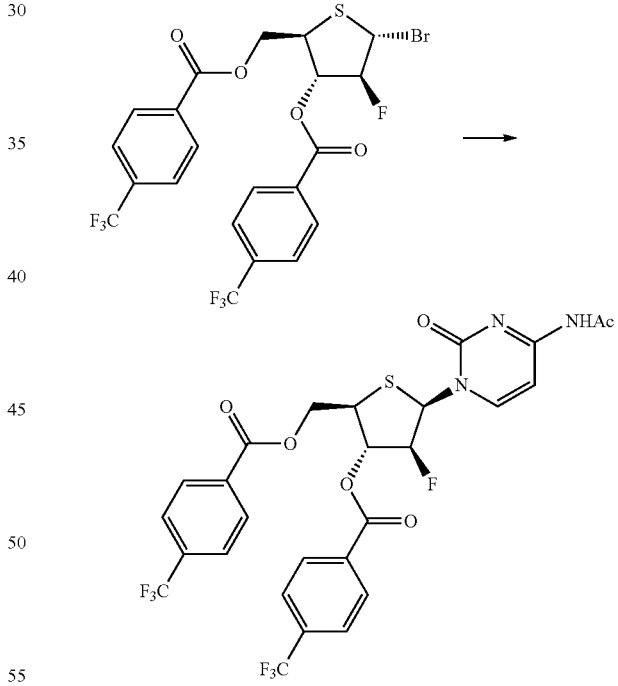

Using a methylene chloride solution of ((2R,3S,4S,5R)-5-bromo-4-fluoro-3-((4-(trifluoromethyl)phenyl)carbonyloxy)thiolan-2-yl)methyl=4-(trifluoromethyl)benzoate, ((2R,3S,4S,5R)-5-(4-acetamido-2-oxo-1,2-dihydropyrimidin-1-yl)-4-fluoro-3-((4-(trifluoromethyl)phenyl)carbonyloxy)thiolan-2-yl)methyl=4-(trifluoromethyl)benzoate was obtained in the form of a light yellow solid in the same manner as that of Example 22(2).

m/z (ESI-positive): 648.5[M+H]$^+$ $^{19}$F-NMR(CDCl$_3$) δ value: −196.23 (1H, ddd, J=49.7, 24.5, 8.7 Hz)

(11)

[Formula 168]

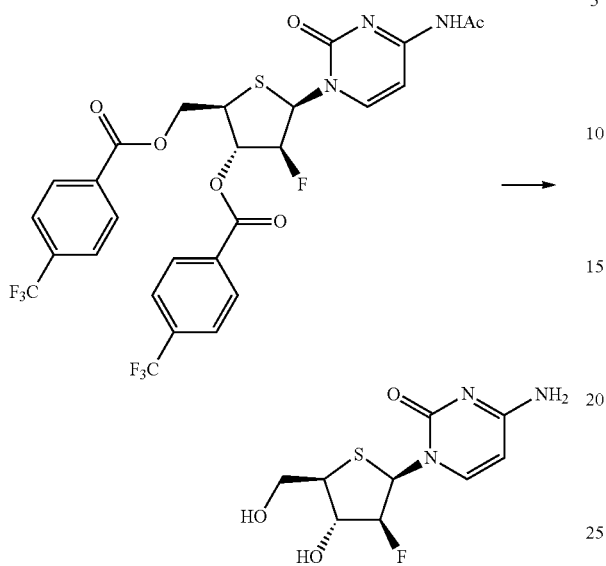

(2R,3S,4S,5R)-3-hydroxy-2-hydroxymethyl-5-(4-amino-2-oxo-1,2-dihydropyrimidin-1-yl)-4-fluorothiolane was obtained in the same manner as that of Example 1(8).

Example 14

(1)

[Formula 169]

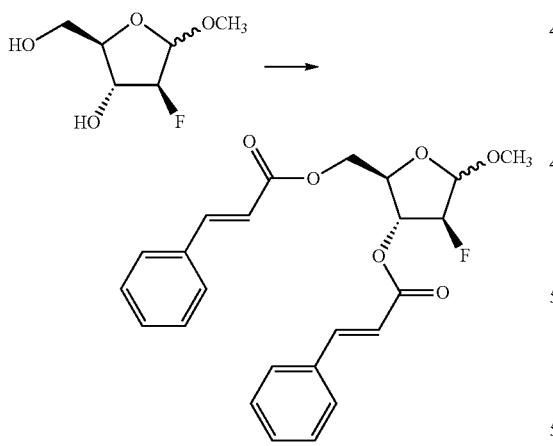

((2R,3R,4S)-4-fluoro-5-methoxy-3-((3-phenyl-2-propenoyl)oxy)oxolan-2-yl)methyl=3-phenyl-2-propenoate was obtained in the form of a white solid in the same manner as that of Example 10(1).

$^1$H-NMR (CDCl$_3$) δ value:

7.74 (2H, dd, J=16.0, 5.6), 7.54-7.51 (4H, m), 7.42-7.36 (6H, m), 6.47 (2H, dd, J=16.0, 6.8 Hz), 50.63 (1H, ddd, J=17.2, 6.0, 6.0 Hz), 5.20 (1H, ddd, J=52.4, 6.4, 4.4 Hz), 5.05 (1H, d, J=4.4 Hz), 4.62 (1H, dd, J=11.6, 4.0 Hz), 4.40 (1H, dd, J=11.6, 7.2 Hz), 4.3-4.24 (1H, m), 3.52 (3H, s)

$^{19}$F-NMR(CDCl$_3$) δ value: −206.91 (1F, dd, J=52.3, 16.9 Hz)

(2)

[Formula 170]

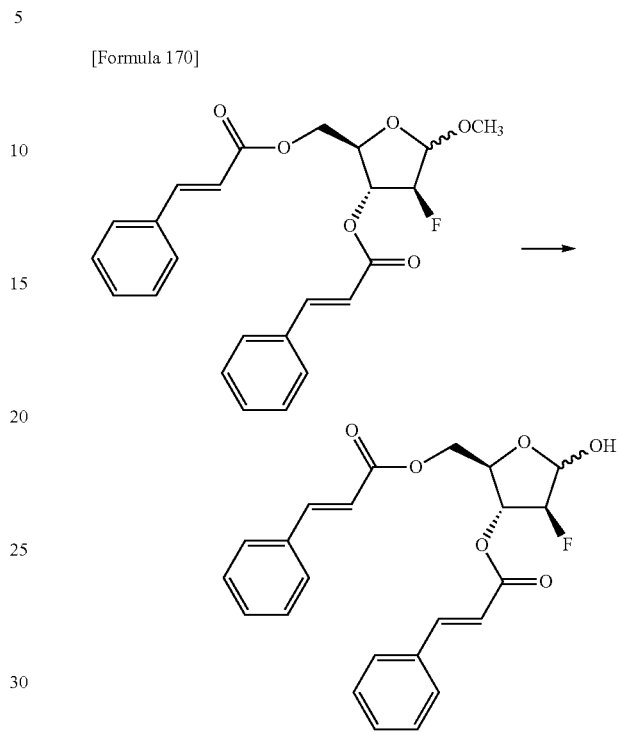

((2R,3R,4S)-4-fluoro-5-hydroxy-3-((3-phenyl-2-propenoyl)oxy)oxolan-2-yl)methyl=3-phenyl-2-propenoate was obtained in the form of a colorless oily product in the same manner as that of Example 10(2), with the exceptions that the reaction temperature was set at 70° C. and that the reaction time was set at 4 hours.

$^1$H-NMR (CDCl$_3$) δ value:

7.75 (2H, dd, J=16.0, 8.0 Hz), 7.54-7.51 (4H, m), 7.41-7.37 (6H, m), 6.48 (2H, dd, J=16.0, 4.4 Hz), 5.67 (1H, dd, J=10.4, 2.8 Hz), 5.51 (1H, dd, J=21.6, 4.0 Hz), 5.32 (1H, dd, J=22.2, 4.2 Hz), 5.09 (1H, d, J=49.2 Hz), 4.65-4.58 (2H, m), 4.48-4.42 (1H, m), 3.15 (1H, brs)

$^{19}$F-NMR(CDCl$_3$) δ value: −190.06 (1F, ddd, J=49.1, 22.1, 10.3 Hz)

(3)

[Formula 171]

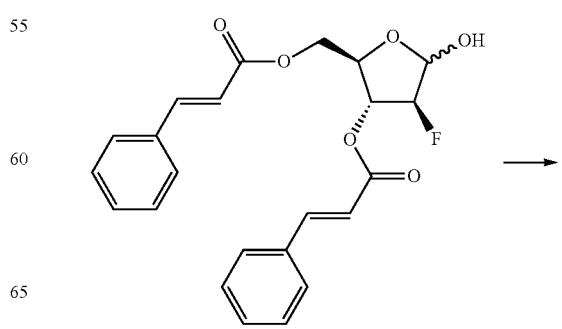

-continued

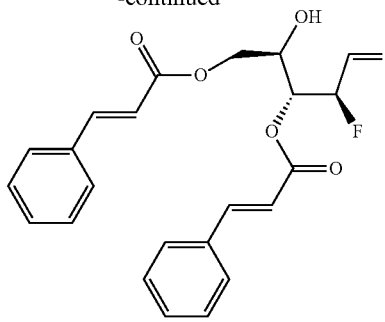

(2R,3R,4R)-2-fluoro-4-hydroxy-1-(methoxyimino)-5-((3-phenyl-2-propenoyl)oxy)pentan-3-yl=3-phenyl-2-propenoate was obtained in the form of a colorless oily product in the same manner as that of Example 1(1).

¹H-NMR (CDCl₃) δ value:
7.75 (2H, dd, J=19.7, 16.1 Hz), 7.53-7.50 (4H, m), 7.41-7.37 (6.77H, m), 6.85 (0.23H, dd, J=11.2, 4.8 Hz), 6.48 (2H, dd, J=16.0, 14.8 Hz), 6.01 (ddd, J=46.4, 4.8, 2.0 Hz), 5.57 (ddd, J=28.4, 8.0, 2.0 Hz), 5.53 (ddd, J=45.4, 6.6, 2.4 Hz), 5.33 (ddd, J=26.0, 8.1, 2.5 Hz), 4.50-4.40 (1H, m), 4.32-4.28 (2H, m), 3.94 (0.7H, s), 3.02-2.99 (1H, m)

¹⁹F-NMR(CDCl₃) δ value:
−200.15 (0.77F, ddd, J=45.6, 26.0, 7.2 Hz), −207.29 (0.23F, ddd, J=46.7, 28.2, 11.3 Hz)
(4)

[Formula 172]

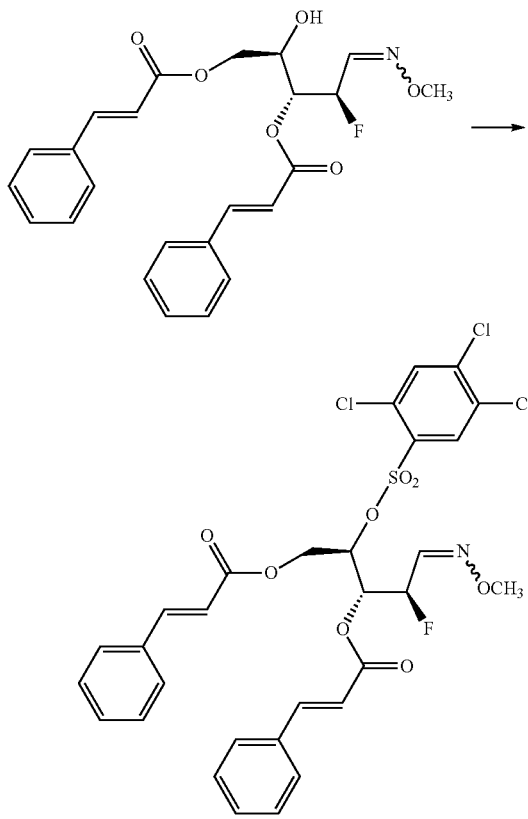

(2R,3R,4R)-2-fluoro-1-(methoxyimino)-5-((3-phenyl-2-propenoyl)oxy)-4-(((2,4,5-trichlorobenzene)sulfonyl)oxy)pentan-3-yl=3-phenyl-2-propenoate was obtained in the form of a colorless oily product in the same manner as that of Example 7(1).

¹H-NMR (CDCl₃) δ value:
8.17 (1H, s), 7.78-7.63 (3H, m), 7.54-7.50 (4H, m), 7.41-7.36 (6.77H, m), 6.81 (0.23H, dd, J=11.1, 4.4 Hz), 6.33 (1.54H, dd, J=77.6, 16.0 Hz), 6.32 (0.46H, dd, J=65.2, 16.0 Hz), 5.89 (0.23H, m), 5.79 (0.23H, ddd, 19.0, 5.5, 2.4 Hz), 5.66 (0.77H, ddd, 23.6, 6.4, 3.2 Hz), 5.37 (0.77H, ddd, 45.8, 6.5, 3.1 Hz), 5.29-5.25 (0.1H, m), 4.59-4.55 (1H, m), 4.43-4.38 (1H, m), 3.94 (0.69H, s), 3.89 (2.31H, s)

¹⁹F-NMR(CDCl₃) δ value:
−197.2 (0.77F, ddd, J=45.6, 23.4, 6.9 Hz), −205.2 (0.23F, ddd, J=46.7, 26.4, 11.3 Hz)
(5)

[Formula 173]

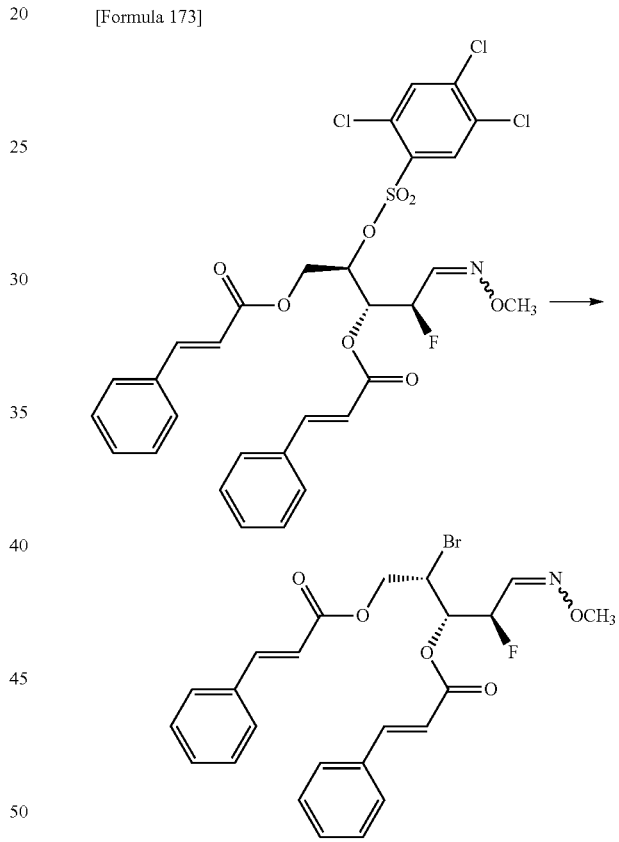

(2S,3S,4R)-2-bromo-4-fluoro-5-(methoxyimino)-1-((3-phenyl-2-propenoyl)oxy)pentan-3-yl=3-phenyl-2-propenoate was obtained in the form of a colorless oily product in the same manner as that of Example 7(2).

¹H-NMR (CDCl₃) δ value:
7.78 (2H, dd, J=28.0, 16.0 Hz), 7.57-7.51 (4H, m), 7.46 (0.87H, dd, J=6.5, 6.5 Hz), 7.41-7.37 (6H, m), 6.87 (0.13H, dd, J=11.0, 4.8 Hz), 6.50 (2H, dd, J=29.6, 16.0 Hz), 6.03 (0.13H, dd, J=47.2, 4.6, 3.3 Hz), 5.75 (0.13H, dd, J=25.1, 5.8, 3.1 Hz), 5.65 (0.87H, ddd, 17.6, 5.6, 3.6 Hz), 5.53 (0.82H, ddd, 46.8, 6.3, 6.3 Hz), 4.66-4.44 (3H, m), 3.92 (3H, s)

¹⁹F-NMR(CDCl₃) δ value: −193.71 (1F, ddd, J=46.7, 17.3, 6.4 Hz)

(6)

[Formula 174]

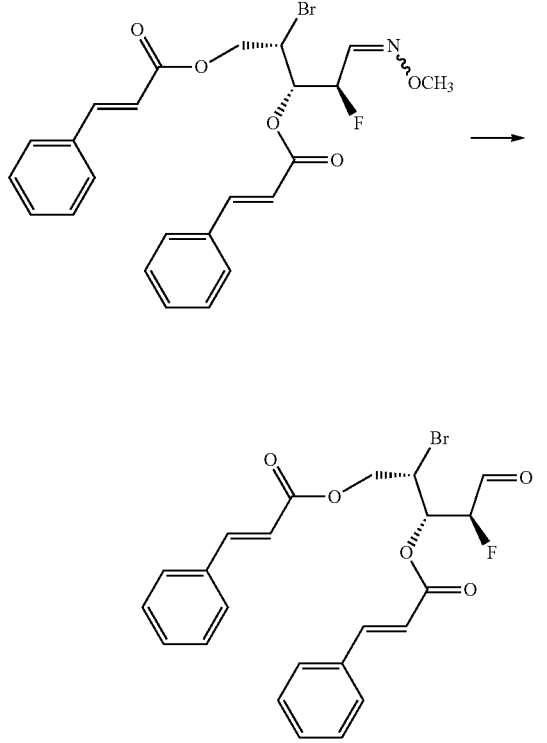

and water adduct thereof

A mixture of (2S,3S,4S)-2-bromo-4-fluoro-5-oxo-1-((3-phenyl-2-propenoyl)oxy)pentan-3-yl=3-phenyl-2-propenoate and a water adduct thereof was obtained in the form of a colorless oily product in the same manner as that of Example 1(4), with the exception that the reaction was carried out at 40° C. for 2 hours, and then at 70° C. for 13 hours.

$^1$H-NMR (CDCl$_3$) δ value:
9.86-9.79 (1H, m), 8.86-7.67 (2H, m), 7.58-7.26 (10H, m), 6.53-6.45 (2H, m), 5.79-4.11 (5H, m)

$^{19}$F-NMR(CDCl$_3$) δ value: −210.09-210.34 (1F, m)

(7)

[Formula 175]

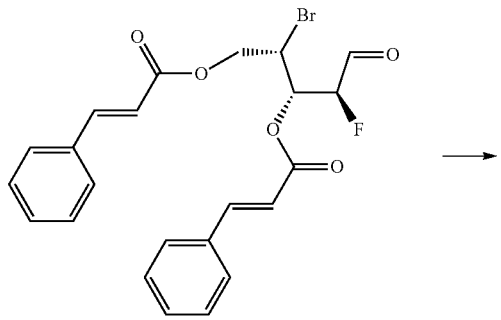

and water adduct thereof

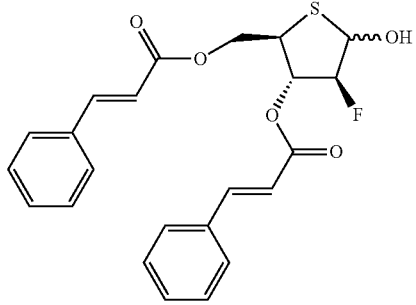

((2R,3S,4S)-4-fluoro-5-hydroxy-3-((3-phenyl-2-propenoyl)oxy)thiolan-2-yl)methyl=3-phenyl-2-propenoate was obtained in the form of a brown oily product in the same manner as that of Example 1(5), with the exception that the reaction was carried out for 4 hours.

$^1$H-NMR (CDCl$_3$) δ value:
7.76-7.69 (2H, m), 7.53-7.46 (4H, m), 7.41-7.31 (6H, m), 6.45 (0.94H, dd, J=15.8, 6.2 Hz), 6.43 (1.06H, dd, J=22.8, 6.0 Hz), 5.91-5.84 (0.53H, m), 5.70 (0.47H, dt, 11.9, 4.8 Hz), 5.59 (0.47H, dd, 9.8, 9.8 Hz), 5.45 (0.53H, dd, J=9.6, 4.8 Hz), 5.30-5.29 (0.23H, m), 5.19-5.16 (0.50H, m), 5.06-5.04 (0.27H, m), 4.53-4.50 (1.3H, m), 4.55-4.53 (0.7H, m), 4.09-4.05 (0.47H, m), 3.62 (0.53H, dd, J=12.3, 6.7 Hz), 2.88 (0.53H, d, J=5.4 Hz), 2.52 (0.47H, d, J=9.0 Hz)

$^{19}$F-NMR(CDCl$_3$) δ value:
−183.75 (0.48F, dd, J=47.1, 11.5 Hz), −192.65 (0.52F, ddd, J=51.2, 11.8, 4.6 Hz)

(8)

[Formula 176]

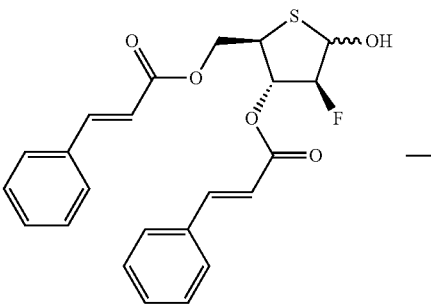

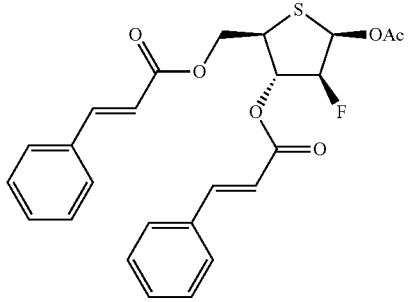

((2R,3S,4S,5R)-5-acetyloxy-4-fluoro-3-((3-phenyl-2-propenoyl)oxy)thiolan-2-yl)methyl=3-phenyl-2-propenoate was obtained in the form of a white solid in the same manner as that of Example 10(8).

$^1$H-NMR (CDCl$_3$) δ value:
7.71 (2H, dd, J=33.8, 16.2 Hz), 7.49-7.29 (10H, m), 6.42 (2H, dd, J=43.2, 16.0 Hz), 6.15 (1H, d, J=4.0 Hz), 5.23-5.86

(1H, m), 5.22 (1H, ddd, J=50.8, 8.9, 4.5 Hz), 4.46 (1H, ddd, J=58.4, 11.3, 6.9 Hz), 3.61 (1H, dd, J=13.8, 7.0 Hz), 2.18 (3H, s)

$^{19}$F-NMR(CDCl$_3$) δ value: −192.04 (1F, dd, J=50.5, 12.0 Hz)

(9)

[Formula 177]

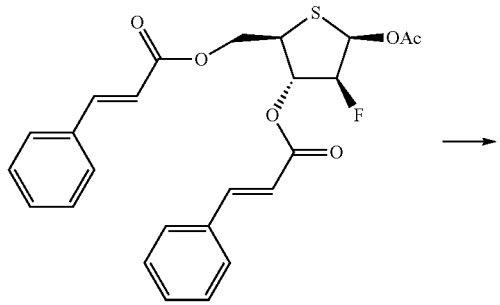

((2R,3S,4S,5R)-5-bromo-4-fluoro-3-((3-phenyl-2-propenoyl)oxy)thiolan-2-yl)methyl=3-phenyl-2-propenoate was obtained in the form of a colorless oily product in the same manner as that of Example 1(7).

$^1$H-NMR (CDCl$_3$) δ value:

7.83-7.69 (2H, m), 7.55-7.45 (4H, m), 7.42-7.31 (6H, m), 6.51-6.38 (2H, m), 5.67-5.66 (1.5H, m), 5.63-5.61 (0.5H, m), 4.65-4.59 (1H, m), 4.54-4.38 (2H, m), 4.23-4.18 (1H, m)

$^{19}$F-NMR(CDCl$_3$) δ value: −163.52 (1F, dd, J=49.1, 15.0 Hz)

(10)

[Formula 178]

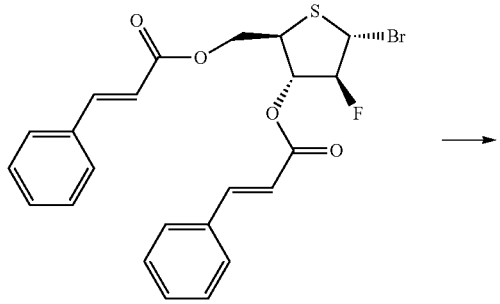

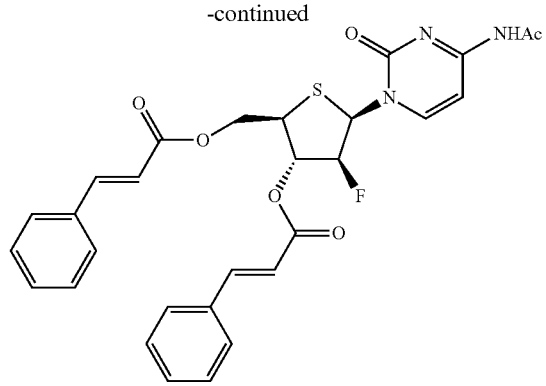

Using a methylene chloride solution of ((2R,3S,4S,5R)-5-bromo-4-fluoro-3-((3-phenyl-2-propenoyl)oxy)thiolan-2-yl)methyl 3-phenyl-2-propenoate, ((2R,3S,4S,5R)-5-(4-acetamido-2-oxo-1,2-dihydropyrimidin-1-yl)-4-fluoro-3-((3-phenyl-2-propenoyl)oxy)thiolan-2-yl)methyl=3-phenyl-2-propenoate was obtained in the form of a yellow-brown solid in the same manner as that of Example 22(2).

m/z (ESI-positive): 564.5[M+H]$^+$ $^{19}$F-NMR(CDCl$_3$) δ value: −195.90 (1F, ddd, J=49.0, 23.5, 9.2 Hz)

(11)

[Formula 179]

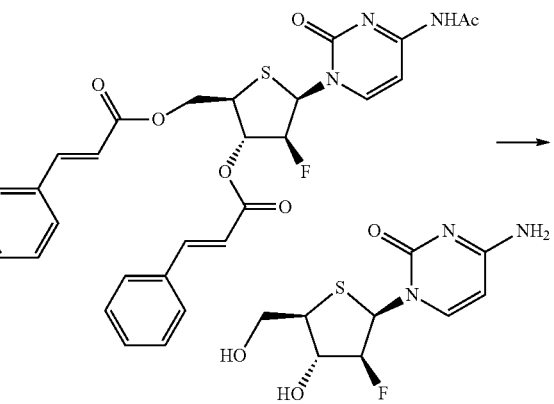

(2R,3S,4S,5R)-3-hydroxy-2-hydroxymethyl-5-(4-amino-2-oxo-1,2-dihydropyrimidin-1-yl)-4-fluorothiolane was obtained in the same manner as that of Example 1(8).

Example 15

[Formula 180]

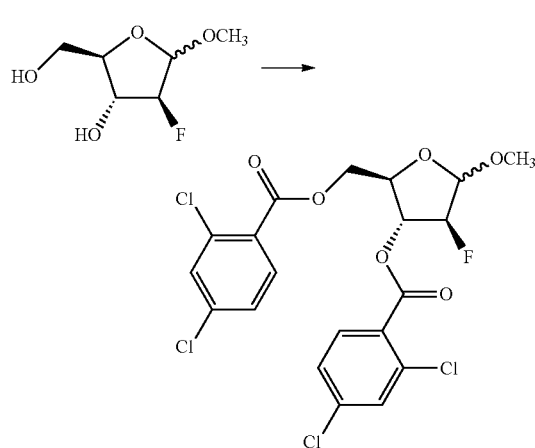

((2R,3R,4S)-3-((2,4-dichlorophenyl)carbonyloxy)-4-fluoro-5-methoxyoxolan-2-yl)methyl=2,4-dichlorobenzoate was obtained in the form of a white solid in the same manner as that of Example 10(1), with the exception that the reaction time was set at 1 hour.

$^1$H-NMR (CDCl$_3$) δ value:

7.89-7.81 (2H, m), 7.50-7.47 (2H, m), 7.34-7.29 (2H, m), 5.44 (1H, dd, J=22.8, 4.8 Hz), 5.20-5.02 (2H, m), 4.77 (1H, dd, J=12.0, 3.6 Hz), 4.61 (1H, dd, J=12.0, 3.6 Hz), 4.49 (1H, dd, J=8.4, 3.6 Hz), 3.44 (3H, s)

$^{19}$F-NMR(CDCl$_3$) δ value: −190.42 (1F, ddd, J=48.9, 22.0, 10.0 Hz)

(2)

[Formula 181]

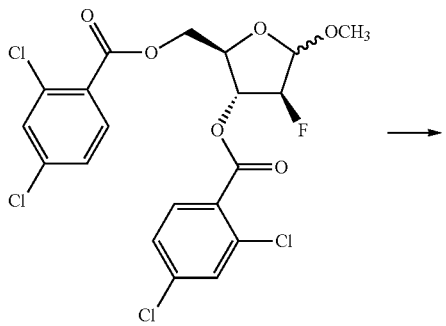

((2R,3R,4S)-3-((2,4-dichlorophenyl)carbonyloxy)-4-fluoro-5-hydroxyoxolan-2-yl)methyl=2,4-dichlorobenzoate was obtained in the form of a colorless oily product in the same manner as that of Example 10(2).

$^1$H-NMR (CDCl$_3$) δ value:

7.87 (2H, dd, J=15.6, 8.4 Hz), 7.50 (2H, dd, J=110.6, 2.0 Hz), 7.35-7.29 (2H, m), 5.68 (1H, d, J=10.0 Hz), 5.46 (1H, dd, J=21.2, 4.0 Hz), 5.15 (1H, d, J=48.8 Hz), 4.77-4.67 (2H, m), 4.62-4.58 (1H, m), 2.87 (1H, brs)

$^{19}$F-NMR(CDCl$_3$) δ value: −190.37 (1F, ddd, J=48.9, 21.4, 10.1 Hz)

(3)

[Formula 182]

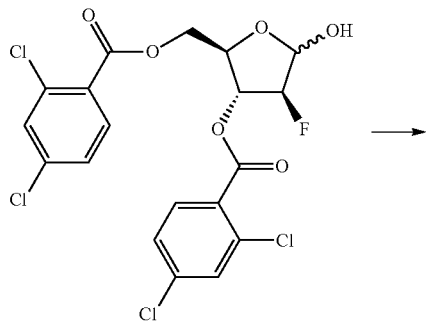

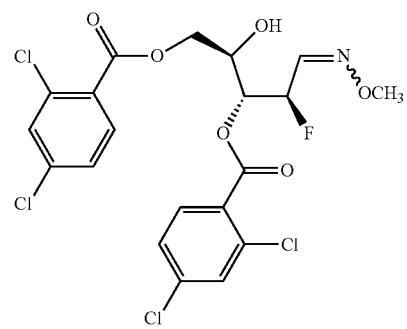

(2R,3R,4R)-3-((2,4-dichlorophenyl)carbonyloxy)-4-fluoro-2-hydroxy-5-(meth oxyimino)pentyl=2,4-dichlorobenzoate was obtained in the form of a colorless oily product in the same manner as that of Example 1(1).

$^1$H-NMR (CDCl$_3$) δ value:

7.84 (2H, dd, J=12.0, 8.4 Hz), 7.50-7.48 (2H, m), 7.44 (0.74H, dd, J=7.4, 6.2 Hz), 7.33-7.30 (2H, m), 6.87 (0.26H, dd, J=11.3, 4.4 Hz), 6.03 (ddd, J=46.4, 4.4, 2.0 Hz), 5.82 (dd, J=8.4, 2.0 Hz), 5.63-5.61 (0.37H, m), 5.54-5.45 (1.1H, m), 4.60-4.55 (1H, m), 4.48-4.39 (2H, m), 3.94 (0.8H, s), 3.86 (2.2H, m)

$^{19}$F-NMR(CDCl$_3$) δ value:

−200.08 (0.74F, ddd, J=44.8, 25.0, 7.3 Hz), −207.25 (0.26F, ddd, J=46.3, 28.0, 11.5 Hz)

(4)

[Formula 183]

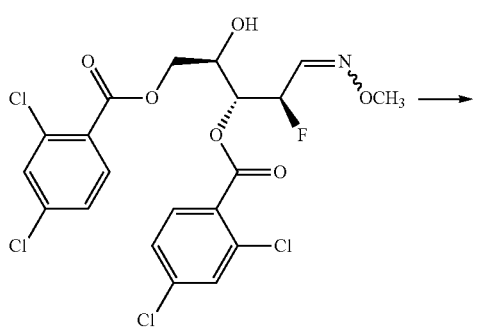

-continued

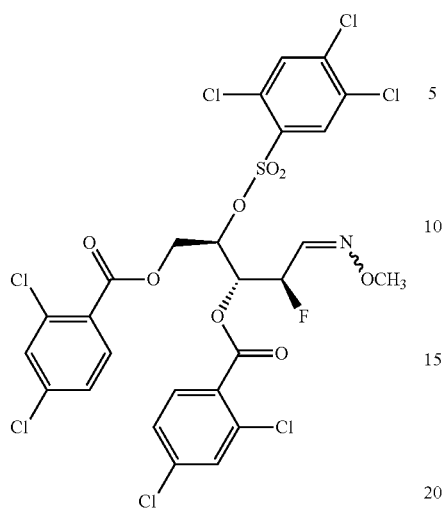

(2R,3R,4R)-1-((2,4-dichlorophenyl)carbonyloxy)-4-fluoro-5-(methoxyimino)-2-(((2,4,5-trichlorobenzene)sulfonyl)oxy)pentan-3-yl=2,4-dichlorobenzoate was obtained in the form of a colorless oily product in the same manner as that of Example 7 (1).

$^1$H-NMR (CDCl$_3$) δ value:

8.07 (1H, s), 7.83-7.75 (2H, m), 7.51-7.42 (3.76H, m), 7.35-7.26 (2H, m), 6.85 (0.24H, dd, J=11.3, 4.4 Hz), 6.00 (0.24H, ddd, J=25.8, 50.8, 2.4 Hz), 5.93-5.91 (0.12H, m) 5.84-5.76 (0.88H, m), 5.49-5.47 (0.38H, m), 5.38-5.29 (1.14H, m), 4.74-4.55 (2H, m), 3.93 (0.72H, s), 3.88 (2.28H, s)

$^{19}$F-NMR(CDCl$_3$) δ value:

−197.30 (0.88F, ddd, J=45.6, 21.6, 7.0 Hz), −204.36 (0.12F, ddd, J=46.7, 25.7, 11.4 Hz)

(5)

[Formula 184]

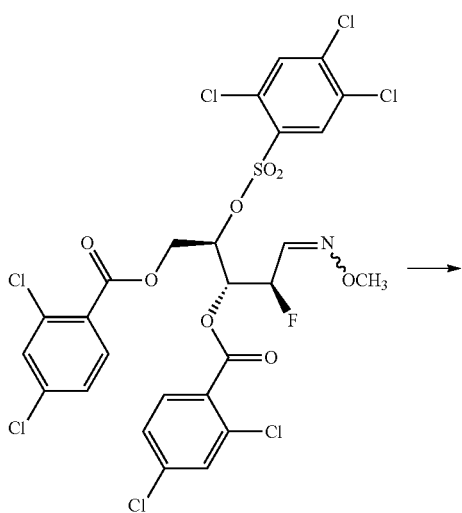

-continued

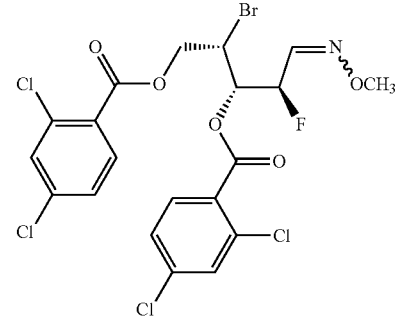

(2S,3S,4R)-2-bromo-3-((2,4-dichlorophenyl)carbonyloxy)-4-fluoro-5-(methoxyimino)pentyl=2,4-dichlorobenzoate was obtained in the form of a colorless oily product in the same manner as that of Example 7(2).

$^1$H-NMR (CDCl$_3$) δ value:

7.88 (2H, dd, J=16.0, 9.6 Hz), 7.51-7.45 (2.77H, m), 7.35-7.30 (2H, m), 6.88 (0.23H, dd, J=11.4, 4.6 Hz), 6.11-6.09 (0.12H, m), 5.99-5.94 (0.23H, m), 5.90-5.88 (0.12H, m), 5.82 (0.77H, ddd, 16.0, 5.8, 3.4 Hz), 5.50 (0.77H, ddd, 46.4, 6.2, 6.2 Hz), 4.79-4.70 (1H, m), 4.60-4.54 (2H, m), 3.93 (0.7H, s), 3.90 (2.3H, s)

$^{19}$F-NMR(CDCl$_3$) δ value:

−193.48 (0.77F, ddd, J=46.7, 15.9, 6.1 Hz), −202.59 (0.23F, ddd, J=47.1, 24.4, 11.2 Hz)

(6)

[Formula 185]

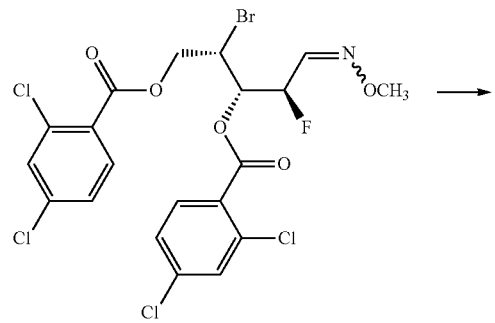

and water adduct thereof

A mixture of (2S,3S,4S)-2-bromo-3-((2,4-dichlorophenyl)carbonyloxy)-4-fluoro-5-oxopentyl=2,4-dichlorobenzoate and a water adduct thereof was obtained in the form of a colorless oily product in the same manner as that of Example 1(4), with the exception that the reaction was carried out at 70° C. for 6 hours.

$^1$H-NMR (CDCl$_3$) δ value:

9.84 (1H, d, J=6.0 Hz), 7.90-7.82 (2H, m), 7.50-7.45 (2H, m), 7.34-7.27 (2H, m), 5.89-4.05 (5H, m)

$^{19}$F-NMR(CDCl$_3$) δ value: −209.92 (1F, ddd, J=46.5, 20.6, 5.7 Hz)

(7)

[Formula 186]

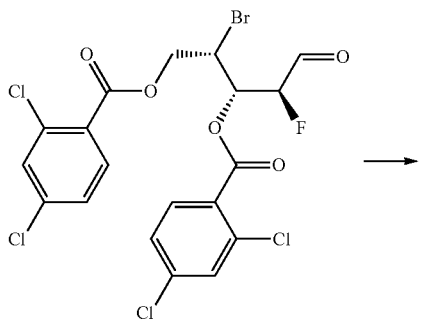

and water adduct thereof

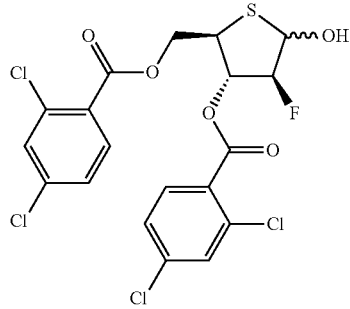

((2R,3S,4S)-3-((2,4-dichlorophenyl)carbonyloxy)-4-fluoro-5-hydroxythiolan-2-yl)methyl=2,4-dichlorobenzoate was obtained in the form of a colorless oily product in the same manner as that of Example 1(5), with the exception that the reaction was carried out for 4 hours.

$^{1}$H-NMR (CDCl$_3$) δ value:
7.93-7.78 (2H, m), 7.50-7.44 (2H, m), 7.35-7.30 (2H, m), 6.01-5.95 (0.59H, m), 5.84 (0.41H, dt, 11.6, 4.3 Hz), 5.63 (0.41H, dd, J=6.0, 6.0 Hz), 5.49 (0.59H, dd, J=7.8, 3.8 Hz), 5.37-5.36 (0.21H, m), 5.26-5.23 (0.50H, m), 5.13-5.10 (0.29H, m), 4.71-4.58 (1.2H, m), 4.53-4.43 (0.8H, m), 4.20-4.16 (0.41H, m), 3.74 (0.59H, dd, J=12.2, 6.7 Hz), 2.84 (0.59H, dd, J=5.5, 1.2 Hz), 2.56 (0.41H, d, J=9.0 Hz)

$^{19}$F-NMR(CDCl$_3$) δ value:
−183.85 (0.41F, dd, J=47.1, 11.1 Hz), −192.53 (0.59F, ddd, J=51.2, 11.3, 4.9 Hz)

(8)

[Formula 187]

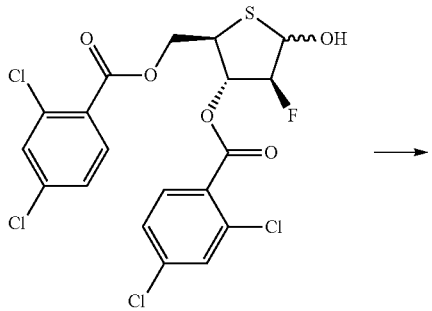

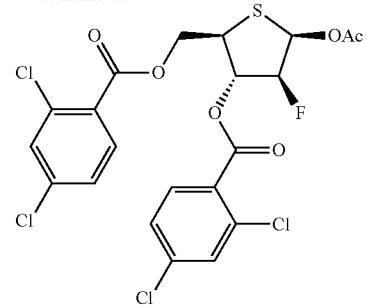

((2R,3S,4S,5R)-5-acetyloxy-3-((2,4-dichlorophenyl)carbonyloxy)-4-fluorothiolan-2-yl)methyl=2,4-dichlorobenzoate was obtained in the form of a colorless oily product in the same manner as that of Example 10(8).

$^{1}$H-NMR (CDCl$_3$) δ value:
7.79 (2H, d, J=8.4 Hz), 7.46 (2H, dd, J=22.8, 2.0 Hz), 7.27 (2H, ddd, J=30.4, 8.4, 2.0 Hz), 6.16 (1H, d, J=4.4 Hz), 6.03-5.98 (1H, m), 5.29 (1H, ddd, J=50.6, 8.8, 4.6 Hz), 4.40 (1H, ddd, J=7.06, 11.4, 6.4 Hz), 3.73 (1H, dd, J=13.6, 6.4 Hz), 2.15 (3H, s)

$^{19}$F-NMR(CDCl$_3$) δ value: −192.62 (1F, dd, J=50.6, 11.5 Hz)

Example 16

(1)

[Formula 188]

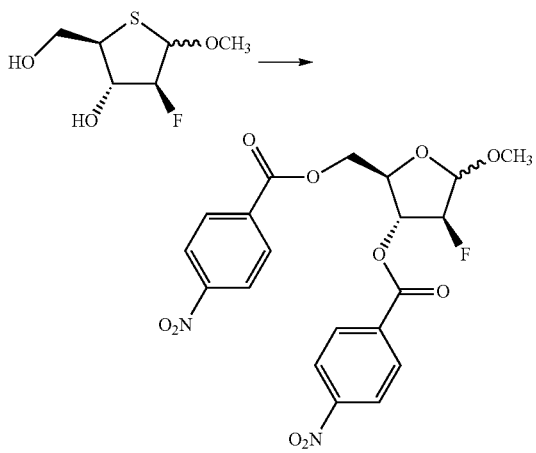

2.2 g of (2R,3R,4S)-4-fluoro-2-(hydroxymethyl)-5-methoxyoxolan-3-ol was dissolved in 26.4 mL of pyridine, and 6.1 g of 4-nitrobenzoyl chloride was then added to the obtained solution under cooling on ice. The obtained mixture was stirred at room temperature for 1 hour. Thereafter, ethyl acetate was added to the reaction mixture. The thus obtained mixture was washed with water twice, and then with a saturated sodium chloride aqueous solution once, and it was then dried over anhydrous sodium sulfate. After that, the solvent was distilled away under reduced pressure. Ethyl acetate was added to the obtained residue, and a solid was collected by filtration, so as to obtain 4.0 g of ((2R,3R,4S)-4-fluoro-5- methoxy-3-((4-nitrophenyl)carbonyloxy)oxolan-2-yl)methyl=4-nitrobenzoate in the form of a white solid.

$^1$H-NMR (DMSO-$d_6$) δ value:

8.38 (4H, d, J=8.6 Hz), 8.25 (2H, d, J=8.9 Hz), 8.22 (2H, d, J=8.9 Hz), 5.72 (1H, td, J=11.5, 5.8 Hz), 5.52 (1H, ddd, J=51.6, 6.5, 4.4 Hz), 5.16 (1H, d, J=4.3 Hz), 4.70 (1H, d, J=7.9 Hz), 4.54-4.50 (2H, m), 3.35 (3H, s)

(2)

[Formula 189]

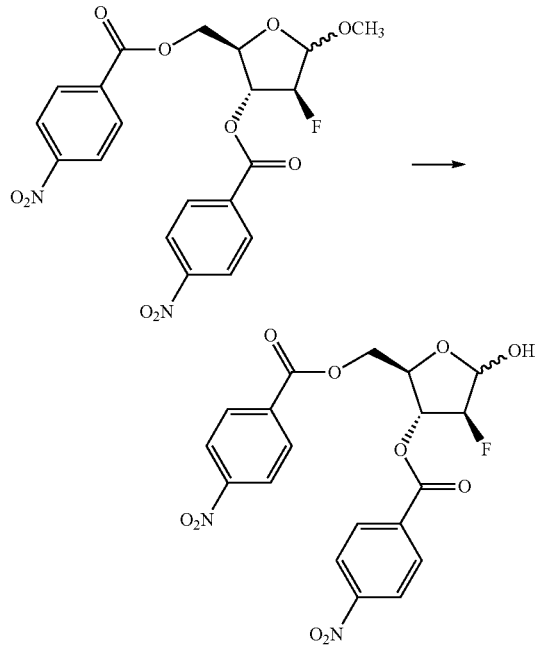

((2R,3R,4S)-4-fluoro-5-hydroxy-3-((4-nitrophenyl)carbonyloxy)oxolan-2-yl)methyl=4-nitrobenzoate was obtained in the form of a white solid in the same manner as that of Example 10(2).

$^1$H-NMR (DMSO-$d_6$) δ value:

8.39 (2H, d, J=5.9 Hz), 8.36 (2H, d, J=5.9 Hz), 8.21 (2H, d, J=5.9 Hz), 8.19 (2H, d, J=5.9 Hz), 5.53 (1H, d, J=10.9 Hz), 5.43 (1H, dd, J=23.1, 5.0 Hz), 5.18 (1H, d, J=49.2 Hz), 4.67 (3H, tdd, J=19.2, 9.9, 4.0 Hz), 3.31 (1H, s)

(3)

[Formula 190]

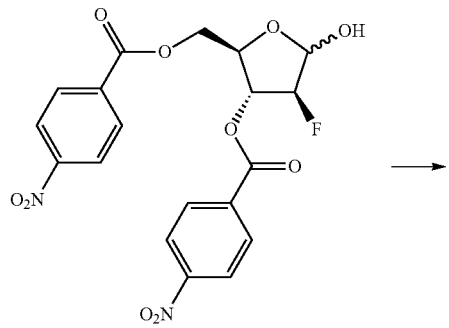

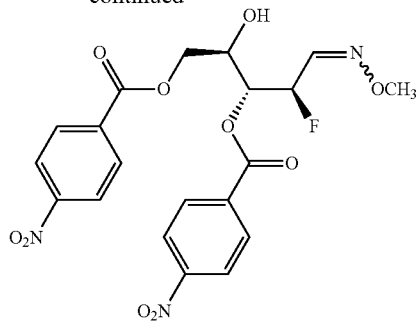

(2R,3R,4R)-3-((4-nitrophenyl)carbonyloxy)-4-fluoro-2-hydroxy-5-(methoxylmino)pentyl=4-nitrobenzoate was obtained in the form of a colorless oily product in the same manner as that of Example 1(1).

$^1$H-NMR (DMSO-$d_6$) δ value:

8.33 (2H, d, J=2.3 Hz), 8.30 (2H, d, J=2.6 Hz), 8.17 (2H, d, J=4.6 Hz), 8.14 (2H, t, J=3.8 Hz), 7.63 (1H, dd, J=8.3, 5.9 Hz), 6.20 (1H, dd, J=22.0, 7.1 Hz), 6.10 (1H, d, J=6.6 Hz), 5.46 (1H, dd, J=24.9, 8.4 Hz), 4.40 (2H, dt, J=14.0, 4.8 Hz), 3.86 (1H, s), 3.71 (3H, s)

(4)

[Formula 191]

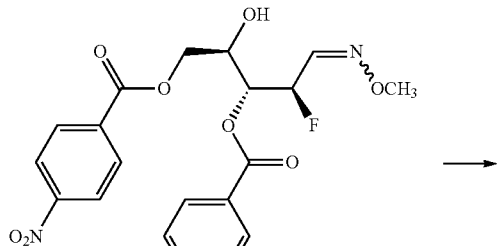

(2R,3R,4R)-3-((4-nitrophenyl)carbonyloxy)-4-fluoro-5-(methoxyimino)-2-(((2,4,5-trichlorophenyl)sulfonyl)oxy)pentyl=4-nitrobenzoate was obtained in the form of a colorless oily product in the same manner as that of Example 7(1).

¹H-NMR (DMSO-d₆) δ value:

8.36 (2H, d, J=5.0 Hz), 8.33 (2H, d, J=5.0 Hz), 8.23 (0.75H, s), 8.22 (0.25H, s), 8.18 (0.75H, s), 8.15 (0.25H, s), 8.11-8.06 (4H, m), 7.71 (0.25H, dd, J=8.1, 5.8 Hz), 7.51 (0.75H, dd, J=8.9, 5.6 Hz), 7.00 (0.25H, dd, J=11.6, 4.6 Hz), 6.14 (0.25H, dd, J=45.2, 4.3 Hz), 5.75-5.67 (1.50H, m), 4.85 (1H, dd, J=12.4, 3.1 Hz), 4.68 (2H, dt, J=26.4, 9.1 Hz), 3.79 (0.75H, s), 3.75 (2.25H, s)

(5)

[Formula 192]

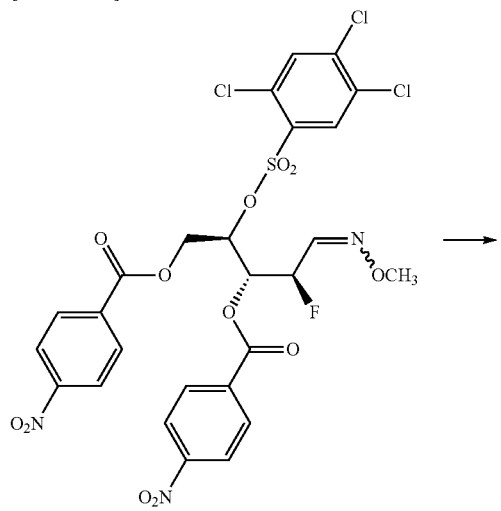

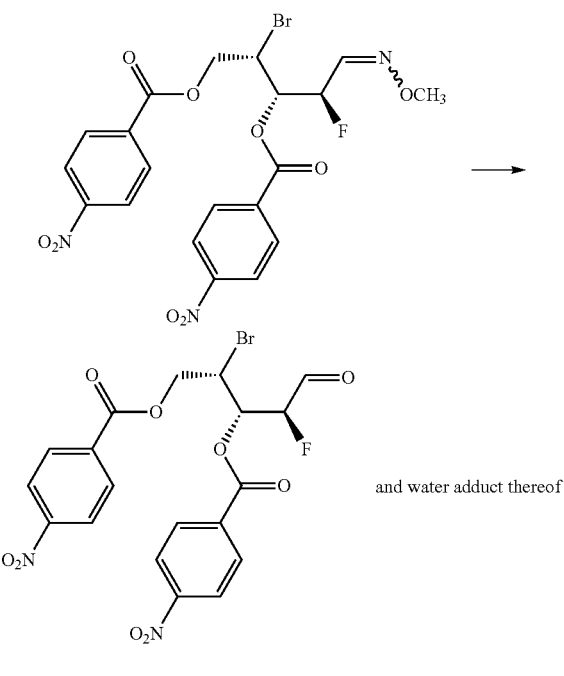

(6)

and water adduct thereof

A mixture of (2S,3S,4S)-3-((4-nitrophenyl)carbonyloxy)-2-bromo-4-fluoro-5-oxopentyl=4-nitrobenzoate and a water adduct thereof was obtained in the form of a colorless oily product in the same manner as that of Example 1(4).

¹H-NMR (DMSO-d₆) δ value:

9.67 (1H, d, J=8.3 Hz), 8.38 (2H, d, J=6.9 Hz), 8.34 (2H, d, J=8.9 Hz), 8.21 (2H, d, J=8.9 Hz), 8.12 (2H, d, J=8.9 Hz), 6.55 (1H, dd, J=21.3, 6.4 Hz), 5.61 (1H, dd, J=45.4, 4.8 Hz), 4.79 (2H, ddd, J=42.4, 21.1, 8.8 Hz), 4.59-4.40 (1H, m)

Example 17

(1)

[Formula 194]

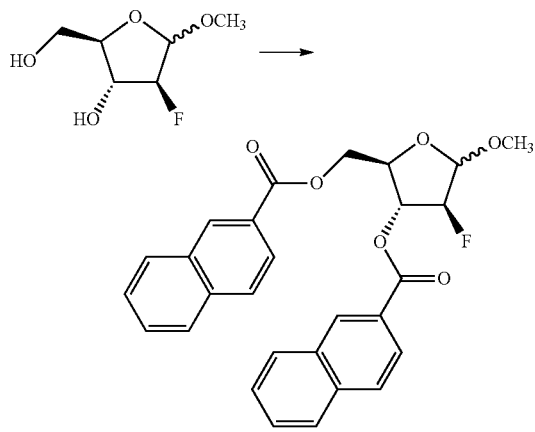

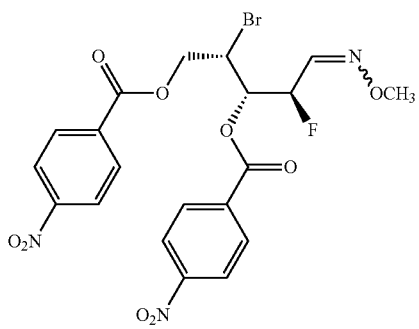

(2S,3S,4R)-3-((4-nitrophenyl)carbonyloxy)-2-bromo-4-fluoro-5-(methoxyimino)pentyl=4-nitrobenzoate was obtained in the form of a white solid in the same manner as that of Example 7(2).

¹H-NMR (DMSO-d₆) δ value:

8.39 (2H, d, J=8.9 Hz), 8.34 (2H, d, J=8.9 Hz), 8.20 (2H, d, J=8.9 Hz), 8.13 (2H, d, J=8.9 Hz), 7.78 (0.2H, t, J=6.4 Hz), 7.64 (0.8H, dd, J=7.6, 5.0 Hz), 5.92-5.88 (1H, m), 5.35 (1H, dt, J=46.0, 7.3 Hz), 5.15 (1H, dt, J=10.3, 4.0 Hz), 4.72 (2H, dt, J=20.0, 8.8 Hz), 3.84 (0.6H, s), 3.63 (2.4H, s)

4.0 g of (2R,3R,4S)-4-fluoro-2-(hydroxymethyl)-5-methoxyoxolan-3-ol was dissolved in 40 mL of pyridine, and 10.1 g of 2-naphthoyl chloride was then added to the obtained solution under cooling on ice. The obtained mixture was stirred at room temperature for 2 hours. Thereafter, water and ethyl acetate were added to the reaction mixture. The organic layer was fractionated, and it was washed with 1 mol/L hydrochloric acid three times, and then with a saturated sodium chloride aqueous solution once, and it was then dried over anhydrous sodium sulfate. After that, the solvent was distilled away under reduced pressure. The obtained residue was purified by column chromatography (ethyl acetate/hexane=1/9 to 5/5), so as to obtain 5.7 g of ((2R,3R,4S)-4-fluoro-5-methoxy-3-((2-naphthoyloxy)oxolan-2-yl)methyl=2-naphthoate in the form of a white solid.

$^1$H-NMR (DMSO-$d_6$) δ value:
8.67 (1H, s), 8.63 (1H, s), 8.14 (1H, d, J=7.9 Hz), 8.07-8.00 (6H, m), 7.69-7.59 (5H, m), 5.55 (1H, dd, J=23.9, 4.8 Hz), 5.38 (1H, d, J=18.2 Hz), 5.28 (1H, d, J=20.5 Hz), 4.76-4.68 (3H, m), 3.42 (3H, s)

(2)

[Formula 195]

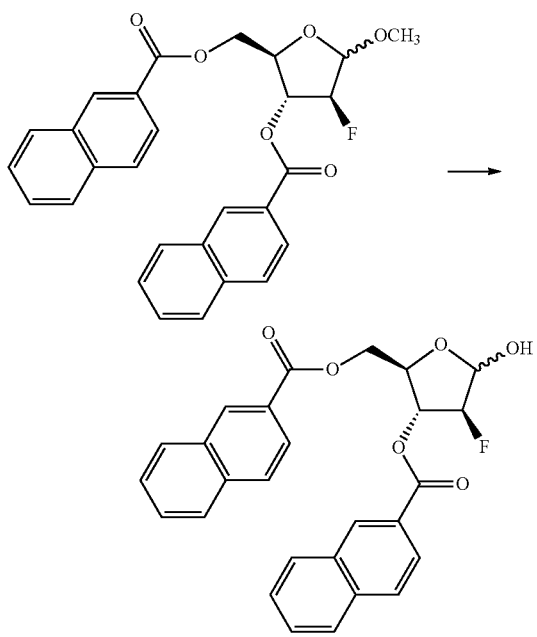

((2R,3R,4S)-4-fluoro-5-hydroxy-3-((2-naphthoyl)oxy)oxolan-2-yl)methyl=2-naphthoate was obtained in the form of a colorless oily product in the same manner as that of Example 10(2).

$^1$H-NMR (CDCl$_3$) δ value:
8.63 (2H, d, J=7.3 Hz), 8.10-8.03 (2H, m), 7.90 (6H, m), 7.56 (4H, m), 5.76 (1H, d, J=10.9 Hz), 5.61 (1H, dd, J=22.1, 4.3 Hz), 5.27 (1H, d, J=49.2 Hz), 4.83 (2H, dt, J=110.7, 4.0 Hz), 4.72 (1H, dd, J=12.9, 6.3 Hz), 3.09 (1H, s)

(3)

[Formula 196]

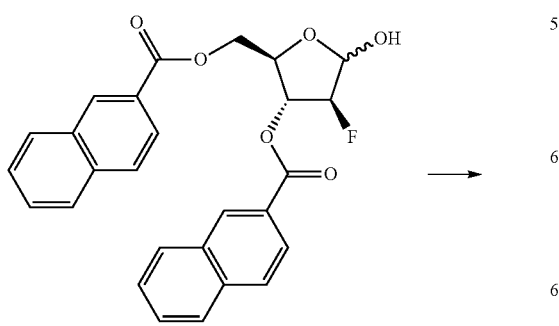

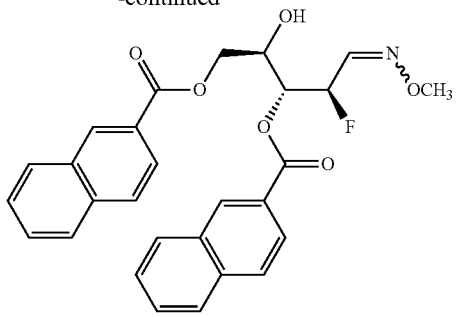

(2R,3R,4R)-4-fluoro-2-hydroxy-5-(methoxyimino)-3-(2-naphthoyloxyl)pentyl=2-naphthoate was obtained in the form of a colorless oily product in the same manner as that of Example 1(1).

$^1$H-NMR (DMSO-$d_6$) δ value:
8.33 (2H, d, J=2.3 Hz), 8.30 (2H, d, J=2.6 Hz), 8.17 (2H, d, J=4.6 Hz), 8.14 (2H, t, J=3.8 Hz), 7.63 (1H, dd, J=8.3, 5.9 Hz), 6.20 (1H, dd, J=22.0, 7.1 Hz), 6.10 (1H, d, J=6.6 Hz), 5.46 (1H, dd, J=24.9, 8.4 Hz), 4.40 (2H, dt, J=14.0, 4.8 Hz), 3.86 (1H, s), 3.71 (3H, s)

(4)

[Formula 197]

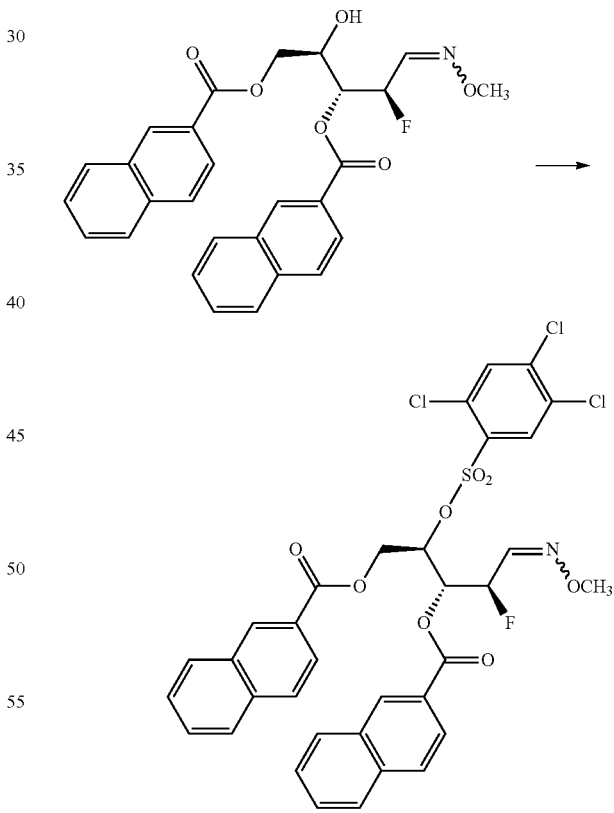

(2R,3R,4R)-4-fluoro-5-(methoxyimino)-3-(2-naphthoyloxy)-2-(((2,4,5-trichlorophenyl)sulfonyl)oxy)pentyl=2-naphthoate was obtained in the form of a white solid in the same manner as that of Example 7(1).

$^1$H-NMR (CDCl$_3$) δ value:
8.61 (1H, s), 8.49 (1H, s), 8.09 (0.3H, s), 8.08 (0.7H, s), 8.03-7.83 (8H, m), 7.65-7.53 (4H, m), 7.47 (0.7H, t, J=6.8

Hz), 7.32 (0.3H, s), 6.89 (0.3H, dd, J=11.1, 4.5 Hz), 6.11 (0.7H, ddd, J=26.3, 5.7, 2.7 Hz), 5.92 (1H, dq, J=22.9, 3.0 Hz), 5.57 (1H, dq, J=16.0, 3.1 Hz), 5.48 (1H, dq, J=20.2, 3.2 Hz), 4.84 (1H, ddd, J=12.6, 7.9, 3.0 Hz), 4.67 (1H, dd, J=12.9, 6.3 Hz), 3.94 (0.9H, s), 3.86 (2.1H, s)

(5)

[Formula 198]

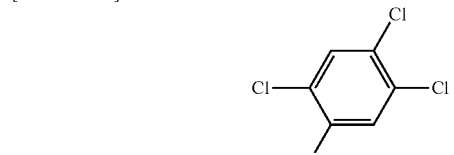

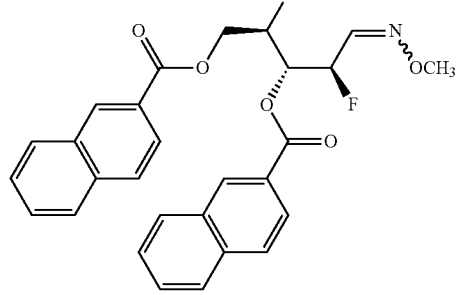

(2S,3S,4R)-2-bromo-4-fluoro-5-(methoxyimino)-3-(2-naphthoyloxyl)pentyl=2-naphthoate was obtained in the form of a colorless oily product in the same manner as that of Example 7(2).

$^1$H-NMR (CDCl$_3$) δ value:

8.67 (0.2H, s), 8.61 (0.8H, s), 8.57 (0.2H, s), 8.11 (0.8H, t, J=4.3 Hz), 8.04 (1H, dd, J=8.6, 1.7 Hz), 7.92-7.87 (7H, m), 7.61-7.54 (5H, m), 6.93 (0.2H, dd, J=11.2, 4.6 Hz), 6.04 (0.8H, dq, J=21.1, 3.1 Hz), 5.92 (1H, dq, J=16.8, 3.0 Hz), 5.61 (1H, dt, J=46.7, 6.2 Hz), 4.88-4.82 (1H, m), 4.78-4.66 (2H, m), 3.89 (2.4H, s), 3.86 (0.6H, s)

(6)

[Formula 199]

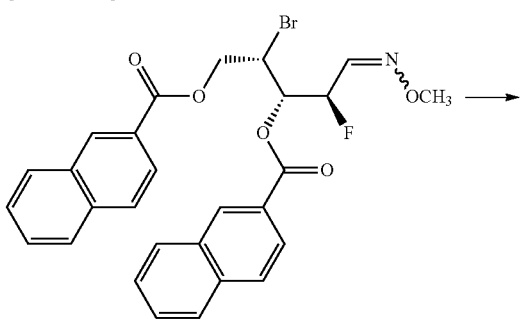

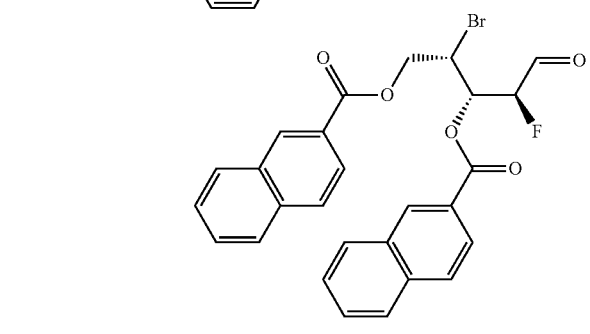

and water adduct thereof

A mixture of (2S,3S,4S)-2-bromo-4-fluoro-3-(2-naphthoyloxy)-5-oxopentyl=2-naphthoate and a water adduct thereof was obtained in the form of a colorless oily product in the same manner as that of Example 1(4).

$^1$H-NMR (CDCl$_3$) δ value:
9.88 (1H, d, J=6.3 Hz), 8.60 (2H, d, J=14.5 Hz), 8.02 (2H, td, J=8.8, 1.8 Hz), 7.92-7.84 (5H, m), 7.59-7.51 (5H, m), 5.95 (1H, dt, J=21.4, 3.8 Hz), 5.56 (1H, d, J=4.0 Hz), 5.41 (1H, d, J=4.0 Hz), 4.81-4.69 (2H, m)

(7)

[Formula 200]

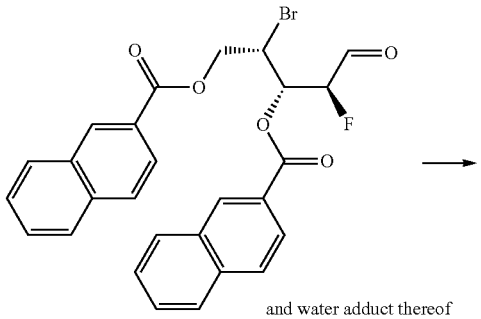

and water adduct thereof

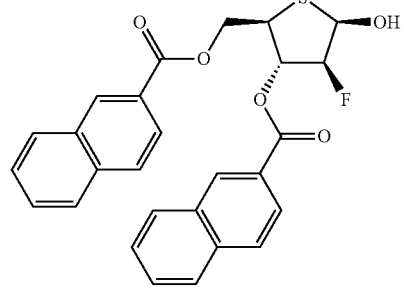

((2R,3S,4S,5R)-4-fluoro-5-hydroxy-3-((2-naphthoyl)oxy)thiolan-2-yl)methyl=2-naphthoate was obtained in the form of a white solid in the same manner as that of Example 1(5).

$^1$H-NMR (CDCl$_3$) δ value:
8.58 (1H, d, J=20.8 Hz), 8.49 (1H, d, J=13.5 Hz), 8.05 (0.5H, dd, J=8.6, 1.7 Hz), 7.97 (1H, dt, J=8.3, 2.1 Hz), 7.90-7.82 (4H, m), 7.71 (2H, td, J=13.8, 5.9 Hz), 7.60-7.46 (4H, m), 7.38 (0.5H, t, J=7.6 Hz), 6.23-6.14 (0.5H, m), 5.96-5.91 (0.5H, m), 5.67 (0.5H, d, J=10.6 Hz), 5.42 (0.5H, dt, J=32.3, 3.1 Hz), 5.32 (0.5H, t, J=6.4 Hz), 5.19 (0.5H, dd, J=7.3, 4.0 Hz), 4.75-4.67 (1H, m), 4.62 (1H, dd, J=14.5, 6.3 Hz), 4.34 (0.5H, dd, J=7.8, 4.1 Hz), 3.88 (0.5H, dd, J=13.4, 6.1 Hz), 3.05 (0.5H, s), 2.67 (0.5H, s)

(8)

[Formula 201]

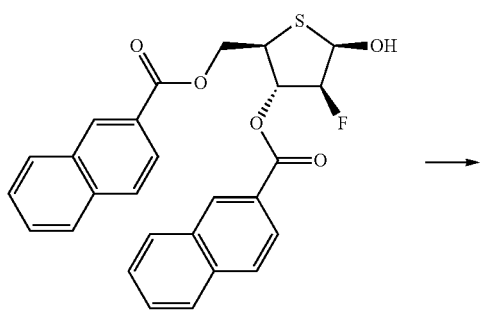

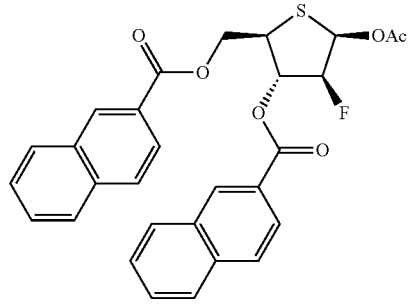

((2R,3S,4S,5R)-5-acetyloxy-4-fluoro-3-((2-naphthoyl)oxy)thiolan-2-yl)methyl=2-naphthoate was obtained in the form of a white solid in the same manner as that of Example 10(8).

$^1$H-NMR (CDCl$_3$) δ value:
8.60 (0.35H, s), 8.58 (0.35H, s), 8.53 (0.65H, s), 8.42 (0.65H, s), 8.03 (0.70H, d, J=8.6 Hz), 7.94 (1.30H, ddd, J=13.2, 8.6, 10.7 Hz), 7.87-7.47 (9.35H, m), 7.35 (0.65H, t, J=6.9 Hz), 6.9-6.08 (2H, m), 5.56-5.28 (1H, m), 4.75 (0.70H, dd, J=11.4, 7.1 Hz), 4.60 (1.30H, t, J=8.1 Hz), 4.24-4.21 (0.35H, m), 3.88 (0.65H, q, J=6.8 Hz), 2.16 (1.05H, s), 2.16 (1.95H, s)

(9)

[Formula 202]

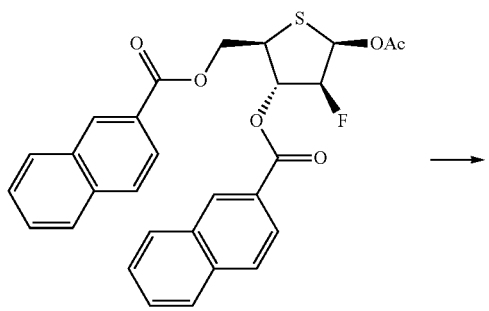

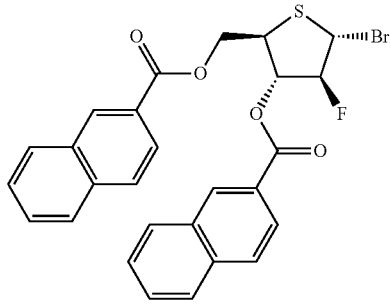

((2R,3S,4S,5R)-5-bromo-4-fluoro-3-((2-naphthoyl)oxy)thiolan-2-yl)methyl=2-naphthoate was obtained in the form of a white solid in the same manner as that of Example 1(7).

$^1$H-NMR (CDCl$_3$) δ value:
8.65 (2H, d, J=27.6 Hz), 8.11-7.80 (8H, m), 7.64-7.47 (4H, m), 5.96 (0.5H, brs), 5.91 (0.5H, brs), 5.82 (0.5H, brs), 5.78 (0.5H, brs), 5.74 (0.5H, brs), 5H, brs), 5.66 (0.5H, brs), 4.76-4.62 (2H, m), 4.48-4.42 (1H, m)

$^{19}$F-NMR(CDCl$_3$) δ value: −163.66 (1F, dd, J=48.0, 14.5 Hz)

(10)

[Formula 203]

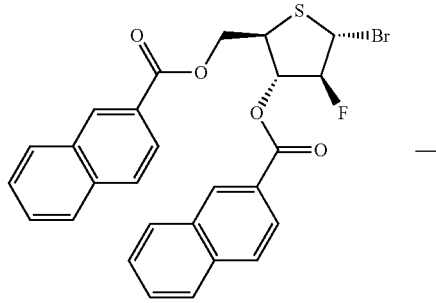

((2R,3S,4S,5R)-5-(4-acetamido-2-oxo-1,2-dihydropyrimidin-1-yl)-4-fluoro-3-((2-naphthoyl)oxy)thiolan-2-yl)methyl=2-naphthoate was obtained in the form of a white solid in the same manner as that of Example 22(2).

m/z (ESI-positive): 664.6[M+H]$^+$ $^{19}$F-NMR(CDCl$_3$) δ value: −195.71 (1F, ddd, J=49.6, 22.7, 9.0 Hz)

(11)

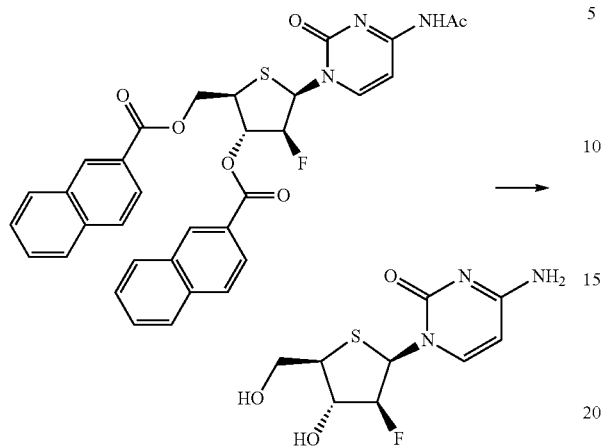

(2R,3S,4S,5R)-3-hydroxy-2-hydroxymethyl-5-(4-amino-2-oxo-1,2-dihydropyrimidin-1-yl)-4-fluorothiolane was obtained in the same manner as that of Example 1(8).

(1)

Example 18

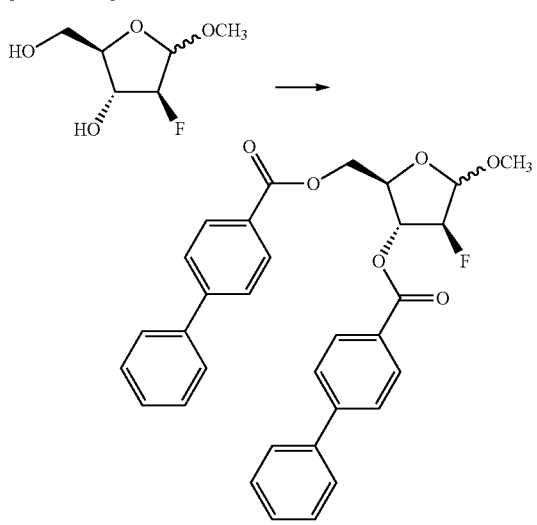

2.5 g of (2R,3R,4S)-4-fluoro-2-(hydroxymethyl)-5-methoxyoxolan-3-ol was dissolved in 25 mL of pyridine, and 7.2 g of 4-phenylbenzoyl chloride was then added to the obtained solution under cooling on ice. The obtained mixture was stirred at room temperature for 2 hours. Thereafter, ethyl acetate was added to the reaction mixture. The thus obtained mixture was washed with water twice, and then with a saturated sodium chloride aqueous solution once, and it was then dried over anhydrous sodium sulfate. After that, the solvent was distilled away under reduced pressure. The obtained residue was purified by column chromatography (ethyl acetate/hexane=1/9 to 6/4), so as to obtain 3.3 g of ((2R,3R,4S)-3-(((1,1-biphenyl)-4-carbonyl)oxy)-4-fluoro-5-methoxyoxolan-2-yl)meth yl=(1,1'-biphenyl)-4-carboxylate in the form of a white solid.

$^1$H-NMR (DMSO-$d_6$) δ value:

8.05 (4H, dd, J=8.4, 1.8 Hz), 7.86 (2H, d, J=8.6 Hz), 7.82 (2H, d, J=8.6 Hz), 7.76-7.72 (4H, m), 7.50-7.45 (6H, m), 5.48 (1H, dd, J=23.8, 5.0 Hz), 5.34 (1H, d, J=9.6 Hz), 5.24 (1H, d, J=28.7 Hz), 4.71-4.59 (3H, m), 3.40 (3H, s)

(2)

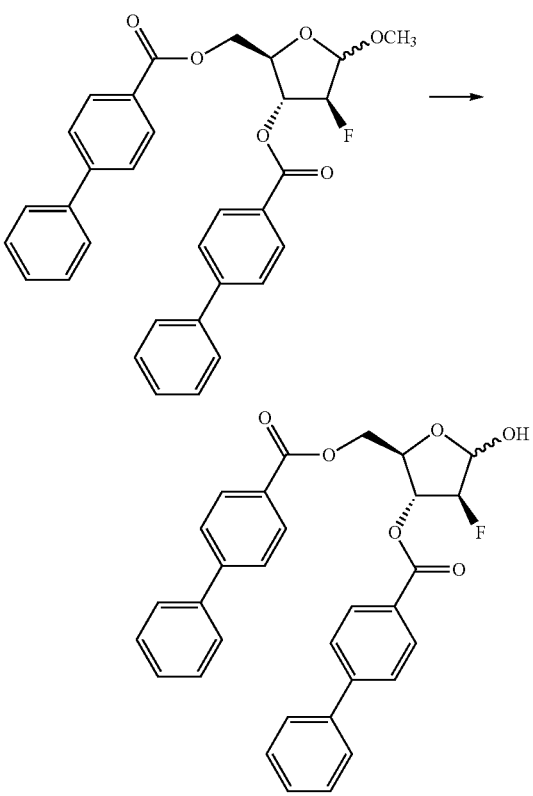

((2R,3R,4S)-3-(((1,1-biphenyl)-4-carbonyl)oxy)-4-fluoro-5-hydroxyoxolan-2-yl)methyl=(1,1'-biphenyl)-4-carboxylate was obtained in the form of a white solid in the same manner as that of Example 10(2).

$^1$H-NMR (DMSO-$d_6$) δ value:

8.06 (4H, t, J=8.6 Hz), 7.86 (2H, d, J=8.6 Hz), 7.81 (2H, d, J=8.6 Hz), 7.77-7.72 (4H, m), 7.52-7.45 (6H, m), 7.07 (1H, dd, J=4.0, 2.6 Hz), 5.54 (1H, dd, J=10.6, 4.3 Hz), 5.44 (1H, dd, J=23.4, 4.6 Hz), 5.15 (1H, d, J=49.9 Hz), 4.68-4.58 (3H, m)

(3)

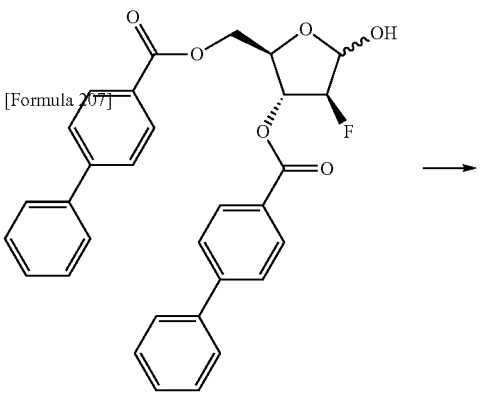

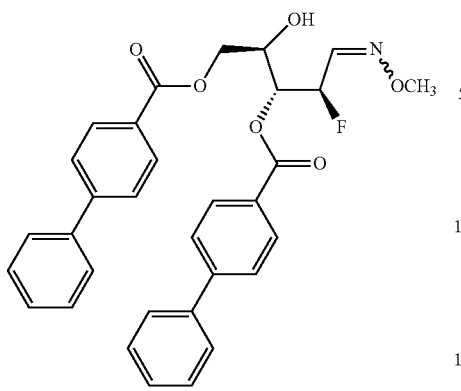

(2R,3R,4R)-3-(((1,1-biphenyl)-4-carbonyl)oxy)-4-fluoro-2-hydroxy-5-(methoxyimino)pentyl=(1,1-biphenyl)-4-carboxylate was obtained in the form of a white solid in the same manner as that of Example 1(1).

$^1$H-NMR (DMSO-$d_6$) δ value:

8.09-7.98 (4H, m), 7.88-7.68 (8H, m), 7.50-7.44 (6H, m), 7.12 (0.3H, dd, J=10.6, 4.6 Hz), 6.06 (1.7H, ddd, J=32.5, 14.2, 5.6 Hz), 5.54 (2H, tt, J=39.1, 7.7 Hz), 5.15 (0.3H, d, J=48.9 Hz), 4.69-4.57 (0.7H, m), 4.41-4.26 (2H, m), 3.88 (0.9H, s), 3.75 (2.1H, s)

(4)

[Formula 208]

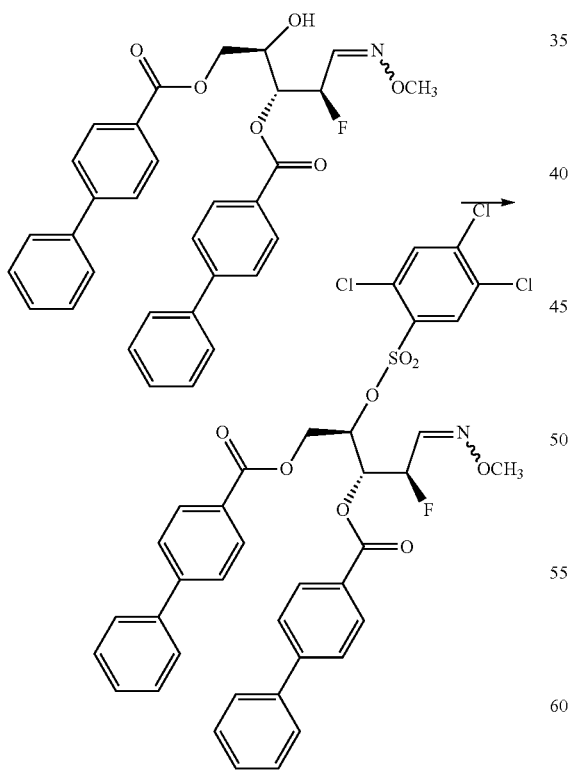

(2R,3R,4R)-3-(((1,1-biphenyl)-4-carbonyl)oxy)-4-fluoro-5-(methoxyimino)-2-(((2,4,5-trichlorophenyl)sulfonyl)oxy)pentyl=(1,1'-biphenyl)-4-carboxylate was obtained in the form of a colorless oily product in the same manner as that of Example 7 (1).

$^1$H-NMR (DMSO-$d_6$) δ value:

8.14 (1H, s), 8.05 (2H, dd, J=19.7, 11.1 Hz), 7.97 (1H, s), 7.81 (8H, m), 7.50 (8H, m), 7.20 (0.5H, dd, J=11.2, 4.6 Hz), 6.09 (0.5H, dq, J=48.2, 3.1 Hz), 5.86 (1H, dt, J=23.1, 3.8 Hz), 5.68 (2H, tt, J=29.9, 9.4 Hz), 4.70 (2H, dt, J=27.4, 9.7 Hz), 3.79 (3H, s)

(5)

[Formula 209]

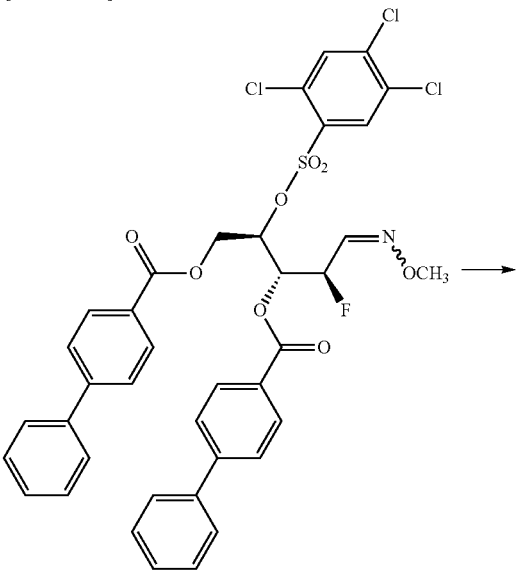

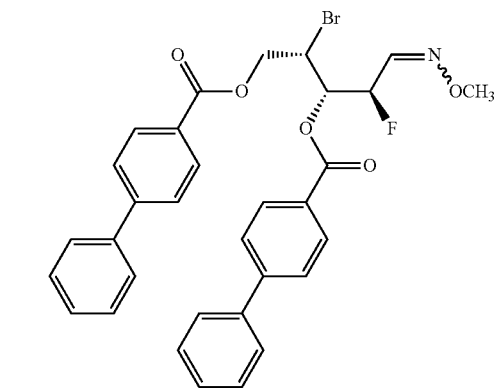

(2S,3S,4R)-3-(((1,1'-biphenyl)-4-carbonyl)oxy)-2-bromo-4-fluoro-5-(methoxy imino)pentyl=(1,1'-biphenyl)-4-carboxylate was obtained in the form of a colorless oily product in the same manner as that of Example 7(2).

$^1$H-NMR (DMSO-$d_6$) δ value:

8.10-8.01 (2H, m), 7.95 (1H, d, J=8.6 Hz), 7.88-7.83 (3H, m), 7.80 (1H, d, J=6.6 Hz), 7.68 (5H, m), 7.47 (6H, m), 6.01-5.93 (1H, m), 5.46 (1H, dt, J=47.4, 6.9 Hz), 5.05 (1H, t, J=45.2 Hz), 4.71 (3H, ddd, J=25.6, 14.5, 7.8 Hz), 3.86 (3H, s)

(6)

[Formula 210]

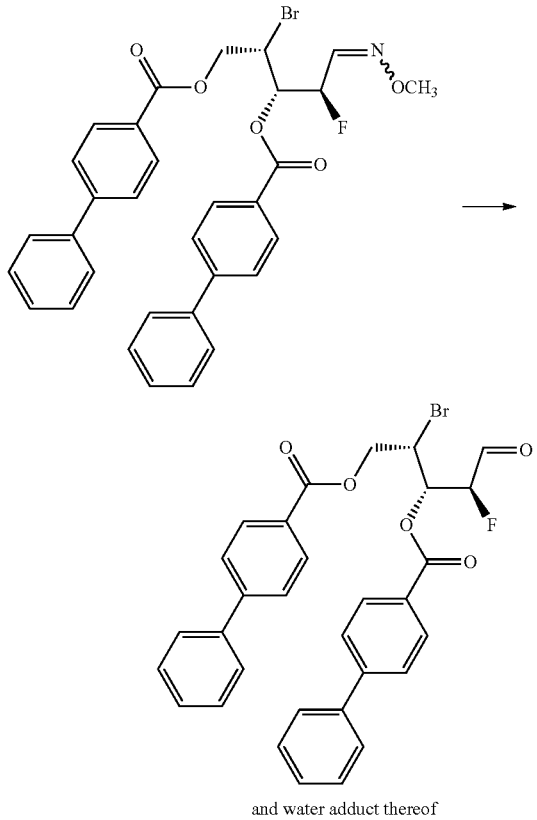

and water adduct thereof

A mixture of (2S,3S,4S)-3-(((1,1-biphenyl)-4-carbonyl)oxy)-2-bromo-4-fluoro-5-oxopentyl=(1,1-biphenyl)-4-carboxylate and a water adduct thereof was obtained in the form of a white solid in the same manner as that of Example 1(4).

¹H-NMR (DMSO-d₆) δ value:
9.69 (1H, d, J=9.9 Hz), 8.06 (2H, m), 8.00 (2H, d, J=7.3 Hz), 7.86 (2H, dd, J=8.6, 2.6 Hz), 7.77 (2H, dd, J=8.4, 4.1 Hz), 7.70 (3H, d, J=12.6 Hz), 7.53-7.43 (7H, m), 6.55 (1H, dd, J=20.1, 5.9 Hz), 6.06 (1H, ddd, J=22.1, 5.0, 3.3 Hz), 5.82 (1H, dq, J=14.9, 4.0 Hz), 5.01-4.95 (1H, m), 4.77-4.67 (1H, m)

(7)

[Formula 211]

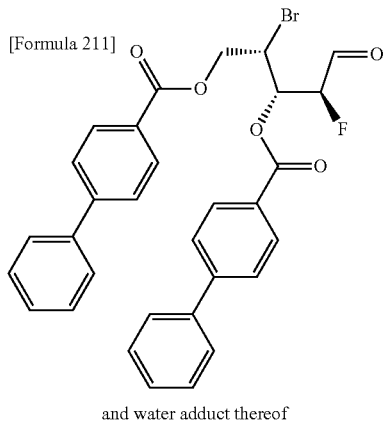

and water adduct thereof

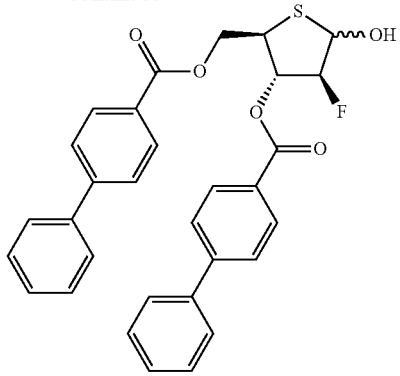

((2R,3S,4S)-3-(((1,1-biphenyl)-4-carbonyl)oxy)-4-fluoro-5-hydroxythiolan-2-yl)methyl=(1,1'-biphenyl)-4-carboxylate was obtained in the form of a white solid in the same manner as that of Example 1(5).

¹H-NMR (DMSO-d₆) δ value:
8.04 (2H, dd, J=8.6, 2.3 Hz), 7.87 (2H, t, J=8.4 Hz), 7.79 (2H, dd, J=8.6, 3.0 Hz), 7.71-7.67 (2H, m), 7.63-7.39 (10 OH, m), 6.84 (1H, dd, J=6.1, 10.8 Hz), 6.09 (0.5H, dt, J=14.2, 5.9 Hz), 5.76 (0.5H, dd, J=14.5, 6.9 Hz), 5.66 (0.5H, dt, J=14.4, 5.4 Hz), 5.39-5.30 (1H, m), 5.18 (0.5H, dt, J=17.2, 5.1 Hz), 4.48 (2H, ddd, J=29.3, 15.8, 9.3 Hz), 4.18 (0.5H, dd, J=12.9, 7.3 Hz), 3.83 (0.5H, dd, J=13.2, 7.3 Hz)

(8)

[Formula 212]

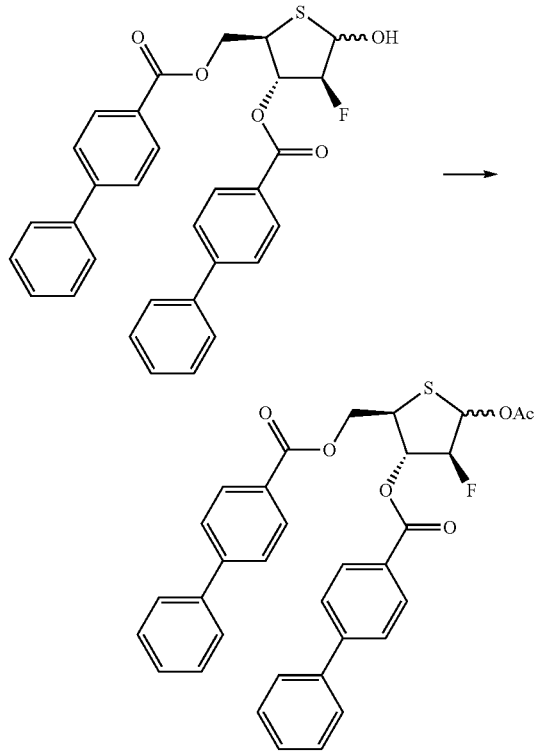

((2R,3S,4S)-3-(((1,1-biphenyl)-4-carbonyl)oxy)-5-acetyloxy-4-fluorothiolan-2-yl)methyl=(1,1'-biphenyl)-4-carboxylate was obtained in the form of a white solid in the same manner as that of Example 10(8).

¹H-NMR (CDCl₃) δ value:
8.11 (0.5H, d, J=8.6 Hz), 8.07 (2H, d, J=8.6 Hz), 7.98 (1.5H, d, J=8.6 Hz), 7.67-7.38 (14H, m), 6.25 (0.25H, t, J=6.9 Hz), 6.14 (1.5H, tt, J=10.7, 3.7 Hz), 5.89 (0.25H, td, J=8.5, 4.2 Hz), 5.42 (0.25H, ddd, J=48.0, 4.0, 2.6 Hz), 5.33 (0.75H, ddd, J=50.7, 9.1, 4.5 Hz), 4.69 (1H, dd, J=11.4, 6.8 Hz), 4.54 (1H, dd, J=10.9, 6.6 Hz), 4.15 (0.25H, ddd, J=13.2, 6.8, 2.1 Hz), 3.79 (0.75H, q, J=6.8 Hz), 2.17 (2.25H, d, J=2.3 Hz), 2.14 (0.75H, s)

(9)

[Formula 213]

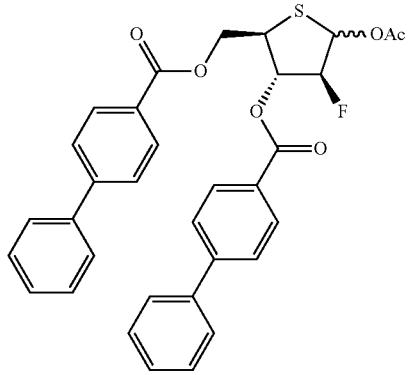

((2R,3S,4S,5R)-3-(((1,1-biphenyl)-4-carbonyl)oxy)-5-bromo-4-fluorothiolan-2-yl)methyl=(1,1-biphenyl)-4-carboxylate was obtained in the form of a colorless oily product in the same manner as that of Example 1(7).

¹H-NMR (CDCl₃) δ value:
8.14 (2H, dd, J=21.0, 8.4 Hz), 7.69-7.37 (16H, m), 5.89-5.70 (0.5H, m), 5.84-5.82 (0.5H, m), 5.78-5.77 (0.5H, m), 5.75 (0.5H, brs), 5.71 (0.5H, brs), 5.62-5.61 (0.5H, m), 4.70-4.56 (2H, m), 4.40-4.34 (1H, m)

¹⁹F-NMR (282.37 MHz, CDCl₃) δ value: -163.62 (1F, dd, J=48.9, 14.3 Hz)

(10)

[Formula 214]

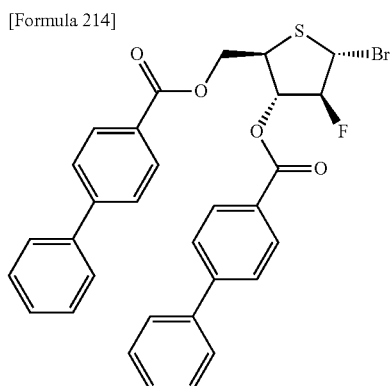

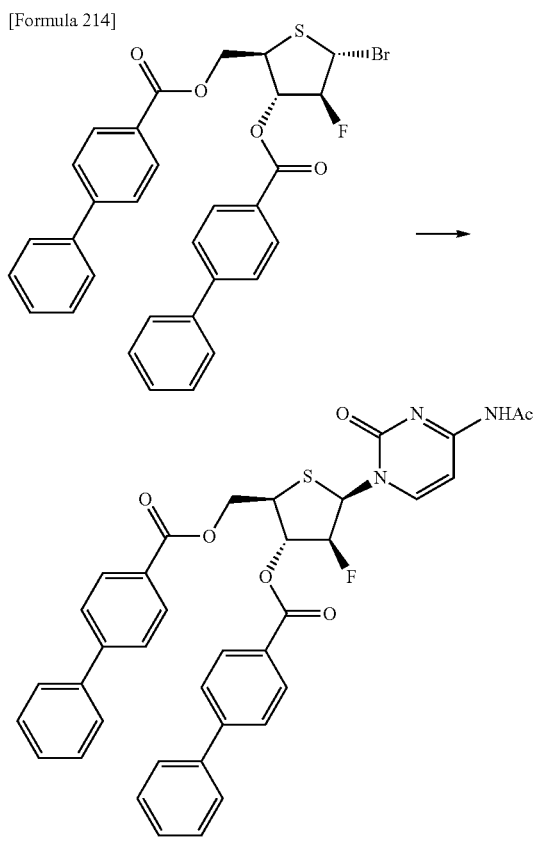

Using a methylene chloride solution of ((2R,3S,4S,5R)-3-(((1,1-biphenyl)-4-carbonyl)oxy)-5-bromo-4-fluorothiolan-2-yl)methyl=(1,1-biphenyl)-4-carboxylate, ((2R,3S,4S,5R)-5-(4-acetamido-2-oxo-1,2-dihydropyrimidin-1-yl)-4-fluoro-3-(((1,1-biphenyl)-4-carbonyl)oxy)thiolan-2-yl)methyl=(1,1'-biphenyl)-4-carboxylate was obtained in the form of a white solid in the same manner as that of Example 22(2).

m/z (ESI-positive): 612.6[M+H]⁺

¹⁹F-NMR(CDCl₃) δ value: -195.70 (1F, ddd, J=49.6, 22.7, 9.0 Hz)

(11)

[Formula 215]

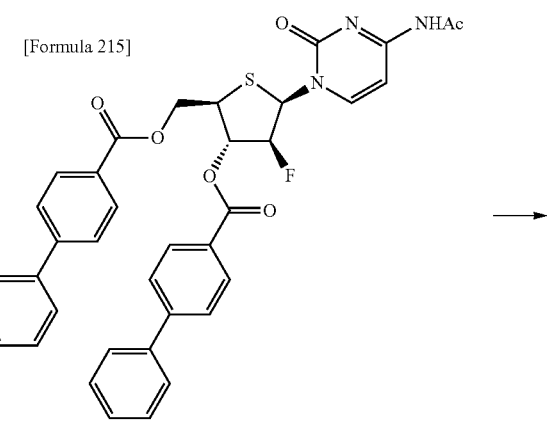

-continued

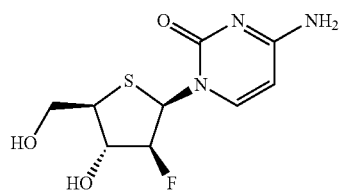

(2R,3S,4S,5R)-3-hydroxy-2-hydroxymethyl-5-(4-amino-2-oxo-1,2-dihydropyrimidin-1-yl)-4-fluorothiolane was obtained in the same manner as that of Example 1(8).

Example 19

(1)

[Formula 216]

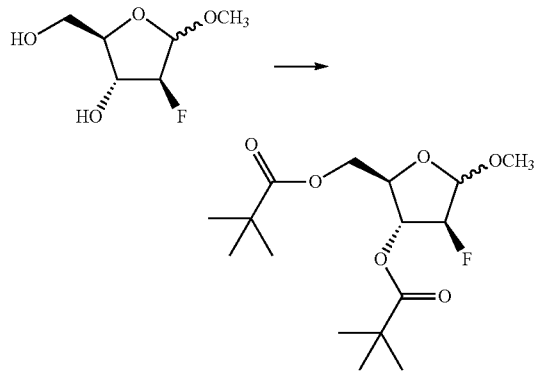

((2R,3R,4S)-3-(2,2-dimethylpropionyloxy)-4-fluoro-5-methoxyoxolan-2-yl)methyl=trimethylacetate was obtained in the form of a white solid in the same manner as that of Example 10(1), with the exception that the reaction time was set at 2 hours.

¹H-NMR (CDCl₃) δ value:

5.11-5.04 (2H, m), 4.80 (1H, d, J=47.6 Hz), 4.42 (1H, dd, J=12.0, 3.6 Hz), 4.27 (1H, dd, J=12.0, 40.4 Hz), 4.17 (1H, m), 3.39 (3H, s), 1.21 (18H, m)

¹⁹F-NMR(CDCl₃) δ value: −190.55 (1F, ddd, J=49.5, 23.0, 10.5 Hz)

(2)

[Formula 217]

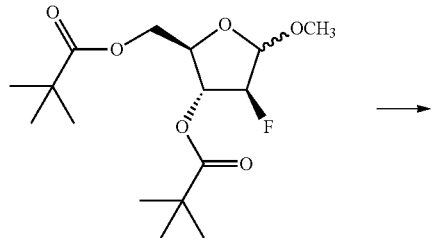

-continued

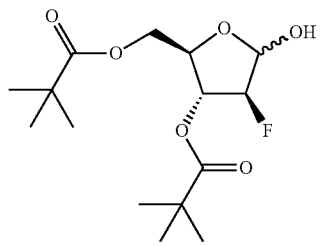

((2R,3R,4S)-3-(2,2-dimethylpropionyloxy)-4-fluoro-5-hydroxyoxolan-2-yl)methyl=trimethylacetate was obtained in the form of a colorless oily product in the same manner as that of Example 10(2).

¹H-NMR (CDCl₃) δ value:

5.57 (1H, dd, J=10.4, 4.0 Hz), 5.11 (1H, dd, J=22.0, 3.6 Hz), 4.92 (1H, d, J=49.6 Hz), 4.42-4.35 (2H, m), 4.27-4.23 (1H, m), 2.96 (1H, dd, J=11.8, 3.2 Hz), 1.21 (9H, s), 1.20 (9H, s)

¹⁹F-NMR(CDCl₃) δ value: −190.09 (1F, ddd, J=49.8, 22.6, 11.2, Hz)

(3)

[Formula 218]

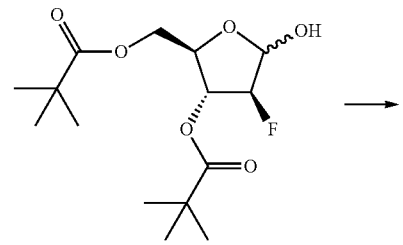

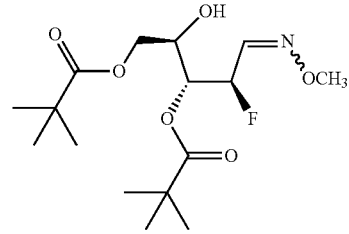

(2R,3R,4R)-3-(2,2-dimethylpropionyloxy)-4-fluoro-2-hydroxy-5-(methoxyimino)pentyl=trimethylacetate was obtained in the form of a white solid in the same manner as that of Example 1(1).

¹H-NMR (CDCl₃) δ value:

7.29 (0.73H, dd, J=8.1, 6.4 Hz), 6.75 (0.27H, dd, J=110.3, 4.6 Hz), 5.91 (0.27H, ddd, J=46.5, 4.6, 1.8 Hz), 5.43 (0.73H, ddd, J=45.3, 6.4, 2.3 Hz), 5.38 (0.27H, ddd, J=28.6, 8.7, 1.8 Hz), 4.74 (0.73H, ddd, J=25.7, 8.8, 2.4 Hz), 4.27-3.91 (3H, m), 3.91 (0.80H, s), 3.88 (2.20H, s), 2.78 (0.73H, d, J=6.4 Hz), 2.73 (0.27H, d, J=6.4 Hz), 1.23 (9H, s), 1.22 (9H, s)

¹⁹F-NMR(CDCl₃) δ value:

−201.5 (0.7F, ddd, J=43.5, 23.8, 6.2 Hz), −208.1 (0.3F, ddd, J=46.5, 28.7, 11.6 Hz)

(4)

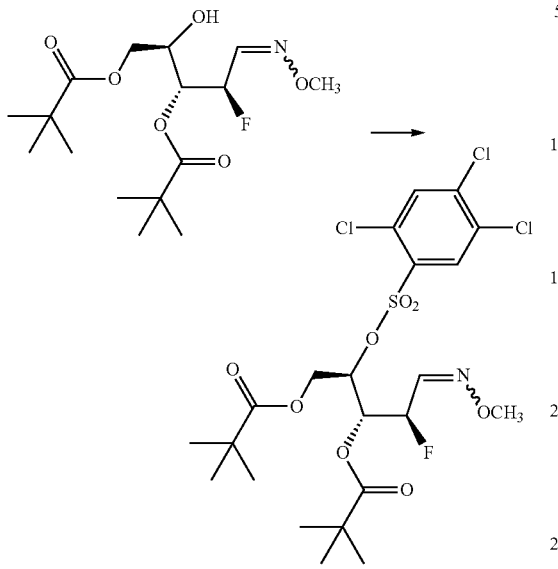

(2R,3R,4R)-5-(2,2-dimethylpropionyloxy)-2-fluoro-1-(methoxyimino)-4-(((2,4,5-trichlorobenzene)sulfonyl)oxy)pentan-3-yl=trimethylacetate was obtained in the form of a colorless oily product in the same manner as that of Example 7(1).

¹H-NMR (CDCl₃) δ value:
8.16 (1H, s), 7.69 (1H, s), 7.22 (0.67H, dd, J=7.8, 6.4 Hz), 6.64 (0.33H, dd, J=11.3, 4.4 Hz), 5.73-5.67 (0.33H, m), 5.63-5.60 (0.33H, m), 5.36 (0.67H, ddd, J=51.9, 6.4, 3.6), 5.38-5.35 (0.34H, m), 5.19-5.53 (1H, m), 5.13-5.09 (0.33H, m), 4.44-4.40 (1H, m), 4.21-4.16 (1H, m), 3.90 (2.01H, s), 3.89 (0.99H, s), 1.19 (9H, s), 1.17 (9H, s)

¹⁹F-NMR(CDCl₃) δ value:
−199.40 (0.71F, ddd, J=48.0, 26.2, 8.0 Hz), −206.33 (0.29F, ddd, J=49.9, 30.1, 12.4 Hz)

(5)

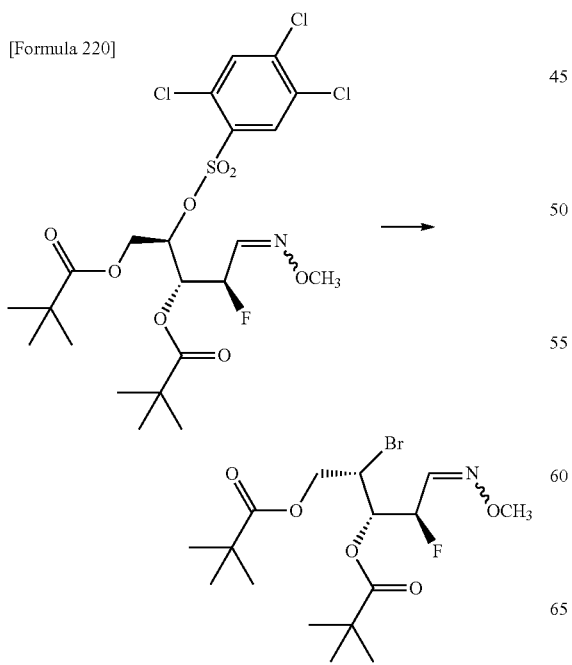

(2S,3S,4R)-2-bromo-3-(2,2-dimethylpropionyloxy)-4-fluoro-5-(methoxyimino)pentyl=trimethylacetate was obtained in the form of a colorless oily product in the same manner as that of Example 7(2).

¹H-NMR (CDCl₃) δ value:
7.38 (0.83H, dd, J=6.5, 6.5 Hz), 6.75 (0.17H, dd, J=11.2, 4.7), 5.85 (0.17H, ddd, J=47.4, 4.7, 3.0), 5.64 (0.17H, m), 5.37-5.47 (2.25H, m), 5.23 (0.41H, m), 4.57-4.18 (2H, m), 3.91 (2.49H, s), 3.89 (0.51H, s), 1.27 (9H, s), 1.23 (9H, s)

¹⁹F-NMR(CDCl₃) δ value: −194.50 (0.84F, ddd, J=46.6, 16.6, 6.6 Hz), −203.81 (0.16F, ddd, J=47.3, 25.7, 11.2 Hz)

(6)

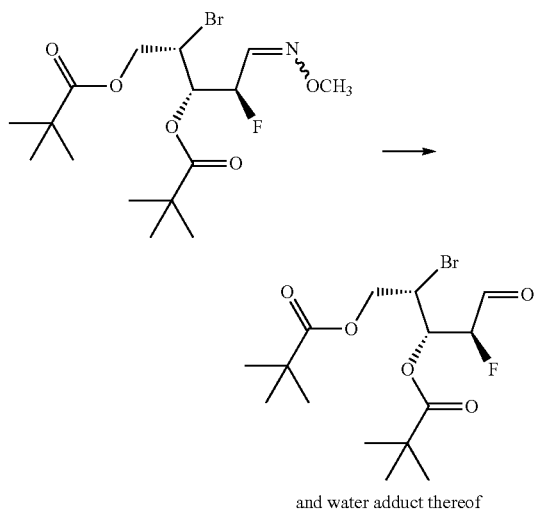

and water adduct thereof

A mixture of (2S,3S,4S)-2-bromo-3-(2,2-dimethylpropionyloxy)-4-fluoro-5-oxopentyl=trimethylacetate and a water adduct thereof was obtained in the form of a colorless oily product in the same manner as that of Example 1(4), with the exception that the reaction was carried out at 60° C. for 8 hours.

¹H-NMR (CDCl₃) δ value: 9.72 (1H, d, J=6.6 Hz), 5.58-4.56 (5H, m), 1.27-1.23 (18H, m)

19F-NMR(CDCl₃) δ value: −210.77 (1F, ddd, J=46.8, 20.9, 6.5 Hz)

(7)

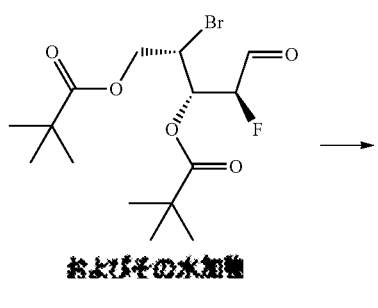

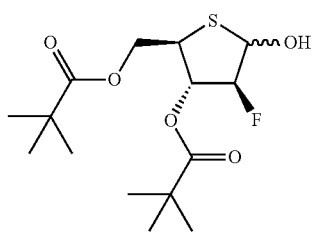

((2R,3S,4S)-3-(2,2-dimethylpropionyloxy)-4-fluoro-5-hydroxythiolan-2-yl)methyl=trimethylacetate was obtained in the form of a colorless oily product in the same manner as that of Example 1(5).

¹H-NMR (CDCl₃) δ value:

5.62-5.44 (1.5H, m), 5.41 (0.5H, m), 5.16 (0.25H, m), 5.06-5.03 (0.5H, m), 4.94-4.90 (0.25H, m), 4.38-4.28 (1H, m), 4.16-4.10 (1H, m), 3.85 (0.5H, dd, J=7.4, 7.4), 3.42 (0.5H, dd, J=3.1, 5.7), 2.97 (0.5H, brs), 2.46 (0.5H, brs), 1.23-1.21 (18H, m)

¹⁹F-NMR(CDCl₃) δ value:

−184.20 (0.54F, ddd, J=47.1, 11.1, 11.1 Hz), −193.48 (0.46F, ddd, J=51.8, 10.9, 5.4 Hz)

(8)

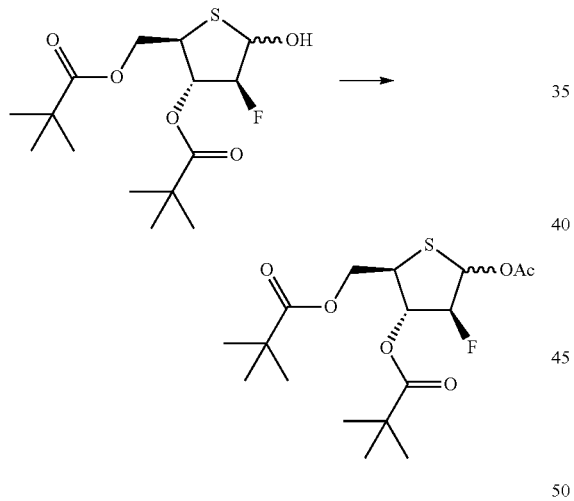

[Formula 223]

14 mg of acetic anhydride was added to a solution of 40 mg of ((2R,3S,4S)-3-(2,2-dimethylpropionyloxy)-4-fluoro-5-hydroxythiolan-2-yl)methyl=trimethylacetate, 0.3 mg of dimethylaminopyridine and 19 mg of 2-picoline in 1.0 mL of tetrahydrofuran at a temperature of 10° C. or lower, and the obtained mixture was then stirred at room temperature for 30 minutes. Thereafter, ethyl acetate was added to the reaction mixture, and the thus obtained mixture was successively washed with a saturated sodium chloride aqueous solution, a saturated sodium hydrogen carbonate aqueous solution and a saturated sodium chloride aqueous solution. After that, the organic layer was dried over anhydrous sodium sulfate, and the solvent was then distilled away under reduced pressure. The obtained residue was purified by column chromatography, so as to obtain 44 mg of ((2R,3S,4S)-5-acetyloxy-3-(2,2-dimethylpropionyloxy)-4-fluorothiolan-2-yl)methyl=trimethylacetate in the form of a colorless oily product.

¹H-NMR (CDCl₃) δ value:

6.14 (0.41H, dd, J=13.8, 2.1 Hz), 6.10 (0.59H, d, J=4.5), 5.64 (0.59H, ddd, J=16.5, 9.0, 7.7), 5.43 (0.41H, ddd, J=12.2, 3.4, 3.4), 5.18 (0.41H, ddd, J=47.4, 3.4, 2.1), 5.10 (0.59H, ddd, J=50.8, 9.0, 4.5), 4.36 (0.59H, dd, J=11.5, 4.7), 4.23 (0.41H, dd, J=11.2, 7.4), 4.12-4.07 (1H, m), 3.78 (0.41H, m), 3.42 (0.59H, ddd, J=7.7, 4.7, 4.7), 2.16 (1.77H, s), 2.10 (1.23H, s), 1.25 (5.31H, s), 1.23 (3.69H, s), 1.21 (5.31H, s), 1.20 (3.96H, s)

¹⁹F-NMR(CDCl₃) δ value:

−187.09 (0.44F, ddd, J=50.5, 13.9, 13.9 Hz), −192.57 (0.56F, dd, J=50.9, 11.8 Hz)

Example 20

(1)

[Formula 224]

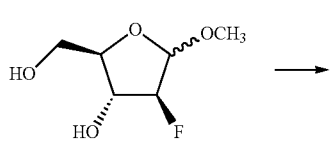

((2R,3R,4S)-3-((3,5-dimethylphenyl)carbonyloxy)-4-fluoro-5-methoxyoxolan-2-yl)methyl=3,5-dimethylbenzoate was obtained in the form of a white solid in the same manner as that of Example 10(1), with the exception that the reaction time was set at 1 hour.

¹H-NMR (CDCl₃) δ value:

7.67-7.64 (4H, m), 7.22-7.17 (2H, m), 5.46 (1H, dd, J=23.8, 4.8 Hz), 5.22-5.03 (2H, m), 4.70 (1H, dd, J=12.0, 4.0 Hz), 4.62 (1H, dd, J=12.0, 4.8 Hz), 4.52-4.49 (1H, m), 3.46 (3H, s), 2.36 (6H, s), 2.32 (6H, s)

¹⁹F-NMR(CDCl₃) δ value: −190.21 (1F, ddd, J=49.1, 23.1, 10.7 Hz)

(2)

[Formula 225]

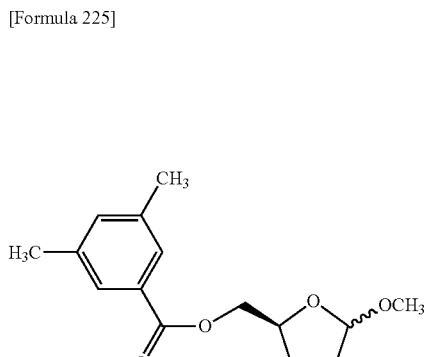

→

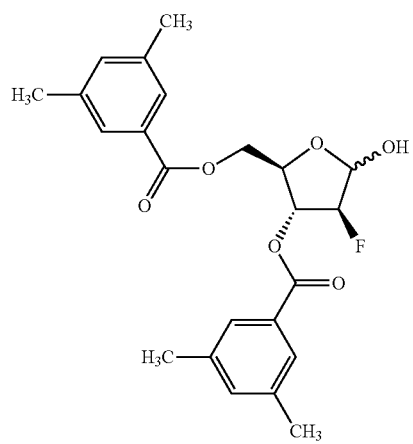

((2R,3R,4S)-3-((3,5-dimethylphenyl)carbonyloxy)-4-fluoro-5-hydroxyoxolan-2-yl)methyl=3,5-dimethylbenzoate was obtained in the form of a white solid in the same manner as that of Example 10(2).

$^1$H-NMR (CDCl$_3$) δ value:

7.68 (2H, s), 7.65 (2H, s), 7.22 (1H, s), 7.17 (1H, s), 5.69 (1H, dd, J=10.4, 3.8 Hz), 5.46 (1H, dd, J=21.8, 3.8 Hz), 5.16 (1H, d, J=49.2 Hz), 4.71-4.69 (3H, m), 2.36 (6H, s), 2.32 (6H, s)

$^{19}$F-NMR(CDCl$_3$) δ value: −190.45 (1F, dddd, J=49.3, 22.3, 10.9, 2.4 Hz)

(3)

[Formula 226]

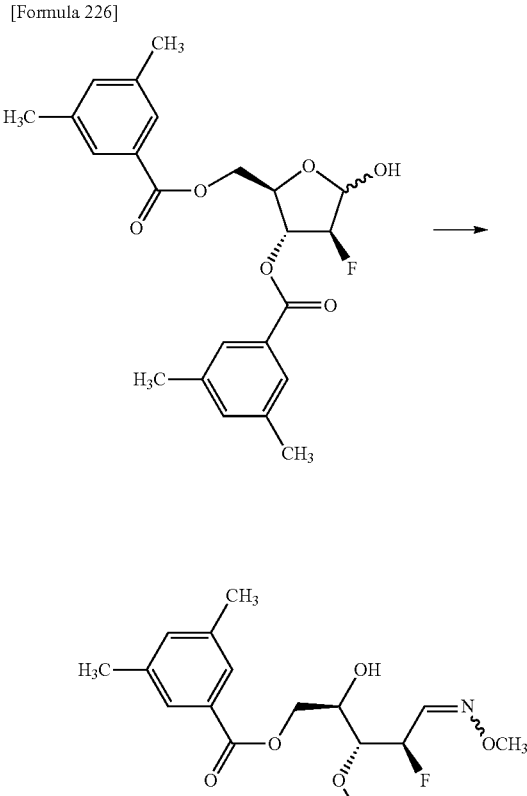

(2R,3R,4R)-3-((3,5-dimethylphenyl)carbonyloxy)-4-fluoro-2-hydroxy-5-(meth oxyimino)pentyl=3,5-dimethylbenzoate was obtained in the form of a colorless oily product in the same manner as that of Example 1(1).

$^1$H-NMR (CDCl$_3$) δ value:

7.67 (2H, s), 7.62 (2H, s), 7.40 (0.80H, dd, J=6.8, 6.8 Hz), 7.23 (1H, s), 7.20 (1H, s), 6.84 (0.20H, dd, J=11.1, 4.6 Hz), 6.06 (0.20H, ddd, J=46.4, 4.6, 2.0 Hz), 5.70 (0.20H, ddd, J=28.5, 8.2, 1.9 Hz), 5.57 (0.80H, ddd, J=45.2, 6.8, 2.4 Hz), 5.43 (0.80H, ddd, J=26.0, 8.4, 2.4 Hz), 4.60-4.51 (1H, m), 4.48-4.34 (2H, m), 3.92 (0.60H, s), 3.84 (2.40H, s), 3.03 (0.80H, d, J=6.2 Hz), 2.98 (0.20H, d, J=13.7 Hz), 2.36 (6H, s), 2.35 (6H, s)

$^{19}$F-NMR(CDCl$_3$) δ value:

−200.07 (0.86F, ddd, J=45.3, 26.0, 7.0 Hz), −207.47 (0.14F, ddd, J=46.3, 28.4, 4.6 Hz)

(4)

[Formula 227]

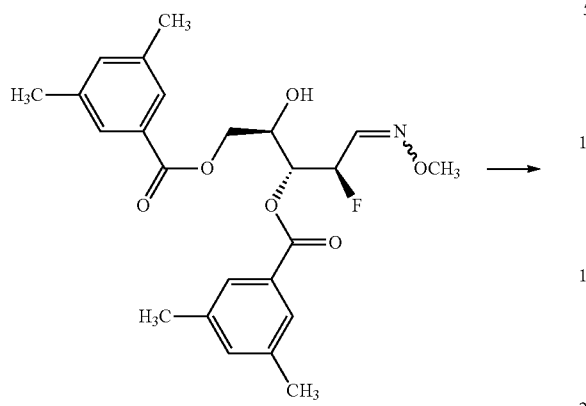

→

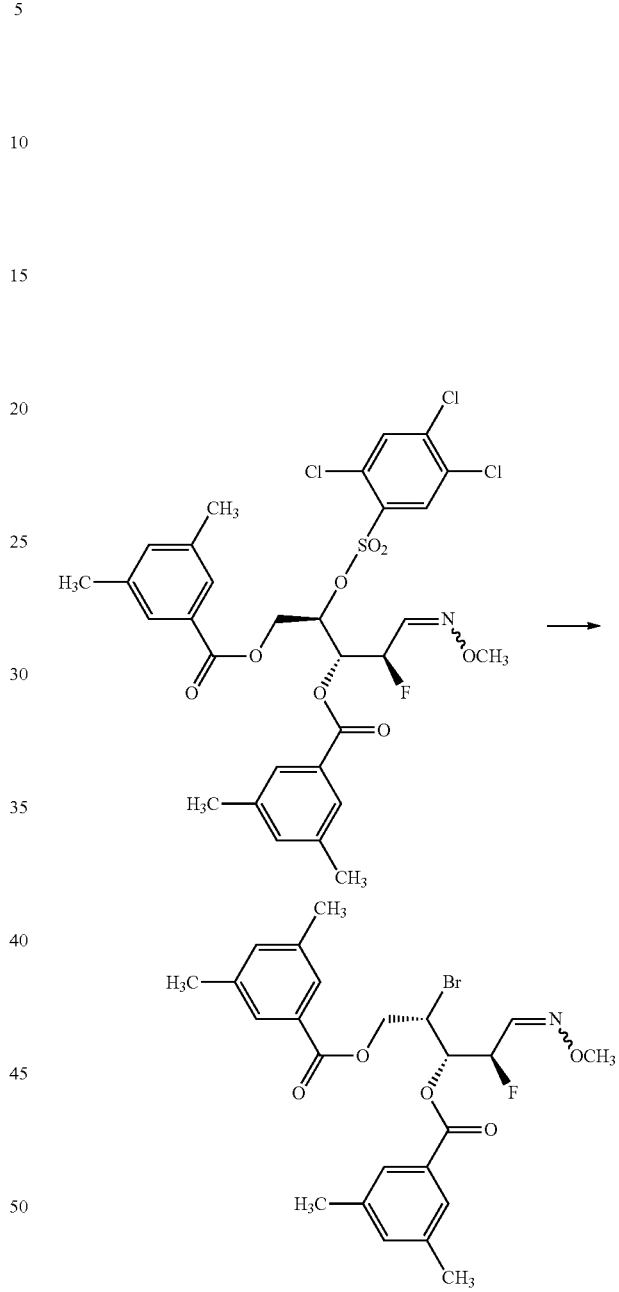

(2R,3R,4R)-1-((3,5-dimethylphenyl)carbonyloxy)-4-fluoro-5-(methoxyimino)-2-(((2,4,5-trichlorobenzene)sulfonyl)oxy)pentan-3-yl=3,5-dimethylbenzoate was obtained in the form of a white solid in the same manner as that of Example 7(1).

$^1$H-NMR (CDCl$_3$) δ value:
8.05 (1H, s), 7.65 (2H, s), 7.51 (2H, s), 7.41 (1H, dd, J=6.6, 6.6 Hz), 7.37 (1H, s), 7.23 (1H, s), 7.20 (1H, s), 5.78 (1H, ddd, J=23.2, 6.1, 3.0 Hz), 5.52-5.50 (0.50H, m), 5.44-5.38 (1.50H, m), 4.67 (1H, dd, J=12.8, 2.9 Hz), 4.53 (1H, dd, J=12.9, 6.2 Hz), 3.87 (3H, s), 2.36 (12H, m,)

$^{19}$F-NMR(CDCl$_3$) δ value: −196.79 (1F, ddd, J=45.7, 23.3, 6.7 Hz)

(5)

[Formula 228]

(2S,3S,4R)-2-bromo-3-((3,5-dimethylphenyl)carbonyloxy)-4-fluoro-5-(methoxyimino)pentyl=3,5-dimethylbenzoate was obtained in the form of a colorless oily product in the same manner as that of Example 7(2).

$^1$H-NMR (CDCl$_3$) δ value:
7.72 (2H, s), 7.65 (2H, s), 7.48 (1H, dd, J=6.4, 6.4 Hz), 7.23 (1H, s), 7.20 (1H, s), 5.80-5.75 (1H, m), 5.53 (1H, ddd, J=46.8, 6.4, 6.2 Hz), 4.76-4.69 (1H, m), 4.63-4.56 (2H, m), 3.89 (3H, s), 2.40 (6H, s), 2.35 (6H, s)

$^{19}$F-NMR(CDCl$_3$) δ value: −193.60 (1F, ddd, J=46.7, 17.3, 6.2 Hz)

(6)

[Formula 229]

A mixture of (2S,3S,4S)-2-bromo-3-((3,5-dimethylphenyl)carbonyloxy)-4-fluoro-5-oxopentyl=3,5-dimethylbenzoate and a water adduct thereof was obtained in the form of a colorless oily product in the same manner as that of Example 1(4), with the exception that the reaction was carried out at 60° C. for 11 hours.

$^{1}$H-NMR (CDCl$_{3}$) δ value:
9.82 (1H, d, J=6.3 Hz), 7.65 (2H, s), 7.29 (2H, s), 7.23 (1H, s), 7.20 (1H, s), 5.82 (1H, ddd, J=21.7, 3.5, 3.5 Hz), 5.41 (1H, dd, J=46.9, 3.5, Hz), 4.61-4.19 (3H, m), 2.37-2.34 (12H, m)
$^{19}$F-NMR(CDCl$_{3}$) δ value: −210.09 (1F, ddd, J=46.8, 21.9, 6.7 Hz)

(7)

[Formula 230]

((2R,3S,4S)-3-((3,5-dimethylphenyl)carbonyloxy)-4-fluoro-5-hydroxythiolan-2-yl)methyl=3,5-dimethylbenzoate was obtained in the form of a yellow oily product in the same manner as that of Example 1(5).

$^{1}$H-NMR (CDCl$_{3}$) δ value:
7.65 (1H, s), 7.61 (1H, s), 7.59 (1H, s), 7.57 (1H, s), 7.21 (0.50H, s), 7.19 (0.50H, s), 7.17 (0.50H, s), 7.12 (0.50H, s), 6.07-6.00 (0.50H, m), 5.80 (0.50H, ddd, J=12.4, 2.5, 2.5 Hz), 5.61 (0.50H, ddd, J=9.3, 9.3, 6.1 Hz), 5.48-5.46 (0.50H, m), 5.37-5.36 (0.25H, m), 5.26-5.23 (0.50H, m), 5.14-5.11 (0.25H, m), 4.65-4.56 (1.25H, m), 4.48-4.46 (0.75H, m), 4.22-4.16 (0.50H, m), 3.77-3.72 (0.50H, m), 2.34-2.33 (6H, m), 2.32 (3H, s), 2.25 (3H, s)

$^{19}$F-NMR(CDCl$_{3}$) δ value:
−183.72 (0.50F, ddd, J=47.7, 12.0, 12.0 Hz), −192.40 (0.50F, ddd, J=51.2, 11.3, 3.7 Hz)

(8)

[Formula 231]

-continued

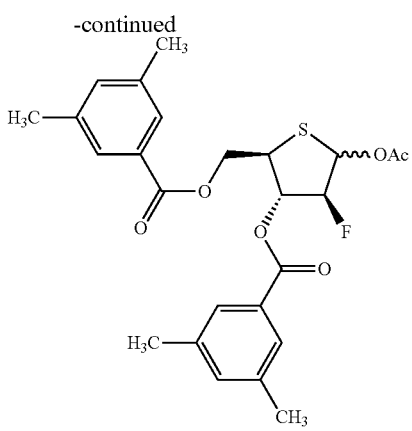

(2)

[Formula 233]

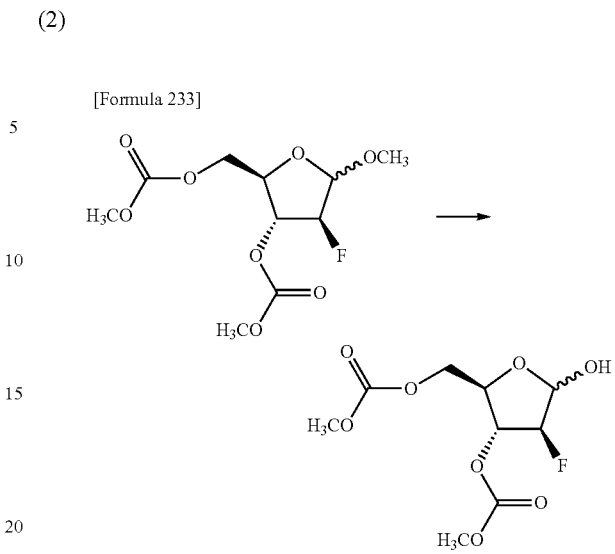

((2R,3S,4S)-5-acetyloxy-3-((3,5-dimethylphenyl)carbonyloxy)-4-fluorothiolan-2-yl)methyl=3,5-dimethylbenzoate was obtained in the form of a yellow oily product in the same manner as that of Example 19(8).

$^1$H-NMR (CDCl$_3$) δ value:
7.64-7.61 (2.9H, m), 7.53 (1.1H, s), 7.45 (0.45H, s), 7.19 (0.55H, s), 7.16 (0.45H, s), 7.08 (0.55H, s), 6.23 (0.45H, dd, J=13.8, 2.3 Hz), 6.16 (0.55H, d, J=4.5 Hz), 6.05 (0.55H, ddd, J=16.2, 9.0, 7.3 Hz), 5.82 (0.45H, ddd, J=12.4, 4.0, 3.8 Hz), 5.38 (0.45H, ddd, J=47.7, 3.8, 2.3 Hz), 5.29 (0.55H, ddd, J=50.7, 9.0, 4.5 Hz), 4.66-4.62 (1H, m), 4.54-4.41 (1.55H, m), 4.13-4.07 (0.45H, m), 2.34-2.31 (9H, m), 2.23 (3H, m) 2.17-2.13 (3H, m)

$^{19}$F-NMR(CDCl$_3$) δ value:
−187.11 (0.5F, ddd, J=48.1, 13.2, 13.2 Hz), −191.86 (0.5F, dd, J=53.8, 12.3 Hz)

((2R,3R,4S)-4-fluoro-5-hydroxy-3-(methoxycarbonyloxy)oxolan-2-yl)methyl=methylformate was obtained in the form of a colorless oily product in the same manner as that of Example 10(2).

$^1$H-NMR (CDCl$_3$) δ value:
5.59 (0.84H, dd, J=10.0, 3.6 Hz), 5.47-5.42 (0.16H, m), 5.20 (0.16H, ddd, J=17.2, 4.0, 4.0 Hz), 5.02 (0.84H, d, J=48.8 Hz), 5.05-4.98 (16H, m), 4.31-4.15 (2H, m), 4.36-4.32 (1H, m), 3.84 (3H, s), 3.80 (3H, s), 3.50 (1H, brs)

$^{19}$F-NMR(CDCl$_3$) δ value:
−191.10 (0.88F, ddd, J=48.9, 21.1, 10.2 Hz), −206.53 (0.12F, ddd, J=51.2, 16.9, 6.0 Hz)

(3)

Example 21

(1)

[Formula 232]

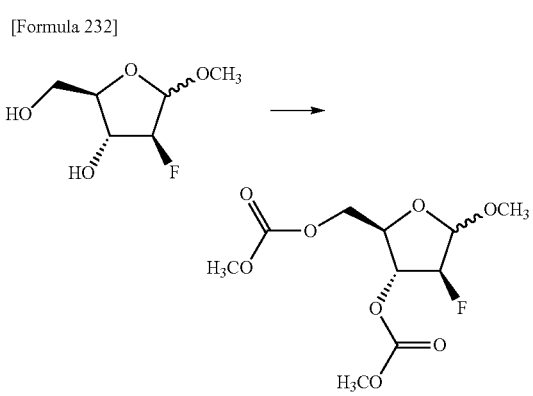

[Formula 234]

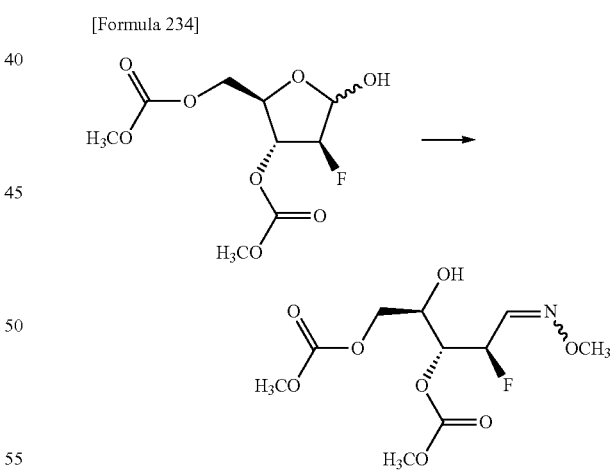

((2R,3R,4S)-4-fluoro-5-methoxy-3-(methoxycarbonyloxy)oxolan-2-yl)methyl=methylformate was obtained in the form of a white solid in the same manner as that of Example 10(1), with the exception that the reaction time was set at 5 hours.

$^1$H-NMR (CDCl$_3$) δ value:
5.11 (1H, d, J=10.0 Hz), 5.03-4.91 (2H, m), 4.50 (1H, dd, J=11.6, 7.2 Hz), 4.33 (1H, dd, J=11.6, 5.2 Hz), 4.31-4.29 (1H, m), 3.83 (3H, s), 3.81 (3H, s), 3.41 (3H, s)

$^{19}$F-NMR(CDCl$_3$) δ value: −191.20 (1F, ddd, J=49.1, 22.2, 10.5 Hz)

(2R,3R,4R)-4-fluoro-2-hydroxy-5-(methoxyimino)-3-(methoxycarbonyloxy)pentyl=methylformate was obtained in the form of a colorless oily product in the same manner as that of Example 1(1).

$^1$H-NMR (CDCl$_3$) δ value:
7.42 (0.78H, dd, J=6.8, 6.8 Hz), 6.6.5 (0.22H, dd, J=11.2, 4.8 Hz), 5.91 (0.22H, ddd, J=46.4, 4.8, 2.0 Hz), 5.41 (0.78H, ddd, J=45.2, 6.8, 2.8 Hz), 5.25-5.15 (0.22H, m), 5.00 (0.78H, ddd, J=24.2, 8.2, 2.8 Hz), 4.52-4.19 (3H, m), 3.89 (3H, s), 3.83 (3H, s), 3.81 (3H, s), 3.08 (1H, brs)

¹⁹F-NMR(CDCl₃) δ value:
−199.93 (0.75F, ddd, J=45.2, 24.3, 4.9 Hz), −207.93 (0.25F, ddd, J=46.3, 27.1, 10.5 Hz)
(4)

[Formula 235]

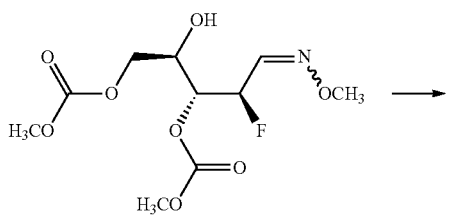

→

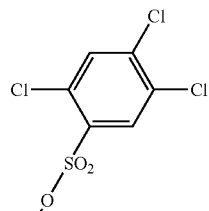

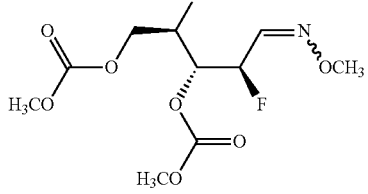

(2R,3R,4R)-2-fluoro-1-(methoxyimino)-5-(methoxycarbonyloxy)-4-(((2,4,5-tri chlorobenzene)sulfonyl)oxy)pentan-3-yl=methylformate was obtained in the form of a colorless oily product in the same manner as that of Example 7(1).
¹H-NMR (CDCl₃) δ value:
8.13-8.08 (1H, m), 7.70-7.68 (1H, m), 7.39-7.30 (0.87H, m), 6.83-6.75 (0.13H, m), 5.80-5.66 (0.24H, m), 5.54-5.45 (0.13H, m), 5.36-5.27 (0.76H, m), 5.19-5.15 (0.50H, m), 5.12-5.01 (1.37H, m), 4.54-4.42 (1.13H, m), 4.34-4.26 (0.87H, m), 3.93-3.73 (9H, m)
¹⁹F-NMR(CDCl₃) δ value:
−196.34 (0.74F, ddd, J=45.3, 20.9, 6.4 Hz), −205.27 (0.26F, ddd, J=46.7, 25.2, 11.1 Hz)
(5)

[Formula 236]

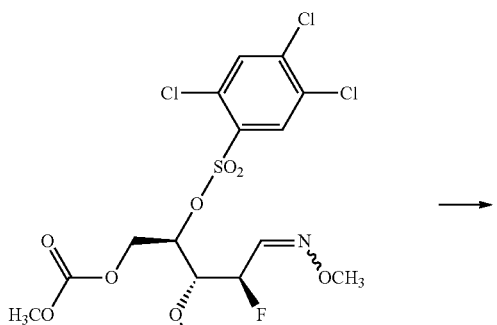

→

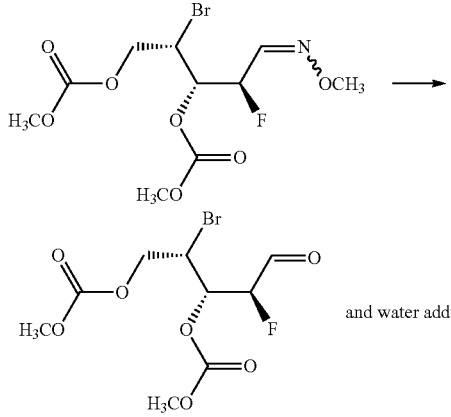

(2S,3S,4R)-2-bromo-4-fluoro-5-(methoxyimino)-3-(methoxycarbonyloxy)pentyl=methylformate was obtained in the form of a colorless oily product in the same manner as that of Example 7(2).
¹H-NMR (CDCl₃) δ value:
7.48-7.41 (0.80H, m), 6.96-6.83 (0.20H, m), 5.95 (0.12H, ddd, J=47.0, 4.8, 3.4 Hz), 5.45-5.09 (1.88H, m), 4.56-4.31 (3H, m), 3.94-3.80 (9H, m)
¹⁹F-NMR(CDCl₃) δ value:
193.89 (0.71F, ddd, J=46.1, 16.6, 6.0 Hz), 203.12 (0.29F, ddd, J=47.1, 24.5, 10.9 Hz)
(6)

[Formula 237]

and water adduct thereof

A mixture of (2S,3S,4S)-2-bromo-4-fluoro-3-(methoxycarbonyloxy)-5-oxopentyl=methylformate and a water adduct thereof was obtained in the form of a colorless oily product in the same manner as that of Example 1(4), with the exception that the reaction was carried out at 60° C. for 9 hours.
¹H-NMR (CDCl₃) δ value:
9.78 (1H, m), 5.48-5.18 (2H, m), 4.57-4.34 (3H, m), 3.84-3.80 (6H, m)
¹⁹F-NMR(CDCl₃) δ value: −210.73 (1F, ddd, J=47.3, 21.8, 6.2 Hz)
(7)

[Formula 238]

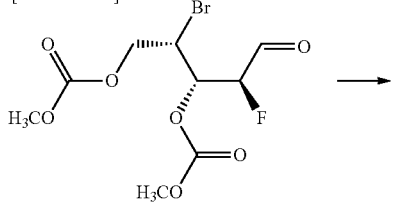 →

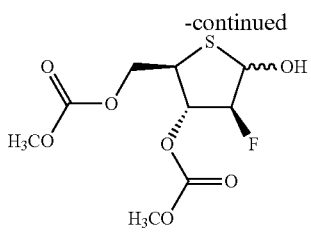

and water adduct thereof ((2R,3S,4S)-4-fluoro-5-hydroxy-3-(methoxycarbony-loxy)thiolan-2-yl)methyl=methylformate was obtained in the form of a colorless oily product in the same manner as that of Example 1(5).

$^1$H-NMR (CDCl$_3$) δ value:

5.57-5.46 (1H, m), 5.38-5.35 (0.80H, m), 5.25-5.23 (0.20H, m), 5.12-5.09 (0.70H, m), 4.99-4.97 (0.30H, m), 4.71-4.31 (1.30H, m), 4.23-4.19 (0.70H, m), 3.84 (3H, s), 3.81 (3H, s), 3.77-3.73 (1H, m)

$^{19}$F-NMR(CDCl$_3$) δ value: −185.10 (0.43F, d, J=46.7 Hz), −192.12 (0.57F, dd, J=51.5, 12.0 Hz)

(8)

[Formula 239]

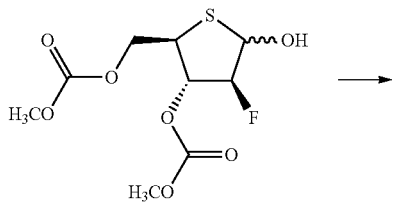

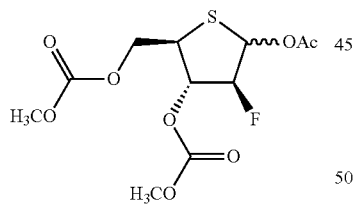

((2R,3S,4S)-5-acetyloxy-4-fluoro-3-(methoxycarbony-loxy)thiolan-2-yl)methyl=methylformate was obtained in the form of a colorless oily product in the same manner as that of Example 19(8).

$^1$H-NMR (CDCl$_3$) δ value:

6.12-6.06 (1H, m), 5.51 (0.60H, ddd, J=15.6, 8.8, 6.8 Hz), 5.38-5.31 (0.60H, m), 5.23-5.19 (0.50H, m), 5.10-5.07 (0.30H, m), 4.45 (0.60H, dd, J=11.2, 5.6 Hz), 4.32-4.20 (1.40, m), 3.95-3.84 (3.40H, m), 3.80-3.79 (3H, m), 3.54-3.51 (0.60H, m), 2.17 (1.80H, s), 2.12 (1.20H, s)

$^{19}$F-NMR(CDCl$_3$) δ value:

−187.31 (0.37F, ddd, J=47.8, 14.1, 14.1 Hz), −191.72 (0.63F, dd, J=50.5, 11.3 Hz)

Example 22

(1)

[Formula 240]

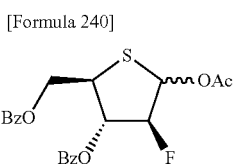

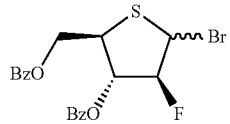

94 mL of a 30% hydrobromic acid/acetic acid solution was added to a solution of 100 g of ((2R,3S,4S)-5-acetyloxy-3-(benzoyloxy)-4-fluorothiolan-2-yl)methyl=benzoate in 600 mL of methylene chloride at room temperature, and the obtained mixture was then stirred for 3 hours. Thereafter, 500 mL of water was added to the reaction mixture, and the thus obtained mixture was then stirred for 10 minutes. Thereafter, the organic layer was fractionated, and was then washed with 600 mL of a 7% sodium hydrogen carbonate aqueous solution, so as to obtain 620 mL of a methylene chloride solution of ((2R,3S,4S)-3-(benzoyloxy)-5-bromo-4-fluorothiolan-2-yl)methyl=benzoate.

(2)

[Formula 240]

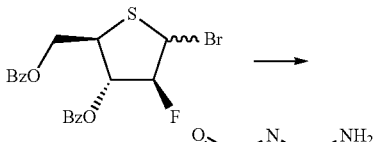

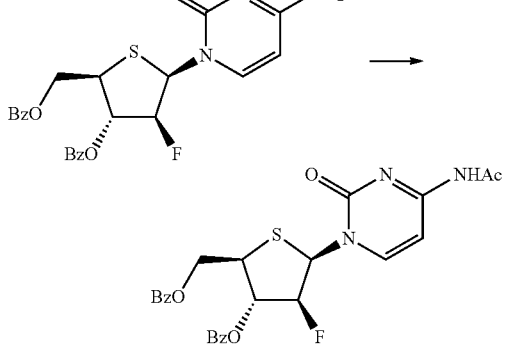

Under a nitrogen gas current, 193 g of 1,1,1,3,3,3-hexamethyldisilazane was added to a suspension of 66.4 g of cytosine and 316 mg of ammonium sulfate in 200 mL of toluene, and the obtained mixture was then stirred under heating to reflux, until the reaction mixture became a homogeneous solution. Thereafter, 620 mL of the methylene chloride solution of ((2R,3S,4S)-3-(benzoyloxy)-5-bromo-4-fluorothiolan-2-yl)methyl=benzoate obtained in (1) above was added dropwise to the reaction mixture at 70° C., and the thus obtained mixture was then stirred at 70° C. for 12 hours, while methylene chloride was distilled away. Thereafter, the reaction mixture was cooled to room temperature, and 146 mg of 4-dimethylaminopyridine was added to the mixture.

Subsequently, 122 g of acetic anhydride was added dropwise to the reaction mixture at 60° C., and the thus obtained mixture was then stirred at a temperature of 60° C. or higher for 1 hour. Thereafter, the reaction mixture was cooled to room temperature, and 2000 mL of methylene chloride and 600 mL of 2 mol/L hydrochloric acid were then added thereto. The organic layer was fractionated, and methylene chloride was then distilled away in an external bath at 45° C. After that, 1500 mL of propyl acetate was added to the obtained residue, and the obtained mixture was then heated to 80° C. Thereafter, the mixture was stirred until distillation of distillate components was terminated. Thereafter, the reaction mixture was cooled to 10° C., and a solid was then collected by filtration, so as to obtain 78.0 g of ((2R,3S,4S,5R)-3-(benzoyloxy)-5-(4-acetamido-2-oxo-1,2-dihydropyrimidin-1-yl)-4-fl uorothiolan-2-yl)methyl=benzoate.
(3)

[Formula 242]

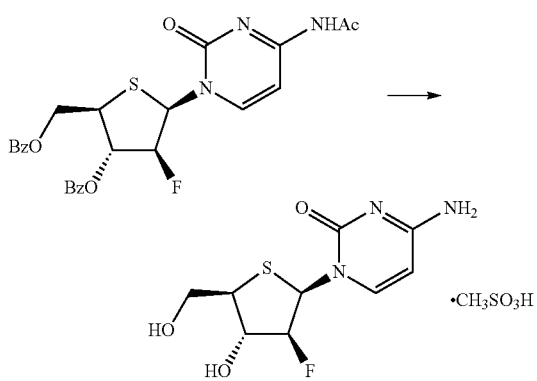

60 mg of a 28% sodium methoxide/methanol solution was added to a suspension of 800 mg of ((2R,3S,4S,5R)-3-(benzoyloxy)-5-(4-acetamido-2-oxo-1,2-dihydropyrimidin-1-yl)-4-fl uorothiolan-2-yl)methyl=benzoate in 10 mL of methanol at 22° C., and the obtained mixture was then stirred for 5 hours. Thereafter, the reaction mixture was cooled to 5° C., and 140 μL of methanesulfonic acid and 2.4 mL of water were then added thereto, so that a solid was dissolved therein. After that, the solvent was distilled away under reduced pressure, and 12.6 mL of acetone was then added to the obtained residue.

The thus obtained mixture was stirred at 20° C. for 90 minutes, and then at 5° C. for 1 hour. A solid was collected by filtration, so as to obtain 478 mg of (2R,3S,4S,5R)-3-hydroxy-2-hydroxymethyl-5-(4-amino-2-oxo-1,2-dihydropyrimidin-1-yl)-4-fluorothiolane methanesulfonate in the form of a white solid.

Example 23

(1)

[Formula 243]

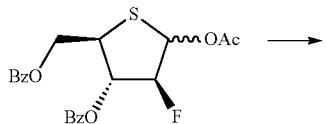

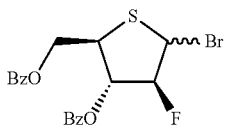

9.4 mL of a 30% hydrobromic acid/acetic acid solution was added to a solution of 10 g of ((2R,3S,4S)-5-acetyloxy-3-(benzoyloxy)-4-fluorothiolan-2-yl)methyl=benzoate in 60 mL of methylene chloride at room temperature, and the obtained mixture was then stirred for 3 hours. Thereafter, 70 mL of water was added to the reaction mixture, and the thus obtained mixture was then stirred for 10 minutes. Thereafter, the organic layer was fractionated, and was then washed with 70 mL of a 7% sodium hydrogen carbonate aqueous solution, so as to obtain 58 mL of a methylene chloride solution of ((2R,3S,4S)-3-(benzoyloxy)-5-bromo-4-fluorothiolan-2-yl) methyl=benzoate.
(2)

[Formula 244]

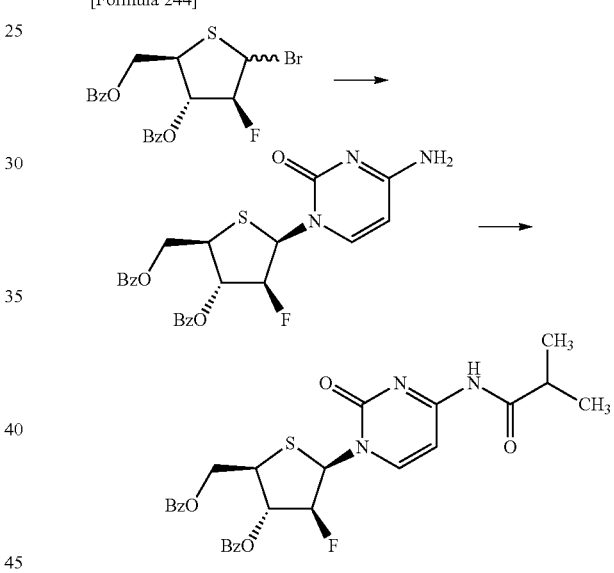

Under a nitrogen gas current, 19.3 g of 1,1,1,3,3,3-hexamethyldisilazane was added to a suspension of 6.6 g of cytosine and 32 mg of ammonium sulfate in 20 mL of toluene, and the obtained mixture was then stirred while heating to reflux, until the reaction mixture became a homogeneous solution. Thereafter, 58 mL of the methylene chloride solution of ((2R, 3S,4S)-3-(benzoyloxy)-5-bromo-4-fluorothiolan-2-yl) methyl=benzoate obtained in (1) above was added dropwise to the reaction mixture at 70° C., and the thus obtained mixture was then stirred at 70° C. for 10 hours, while methylene chloride was distilled away. Thereafter, the reaction mixture was cooled to room temperature, and 15 mg of 4-dimethylaminopyridine was then added to the mixture. After that, 20 mL of isobutyric anhydride was added to the mixture at 60° C., and the thus obtained mixture was then stirred at a temperature of 70° C. to 80° C. for 1 hour. Thereafter, the reaction mixture was cooled to room temperature, and 30 mL of methylene chloride and 30 mL of 2 mol/L hydrochloric acid were added to the mixture. The organic layer was fractionated, 6 mL of triethylamine was then added thereto, and methylene chloride was then distilled away. The reaction mixture was cooled to 5° C., and a solid was then collected by filtration, so as to obtain 5.7 g of ((2R,3S,4S,5R)-3-(benzoyloxy)-5-(4-(2-methylpropanamido)-2-oxo-1,2-dihydropyrimidin-1-yl)-4-fluorothiolan-2-yl)methyl=benzoate.

$^1$H-NMR (DMSO-$d_6$) δ value:

1.07 (dd, J=6.8, 1.2 Hz, 6H), 2.71 (hept, J=6.8 Hz, 1H), 4.07 (dd, J=12.0, 7.0 Hz, 1H), 4.65 (dd, J=9.9, 6.5 Hz, 1H), 4.74 (dd, 11.3, 7.5 Hz, 1H), 5.71 (ddd, J=49.4, 5.4, 5.4 Hz, 1H), 5.99 (ddd, J=11.1, 5.4, 5.4 Hz, 1H), 6.63 (dd, J=13.5, 5.4 Hz, 1H), 7.31 (d, J=7.6 Hz, 1H), 7.48 (dd, J=7.8, 7.8 Hz, 2H), 7.57 (dd, J=7.7, 7.7 Hz, 2H), 7.66 (dd, J=7.5, 7.5 Hz, 1H), 7.72 (dd, J=7.4, 7.4 Hz, 1H), 7.95 (dd, J=1.3, 8.4 Hz, 2H), 8.01 (dd, J=1.3, 8.4 Hz, 2H), 8.45 (d, J=7.4 Hz, 1H), 10.98 (brs, 1H)

Example 24

[Formula 245]

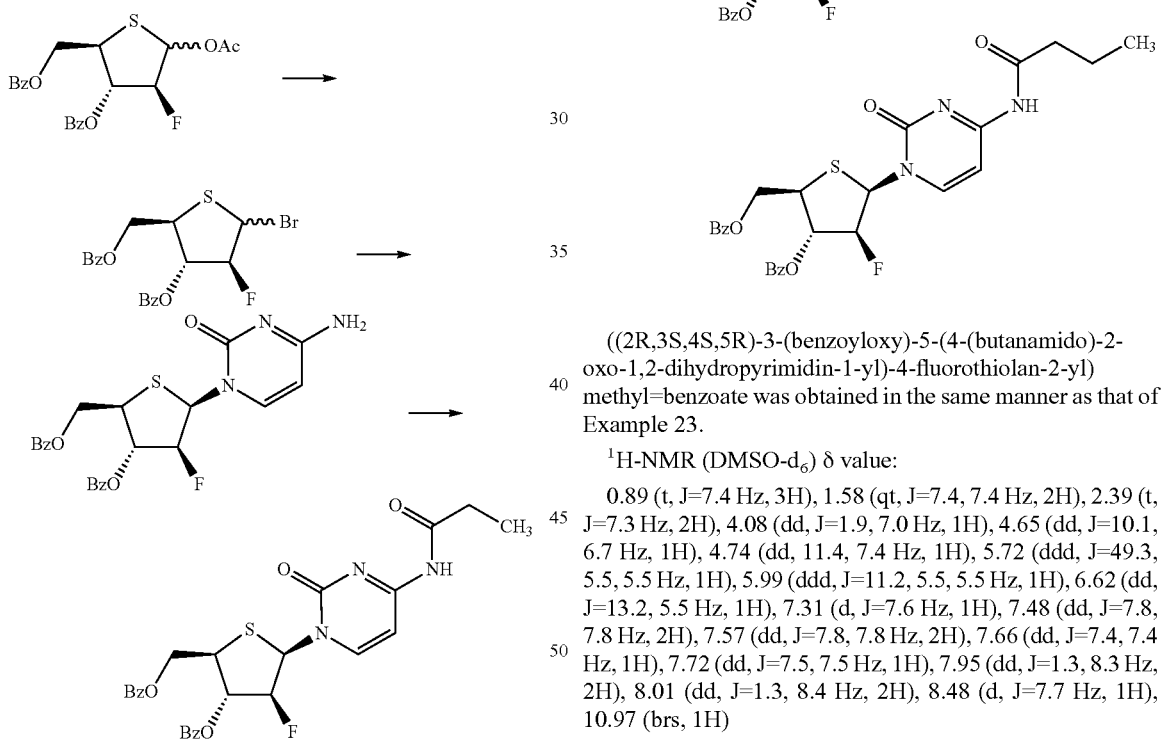

((2R,3S,4S,5R)-3-(benzoyloxy)-5-(4-(propanamido)-2-oxo-1,2-dihydropyrimidin-1-yl)-4-fluorothiolan-2-yl)methyl=benzoate was obtained in the same manner as that of Example 23.

$^1$H-NMR (DMSO-$d_6$) δ value:

1.04 (t, J=7.4 Hz, 3H), 2.43 (q, J=7.4 Hz, 2H), 4.07 (dd, J=11.9, 6.7 Hz, 1H), 4.65 (dd, J=10.5, 6.8 Hz, 1H), 4.74 (dd, 11.3, 7.4 Hz, 1H), 5.72 (ddd, J=49.3, 5.5, 5.5 Hz, 1H), 5.99 (ddd, J=11.1, 5.4, 5.4 Hz, 1H), 6.62 (dd, J=13.1, 5.6 Hz, 1H), 7.30 (d, J=7.4 Hz, 1H), 7.48 (dd, J=7.8, 7.8 Hz, 2H), 7.57 (dd, J=7.8, 7.8 Hz, 2H), 7.66 (dd, J=7.4, 7.4 Hz, 1H), 7.72 (dd, J=7.6, 7.6 Hz, 1H), 7.95 (d, J=7.2 Hz, 2H), 8.01 (d, J=7.3 Hz, 2H), 8.48 (d, J=7.6 Hz, 1H), 10.96 (brs, 1H)

Example 25

[Formula 246]

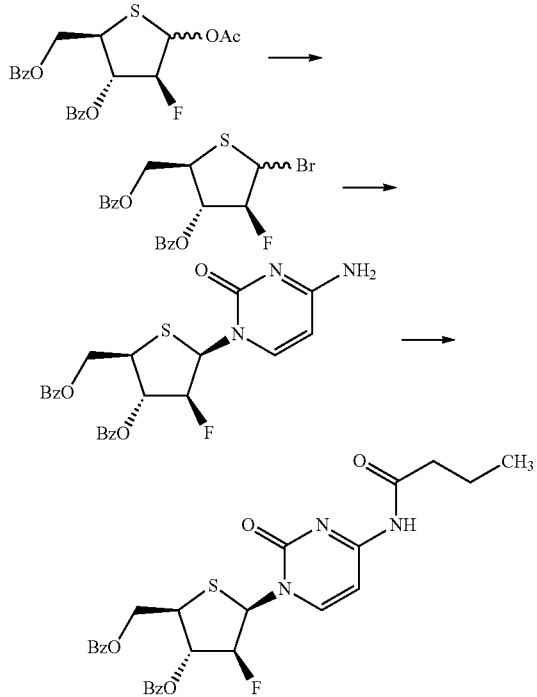

((2R,3S,4S,5R)-3-(benzoyloxy)-5-(4-(butanamido)-2-oxo-1,2-dihydropyrimidin-1-yl)-4-fluorothiolan-2-yl)methyl=benzoate was obtained in the same manner as that of Example 23.

$^1$H-NMR (DMSO-$d_6$) δ value:

0.89 (t, J=7.4 Hz, 3H), 1.58 (qt, J=7.4, 7.4 Hz, 2H), 2.39 (t, J=7.3 Hz, 2H), 4.08 (dd, J=1.9, 7.0 Hz, 1H), 4.65 (dd, J=10.1, 6.7 Hz, 1H), 4.74 (dd, J=11.4, 7.4 Hz, 1H), 5.72 (ddd, J=49.3, 5.5, 5.5 Hz, 1H), 5.99 (ddd, J=11.2, 5.5, 5.5 Hz, 1H), 6.62 (dd, J=13.2, 5.5 Hz, 1H), 7.31 (d, J=7.6 Hz, 1H), 7.48 (dd, J=7.8, 7.8 Hz, 2H), 7.57 (dd, J=7.8, 7.8 Hz, 2H), 7.66 (dd, J=7.4, 7.4 Hz, 1H), 7.72 (dd, J=7.5, 7.5 Hz, 1H), 7.95 (dd, J=1.3, 8.3 Hz, 2H), 8.01 (dd, J=1.3, 8.4 Hz, 2H), 8.48 (d, J=7.7 Hz, 1H), 10.97 (brs, 1H)

Example 26

(1)

[Formula 247]

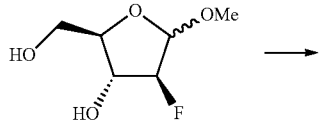

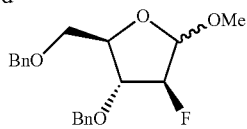

438 mg of 60% sodium hydride was added to a solution of 727 mg of 2-deoxy-2-fluoro-1-O-methyl-D-arabinofuranoside in 15 mL of N,N-dimethylformamide under cooling on ice, and the obtained mixture was then stirred at the same temperature as described above for 15 minutes. Thereafter, 1.20 mL of benzyl bromide was added to the reaction mixture, and the thus obtained mixture was then stirred for 5 minutes. The mixture was further stirred at room temperature for 1.5 hours. Thereafter, ethyl acetate and water were added to the reaction mixture. The organic layer was fractionated. The obtained organic layer was washed with a saturated sodium chloride aqueous solution, and was then dried over anhydrous magnesium sulfate. The solvent was distilled away under reduced pressure. The obtained residue was purified by silica gel column chromatography (hexane/ethyl acetate=100/0 to 75/25), so as to obtain 1.35 g of 2-deoxy-2-fluoro-1-O-methyl-3,5-bis-O-benzyl-D-arabinofuranoside in the form of a colorless oily product.

As a result of the measurement of $^1$H-NMR, the anomeric ratio was found to be 1:1.

RT(min): 1.80.

$^1$H-NMR (CDCl$_3$) δ value:

7.38-7.25 (1 OH, m), 5.11 (0.5H, dd, J=6.3, 4.3 Hz), 4.96-4.92 (1.5H, m), 4.64 (2H, ABq, J=21.9, 11.2 Hz), 4.57 (2H, s), 4.28-4.11 (2H, m), 3.62-3.50 (2H, m), 3.40 (3H, s)

(2)

[Formula 248]

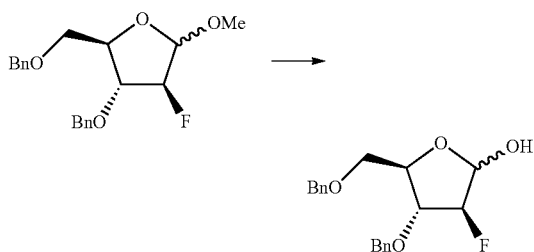

1.26 mL of trifluoroacetic acid and 0.14 mL of water were added to 1.35 g of 2-deoxy-2-fluoro-1-O-methyl-3,5-bis-O-benzyl-D-arabinofuranoside, and the obtained mixture was then stirred at a temperature of 55° C. to 60° C. for 3 hours. Thereafter, ethyl acetate and a saturated sodium hydrogen carbonate aqueous solution were added to the reaction mixture. The organic layer was fractionated. The obtained organic layer was washed with water once and then with a saturated sodium hydrogen carbonate aqueous solution twice, and it was then dried over anhydrous sodium sulfate. After that, the solvent was distilled away under reduced pressure. The obtained residue was purified by silica gel column chromatography (hexane/ethyl acetate=100/0 to 65/35), so as to obtain 954 mg of 2-deoxy-2-fluoro-3,5-bis-O-benzyl-D-arabinofuranoside in the form of a colorless oily product.

As a result of the measurement of $^1$H-NMR, the anomeric ratio was found to be 8/2.

RT(min): 1.54.

$^1$H-NMR (CDCl$_3$) δ value:

7.40-7.25 (1 OH, m), 5.48 (0.8H, dd, J=9.9, 6.6 Hz), 5.30 (0.2H, dq, J=10.4, 2.1 Hz), 4.96 (0.2H, d t, J=52.8, 4.6 Hz), 4.95 (0.8H, dd, J=50.1, 1.3 Hz), 4.69 (0.4H, dd, J=11.2, 2.6 Hz), 4.62 (1H, d, 5.3 Hz), 4.60 (0.6H, dd, J=3.3, 11.2 Hz), 4.55 (2H, s), 4.52-4.43 (1H, m), 4.38-4.27 (0.2H, m), 4.07-3.97 (0.8H, m), 3.64-3.44 (2H, m), 2.99 (1H, m)

(3)

[Formula 249]

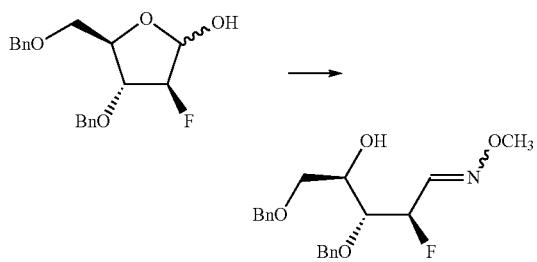

325 mg of O-methylhydroxylammonium chloride and 0.415 mL of triethylamine were added to a solution of 954 mg of 2-deoxy-2-fluoro-3,5-bis-O-benzyl-D-arabinofuranoside in 10 mL of methanol, and the obtained mixture was then stirred at room temperature for 2 hours. Thereafter, the solvent was distilled away under reduced pressure, and ethyl acetate and water were then added to the obtained residue. The organic layer was fractionated, and was then dried over anhydrous sodium sulfate. After that, the solvent was distilled away under reduced pressure. The obtained residue was purified by silica gel column chromatography (hexane/ethyl acetate=100/0 to 70/30), so as to obtain 1.09 g of (2R,3R,4R)-2-fluoro-4-hydroxy-3,5-bis(benzyloxy)pentanal O-methyloxime in the form of a colorless oily product.

$^1$H-NMR was measured. As a result, the syn-anti ratio was found to be 63:37.

RT(min): 1.66.

$^1$H-NMR (CDCl$_3$) δ value:

7.51 (0.63H, t, J=6.9 Hz), 7.40-7.20 (10H, m), 7.01 (0.37H, dd, J=11.9, 4.6 Hz), 5.82 (0.37H, ddd, J=46.9, 4.6, 1.3 Hz), 5.31 (0.63H, ddd, J=46.1, 6.6, 3.3 Hz), 4.72-4.42 (4H, m), 3.97 (1H, brs), 3.91-3.56 (1H, m), 3.90 (1.11H, s), 3.87 (1.89H, s), 3.71-3.64 (2H, m), 2.47 (1H, brs)

(4)

[Formula 250]

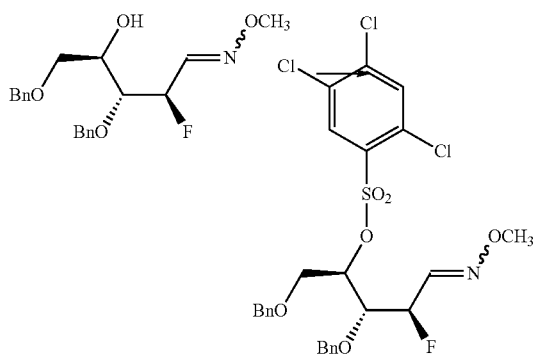

1.26 g of 2,4,5-trichlorobenzenesulfonyl chloride and 0.430 mL of 1-methylimidazole were added to a solution of 1.09 g of (2R,3R,4R)-2-fluoro-4-hydroxy-3,5-bis(benzyloxy)pentanal O-methyloxime in 10.4 mL of acetonitrile at room temperature, and the obtained mixture was then stirred at room temperature for 14.5 hours. Thereafter, ethyl acetate and a saturated sodium hydrogen carbonate aqueous solution were added to the reaction mixture. A solid was removed by filtration, and the organic layer was then fractionated. The obtained organic layer was dried over anhydrous magnesium sulfate, and the solvent was then distilled away under reduced pressure. The obtained residue was purified by silica gel column chromatography (hexane/ethyl acetate), so as to obtain 1.50 g of (2R,3R,4R)-2-fluoro-3,5-bis(benzyloxy)-4-(2,4,5-trichlorophenoxy)pentanal O-methyloxime in the form of a colorless oily product.

$^1$H-NMR was measured. As a result, the syn-anti ratio was found to be 68:32.

RT(min): 2.22.

$^1$H-NMR (CDCl$_3$) δ value:

8.09 (0.32H, s), 8.09 (0.68H, s), 7.43 (1H, s), 7.40 (0.68H, t, J=7.7 Hz), 7.37-7.15 (10H, m), 6.88 (0.32H, dd, J=11.2, 4.6 Hz), 5.61 (0.32H, ddd, J=47.6, 4.6, 2.4 Hz), 5.14 (0.68H, ddd, J=46.4, 6.6, 4.0 Hz), 4.88-4.75 (1H, m), 4.72-4.54 (2H, m), 4.45-4.25 (2.32H, m), 4.20-4.07 (0.68H, ddd, J=22.5, 5.3, 4.0 Hz), 3.88 (3H, s), 3.86-3.75 (2H, m)

(5)

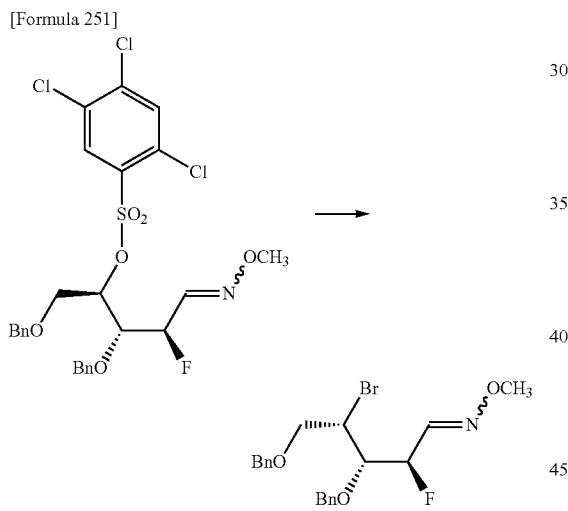

[Formula 251]

430 mg of lithium bromide was added to a solution of 1.50 g of (2R,3R,4R)-2-fluoro-3,5-bis(benzyloxy)-4-(2,4,5-trichlorophenoxy)pentanal O-methyloxime in 6 mL of tetrahydrofuran and 5.4 mL of 1,3-dimethyl-2-imidazolidinone, and the obtained mixture was then stirred at 60° C. for 6 hours. Thereafter, ethyl acetate and water were added to the reaction mixture. The organic layer was fractionated. The obtained organic layer was washed with a saturated sodium chloride aqueous solution, and was then dried over anhydrous magnesium sulfate. The solvent was distilled away under reduced pressure. The obtained residue was purified by silica gel column chromatography (hexane/ethyl acetate=100/0 to 75/25), so as to obtain 662 mg of (2S,3S,4S)-4-bromo-2-fluoro-3,5-bis(benzyloxy)pentanal O-methyloxime in the form of a colorless oily product.

$^1$H-NMR was measured. As a result, the syn-anti ratio was found to be 86:14.

RT(min): 2.00.

$^1$H-NMR (CDCl$_3$) δ value:

7.42 (0.86H, t, J=6.9 Hz), 7.33 (10H, m), 6.90 (0.14H, dd, J=11.2, 5.3 Hz), 5.81 (0.14H, dq, J=47.6, 2.6 Hz), 5.32 (0.86H, dt, J=46.9, 6.6 Hz), 4.75 (1.72H, ABq, 40.3, 110.2 Hz), 4.68 (0.28H, ABq, 19.8, 8.6 Hz), 4.55 (0.28H, ABq, 12.6, 10.6 Hz), 4.48 (1.72H, s), 4.33-4.21 (0.14H, m), 4.19-4.10 (1H, m), 4.09-3.98 (0.86H, m), 3.91 (2.58H, s), 3.90 (0.42H, m), 3.93-3.83 (1H, m), 3.83-3.76 (0.14H, m), 3.71 (0.86H, m)

(6)

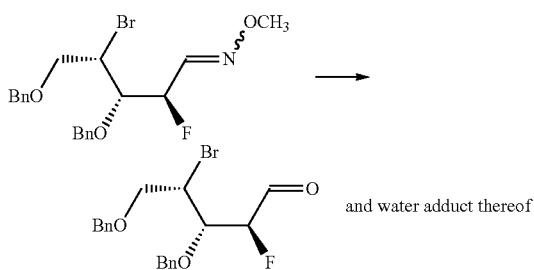

[Formula 252]

3.3 mL of a 50% glyoxylic acid aqueous solution was added to a solution of 662 mg of the (2S,3S,4S)-4-bromo-2-fluoro-3,5-bis(benzyloxy)pentanal O-methyloxime in 6.6 mL of tetrahydrofuran, and the obtained mixture was then stirred at 70° C. for 4.83 hours. Thereafter, ethyl acetate and water were added to the reaction mixture. The organic layer was fractionated, and it was washed with a sodium hydrogen carbonate aqueous solution, and was then dried over anhydrous magnesium sulfate. The solvent was distilled away under reduced pressure, so as to obtain 655 mg of colorless oily (2S,3S,4S)-4-bromo-2-fluoro-3,5-bis(benzyloxy)pentanal and a water adduct thereof.

RT(min): 1.54

(7)

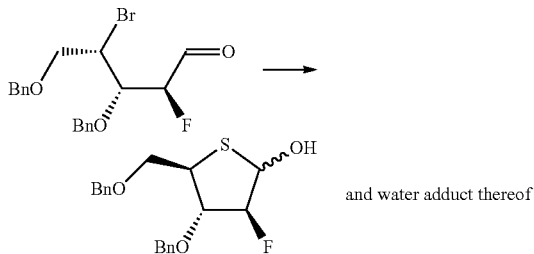

[Formula 253]

289 mg of a sodium monohydrogen sulfide n-hydrate was added to a solution of 655 mg of (2S,3S,4S)-4-bromo-2-fluoro-3,5-bis(benzyloxy)pentanal and a water adduct thereof in 6 mL of 1-methylpyrrolidone under cooling on ice, and the obtained mixture was then stirred at the same temperature as described above for 1.25 hours. Thereafter, ethyl acetate and water were added to the reaction mixture. The organic layer was fractionated, and it was washed with a saturated sodium chloride aqueous solution, and was then dried over anhydrous magnesium sulfate. The solvent was distilled away under reduced pressure, so as to obtain a 1-methylpyrrolidone solution of 2-deoxy-2-fluoro-3,5-bis-O-benzyl-4-thio-D-arabinofuranoside in the form of a colorless oily product.

As a result of the measurement of $^1$H-NMR, the anomeric ratio was found to be 57/43.

RT(min): 1.66, 1.68.

$^1$H-NMR (CDCl$_3$) δ value:

7.39-7.21 (10H, m), 6.14 (0.57H, d, J=5.9 Hz), 5.77 (0.43H, d, J=7.9 Hz), 5.51-5.40 (0.43H, m), 5.29-5.23 (0.57H, m), 5.08 (0.43H, ddd, J=50.2, 4.6, 3.3 Hz), 4.96 (0.57H, ddd, J=52.2, 7.9, 4.0 Hz), 4.77-4.57 (2H, m), 4.54 (1.14H, s), 4.50 (0.86, s), 4.42-4.3 (0.57H, m), 4.17-1.06 (0.43H, m), 3.88-3.51 (2H, m), 3.19-3.15 (1H, m), 3.08 (2H, t, J=5.0 Hz), 2.99 (1H, t, J=6.6 Hz)

(8)

[Formula 254]

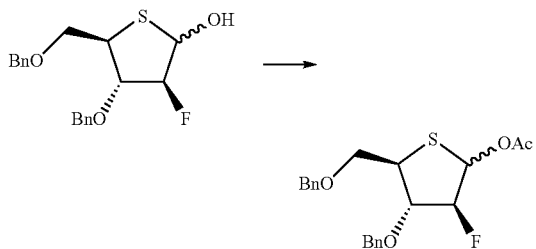

5.4 mL of tetrahydrofuran, 0.293 mL of acetic anhydride, 0.541 mL of triethylamine and a piece of 4-dimethylaminopyridine were added to the 1-methylpyrrolidone solution of 2-deoxy-2-fluoro-3,5-bis(benzyloxy)-4-thio-D-arabinofuranoside obtained in Example 26 (7), and the obtained mixture was then stirred at room temperature for 1.25 hours. Thereafter, ethyl acetate and water were added to the reaction mixture. The organic layer was fractionated, and it was washed with a saturated sodium chloride aqueous solution, and was then dried over anhydrous magnesium sulfate. The solvent was distilled away under reduced pressure. The obtained residue was purified by silica gel column chromatography (hexane/ethyl acetate=95/5 to 60/40), so as to obtain 394 mg of I-acetyl-2-deoxy-2-fluoro-3,5-bis-O-benzyl-4-thio-D-arabinofuranoside in the form of a colorless oily product.

As a result of the measurement of $^1$H-NMR, the α/β ratio was found to be 55/45.

RT(min): 1.89.

$^1$H-NMR (CDCl$_3$) δ value:

7.39-7.22 (1 OH, m), 6.05 (0.55H, t, J=4.5 Hz), 6.02 (0.45H, dd, J=10.6, 3.3 Hz), 5.20 (0.45H, ddd, J=50.1, 5.3, 3.3 Hz), 5.14 (0.55H, ddd, J=51.0, 8.6, 4.6 Hz), 4.80-4.46 (4H, m), 4.36-4.23 (0.55H, m), 4.21-4.09 (0.45H, m), 3.81-3.37 (3H, m), 2.11 (1.65H, s), 2.06 (1.35H, s)

(9)

[Formula 255]

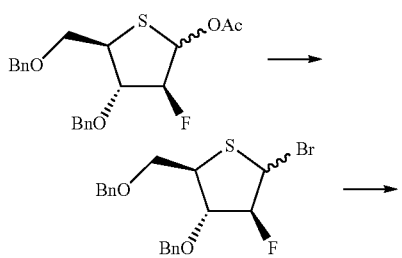

[Formula 256]

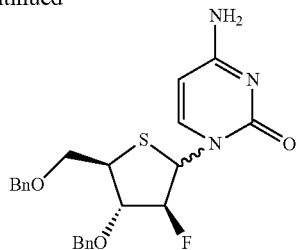

0.119 mL of a 30% hydrogen bromide-acetic acid solution was added to a solution of 116.2 mg of 1-acetyl-2-deoxy-2-fluoro-3,5-bis-O-benzyl-4-thio-D-arabinofuranoside in 2.3 mL of dichloromethane, and the obtained mixture was then stirred at room temperature for 1 hour. Thereafter, water was added to the reaction mixture. The organic layer was fractionated, and it was washed with a saturated sodium hydrogen carbonate aqueous solution and was then dried over magnesium sulfate, so as to obtain a dichloromethane solution of 1-bromo-2-deoxy-2-fluoro-3,5-bis-O-benzyl-4-thio-D-arabinofuranoside.

0.521 mL of N,O-bistrimethylsilyl acetamide was added to 83 mg of cytosine at room temperature, and the obtained mixture was then stirred in a nitrogen atmosphere at 80° C. for 1.5 hours. Thereafter, a dichloromethane solution of 1-bromo-2-deoxy-2-fluoro-3,5-bis-O-benzyl-4-thio-D-arabinofuranoside was added to the reaction mixture, and the solvent was then distilled away. After that, the obtained residue was further stirred at 80° C. for 2.5 hours. Thereafter, ethyl acetate and 2 mol/L hydrochloric acid were added to the reaction mixture. The organic layer was fractionated, and it was washed with water and was then dried over anhydrous sodium sulfate. Subsequently, the solvent was distilled away under reduced pressure. The obtained residue was purified by silica gel column chromatography (ethyl acetate/methanol), so as to obtain 61.3 mg of 1-(3,5-bis-O-benzyl-2-deoxy-2-fluoro-4-thio-D-arabinofuranosyl)cytosine in the form of a colorless oily product.

As a result of the measurement of $^1$H-NMR, the α/β ratio was found to be 31/69.

RT(min): 1.30.

$^1$H-NMR (CDCl$_3$) δ value:

7.99 (0.69H, dd, J=7.6, 1.7 Hz), 7.83 (0.31H, d, J=7.3 Hz), 7.40-7.24 (1 OH, m), 7.21-7.16 (1H, m), 6.68 (0.69H, dd, J=18.5, 4.6 Hz), 6.34 (0.31H, dd, J=15.9, 2.0 Hz), 6.20-5.80 (1H, brs), 5.69 (0.31H, d, J=7.3 Hz), 5.60 (0.69H, d, J=7.3 Hz), 5.15 (0.31H, dt, J=47.4, 2.5 Hz), 5.11 (0.69H, dt, J=51.0, 4.5 Hz), 4.61 (1.38H, ABq, J=12.6, 11.7), 4.52 (1.24H, brs), 4.48 (1.38H, ABq, 12.9, 4.8 Hz), 4.26 (1H, m), 3.93 (0.31H, t, J=5.9 Hz), 3.70-3.55 (2.38H, m), 3.53-3.47 (0.31H, m)

(10)

[Formula 256]

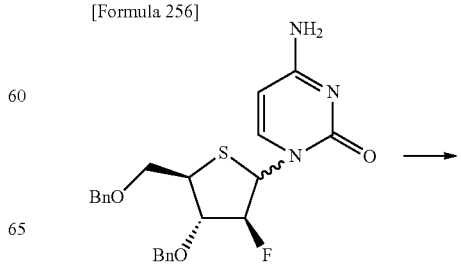

-continued

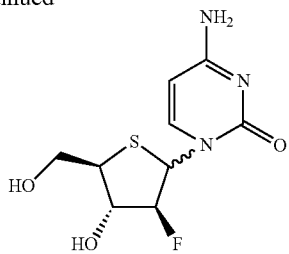

0.065 mL of a 1 mol/L boron tribromide-dichloromethane solution was added to a solution of 9.6 mg of 1-(3,5-bis-O-benzyl-2-deoxy-2-fluoro-4-thio-D-arabinofuranosyl)cytosine in 1 mL of dichloromethane under cooling on ice. While the temperature was gradually increased to room temperature, the obtained mixture was stirred for 2 hours. Thereafter, hexane was added to the reaction mixture, and a solid was then collected by filtration. The obtained solid was washed with toluene and ethyl acetate, so as to obtain 5.3 mg of 1-(2-deoxy-2-fluoro-4-thio-D-arabinofuranosyl)cytosine in the form of a white solid.

As a result of the measurement of $^1$H-NMR, the α/β ratio was found to be 36/64.

RT(min): 0.22, 0.27.

$^1$H-NMR (DMSO-d$_6$) δ value:

8.02-7.93 (1H, m), 7.40-7.15 (2H, m), 6.46 (0.64H, dd, J=14.5, 5.3 Hz), 6.15 (0.36H, dd, J=17.2, 5.9 Hz), 5.93 (0.36H, d, J=4.6 Hz), 5.84 (0.64H, d, J=4.6 Hz), 5.82-5.71 (1H, m), 5.26 (0.64H, t, J=5.3 Hz), 5.06 (0.36H, dt, J=52.2, 5.9 Hz), 5.03 (1H, dd, J=11.2, 4.6 Hz), 4.91 (0.64H, dt, J=46.2, 5.3 Hz), 4.29-4.18 (0.64H, m), 4.15-4.02 (0.36H, m), 3.82-3.67 (0.36H, m), 3.65-3.54 (1H, m), 3.51-3.28 (1H, m), 3.26-3.15 (0.64H, m)

Example 27

(1)

[Formula 257]

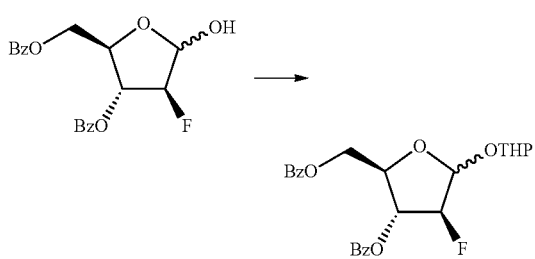

0.941 mL of 3,4-dihydro-2H-pyran was added to a solution of 1.87 g of 3,5-bis-O-benzoyl-2-deoxy-2-fluoro-D-arabinofuranoside in 37.5 mL of dichloromethane at room temperature, and thereafter, 49 mg of p-toluenesulfonic acid monohydrate was added to the obtained mixture under cooling on ice. The thus obtained mixture was stirred at the same temperature as described above for 1.5 hours. Thereafter, a saturated sodium hydrogen carbonate aqueous solution was added to the reaction mixture. The organic layer was fractionated, and was then dried over anhydrous sodium sulfate. After that, the solvent was distilled away under reduced pressure. The obtained residue was purified by silica gel column chromatography (hexane/ethyl acetate=100/0 to 60/40), so as to obtain 2.33 g of 3,5-bis-O-benzoyl-2-deoxy-2-fluoro-1-O-(tetrahydro-2H-pyran-2-yl)-D-arabinofuranoside in the form of a colorless oily product.

RT(min): 1.96.

$^1$H-NMR (CDCl$_3$) δ value:

8.06 (4H, m), 7.51 (6H, m), 5.68 (1H, d, J=10.6 Hz), 5.59-5.48 (1H, dd, 21.9, 4.5 Hz), 5.20 (1H, d, J=49.5 Hz), 5.06-5.02 (1H, m), 4.77-4.59 (2H, m), 4.53 (1H, q, 4.2 Hz), 3.94-3.84 (1H, m), 3.64-3.53 (1H, m), 1.90-1.40 (6H, m)

(2)

[Formula 258]

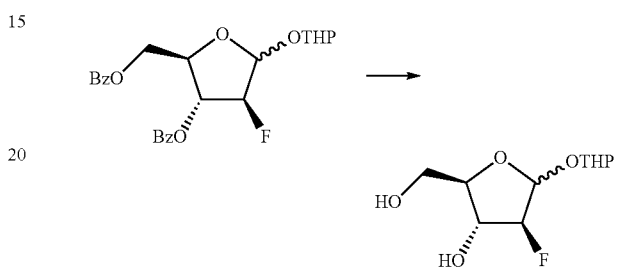

A 28% sodium methoxide/methanol solution was added to a methanol solution of 2.33 g of the 3,5-bis-O-benzoyl-2-deoxy-2-fluoro-1-O-(tetrahydro-2H-pyran-2-yl)-D-arabinofuranoside, and the obtained mixture was then stirred at room temperature for 1 hour. Thereafter, the solvent was distilled away, and ethyl acetate and water were then added to the obtained residue. The organic layer was fractionated, and was then dried over anhydrous sodium sulfate. After that, the solvent was distilled away under reduced pressure. The obtained residue was purified by silica gel column chromatography (hexane/ethyl acetate=50/50 to 0/100), so as to obtain 1.08 g of 2-deoxy-2-fluoro-1-O-(tetrahydro-2H-pyran-2-yl)-D-arabinofuranoside in the form of a colorless oily product.

RT(min): 0.69.

$^1$H-NMR (CDCl$_3$) δ value:

5.58-5.50 (1H, m), 5.03 (1H, brs), 4.94 (1H, dd, 44.7, 2.7 Hz), 4.30-4.07 (3H, m), 3.92-3.52 (3H, m), 2.33 (1H, d, J=9.2 Hz), 2.14-2.08 (1H, m), 1.84-1.54 (7H, m)

(3)

[Formula 259]

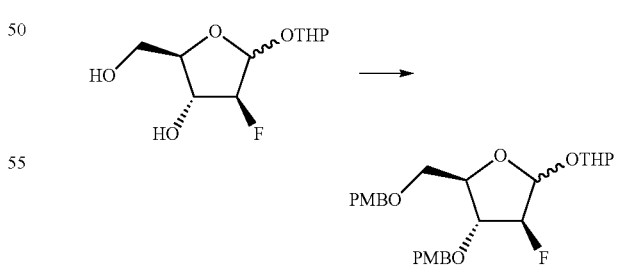

456 mg of 60% sodium hydride was added to a solution of 1.08 g of the 2-deoxy-2-fluoro-1-O-(tetrahydro-2H-pyran-2-yl)-D-arabinofuranoside in 20 mL of N,N-dimethylformamide under cooling on ice, and the obtained mixture was then stirred at the same temperature as described above for 25 minutes. Thereafter, 1.43 mL of 4-methoxybenzyl chloride was added to the reaction mixture, and the thus obtained mixture was then stirred for 1 hour. The reaction mixture was further stirred at room temperature for 1 hour, and it was then left at rest overnight at room temperature. Thereafter, ethyl acetate and water were added to the reaction mixture. The organic layer was fractionated, and it was washed with a saturated sodium chloride aqueous solution and was then dried over anhydrous sodium sulfate. After that, the solvent was distilled away under reduced pressure. The obtained residue was purified by silica gel column chromatography (hexane/ethyl acetate=100/0 to 60/40), so as to obtain 1.42 g of 2-deoxy-2-fluoro-1-O-(tetrahydro-2H-pyran-2-yl)-3,5-bis-O-(4-methoxybenzyl)-D-ara binofuranoside in the form of a colorless oily product.

As a result of the measurement of $^1$H-NMR, the anomeric ratio was found to be 8:2.

RT(min): 1.92.

$^1$H-NMR (CDCl$_3$) δ value:

7.25-7.20 (4H, m), 6.90-6.83 (4H, m), 5.49 (0.8H, d, J=12.6 Hz), 5.40-5.34 (0.2H, m), 5.12 (0.4H, d, J=2.0 Hz), 4.99-4.89 (1.6H, m), 4.64-4.62 (4H, m), 4.22-4.15 (1H, m), 4.12-3.84 (2H, m), 3.81 (3H, s), 3.80 (3H, s), 3.75-3.63 (3H, m), 1.89-1.43 (6H, m)

(4)

[Formula 260]

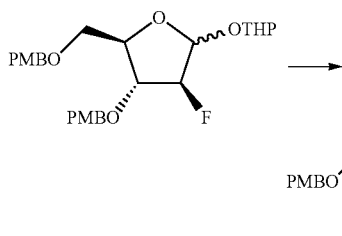

1.42 mL of 2 mol/L hydrochloric acid was added to a solution of 1.42 g of the 2-deoxy-2-fluoro-1-O-(tetrahydro-2H-pyran-2-yl)-3,5-bis-O-(4-methoxybenzyl)-D-ara binofuranoside in 14.2 mL of acetone, and the obtained mixture was then stirred at 50° C. for 1.25 hours. Thereafter, ethyl acetate and a saturated sodium hydrogen carbonate aqueous solution were added to the reaction mixture. The organic layer was fractionated, and it was washed with a saturated sodium chloride aqueous solution and was then dried over anhydrous sodium sulfate. After that, the solvent was distilled away under reduced pressure. The obtained residue was purified by silica gel column chromatography (hexane/ethyl acetate=100/0 to 50/50), so as to obtain 1.14 g of 2-deoxy-2-fluoro-3,5-bis-O-(4-methoxybenzyl)-D-arabinofuranoside in the form of a colorless oily product.

As a result of the measurement of $^1$H-NMR, the anomeric ratio was found to be 8:2.

RT(min): 1.50.

$^1$H-NMR (CDCl$_3$) δ value:

7.29-7.17 (4H, m), 6.92-6.83 (4H, m), 5.46 (0.8H, dd, J=10.2, 7.6 Hz), 5.28 (0.2H, ddd, J=11.4, 3.9, 10.2 Hz), 4.94 (0.2H, dt, J=52.8, 4.8 Hz), 4.91 (0.8H, dd, J=50.4, 1.3 Hz), 4.93-4.87 (0.2H, d, J=1.3 Hz), 4.62-4.39 (4.8H, m), 4.10-3.91 (1H, m), 3.81 (3H, s), 3.81 (3H, s), 3.77-3.67 (0.8H, m), 3.58-3.43 (2.2H, m)

(5)

[Formula 261]

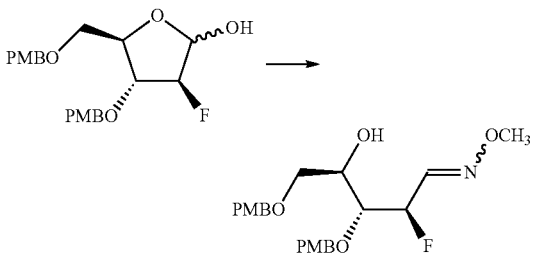

315 mg of O-methylhydroxylammonium chloride and 0.403 mL of triethylamine were added to a solution of 1.14 g of 2-deoxy-2-fluoro-3,5-bis-O-(4-methoxybenzyl)-D-arabinofuranoside in 11 mL of methanol, and the obtained mixture was then stirred at room temperature for 1 hour. Thereafter, the solvent was distilled away under reduced pressure, and ethyl acetate and water were then added to the obtained residue. The organic layer was fractionated, and it was washed with a saturated sodium chloride aqueous solution and was then dried over anhydrous sodium sulfate. After that, the solvent was distilled away under reduced pressure. The obtained residue was purified by silica gel column chromatography (hexane/ethyl acetate=95/5 to 50/50), so as to obtain 1.02 g of (2R,3R,4R)-2-fluoro-4-hydroxy-3,5-bis((4-methoxybenzyl)oxy)pentanal O-methyloxime in the form of a colorless oily product.

$^1$H-NMR was measured. As a result, the syn-anti ratio was found to be 69:31.

RT(min): 1.58.

$^1$H-NMR (CDCl$_3$) δ value:

7.47 (0.69H, t, J=6.9 Hz), 7.29-7.21 (2H, m), 7.18-7.10 (2H, m), 7.00 (0.31H, dd, J=11.2, 4.6 Hz), 6.87 (4H, m), 5.80 (0.31H, ddd, J=47.1, 4.6, 2.0 Hz), 5.35 (0.69H, ddd, J=46.2, 6.9, 3.0 Hz), 4.56-4.34 (4H, m), 3.95-3.90 (1H, m), 3.90 (0.93H, m), 3.86 (2.07H, s), 3.82-3.78 (1H, m), 3.81 (3H, s), 3.80 (3H, s), 3.71 (0.31H, dd, J=7.8, 3.3 Hz), 3.64-3.56 (1.69H, m)

(6)

[Formula 262]

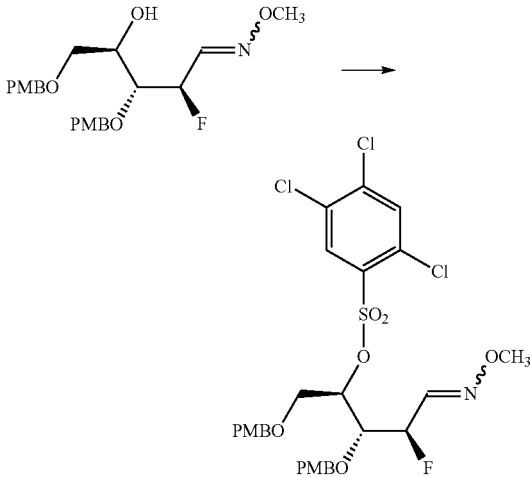

2.03 g of 2,4,5-trichlorobenzenesulfonyl chloride and 0.772 mL of 1-methylimidazole were added to a solution of 1.02 g of the (2R,3R,4R)-2-fluoro-4-hydroxy-3,5-bis((4-methoxybenzyl)oxy)pentanal O-methyloxime in 20 mL of acetonitrile at room temperature, and the obtained mixture was stirred at room temperature for 1.75 hours, and then at 40° C. for 1.25 hours. Thereafter, ethyl acetate and a saturated sodium hydrogen carbonate aqueous solution were added to the reaction mixture. The organic layer was fractionated, and a solid was removed by filtration. The organic layer was dried over anhydrous sodium sulfate, and the solvent was then distilled away under reduced pressure. The obtained residue was purified by silica gel column chromatography (hexane/ethyl acetate=100/0 to 75/25), so as to obtain 1.15 g of (2R,3R,4R)-2-fluoro-3,5-bis((4-methoxybenzyl)oxy)-4-(2,4,5-trichlorophenoxy)pentan al O-methyloxime in the form of a colorless oily product.

$^1$H-NMR was measured. As a result, the syn-anti ratio was found to be 65:35.

RT(min): 2.15.

$^1$H-NMR (CDCl$_3$) δ value:

8.08 (0.35H, s), 8.08 (0.65H, s), 7.43 (1H, s), 7.36 (0.65H, t, J=6.9 Hz), 7.18-7.10 (4H, m), 6.92-6.80 (4.35H, m), 5.58 (0.35H, dq, J=47.6, 2.4 Hz), 5.10 (0.65H, dq, J=46.6, 3.5 Hz), 4.85-4.72 (1H, m), 4.62-4.46 (2H, m), 4.40-4.2 (2.35H, m), 4.08 (0.65H, dq, J=23.8, 2.9 Hz), 3.87 (1.95H, s), 3.87 (1.05H, s), 3.81 (3.90H, s), 3.80 (2.10H, s), 3.81-3.72 (2H, m)

(7)

[Formula 263]

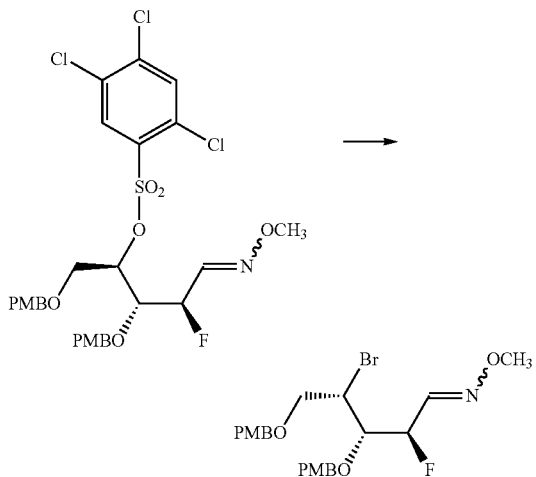

451 mg of lithium bromide was added to a solution of 1.15 g of (2R,3R,4R)-2-fluoro-3,5-bis((4-methoxybenzyl)oxy)-4-(2,4,5-trichlorophenoxy)pentan al O-methyloxime in 6 mL of tetrahydrofuran and 6 mL of 1,3-dimethyl-2-imidazolidinone, and the obtained mixture was then stirred at 65° C. for 7 hours. Thereafter, ethyl acetate and a 25% lithium bromide aqueous solution were added to the reaction mixture. The organic layer was fractionated, and it was washed with a 12% lithium bromide aqueous solution and was then dried over anhydrous sodium sulfate. After that, the solvent was distilled away under reduced pressure. The obtained residue was purified by silica gel column chromatography (hexane/ethyl acetate=100/0 to 60/40), so as to obtain 857 mg of (2S,3S,4S)-4-bromo-2-fluoro-3,5-bis((4-methoxybenzyl)oxy)pentanal O-methyloxime in the form of a colorless oily product.

$^1$H-NMR was measured. As a result, the syn-anti ratio was found to be 82:18.

RT(min): 1.92.

$^1$H-NMR (CDCl$_3$) δ value:

7.40 (0.82H, t, J=6.9 Hz), 7.24 (4H, m), 6.92-6.83 (4.18H, m), 5.79 (0.18H, ddd, J=50.9, 6.0, 2.4 Hz), 5.29 (0.82H, dt, J=46.9, 6.6 Hz), 4.66 (1.64H, ABq, J=10.5, 24.3 Hz), 4.58 (0.36H, ABq, J=18.0, 10.5 Hz), 4.48 (0.36H, s), 4.42 (1.64H, ABq, J=12.0, 1.3 Hz), 4.29-4.06 (1H, m), 3.98 (0.82H, dq, J=17.3, 3.3 Hz), 3.90 (3H, s), 3.88-3.70 (0.18H, m), 3.81 (1H, s), 3.81 (3H, s), 3.80 (3H, s), 3.71-3.63 (1H, m)

(8)

[Formula 264]

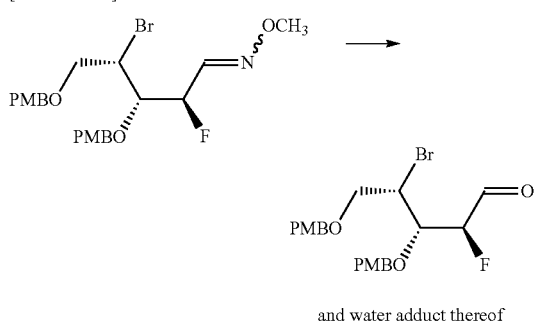

and water adduct thereof 4.2 mL of a 35% formaldehyde solution and 4.2 mL of 2 mol/L hydrochloric acid were added to a solution of 857 mg of (2S,3S,4S)-4-bromo-2-fluoro-3,5-bis((4-methoxybenzyl)oxy)pentanal O-methyloxime in 17 mL of acetone at room temperature, and the obtained mixture was then stirred at room temperature for 1.75 hours. Thereafter, ethyl acetate and a saturated sodium hydrogen carbonate aqueous solution were added to the reaction mixture. The organic layer was fractionated, and it was washed with a saturated sodium chloride aqueous solution and was then dried over anhydrous sodium sulfate. After that, the solvent was distilled away under reduced pressure. The obtained residue was purified by silica gel column chromatography (hexane/ethyl acetate=100/0 to 60/40), so as to obtain 598 mg of colorless oily (2S,3S,4S)-4-bromo-2-fluoro-3,5-bis((4-methoxybenzyl)oxy)pentanal and a water adduct thereof.

RT(min): 1.66.

(9)

[Formula 265]

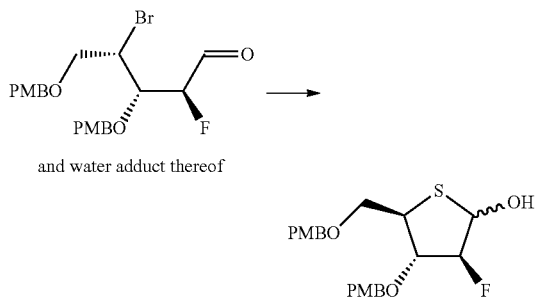

and water adduct thereof 210 mg of a sodium monohydrogen sulfide n-hydrate was added to a solution of 598 mg of (2S,3S,4S)-4-bromo-2-fluoro-3,5-bis((4-methoxybenzyl)oxy)pentanal in 6 mL of 1-methylpyrrolidone and the water adduct thereof under cooling on ice, and the obtained mixture was then stirred at the same temperature as described above for 1.5 hours. Thereafter, ethyl acetate and a saturated saline were added to the reaction mixture. The organic layer was fractionated, and it was washed with a saturated sodium chloride aqueous solution and was then dried over anhydrous sodium sulfate. After that, the solvent was distilled away under reduced pressure. The obtained residue was purified by silica gel column chromatography (hexane/ethyl acetate=90/10 to 30/70), so as to obtain 453 mg of 2-deoxy-2-fluoro-3,5-bis-O-(4-methoxybenzyl)-4-thio-D-arabinofuranoside in the form of a colorless oily product.

RT(min): 1.58, 1.61.

m/z (ESI-positive): 409.3[M+H]$^+$ (10)

[Formula 266]

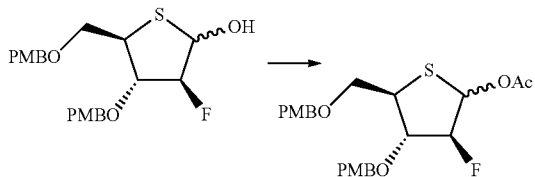

0.210 mL of acetic anhydride, 0.462 mL of triethylamine and 5 mg of 4-dimethylaminopyridine were added to a solution of 453 mg of 2-deoxy-2-fluoro-3,5-bis((4-methoxybenzyl)oxy)-4-thio-D-arabinofuranoside in 9 mL of tetrahydrofuran at room temperature, and the obtained mixture was then stirred at the same temperature as described above for 1.5 hours. Thereafter, ethyl acetate and water were added to the reaction mixture. The organic layer was fractionated, and it was washed with a saturated sodium chloride aqueous solution and was then dried over anhydrous sodium sulfate. After that, the solvent was distilled away under reduced pressure. The obtained residue was purified by silica gel column chromatography (hexane/ethyl acetate=90/10 to 50/50), so as to obtain 447 mg of 1-acetyl-2-deoxy-2-fluoro-3,5-bis-O-(4-methoxybenzyl)-4-thio-D-arabinofuranoside in the form of a colorless oily product.

As a result of the measurement of $^1$H-NMR, the anomeric ratio was found to be 1/1.

RT(min): 1.79, 1.81.

$^1$H-NMR (CDCl$_3$) δ value:

7.25-7.18 (4H, m), 6.90-6.83 (4H, m), 6.03 (0.5H, t, J=3.3 Hz), 6.01 (0.5H, J=13.8, 3.3 Hz), 5.25 (0.5H, ddd, J=50.1, 5.1, 3.3 Hz), 5.09 (0.5H, ddd, J=51.0, 8.4, 4.8 Hz), 4.73-4.46 (2H, m), 4.46 (1H, s), 4.42 (1H, ABq, J=2.0, 3.3 Hz), 4.30-4.07 (1H, m), 3.80 (6H, s), 3.79-3.55 (1.5H, m), 3.50-3.31 (1.5H, m), 2.10 (1.5H, s), 2.07 (1.5H, s)

(11)

[Formula 267]

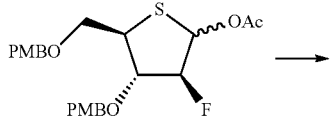

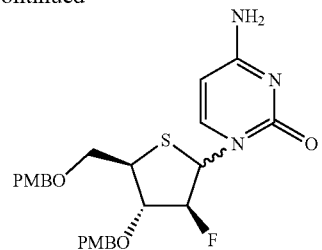

0.277 mL of N,O-bistrimethylsilyl acetamide was added to a solution of 47.2 mg of cytosine and 95.7 mg of 1-acetyl-2-deoxy-2-fluoro-3,5-bis-O-(4-methoxybenzyl)-4-thio-D-arabinofuranoside in 1 mL of acetonitrile at room temperature, and the obtained mixture was then stirred in a nitrogen atmosphere at 75° C. for 2 hours. Thereafter, 0.154 mL of trimethylsilyl trifluoromethanesulfonate was added to the reaction mixture, and the thus obtained mixture was then stirred at the same temperature as described above for 1 hour. Thereafter, dichloromethane and water were added to the reaction mixture. The organic layer was fractionated, and was then dried over anhydrous sodium sulfate. After that, the solvent was distilled away under reduced pressure. The obtained residue was purified by silica gel column chromatography (ethyl acetate/methanol=100/0 to 50/50), and then by silica gel column chromatography (NH column, chloroform/methanol=100/0 to 90/10), so as to obtain 8.8 mg of 1-(2-deoxy-2-fluoro-3,5-bis-O-(4-methoxybenzyl)-4-thio-D-arabinofuranosyl)cytosine in the form of a colorless oily product.

As a result of the measurement of $^1$H-NMR, the α/β ratio was found to be 53/47.

RT(min): 1.30.

$^1$H-NMR (CDCl$_3$) δ value:

8.04 (0.47H, dd, J=7.3, 10.3 Hz), 7.90 (0.53H, d, J=7.3 Hz), 7.25-7.19 (3H, m), 7.13-7.07 (1H, m), 6.92-6.79 (4H, m), 6.68 (0.47H, dd, J=17.8, 4.6 Hz), 6.36 (0.53H, dd, J=15.5, 2.3 Hz), 5.58 (0.53H, d, J=7.9 Hz), 5.52 (0.47H, d, J=7.3 Hz), 5.13 (0.53H, dt, J=46.9, 2.6 Hz), 5.09 (0.47H, dt, J=50.2, 4.6 Hz), 4.47-4.36 (3H, m), 4.28-4.19 (1H, m), 3.89 (1H, q, J=6.8 Hz), 3.83-3.75 (1H, m), 3.82 (1.41H, s), 3.81 (1.59H, s), 3.79 (3H, s), 3.64-3.42 (2H, m)

(12)

[Formula 268]

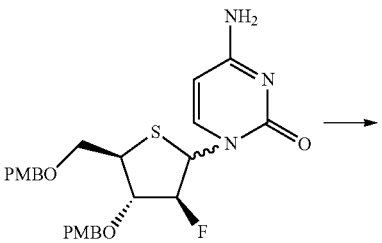

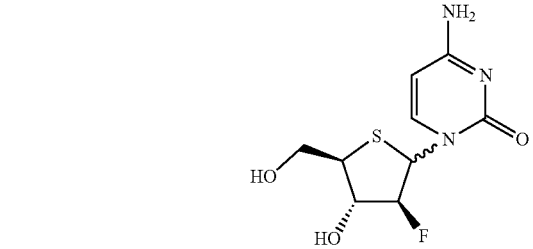

0.2 mL of trifluoroacetic acid was added to a solution of 8.8 mg of 1-(2-deoxy-2-fluoro-3,5-bis-O-(4-methoxybenzyl)-4-thio-D-arabinofuranosyl)cytosine in 2 mL of dichloromethane, and the obtained mixture was then stirred at room temperature for 1.5 hours. Thereafter, the solvent was distilled away from the reaction mixture under reduced pressure. The obtained residue was purified by silica gel column chromatography (NH column, chloroform/methanol=90/10 to 60/40), so as to obtain 3.1 mg of 1-(2-deoxy-2-fluoro-4-thio-D-arabinofuranosyl)cytosine in the form of a white solid.

As a result of the measurement of $^1$H-NMR, the α/β ratio was found to be 56/44.

RT(min): 0.22.

$^1$H-NMR (DMSO-d$_6$) δ value:

8.02-7.94 (1H, m), 7.34-7.15 (2H, m), 6.46 (0.44H, dd, J=14.5, 5.3 Hz), 6.15 (0.56H, dd, J=17.8, 5.9 Hz), 5.92 (0.56H, d, J=5.3 Hz), 5.87 (0.44H, d, J=4.6 Hz), 5.79 (0.56H, d, J=7.3 Hz), 5.77 (0.44H, d, J=7.3 Hz), 5.24 (1H, t, J=5.6 Hz), 5.06 (0.56H, dt, J=52.2, 5.9 Hz), 5.03 (1H, dd, J=11.2, 40.6 Hz), 4.91 (0.44H, dt, J=46.2, 5.3 Hz), 4.24 (0.44H, dt, J=10.7, 5.3 Hz), 4.09 (0.56H, dt, J=2.7, 6.4 Hz), 3.82-3.67 (0.66H, m), 3.65-3.54 (1H, m), 3.51-3.28 (1H, m), 3.26-3.15 (0.44H, m)

Example 28

(1)

[Formula 269]

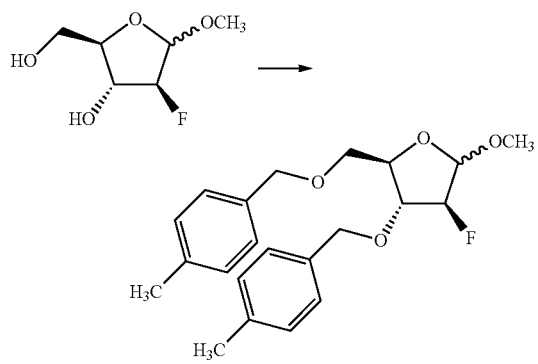

In a nitrogen atmosphere, 0.44 g of sodium hydride and 2.03 g of 4-methylbenzyl bromide were added to a solution of 0.70 g of (2R,3R,4S)-4-fluoro-2-(hydroxymethyl)-5-methoxyoxolan-3-ol in 7.0 mL of N,N-dimethylformamide under cooling on ice, and the obtained mixture was then stirred at room temperature for 2 hours. Thereafter, 2.5 mL of methanol was added to the reaction mixture to terminate the reaction, and ethyl acetate and hexane were then added thereto. The reaction mixture was successively washed with water and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 60/40), so as to obtain 1.33 g of (3S,4R,5R)-3-fluoro-2-methoxy-4-((4-methylbenzyl)oxy)-5-(((4-methylbenzyl)oxy)methyl)oxolane in the form of a colorless oily product.

$^1$H-NMR (CDCl$_3$) δ value:

7.23-7.11 (8H, m), 5.10 (0.5H, dd, J=5.9, 4.3 Hz), 4.93-4.91 (1.5H, m), 4.66-4.52 (4H, m), 4.23-4.09 (2H, m), 3.57-3.48 (2H, m), 3.40 (3H, s), 2.35 (3H, s), 2.34 (3H, s)

(2)

[Formula 270]

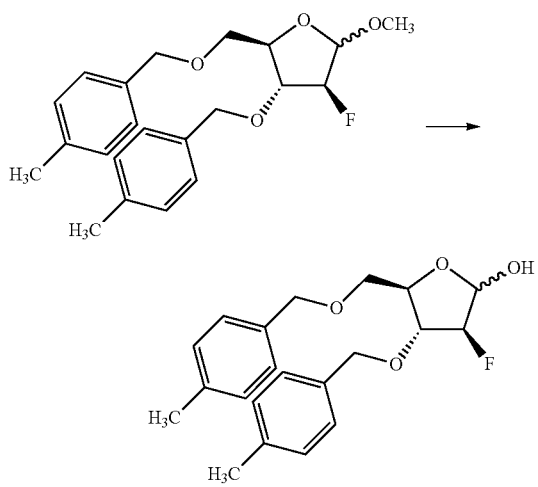

9.8 mL of acetic acid, 3.3 mL of water and 0.56 mL of concentrated sulfuric acid were added to 1.31 g of (3S,4R,5R)-3-fluoro-2-methoxy-((4-methylbenzyl)-(((4-methylbenzyl)oxy)methyl)oxolane, and the obtained mixture was then stirred at 70° C. for 2 hours. Thereafter, ethyl acetate and hexane were added to the reaction mixture, and the thus obtained mixture was successively washed with water and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 30/70), so as to obtain 0.74 g of (3S,4R,5R)-3-fluoro-4-((4-methylbenzyl)oxy)-5-(((4-methylbenzyl)oxy)methyl)oxolan-2-ol in the form of a colorless oily product.

As a result of the measurement of $^1$H-NMR, the α/β ratio was found to be 22:78.

$^1$H-NMR (CDCl$_3$) δ value:

7.21-7.12 (8H, m), 5.46 (0.78H, dd, J=10.1, 7.1 Hz), 5.28 (0.22H, dd, J=10.6, 2.1 Hz), 4.94 (0.22H, dt, J=52.6, 4.8 Hz), 4.92 (0.78H, dd, J=50.4, 1.0 Hz), 4.67-4.42 (5H, m), 4.30 (0.22H, dt, J=17.8, 4.8 Hz), 4.00 (0.78H, ddt, J=19.0, 3.8, 1.0 Hz), 3.92 (0.22H, dd, J=10.6, 1.3 Hz), 3.57-3.42 (2H, m), 2.97 (0.78H, dd, J=7.1, 1.0 Hz), 2.35 (6H, s)

(3)

[Formula 271]

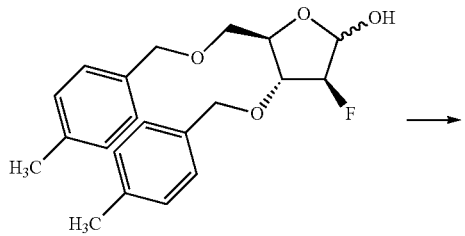

-continued

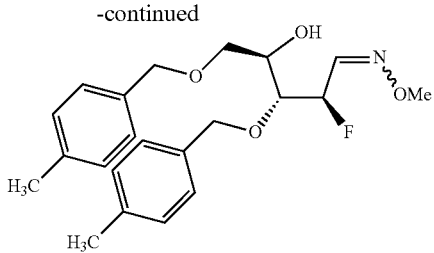

In a nitrogen atmosphere, 3.6 mL of methanol and 0.20 g of O-methylhydroxylamine hydrochloride were added to 0.72 g of (3S,4R,5R)-3-fluoro-4-((4-methylbenzyl)oxy)-5-(((4-methylbenzyl)oxy)methyl)oxoan-2-ol, and thereafter, 0.34 mL of triethylamine was added dropwise to the mixture. The obtained mixture was stirred at room temperature for 16 hours. Thereafter, 0.10 g of O-methylhydroxylamine hydrochloride and 0.25 mL of triethylamine were added to the reaction mixture, and the thus obtained mixture was further stirred at 50° C. for 2 hours. Thereafter, ethyl acetate was added to the reaction mixture, and the thus obtained mixture was successively washed with water and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 50/50), so as to obtain 0.65 g of (2R,3R,4R)-2-fluoro-4-hydroxy-3,5-bis((4-methylbenzyl)oxy)pentanal=O-methyl=oxime in the form of a colorless oily product.

$^1$H-NMR was measured. As a result, the syn-anti ratio was found to be 67:33.

$^1$H-NMR (CDCl$_3$) δ value:
7.48 (0.67H, t, J=7. Hz), 7.23-7.11 (8H, m), 7.00 (0.33H, dd, J=11.6, 4.6 Hz), 5.81 (0.33H, ddd, J=46.2, 4.6, 1.8 Hz), 5.28 (0.67H, ddd, J=46.2, 7.1, 3.1 Hz), 4.58-4.28 (4H, m), 3.97-3.82 (4.33H, m), 3.74-3.60 (2.67H, m), 2.45 (0.33H, d, J=6.9 Hz), 2.43 (0.67H, d, J=6.9 Hz), 2.35 (3H, s), 2.34 (3H, s)
(4)

[Formula 272]

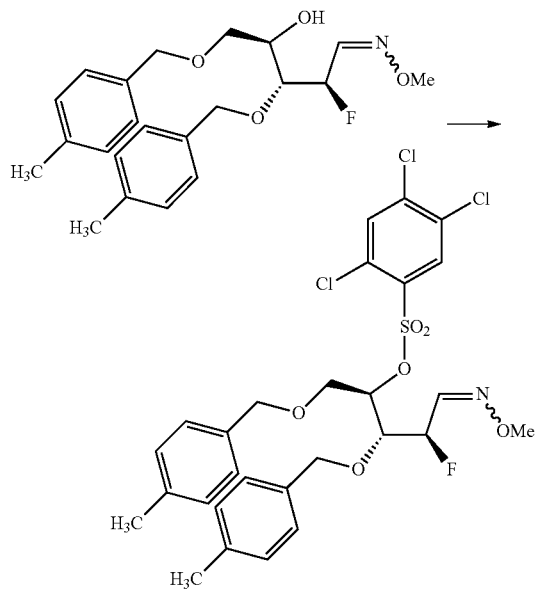

In a nitrogen atmosphere, 6.4 mL of acetonitrile, 0.60 g of 2,4,5-trichlorobenzenesulfonyl chloride and 0.21 mL of N-methylimidazole were added to 0.64 g of (2R,3R,4R)-2-fluoro-4-hydroxy-3,5-bis((4-methylbenzyl)oxy)pentanal=O-methyl=oxime, and the obtained mixture was then stirred at room temperature for 16 hours. Thereafter, ethyl acetate was added to the reaction mixture, and the thus obtained mixture was successively washed with water, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=100/0 to 70/30), so as to obtain 1.01 g of (2R,3R,4R)-4-fluoro-5-(methoxyimino)-1,3-bis((4-methylbenzyl)oxy)pentan-2-yl=2,4,5-trichlorobenzenesulfonate in the form of a colorless oily product.

$^1$H-NMR was measured. As a result, the syn-anti ratio was found to be 66:34.

$^1$H-NMR (CDCl$_3$) δ value:
8.08 (0.34H, s), 8.07 (0.66H, s), 7.40 (1H, s), 7.38 (0.66H, t, J=6.9 Hz), 7.14-7.05 (8H, m), 6.88 (0.34H, dd, J=11.6, 4.6 Hz), 5.59 (0.34H, ddd, J=47.6, 4.6, 2.6 Hz), 5.12 (0.66H, ddd, J=46.5, 6.9, 3.8 Hz), 4.82 (0.66H, td, J=5.3, 3.3 Hz), 4.77 (0.34H, td, J=5.6, 2.4 Hz), 4.65-4.49 (2H, m), 4.40-4.23 (2.34H, m), 4.10 (0.66H, ddd, J=23.7, 5.3, 3.8 Hz), 3.87 (3H, s), 3.85-3.82 (2H, m), 2.35-2.33 (6H, m)
(5)

[Formula 273]

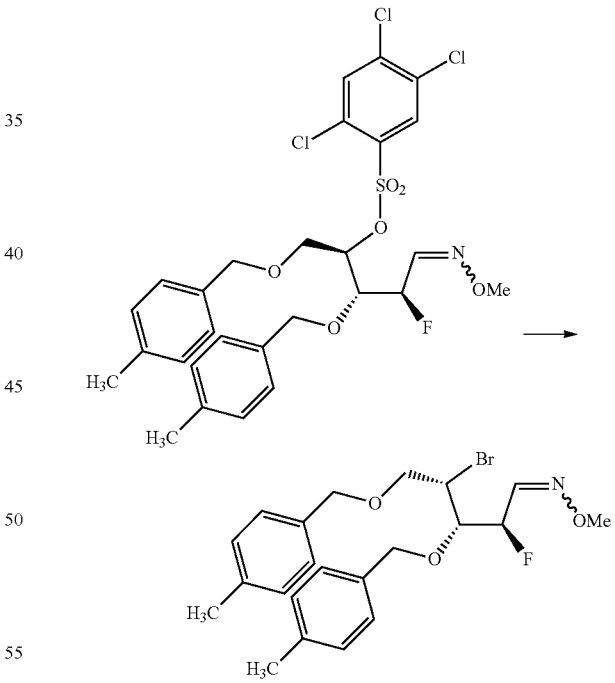

In a nitrogen atmosphere, 10 mL of 1,3-dimethyl-2-imidazolidinone and 0.82 g of anhydrous lithium bromide were added to 1.00 g of (2R,3R,4R)-4-fluoro-5-(methoxyimino)-1,3-bis((4-methylbenzyl)oxy)pentan-2-yl=2,4,5-trichlorobenzenesulfonate, and the obtained mixture was then stirred at 50° C. for 17 hours. Thereafter, ethyl acetate and n-hexane were added to the reaction mixture, and the thus obtained mixture was successively washed with water, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=100/0 to 60/40), so as to obtain 0.56 g of (2R,3S,4S)-4-bromo-2-fluoro-3,5-bis((4-methylbenzyl)oxy)pentanal=O-methyl=oxime in the form of a light yellow oily product.

¹H-NMR was measured. As a result, the syn-anti ratio was found to be 84:16.

¹H-NMR (CDCl₃) δ value:

7.40 (0.84H, t, J=6.6 Hz), 7.23-7.11 (8H, m), 6.89 (0.16H, dd, J=10.2, 5.0 Hz), 5.79 (0.16H, ddd, J=47.7, 5.0, 3.0 Hz), 5.29 (0.84H, dt, J=47.2, 6.6 Hz), 4.77-4.43 (4H, m), 4.28-4.08 (1.16H, m), 4.00 (0.84H, ddd, J=17.2, 6.6, 3.3 Hz), 3.92-3.87 (3.16H, m), 3.83 (0.84H, dd, J=10.2, 7.3 Hz), 3.77 (0.16H, ddd, J=1.2, 5.9, 2.3 Hz), 3.69 (0.84H, ddd, J=10.2, 5.9, 2.3 Hz), 2.35 (3H, s), 2.34 (3H, s)

[Formula 274]

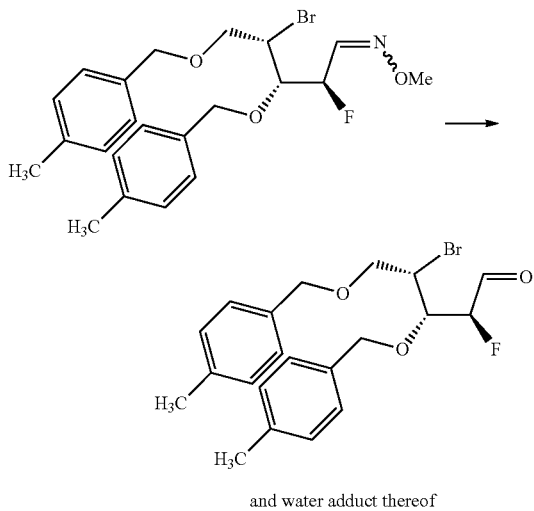

and water adduct thereof

In a nitrogen atmosphere, 11 mL of acetone, 2.7 mL of 2 mol/L hydrochloric acid and 1.0 mL of a 37% formaldehyde aqueous solution were added to 0.55 g of (2R,3S,4S)-4-bromo-2-fluoro-3,5-bis((4-methylbenzyl)oxy)pentanal=O-methyl=oxime, and the obtained mixture was then stirred at room temperature for 4 hours. Thereafter, ethyl acetate was added to the reaction mixture, and the thus obtained mixture was successively washed with water, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 50/50), to obtain 0.50 g of a colorless oily product.

The obtained oily product was a mixture of (2S,3S,4S)-4-bromo-2-fluoro-3,5-bis((4-methylbenzyl)oxy)pentanal and a water adduct thereof.

¹H-NMR (CDCl₃) δ value:

9.76 (1H, d, J=6.6 Hz), 7.23-7.13 (8H, m), 5.06 (1H, dd, J=47.7, 3.8 Hz), 4.66-4.48 (4H, m), 4.34 (1H, td, J=5.9, 4.8 Hz), 4.22 (1H, ddd, J=22.6, 4.8, 3.8 Hz), 3.94 (1H, dd, J=10.9, 5.4 Hz), 3.76 (1H, ddd, J=10.9, 6.4, 2.5 Hz), 2.35 (3H, s), 2.34 (3H, s)

(7)

[Formula 275]

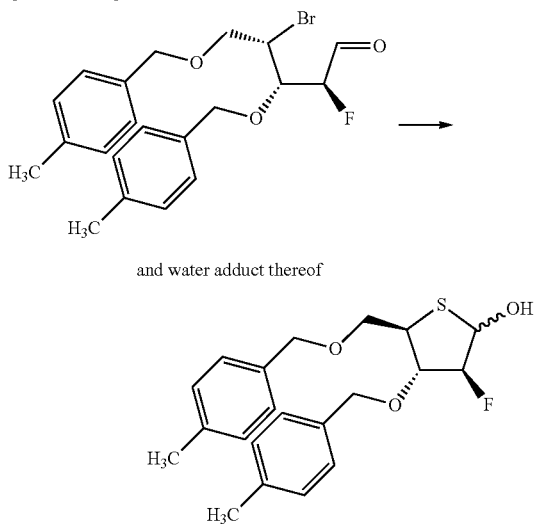

and water adduct thereof 0.19 g of a sodium hydrogen sulfide x-hydrate was added to a solution of 0.50 g of the colorless oily product obtained in Example 28(6) in 4.8 mL of 1-methyl-2-pyrrolidone under cooling on ice, and the obtained mixture was then stirred under cooling on ice for 2 hours. Thereafter, ethyl acetate was added to the reaction mixture, and the thus obtained mixture was successively washed with water, 0.5 M hydrochloric acid, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 50/50), so as to obtain 0.36 g of (3S,4S,5R)-3-fluoro-4-((4-methylbenzyl)oxy)-5-(((4-methylbenzyl)oxy)methyl)thiolan-2-ol in the form of a light yellow oily product.

As a result of the measurement of ¹H-NMR, the α/β ratio was found to be 40:60.

¹H-NMR (CDCl₃) δ value:

7.23-7.13 (8H, m), 5.43 (0.40H, ddt, J=12.2, 8.9, 1.3 Hz), 5.20-5.03 (1.30H, m), 4.90 (0.30H, dd, J=7.3, 4.0 Hz), 4.72-4.46 (4H, m), 4.36 (0.60H, dd, J=7.4, 1.8 Hz), 4.31 (0.40H, dd, J=7.1, 4.6 Hz), 3.95 (0.40H, t, J=7.9 Hz), 3.66-3.37 (3.20H, m), 3.03 (0.40H, dd, J=12.2, 1.3 Hz), 2.35 (6H, s)

(8)

[Formula 276]

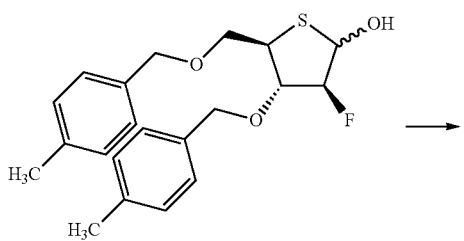

-continued

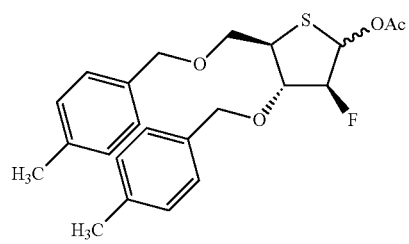

In a nitrogen atmosphere, 0.17 mL of acetic anhydride and 0.38 mL of triethylamine were added to a solution of 0.34 g of (3S,4S,5R)-3-fluoro-4-((4-methylbenzyl)oxy)-5-(((4-methylbenzyl)oxy)methyl)thiolan-2-ol in 3.4 mL of tetrahydrofuran under cooling on ice, and the obtained mixture was then stirred at room temperature for 21 hours. Thereafter, ethyl acetate was added to the reaction mixture, and the thus obtained mixture was successively washed with a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 60/40), so as to obtain 0.31 g of (3S,4S,5R)-3-fluoro-4-((4-methylbenzyl)oxy)-5-(((4-methylbenzyl)oxy)methyl)thiolan-2-yl=acetate in the form of a colorless oily product.

As a result of the measurement of $^1$H-NMR, the α/β ratio was found to be 40:60.

$^1$H-NMR (CDCl$_3$) δ value:

7.21-7.12 (8H, m), 6.03 (0.40H, d, J=4.6 Hz), 6.02 (0.60H, dd, J=16.7, 3.2 Hz), 5.17 (0.60H, ddd, J=50.1, 5.4, 3.2 Hz), 5.09 (0.40H, ddd, J=50.9, 8.6, 4.6 Hz), 4.74-4.41 (4H, m), 4.26 (0.40H, ddd, J=12.6, 8.6, 4.9 Hz), 4.12 (0.60H, ddd, J=15.4, 6.9, 5.4), 3.74 (0.60H, ddd, J=6.9, 5.3, 1.1 Hz), 3.66-3.60 (1H, m), 3.51-3.34 (1.40H, m), 2.35 (6H, s), 2.10 (1.80H, s), 2.06 (1.20H, s)

(9)

[Formula 277]

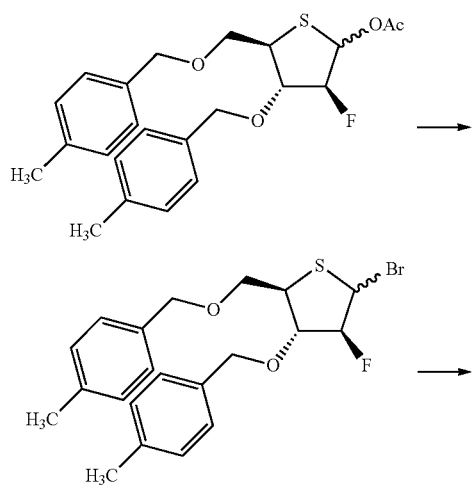

-continued

In a nitrogen atmosphere, 0.14 mL of a 30% hydrogen bromide/acetic acid solution was added to a solution of 0.15 g of (3S,4S,5R)-3-fluoro-4-((4-methylbenzyl)oxy)-5-(((4-methylbenzyl)oxy)methyl)thiolan-2-yl=acetate in 0.60 mL of methylene chloride, and the obtained mixture was then stirred at room temperature for 1.5 hours. Thereafter, methylene chloride was added to the reaction mixture, and the thus obtained mixture was successively washed with water and a saturated sodium hydrogen carbonate aqueous solution, and was then dried over anhydrous sodium sulfate, to obtain a methylene chloride solution containing (3S,4S,5R)-2-bromo-3-fluoro-4-((4-methylbenzyl)oxy)-5-(((4-methylbenzyl)oxy)meth yl)thiolane.

To another reaction vessel, 0.10 g of cytosine and 0.58 mL of N,O-bis(trimethylsilyl)acetamide were added in a nitrogen atmosphere, and the obtained mixture was then stirred at 80° C. for 1.5 hours. After cooling in air, the methylene chloride solution containing (3S,4S,5R)-2-bromo-3-fluoro-4-((4-methylbenzyl)oxy)-5-(((4-methylbenzyl)oxy)meth yl)thiolane was added to the reaction mixture, and the obtained mixture was then stirred at 60° C. for 2.5 hours. Thereafter, methylene chloride was added to the reaction mixture, and the thus obtained mixture was washed with a saturated sodium hydrogen carbonate aqueous solution, and was then dried over anhydrous magnesium sulfate. After that, the solvent was distilled away under reduced pressure. The obtained residue was purified by silica gel column chromatography (chloroform/methanol=100/0 to 90/10), so as to obtain 72 mg of (3S,4S,5R)-2-(4-amino-2-oxo-1,2-dihydropyrimidin-1-yl)-3-fluoro-4-((4-methylbenzyl)oxy)-5-(((4-methylbenzyl)oxy)methyl)thiolane in the form of a light yellow solid.

As a result of the measurement of $^1$H-NMR, the α/β ratio was found to be 38:62.

$^1$H-NMR (CDCl$_3$) δ value:

8.08 (0.62H, dd, J=7.3, 1.7 Hz), 7.95 (0.38H, d, J=7.3 Hz), 7.23-7.05 (8H, m), 6.69 (0.62H, dd, J=18.0, 4.5 Hz), 6.39 (0.38H, dd, J=15.2, 2.0 Hz), 5.56 (0.38H, d, J=7.3 Hz), 5.50 (0.62H, d, J=7.3 Hz), 5.14 (0.38H, dt, J=46.6, 2.0 Hz), 5.11 (0.62H, dt, J=50.5, 4.5 Hz), 4.63-4.40 (4H, m), 4.29-4.15 (1H, m), 3.92 (0.38H, t, J=7.6 Hz), 3.65-3.56 (2.24H, m), 3.49 (0.38H, ddd, J=9.2, 6.8, 2.0 Hz), 2.37-2.34 (6H, m)

(10)

[Formula 278]

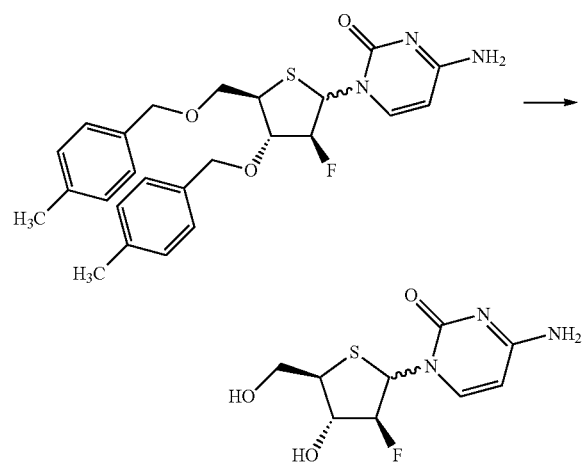

In a nitrogen atmosphere, 3.0 mL of a methylene chloride solution 1 mol/L boron trichloride was added to a solution of 70 mg of (3S,4S,5R)-2-(4-amino-2-oxo-1,2-dihydropyrimidin-1-yl)-3-fluoro-4-((4-methylbenzyl)oxy)-5-(((4-methylbenzyl)oxy)methyl)thiolane in 4.6 mL of methylene chloride under cooling on dry ice/acetone, and the obtained mixture was then stirred at the same temperature as described above for 3.5 hours. Thereafter, the temperature of the reaction mixture was increased to 0° C., and the mixture was then stirred for 30 minutes. Thereafter, 3.0 mL of methanol was added to the reaction mixture, and the thus obtained mixture was then stirred at room temperature for 30 minutes. Thereafter, a solid was then collected by filtration, and it was then purified by silica gel column chromatography (chloroform/methanol=100/0 to 60/40), so as to obtain 63 mg of (2R,3S,4S)-5-(4-amino-2-oxo-1,2-dihydropyrimidin-1-yl)-4-fluoro-2-(hydroxymethyl)thiolan-3-ol in the form of a white solid.

As a result of the measurement of $^1$H-NMR, the α/β ratio was found to be 24:76.

$^1$H-NMR (DMSO-d$_6$) δ value:
7.99 (0.76H, dd, J=7.3, 1.3 Hz), 7.97 (0.24H, d, J=7.3 Hz), 7.31-7.20 (2H, br), 6.46 (0.76H, dd, J=14.5, 5.0 Hz), 6.15 (0.24H, dd, J=17.5, 5.9 Hz), 5.95 (0.24H, d, J=5.0 Hz), 5.90 (0.76H, d, J=5.0 Hz), 5.80 (0.24H, d, J=7.3 Hz), 5.78 (0.76H, d, J=7.3 Hz), 5.26 (0.76H, t, J=5.3 Hz), 5.18-4.82 (1.24H, m), 4.29-4.20 (0.76H, m), 4.14-4.03 (0.27H, m), 3.80-3.56 (2H, m), 3.25-3.19 (1H, m)

Example 29

(1)

[Formula 279]

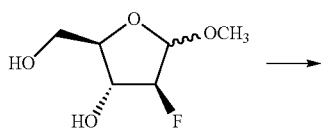

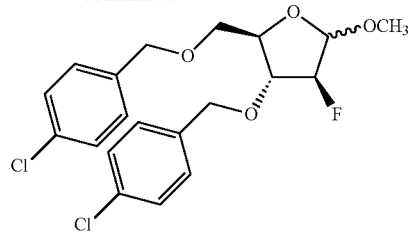

In a nitrogen atmosphere, 0.97 g of sodium hydride and 4.66 g of 4-chlorobenzyl bromide were added to a solution of 1.35 g of (2R,3R,4S)-4-fluoro-2-(hydroxymethyl)-5-methoxyoxolan-3-ol in 13 mL of N,N-dimethylformamide under cooling on ice, and the obtained mixture was then stirred at room temperature for 1 hour. Thereafter, 5 mL of methanol was added to the reaction mixture to terminate the reaction, and ethyl acetate and hexane were then added to the mixture. The thus obtained mixture was successively washed with water, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=100/0 to 60/40), so as to obtain 3.32 g of (2R,3R,4S)-3-((4-chlorobenzyl)oxy)-2-(((4-chlorobenzyl)oxy)methyl)-4-fluoro-5-methoxyoxolane in the form of a colorless oily product.

$^1$H-NMR (CDCl$_3$) δ value:
7.33-7.20 (8H, m), 5.10 (0.5H, dd, J=6.1, 4.5 Hz), 4.93-4.91 (1.5H, m), 4.68-4.52 (4H, m), 4.13-4.07 (2H, m), 3.59-3.49 (2H, m), 3.40 (3H, s)

(2)

[Formula 280]

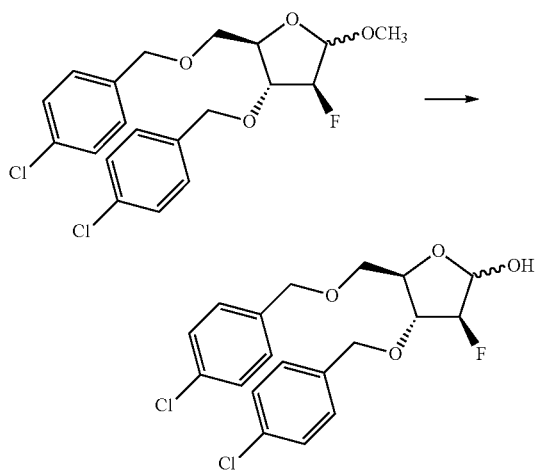

27 mL of acetic acid, 6.6 mL of water and 1.06 mL of concentrated sulfuric acid were added to 3.32 g of (2R,3R,4S)-3-((4-chlorobenzyl)oxy)-2-(((4-chlorobenzyl)oxy)methyl)-4-fluoro-5-methoxyoxolane, and the obtained mixture was then stirred at 70° C. for 2 hours. Thereafter, 4.5 mL of water and 0.53 mL of concentrated sulfuric acid were added to the reaction mixture, and the obtained mixture was then stirred at 70° C. for 5 hours. Thereafter, ethyl acetate and hexane were added to the reaction mixture, and the thus obtained mixture was successively washed with water and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 30/70), so as to obtain 2.92 g of (3S,4R,5R)-4-((4-chlorobenzyl)oxy)-5-(((4-chlorobenzyl)oxy)methyl)-3-fluorooxolan-2-ol in the form of a colorless oily product.

As a result of the measurement of $^1$H-NMR, the α/β ratio was found to be 18:82.

$^1$H-NMR (CDCl$_3$) δ value:
7.35-7.29 (4H, m), 7.25-7.20 (4H, m), 5.49 (0.82H, dd, J=10.2, 6.3 Hz), 5.31 (0.18H, ddd, J=10.2, 3.8, 2.3 Hz), 4.95 (0.18H, dt, J=52.8, 4.6 Hz), 4.95 (0.82H, dd, J=50.2, 1.3 Hz), 4.68-4.48 (4H, m), 4.43 (0.82H, td, J=5.6, 4.3 Hz), 4.26 (0.18H, dt, J=17.6, 4.6 Hz), 4.10 (0.18H, dt, J=5.0, 3.8 Hz), 3.99 (0.82H, ddt, J=19.8, 4.3, 0.9 Hz), 3.70 (0.18H, dd, J=10.2, 1.5 Hz), 3.62-3.48 (2H, m), 2.88 (0.82H, dd, J=6.6, 1.3 Hz)

(3)

[Formula 281]

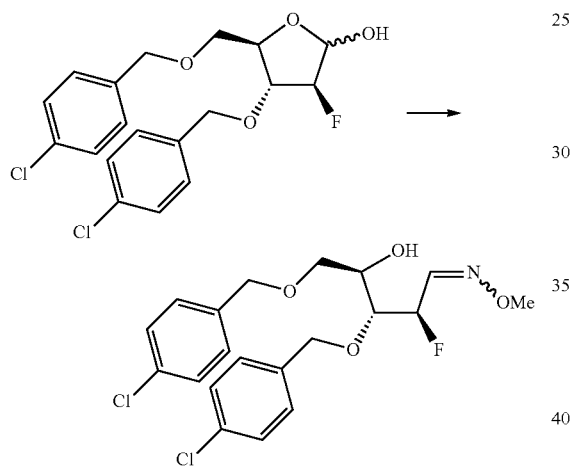

In a nitrogen atmosphere, 14 mL of methanol and 0.72 g of O-methylhydroxylamine hydrochloride were added to 2.89 g of (3S,4R,5R)-4-((4-chlorobenzyl)oxy)-5-(((4-chlorobenzyl)oxy)methyl)-3-fluorooxolan-2-ol, and thereafter, 1.21 mL of triethylamine was added dropwise to the mixture. The thus obtained mixture was stirred at room temperature for 12 hours. Thereafter, ethyl acetate was added to the reaction mixture, and the thus obtained mixture was successively washed with water and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 50/50), so as to obtain 3.09 g of (2R,3R,4R)-3,5-bis((4-chlorobenzyl)oxy)-2-fluoro-4-hydroxypentanal=O-methyl=oxime in the form of a white solid.

$^1$H-NMR was measured. As a result, the syn-anti ratio was found to be 65:35.

$^1$H-NMR (CDCl$_3$) δ value:
7.47 (0.65H, t, J=6.9 Hz), 7.35-7.13 (8H, m), 6.99 (0.35H, dd, J=11.6, 4.6 Hz), 5.80 (0.35H, ddd, J=46.9, 4.6, 1.7 Hz), 5.28 (0.65H, ddd, J=45.9, 6.9, 3.3 Hz), 4.62-4.39 (4H, m), 4.00-3.83 (4.35H, m), 3.76-3.56 (2.65H, m), 2.42 (0.35H, d, J=6.6 Hz), 2.40 (0.65H, d, J=6.6 Hz)

(4)

[Formula 282]

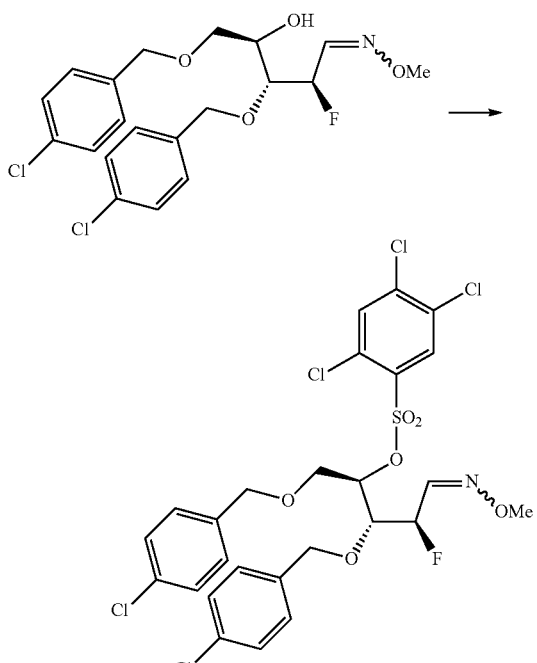

In a nitrogen atmosphere, 31 mL of acetonitrile, 2.81 g of 2,4,5-trichlorobenzenesulfonyl chloride and 1.02 mL of N-methylimidazole were added to 3.08 g of (2R,3R,4R)-3,5-bis((4-chlorobenzyl)oxy)-2-fluoro-4-hydroxypentanal=O-methyl=oxime, and the obtained mixture was then stirred at room temperature for 4.5 hours. Thereafter, ethyl acetate was added to the reaction mixture, and the thus obtained mixture was successively washed with water, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=100/0 to 70/30), so as to obtain 4.72 g of (2R,3R,4R)-1,3-bis((4-chlorobenzyl)oxy)-4-fluoro-5-(methoxyimino) pentan-2-yl=2,4,5-trichlorobenzenesulfonate in the form of a colorless oily product.

$^1$H-NMR was measured. As a result, the syn-anti ratio was found to be 68:32.

$^1$H-NMR (CDCl$_3$) δ value:
8.08 (0.32H, s), 8.07 (0.68H, s), 7.42 (1H, s), 7.37 (0.68H, t, J=6.7 Hz), 7.33-7.27 (4H, m), 7.21-7.08 (4H, m), 6.87 (0.32H, dd, J=11.6, 4.6 Hz), 5.58 (0.32H, ddd, J=47.6, 4.6, 3.0 Hz), 5.12 (0.68H, ddd, J=46.5, 6.7, 4.2 Hz), 4.84 (0.68H, ddd, J=5.6, 4.8, 3.0 Hz), 4.77 (0.32H, td, J=5.6, 2.3 Hz), 4.68-4.53 (2H, m), 4.41-4.29 (2.16H, m), 4.25 (0.16H, dd, J=5.6, 2.3 Hz), 4.10 (0.68H, td, J=23.1, 4.5 Hz), 3.88 (3H, s), 3.86-3.73 (2H, m)

(5)

[Formula 283]

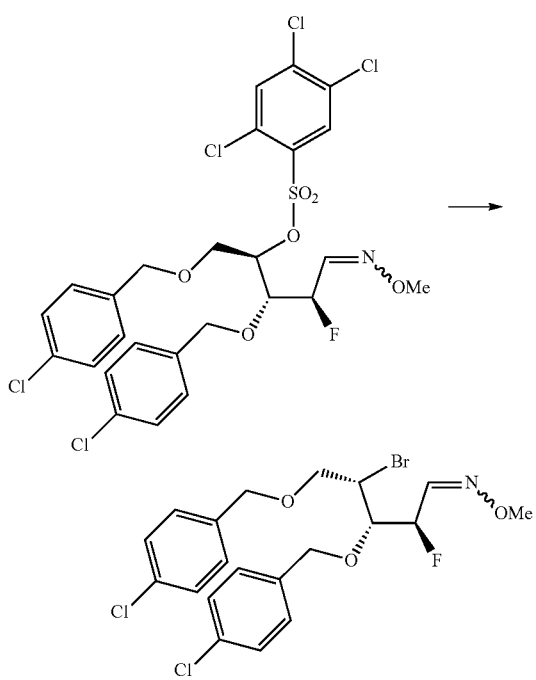

In a nitrogen atmosphere, 47 mL of 1,3-dimethyl-2-imidazolidinone and 3.64 g of anhydrous lithium bromide were added to 4.71 g of (2R,3R,4R)-1,3-bis((4-chlorobenzyl)oxy)-4-fluoro-5-(methoxyimino)pentan-2-yl=2,4,5-trichlorobenzenesulfonate, and the obtained mixture was then stirred at 50° C. for 14 hours. Thereafter, ethyl acetate and hexane were added to the reaction mixture, and the thus obtained mixture was successively washed with water, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=100/0 to 60/40), so as to obtain 2.78 g of (2R,3S,4S)-4-bromo-3,5-bis((4-chlorobenzyl)oxy)-2-fluoropentanal=O-methyl=oxime in the form of a light yellow oily product.

$^1$H-NMR was measured. As a result, the syn-anti ratio was found to be 81:19.

$^1$H-NMR (CDCl$_3$) δ value:

7.42 (0.81H, t, J=6.6 Hz), 7.34-7.21 (8H, m), 6.89 (0.19H, dd, J=11.6, 4.8 Hz), 5.79 (0.19H, ddd, J=47.6, 4.8, 3.0 Hz), 5.31 (0.81H, dt, J=47.2, 6.6 Hz), 4.80-4.39 (4H, m), 4.30-4.11 (1.19H, m), 4.00 (0.81H, ddd, J=16.8, 6.6, 3.3 Hz), 3.913 (2.43H, s), 3.905 (0.57H, s), 3.89-3.77 (1.19H, m), 3.70 (0.81H, ddd, J=10.2, 5.9, 2.3 Hz)

(6)

[Formula 284]

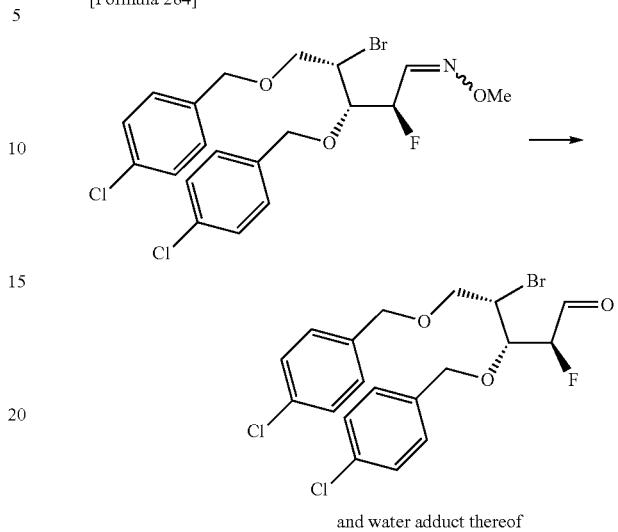

and water adduct thereof

In a nitrogen atmosphere, 55 mL of acetone, 14 mL of 2 mol/L hydrochloric acid and 4.80 mL of a 37% formaldehyde aqueous solution were added to 2.75 g of (2R,3S,4S)-4-bromo-3,5-bis((4-chlorobenzyl)oxy)-2-fluoropentanal=O-methyl=oxime, and the obtained mixture was then stirred at room temperature for 5.5 hours. Thereafter, ethyl acetate was added to the reaction mixture, and the thus obtained mixture was successively washed with water, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=80/20 to 20/80), so as to obtain 2.56 g of a light yellow oily product.

The obtained oily product was a mixture of (2S,3S,4S)-4-bromo-3,5-bis((4-chlorobenzyl)oxy)-2-fluoropentanal and a water adduct thereof.

$^1$H-NMR (CDCl$_3$) δ value:

9.80 (1H, d, J=5.9 Hz), 7.35-7.15 (8H, m), 5.13 (1H, dd, J=47.6, 3.6 Hz), 4.66-4.44 (4H, m), 4.37 (1H, dt, J=5.9, 5.1 Hz), 4.22 (1H, ddd, J=23.0, 5.1, 3.6 Hz), 3.94 (1H, dd, J=0.9, 5.3 Hz), 3.78 (1H, ddd, J=10.9, 5.9, 2.5 Hz)

(7)

[Formula 285]

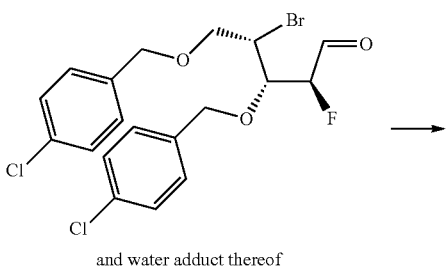

and water adduct thereof

-continued

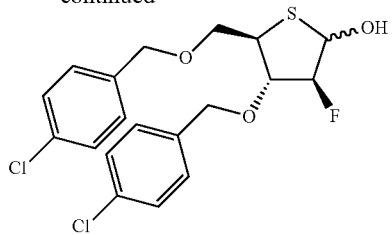

0.91 g of a sodium hydrogen sulfide x-hydrate was added to a solution of 2.50 g of the light yellow oily product obtained in Example 29(6) in 25 mL of 1-methyl-2-pyrrolidone under cooling on ice, and the obtained mixture was then stirred under cooling on ice for 1.5 hours. Thereafter, ethyl acetate was added to the reaction mixture, and the thus obtained mixture was successively washed with water, 0.5 mol/L hydrochloric acid, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 50/50), so as to obtain 1.92 g of (3S,4S,5R)-4-((4-chlorobenzyl)oxy)-5-(((4-chlorobenzyl)oxy)methyl)-3-fluorothiolan-2-ol in the form of a light yellow oily product.

As a result of the measurement of $^1$H-NMR, the α/β ratio was found to be 63:37.

$^1$H-NMR (CDCl$_3$) δ value:
7.42-7.19 (8H, m), 5.45 (0.37H, ddd, J=11.6, 9.2, 1.2 Hz), 5.15 (0.63H, ddd, J=8.3, 3.6, 3.0 Hz), 5.13 (0.37H, dt, J=47.9, 1.2 Hz), 5.01 (0.63H, ddd, J=52.2, 7.1, 4.1 Hz), 4.72-4.41 (4H, m), 4.35-4.36 (1H, m), 3.93 (0.37H, t, J=7.8 Hz), 3.59-3.34 (3.26H, m), 2.89 (0.37H, dd, J=11.6, 1.0 Hz)

(8)

[Formula 286]

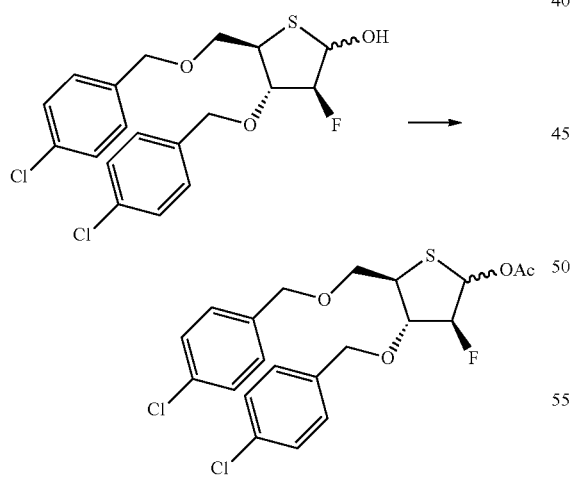

0.86 mL of acetic anhydride and 1.90 mL of triethylamine were added to a solution of 1.89 g of (3S,4S,5R)-4-((4-chlorobenzyl)oxy)-5-(((4-chlorobenzyl)oxy)methyl)-3-fluorothiolan-2-ol in 19 mL of tetrahydrofuran under cooling on ice, and the obtained mixture was then stirred at room temperature for 24 hours. Thereafter, ethyl acetate was added to the reaction mixture, and the thus obtained mixture was successively washed with a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 60/40), so as to obtain 1.77 g of (3S,4S,5R)-4-((4-chlorobenzyl)oxy)-5-(((4-chlorobenzyl)oxy)methyl)-3-fluorothiolan-2-yl=acetate in the form of a light yellow oily product.

As a result of the measurement of $^1$H-NMR, the α/β ratio was found to be 40:60.

$^1$H-NMR (CDCl$_3$) δ value:
7.33-7.20 (8H, m), 6.04 (0.40H, d, J=4.3 Hz), 6.02 (0.60H, dd, J=16.8, 3.0 Hz), 5.19 (0.60H, ddd, J=50.0, 5.4, 3.0 Hz), 5.11 (0.40H, ddd, J=50.9, 8.3, 4.3 Hz), 4.76-4.41 (4H, m), 4.24 (0.40H, ddd, J=12.2, 8.3, 6.6 Hz), 4.12 (0.60H, ddd, J=15.4, 6.6, 5.4), 3.75 (0.60H, qd, J=6.6, 1.0 Hz), 3.65-3.60 (1H, m), 3.50 (0.60H, dd, J=9.6, 6.6 Hz), 3.47 (0.40H, ddd, J=9.7, 6.6, 1.0 Hz), 3.37 (0.40H, q, J=6.6 Hz), 2.11 (1.8H, s), 2.08 (1.2H, s)

(9)

[Formula 287]

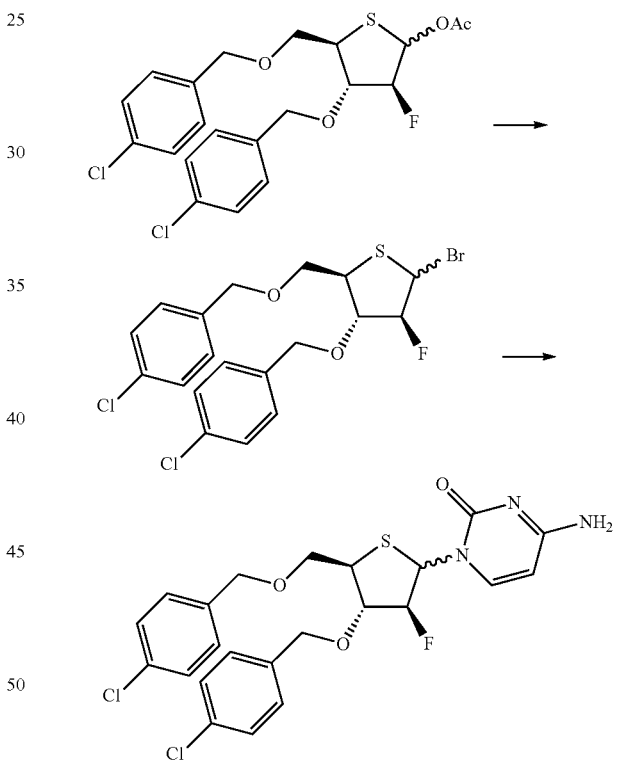

In a nitrogen atmosphere, 0.17 mL of a 30% hydrogen bromide/acetic acid solution was added to a solution of 0.20 g of (3S,4S,5R)-4-((4-chlorobenzyl)oxy)-5-(((4-chlorobenzyl)oxy)methyl)-3-fluorothiolan-2-yl=acetate in 0.80 mL of methylene chloride, and the obtained mixture was then stirred at room temperature for 2 hours. Thereafter, methylene chloride was added to the reaction mixture, and the thus obtained mixture was successively washed with water and a saturated sodium hydrogen carbonate aqueous solution, and was then dried over anhydrous magnesium sulfate, to obtain a methylene chloride solution containing (3S,4S,5R)-2-bromo-4-((4-chlorobenzyl)oxy)-5-(((4-chlorobenzyl)oxy)methyl)-3-fluorothiolane.

To another reaction vessel, 0.12 g of cytosine and 0.53 mL of N,O-bis(trimethylsilyl)acetamide were added in a nitrogen atmosphere, and the obtained mixture was then stirred at 80° C. for 2 hours. After cooling in air, a methylene chloride solution containing (3S,4S,5R)-2-bromo-4-((4-chlorobenzyl)oxy)-5-(((4-chlorobenzyl)oxy)methyl)-3-fluorothiolane was added to the reaction mixture, and the obtained mixture was then stirred 60° C. for 2 hours. Thereafter, methylene chloride was added to the reaction mixture, and the thus obtained mixture was washed with a saturated sodium hydrogen carbonate aqueous solution, and was then dried over anhydrous sodium sulfate. After that, the solvent was distilled away under reduced pressure. The obtained residue was purified by silica gel column chromatography (chloroform/methanol=100/0 to 80/20), so as to obtain 0.18 g of (3S,4S,5R)-2-(4-amino-2-oxo-1,2-dihydropyrimidin-1-yl)-4-((4-chlorobenzyl)oxy)-5-(((4-chlorobenzyl)oxy)methyl)-3-fluorothiolane in the form of a light yellow solid.

As a result of the measurement of ¹H-NMR, the α/β ratio was found to be 36:64.

¹H-NMR (CDCl₃) δ value:
8.01 (0.64H, dd, J=7.6, 1.8 Hz), 7.93 (0.36H, d, J=7.6 Hz), 7.36-7.09 (8H, m), 6.73 (0.64H, dd, J=19.2, 4.3 Hz), 6.38 (0.36H, dd, J=15.0, 2.3 Hz), 5.54 (0.36H, d, J=7.6 Hz), 5.53 (0.64H, d, J=7.6 Hz), 5.20 (0.36H, dt, J=47.2, 2.3 Hz), 5.14 (0.64H, dt, J=50.5, 4.3 Hz), 4.65-4.41 (4H, m), 4.28-4.21 (1H, m), 3.95-3.89 (0.36H, m), 3.66-3.60 (2.28H, m), 3.54-3.48 (0.36H, m)

(10)

[Formula 288]

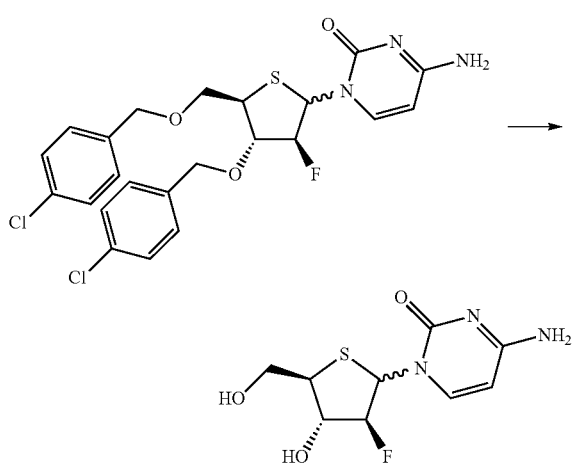

In a nitrogen atmosphere, 6.8 mL of a methylene chloride solution of 1 mol/L boron trichloride was added to a solution of 0.17 g of (3S,4S,5R)-2-(4-amino-2-oxo-1,2-dihydropyrimidin-1-yl)-4-((4-chlorobenzyl)oxy)-5-(((4-chlorobenzyl)oxy)methyl)-3-fluorothiolane in 11 mL of methylene chloride under cooling on dry ice/acetone, and the obtained mixture was then stirred at the same temperature as described above for 3.5 hours. Thereafter, the temperature of the reaction mixture was increased to 0° C., and the reaction mixture was then stirred for 30 minutes. Thereafter, 7.5 mL of methanol was added to the reaction mixture, and the thus obtained mixture was then stirred at room temperature for 30 minutes. Thereafter, a solid was collected by filtration, and it was successively washed with ethyl acetate and hexane. The obtained solid was purified by silica gel column chromatography (chloroform/methanol=100/0 to 60/40), so as to obtain 63 mg of (2R,3S,4S)-5-(4-amino-2-oxo-1,2-dihydropyrimidin-1-yl)-4-fluoro-2-(hydroxymethyl)thiolan-3-ol in the form of a white solid.

As a result of the measurement of ¹H-NMR, the α/β ratio was found to be 27:73.

¹H-NMR (DMSO-d₆) δ value:
7.99 (0.73H, dd, J=7.3, 1.3 Hz), 7.97 (0.27H, d, J=7.3 Hz), 7.31-7.20 (2H, br), 6.46 (0.73H, dd, J=14.7, 5.3 Hz), 6.15 (0.27H, dd, J=17.5, 5.9 Hz), 5.95 (0.27H, d, J=5.3 Hz), 5.89 (0.73H, d, J=5.3 Hz), 5.80 (0.27H, d, J=7.3 Hz), 5.78 (0.73H, d, J=7.3 Hz), 5.26 (0.73H, t, J=5.3 Hz), 5.18-4.82 (1.27H, m), 4.29-4.20 (0.73H, m), 4.14-4.03 (0.27H, m), 3.80-3.54 (2H, m), 3.25-3.19 (1H, m)

Example 30

(1)

[Formula 289]

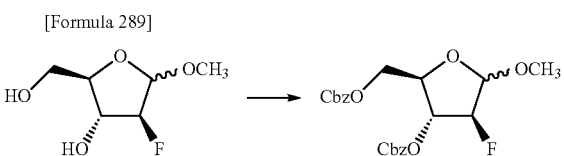

In a nitrogen atmosphere, 55 mL of methylene chloride and 2.60 mL of 1-methylimidazole were added to 1.37 g of (2R,3R,4S)-4-fluoro-2-(hydroxymethyl)-5-methoxyoxolan-3-ol, and thereafter, 3.52 mL of (benzyloxy)carbonyl chloride was added dropwise to the mixture under cooling on ice. The obtained mixture was stirred at room temperature for 3 hours. Thereafter, the solvent was distilled away under reduced pressure, and the obtained residue was then dissolved in ethyl acetate. The resultant was successively washed with water and a saturated sodium hydrogen carbonate aqueous solution, and was then dried over anhydrous magnesium sulfate. After that, the solvent was distilled away under reduced pressure. The obtained residue was purified by silica gel column chromatography (hexane/ethyl acetate=95/5 to 70/30), so as to obtain 2.91 g of benzyl=((2R,3R,4S)-3-(((benzyloxy)carbonyl)oxy)-4-fluoro-5-methoxyoxolan-2-yl)methyl=carbonate in the form of a colorless oily product.

¹H-NMR (CDCl₃) δ value:
7.40-7.33 (10H, m), 5.33-5.22 (1H, m), 5.14 (0.5H, dd, J=5.6, 4.3 Hz), 4.97-4.96 (1.5H, m), 4.53 (1H, dd, J=11.2, 4.0 Hz), 4.31 (1H, dd, J=11.2, 7.6 Hz), 4.21 (1H, ddd, J=7.6, 5.1, 4.0 Hz), 3.45 (3H, s)

(2)

[Formula 290]

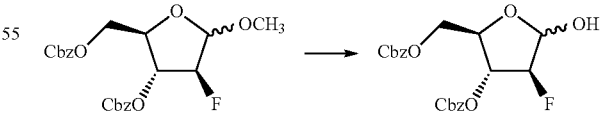

21 mL of acetic acid, 5.2 mL of water and 0.67 mL of concentrated sulfuric acid were added to 2.58 g of benzyl=((2R,3R,4S)-3-(((benzyloxy)carbonyl)oxy)-4-fluoro-5-methoxyoxolan-2-yl)methyl=carbonate, and the obtained mixture was then stirred at 70° C. for 8 hours. Thereafter, 0.30 mL of concentrated sulfuric acid was added to the reaction mixture, and the obtained mixture was further stirred at 70° C. for 7 hours. Thereafter, ethyl acetate was added to the reaction mixture, and the thus obtained mixture was successively washed with water and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=95/5 to 50/50), so as to obtain 1.69 g of benzyl=((2R,3R,4S)-3-(((benzyloxy)carbonyl)oxy)-4-fluoro-5-hydroxyoxolan-2-yl)methyl=carbonate in the form of a colorless oily product.

As a result of the measurement of ¹H-NMR, the α/β ratio was found to be 20:80.

¹H-NMR (CDCl₃) δ value:

7.40-7.33 (10H, m), 5.56 (0.80H, dd, J=10.2, 4.0 Hz), 5.42 (0.20H, ddd, J=8.6, 6.6, 3.6 Hz), 5.23-5.14 (4.20H, m), 5.03 (0.80H, dd, J=21.3, 4.1 Hz), 5.02 (0.80H, dd, J=48.2, 1.0 Hz), 4.96 (0.20H, dt, J=50.9, 3.6 Hz), 4.53-4.43 (2H, m), 4.34 (0.80H, dd, J=12.4, 6.8 Hz), 4.17 (0.20H, dd, J=5.9, 4.1 Hz), 3.34 (0.20H, dd, J=8.6, 2.0 Hz), 2.70 (0.80H, dd, J=4.0, 2.8 Hz)

(3)

[Formula 291]

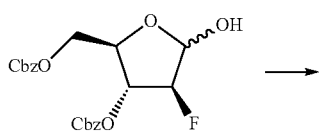

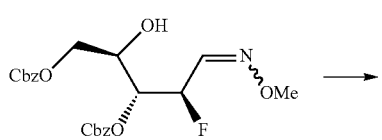

8.4 mL of methanol and 0.37 g of O-methylhydroxylamine hydrochloride were added to 1.68 g of benzyl=((2R,3R,4S)-3-(((benzyloxy)carbonyl)oxy)-4-fluoro-5-hydroxyoxolan-2-yl)methyl=carbonate, and thereafter, 0.61 mL of triethylamine was added dropwise to the mixture. The obtained mixture was stirred at room temperature for 2 hours. Thereafter, ethyl acetate was added to the reaction mixture, and the thus obtained mixture was successively washed with water and a saturated sodium hydrogen carbonate aqueous solution, and was then dried over anhydrous magnesium sulfate. After that, the solvent was distilled away under reduced pressure. The obtained residue was purified by silica gel column chromatography (hexane/ethyl acetate=95/5 to 60/40), so as to obtain 1.66 g of dibenzyl=((2R,3R,4R)-4-fluoro-2-hydroxy-5-(methoxyimino)pentane-1,3-diyl)=dicarbonate in the form of a colorless oily product.

¹H-NMR was measured. As a result, the syn-anti ratio was found to be 77:23.

¹H-NMR (CDCl₃) δ value:

7.41-7.33 (10.77H, m), 6.82 (0.23H, dd, J=110.2, 4.6 Hz), 5.89 (0.23H, ddd, J=46.2, 4.6, 2.1 Hz), 5.39 (0.77H, ddd, J=45.2, 6.4, 2.8 Hz), 5.29-5.13 (4.23H, m), 5.01 (0.77H, ddd, J=24.0, 8.0, 2.9 Hz), 4.35-4.09 (3H, m), 3.89 (0.69H, s), 3.84 (2.31H, s), 2.62 (0.77H, d, J=5.9 Hz), 2.60 (0.23H, d, J=6.9 Hz)

(4)

[Formula 292]

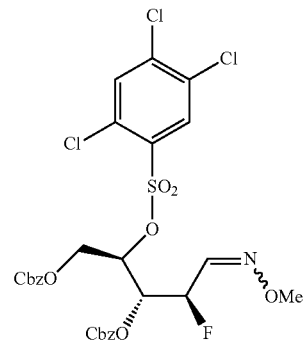

In a nitrogen atmosphere, 10 mL of acetonitrile, 1.55 g of 2,4,5-trichlorobenzenesulfonyl chloride and 0.87 mL of N-methylimidazole were added to 1.66 g of the dibenzyl=((2R,3R,4R)-4-fluoro-2-hydroxy-5-(methoxyimino)pentane-1,3-diyl)=dicarbonate, and the obtained mixture was then stirred at room temperature for 1.5 hours. Thereafter, ethyl acetate was added to the reaction mixture, and the thus obtained mixture was successively washed with a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=100/0 to 75/25), so as to obtain 2.40 g of dibenzyl ((2R,3R,4R)-4-fluoro-5-(methoxyimino)-2-(((2,4,5-trichlorobenzene)sulfonyl)oxy)pentane-1,3-diyl) =dicarbonate in the form of a colorless oily product.

¹H-NMR was measured. As a result, the syn-anti ratio was found to be 78:22.

¹H-NMR (CDCl₃) δ value:

8.11 (0.22H, s), 8.10 (0.78H, s), 7.51 (1H, s), 7.43-7.33 (10.78H, m), 6.78 (0.22H, dd, J=11.4, 4.5 Hz), 5.71 (0.22H, ddd, J=46.9, 4.5, 2.8 Hz), 5.54 (0.22H, ddd, J=25.1, 5.8, 2.8 Hz), 5.37 (0.78H, ddd, J=21.5, 5.6, 4.0 Hz), 5.31 (0.39H, dd, J=6.3, 4.0 Hz), 5.22-5.03 (5.17H, m), 5.00 (0.22H, td, J=5.8, 2.6 Hz), 4.46-4.39 (1H, m), 4.36-4.30 (1H, m), 3.87 (0.66H, s), 3.85 (2.34H, s)

(5)

[Formula 293]

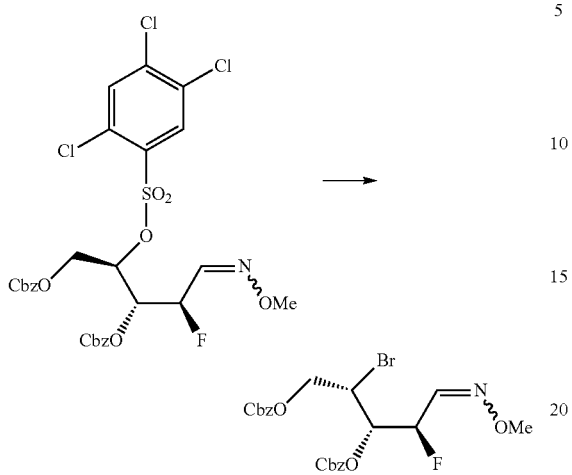

In a nitrogen atmosphere, 24 mL of 1,3-dimethyl-2-imidazolidinone and 1.65 g of anhydrous lithium bromide were added to 2.40 g of the dibenzyl=((2R,3R,4R)-4-fluoro-5-(methoxyimino)-2-(((2,4,5-trichlorobenzene)sulfonyl)oxy) pentane-1,3-diyl)=dicarbonate, and the obtained mixture was then stirred at 50° C. for 9 hours. Thereafter, ethyl acetate was added to the reaction mixture, and the thus obtained mixture was successively washed with water, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=100/0 to 80/20), so as to obtain 1.25 g of dibenzyl= ((2R,3S,4S)-2-bromo-4-fluoro-5-(methoxyimino)pentane-1,3-diyl)=dicarbonate in the form of a colorless oily product.

$^1$H-NMR was measured. As a result, the syn-anti ratio was found to be 79:21.

$^1$H-NMR (CDCl$_3$) δ value:
7.42-7.34 (10.79H, m), 6.82 (0.21H, dd, J=11.2, 4.8 Hz), 5.94 (0.21H, ddd, J=46.9, 4.8, 3.1 Hz), 5.47-5.16 (5.79H, m), 4.59-4.31 (3H, m), 3.89 (3H, s)

(6)

[Formula 294]

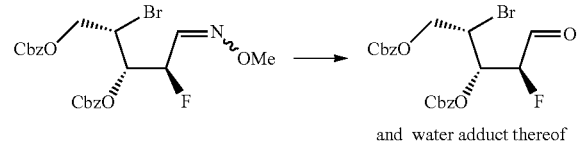

and water adduct thereof

In a nitrogen atmosphere, 22 mL of acetone, 5.6 mL of 2 mol/L hydrochloric acid and 1.87 mL of a 37% formaldehyde aqueous solution were added to 1.11 g of dibenzyl=((2R,3S, 4S)-2-bromo-4-fluoro-5-(methoxyimino)pentane-1,3-diyl) =dicarbonate, and the obtained mixture was then stirred at room temperature for 4 hours. Thereafter, ethyl acetate was added to the reaction mixture, and the thus obtained mixture was successively washed with water, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=85/15 to 20/80), so as to obtain 1.07 g of a colorless oily product.

The obtained oily product was a mixture of dibenzyl=((2R, 3S,4S)-2-bromo-4-fluoro-5-oxopentane-1,3-diyl)=dicarbonate and a water adduct thereof.

$^1$H-NMR (CDCl$_3$) δ value:
9.74 (1H, d, J=5.6 Hz), 7.39-7.31 (10H, m), 5.38 (1H, dt, J=22.0, 4.0 Hz), 5.20-5.13 (5H, m), 4.62-4.31 (3H, m)

(7)

[Formula 295]

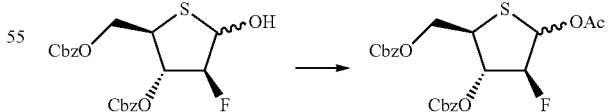

and water adduct thereof 0.37 g of a sodium hydrogen sulfide x-hydrate was added to a solution of 1.05 g of the colorless oily product obtained in Example 30(6) in 11 mL of 1-methyl-2-pyrrolidone under cooling on ice, and the obtained mixture was then stirred under cooling on ice for 1.5 hours. Thereafter, ethyl acetate was added to the reaction mixture, and the thus obtained mixture was successively washed with water, 0.5 mol/L hydrochloric acid, a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 40/60), so as to obtain 0.64 g of benzyl=((2R,3S,4S)-3-(((benzyloxy)carbonyl)oxy)-4-fluoro-5-hydroxythiolan-2-yl)methyl=carbonate in the form of a light yellow oily product.

As a result of the measurement of $^1$H-NMR, the α/β ratio was found to be 36:64.

$^1$H-NMR (CDCl$_3$) δ value:
7.40-7.31 (10H, m), 5.53-5.45 (1H, m), 5.40 (0.36H, dtd, J=10.2, 2.0, 1.0 Hz), 5.34 (0.64H, t, J=4.0 Hz), 5.27-5.10 (4.68H, m), 4.95 (0.32H, dd, J=7.3, 4.0 Hz), 4.46 (0.64H, dd, J=10.6, 6.4 Hz), 4.37 (0.64H, dd, J=10.6, 6.4 Hz), 4.22 (0.72H, dd, J=7.3, 1.0 Hz), 4.03-3.97 (0.36H, m), 3.54 (0.64H, td, J=6.4, 5.3 Hz)

(8)

[Formula 296]

0.28 mL of acetic anhydride and 0.61 mL of triethylamine were added to a solution of 0.64 g of benzyl=((2R,3S,4S)-3-(((benzyloxy)carbonyl)oxy)-4-fluoro-5-hydroxythiolan-2-yl)methyl=carbonate in 6.4 mL of tetrahydrofuran under cooling on ice, and the obtained mixture was then stirred at room temperature for 4 hours. Thereafter, ethyl acetate was added to the reaction mixture, and the thus obtained mixture was successively washed with a saturated sodium hydrogen carbonate aqueous solution and a saturated sodium chloride aqueous solution, and was then dried over anhydrous magnesium sulfate. After that, the solvent was distilled away under reduced pressure. The obtained residue was purified by silica gel column chromatography (hexane/ethyl acetate=90/10 to 40/60), so as to obtain 0.58 g of (3S,4S,5R)-4-(((benzyloxy)carbonyl)oxy)-5-((((benzyloxy)carbonyl)oxy)methyl)-3-fluorothiolan-2-yl=acetate in the form of a light yellow oily product.

As a result of the measurement of $^1$H-NMR, the α/β ratio was found to be 40:60.

$^1$H-NMR (CDCl$_3$) δ value:
7.39-7.34 (1 OH, m), 6.08 (0.60H, dd, J=14.5, 1.7 Hz), 6.05 (0.40H, d, J=4.3 Hz), 5.51 (0.40H, ddd, J=11.9, 8.8, 7.1 Hz), 5.38-5.03 (5.60H, m), 4.47 (0.40H, dd, J=11.1, 5.8 Hz), 4.34-4.20 (1.60 H, m), 3.89 (0.60H, q, J=6.4 Hz), 3.51 (0.40H, q, J=6.5 Hz), 2.11 (1.20H, s), 2.07 (1.80H, s)

(9)

[Formula 297]

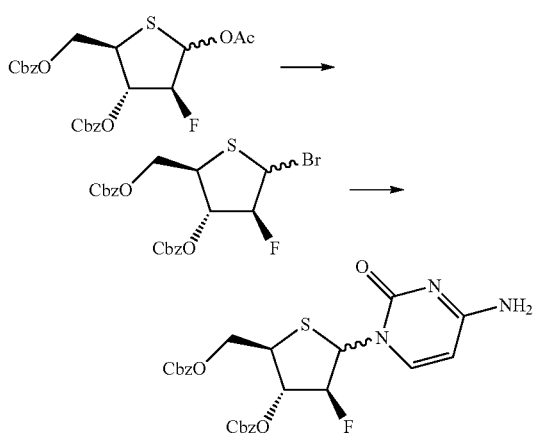

In a nitrogen atmosphere, 0.08 mL of a 30% hydrogen bromide/acetic acid solution was added to a solution of 100 mg of (3S,4S,5R)-4-(((benzyloxy)carbonyl)oxy)-5-((((benzyloxy)carbonyl)oxy)methyl)-3-fluorothiolan-2-yl=acetate in 0.40 mL of methylene chloride, and the obtained mixture was then stirred at room temperature for 2 hours. Thereafter, methylene chloride was added to the reaction mixture, and the thus obtained mixture was successively washed with water and a saturated sodium hydrogen carbonate aqueous solution, and was then dried over anhydrous sodium sulfate, to obtain a methylene chloride solution containing benzyl=((2R,3S,4S)-3-(((benzyloxy)carbonyl)oxy)-5-bromo-4-fluorothiolan-2-yl)methyl=carbonate.

To another reaction vessel, 59 mg of cytosine and 0.36 mL of N,O-bis(trimethylsilyl)acetamide were added in a nitrogen atmosphere, and the obtained mixture was then stirred at 80° C. for 1.5 hours. After cooling in air, the methylene chloride solution containing benzyl=((2R,3S,4S)-3-(((benzyloxy)carbonyl)oxy)-5-bromo-4-fluorothiolan-2-yl)methyl=carbonate was added to the reaction mixture, and the obtained mixture was then stirred at 60° C. for 3 hours. Thereafter, methylene chloride was added to the reaction mixture, and the thus obtained mixture was successively washed with water and a saturated sodium hydrogen carbonate aqueous solution, and was then dried over anhydrous sodium sulfate. After that, the solvent was distilled away under reduced pressure. The obtained residue was purified by silica gel column chromatography (chloroform/methanol=100/0 to 80/20), so as to obtain 15 mg of benzyl=((2R,3S,4S)-5-(4-amino-2-oxo-1,2-dihydropyrimidin-1-yl)-3-(((benzyloxy)carbonyl)oxy)-4-fluorothiolan-2-yl)methyl=carbonate in the form of a white solid.

As a result of the measurement of $^1$H-NMR, the α/β ratio was found to be 24:76.

$^1$H-NMR (CDCl$_3$) δ value:
7.96 (0.76H, dd, J=7.3, 2.1 Hz), 7.96 (0.24H, d, J=7.3 Hz), 7.41-7.34 (10H, m), 6.82 (0.76H, dd, J=23.8, 4.0 Hz), 6.35 (0.24H, dd, J=15.2, 2.3 Hz), 5.77-5.66 (1.24H, m), 5.43-5.07 (5.76H, m), 4.45-4.30 (2H, m), 4.08 (0.24H, t, J=7.6 Hz), 3.80 (0.76H, t, J=7.6 Hz)

(10)

[Formula 298]

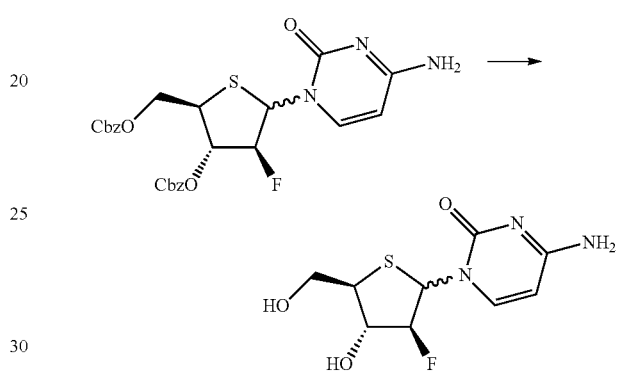

1.0 mL of a 7 mol/L ammonia/methanol solution was added to 15 mg of benzyl=((2R,3S,4S)-5-(4-amino-2-oxopyrimidin-(2H)-yl)-3-(((benzyloxy)carbonyl)oxy)-4-fluorothiolan-2-yl)methyl=carbonate, and the obtained mixture was then stirred at room temperature for 1.5 hours. Thereafter, the solvent was distilled away under reduced pressure, and the obtained residue was then purified by silica gel column chromatography (chloroform/methanol=100/0 to 65/35), so as to obtain 6.6 mg of (2R,3S,4S)-5-(4-amino-2-oxo-1,2-dihydropyrimidin-1-yl)-4-fluoro-2-(hydroxymethyl)thiolan-3-ol in the form of a white solid.

As a result of the measurement of $^1$H-NMR, the α/β ratio was found to be 26:74.

$^1$H-NMR (DMSO-d$_6$) δ value:
7.99 (0.74H, dd, J=7.3, 1.3 Hz), 7.97 (0.26H, d, J=7.3 Hz), 7.29-7.19 (2H, br), 6.46 (0.74H, dd, J=14.5, 5.0 Hz), 6.15 (0.26H, dd, J=17.5, 5.9 Hz), 5.94 (0.26H, d, J=5.0 Hz), 5.88 (0.74H, d, J=5.0 Hz), 5.79 (0.26H, d, J=7.3 Hz), 5.78 (0.74H, d, J=7.3 Hz), 5.26 (0.74H, t, J=5.3 Hz), 5.17-4.82 (1.26H, m), 4.29-4.20 (0.74H, m), 4.14-4.03 (0.26H, m), 3.79-3.56 (2H, m), 3.25-3.19 (1H, m)

Example 31

(1)

[Formula 299]

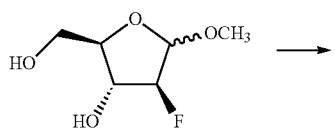

-continued

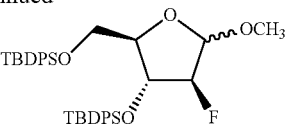

(3)

A mixture of 1.15 g of (2R,3R,4S)-4-fluoro-2-(hydroxymethyl)-5-methoxyoxolan-3-ol, 20 mL of N,N-dimethylformamide, 5.33 mL of tert-butyl diphenylchlorosilane and 2.83 g of imidazole was stirred at room temperature for 1 hour, and the reaction mixture was then left at room temperature for 1 day. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/0 to 9/1), so as to obtain 3.15 g of (3S,4R,5R)-4-((tert-butyldiphenylsilyl)oxy)-5-(((tert-butyldiphenylsilyl)oxy)methyl)-3-fluoro-2-methoxyoxolane in the form of a colorless oily product.

$^1$H-NMR (CDCl$_3$) δ value:
7.59-7.51 (8H, m), 7.41-7.24 (12H, m), 4.94 (1H, d, J=5.3 Hz), 4.92 (1H, ddd, J=52.8, 5.9, 4.6 Hz), 4.32 (1H, dt, J=16.5, 5.3 Hz), 4.13-4.07 (1H, m), 3.38 (2H, d, J=5.3 Hz), 3.29 (3H, s), 1.06 (9H, s), 0.97 (9H, s)

(2)

[Formula 300]

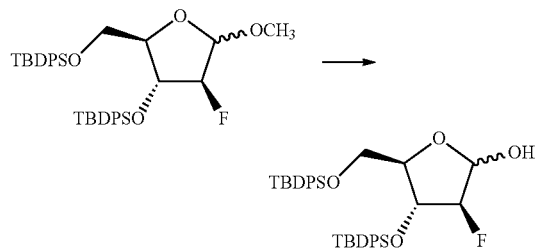

1.0 mL of 30% hydrogen bromide/acetic acid was added dropwise to a solution of 1.66 g of (3S,4R,5R)-4-((tert-butyldiphenylsilyl)oxy)-5-(((tert-butyldiphenylsilyl)oxy)methyl)-3-fluoro-2-methoxyoxolane in 10 mL of methylene chloride at room temperature, and the obtained mixture was then stirred at room temperature for 3 hours. Thereafter, ethyl acetate and water were added to the reaction mixture, and the obtained mixture was then stirred for 5 minutes. Thereafter, the organic layer was fractionated, and it was washed with a 10% sodium hydrogen carbonate aqueous solution. After that, the solvent was distilled away under reduced pressure. 10 mL of acetonitrile and 10 mL of a 10% sodium hydrogen carbonate aqueous solution were added to the obtained residue, and the obtained mixture was then stirred at room temperature for 3 hours. Subsequently, the reaction mixture was left overnight. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/0 to 9/1), so as to obtain 0.65 g of (3S,4R,5R)-4-((tert-butyldiphenylsilyl)oxy)-5-(((tert-butyldiphenylsilyl)oxy)methyl)-3-fluorooxolan-2-ol in the form of a colorless oily product.

$^1$H-NMR (CDCl$_3$) δ value:
7.65-7.24 (20H, m), 5.37 (1H, t, J=9.2 Hz), 4.76 (1H, dd, J=50.2, 1.3 Hz), 4.45 (1H, td, J=5.4, 2.9 Hz), 4.38-4.32 (1H, m), 3.47-4.43 (2H, m), 3.15 (1H, d, J=8.6z), 1.07 (9H, s), 0.91 (9H, s)

[Formula 301]

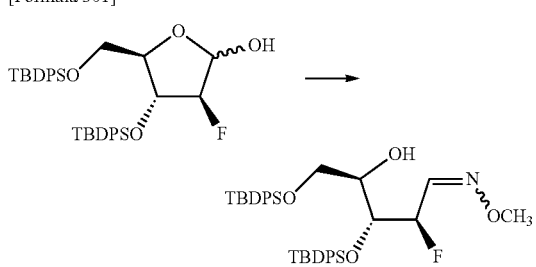

0.13 g of O-methylhydroxylamine hydrochloride and 1.0 mL of methanol were added to 0.65 g of (3S,4R,5R)-4-((tert-butyldiphenylsilyl)oxy)methyl)-3-fluorooxolan-2-ol, and thereafter, 0.19 mL of triethylamine was added dropwise to the mixture under cooling on ice. The obtained mixture was stirred at room temperature for 3 hours. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/0 to 9/1), so as to obtain 0.32 g of (2R,3R,4R)-3,5-bis((tert-butyldiphenylsilyl)oxy)-2-fluoro-4-hydroxypentanal=O-methyloxime in the form of a colorless oily product.

$^1$H-NMR was measured. As a result, the syn-anti ratio was found to be 4:1.

$^1$H-NMR (CDCl$_3$) δ value:
7.63-7.50 (8H, m), 7.46-7.28 (12.75H, m), 6.72 (0.25H, dd, J=11.2, 4.6 Hz), 5.73 (0.25H, ddd, J=46.6, 4.6, 2.0 Hz), 5.10 (0.75H, ddd, J=46.1, 7.3, 4.0 Hz), 4.10 (0.25H, ddd, J=28.1, 6.3, 1.7 Hz), 3.98-3.77 (2.75H, m), 3.76 (2.25H, s), 3.60-3.50 (1.75H, m), 2.66 (0.25H, dd, J=4.0, 1.3 Hz), 2.55 (0.25H, ddd, J=28.1, 6.3, 1.7 Hz), 1.01 (9H, s), 0.97 (6.75H, s), 0.94 (2.25H, s)

(4)

[Formula 302]

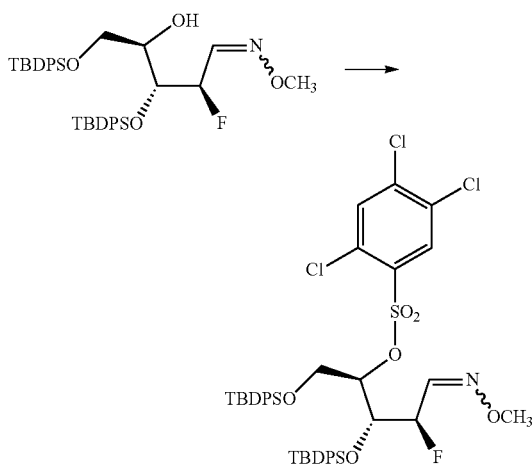

A mixture of 0.32 g of (2R,3R,4R)-3,5-bis((tert-butyldiphenylsilyl)oxy)-2-fluoro-4-hydroxypentanal=O-methyloxime, 2 mL of acetonitrile, 1 mL of tetrahydrofuran, 0.1 mL of N-methylimidazole and 0.15 g of 2,4,5-trichlorobenzenesulfonyl chloride was stirred at room temperature for 8 hours, and the reaction mixture was then left at room temperature for 3 days. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/0 to 19/1), so as to obtain 0.24 g of (2R,3R,4R)-3,5-bis((tert-butyldiphenylsilyl)oxy)-2-fluoro-4-(((2,4,5-trichlorobenzene) sulfonyl)oxy)pentanal=O-methyloxime in the form of a colorless oily product.

$^1$H-NMR (CDCl$_3$) δ value:

8.01 (1H, s), 7.63-7.56 (8H, m), 7.46-7.28 (13H, m), 7.15 (1H, t, J=6.9 Hz), 5.01 (1H, dt, J=47.6, 7.3 Hz), 4.90 (1H, t, J=7.3 Hz), 4.32 (1H, ddd, J=13.2, 6.6, 1.3 Hz), 4.03 (1H, dd, J=11.2, 5.9 Hz), 3.83 (1H, dd, J=11.2, 6.6 Hz), 3.79 (3H, s), 0.99 (9H, s), 0.97 (9H, s)

(5)

[Formula 303]

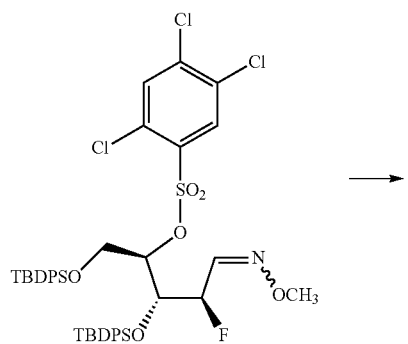

114 mg of anhydrous lithium bromide and 1.0 mL of 1,3-dimethyl-2-imidazolidinone were added to a solution of 236 mg of (2R,3R,4R)-3,5-bis((tert-butyldiphenylsilyl)oxy)-2-fluoro-4-(((2,4,5-trichlorobenzene) sulfonyl)oxy)pentanal=O-methyloxime in 1.0 mL of tetrahydrofuran, and the obtained mixture was then stirred at 50° C. for 10 hours. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/0 to 19/1), so as to obtain 173 mg of (2R,3S,4S)-4-bromo-3,5-bis((tert-butyldiphenylsilyl)oxy)-2-fluoropentanal=O-methyloxime in the form of a colorless oily product.

$^1$H-NMR (CDCl$_3$) δ value:

7.71-7.53 (8H, m), 7.46-7.29 (12H, m), 7.17 (0.86H, t, J=7.3 Hz), 6.57 (0.14H, dd, J=10.6, 5.3 Hz), 5.75 (0.14H, dt, J=47.3, 4.6 Hz), 5.13 (0.86H, dt, J=46.9, 6.6 Hz), 4.26-4.19 (1H, m), 4.08-4.00 (1H, m), 3.87-3.78 (4.58H, m), 3.65 (0.42H, s), 1.03 (9H, s), 1.00 (9H, s)

(6)

[Formula 304]

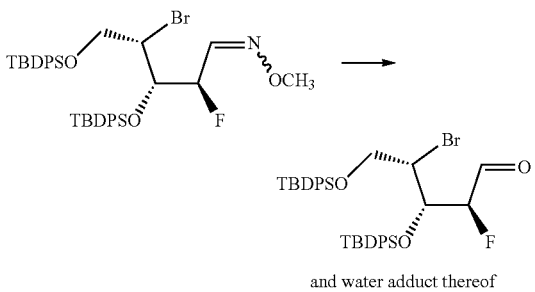

and water adduct thereof 0.18 mL of a 37% formaldehyde aqueous solution, 0.20 mL of water and 0.04 mL of concentrated hydrochloric acid were added to a solution of 173 mg of (2R,3S,4S)-4-bromo-3,5-bis((tert-butyldiphenylsilyl)oxy)-2-fluoropentanal=O-methyloxime in 1.0 mL of acetone, and the obtained mixture was then stirred at room temperature for 48 hours. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/0 to 7/3), so as to obtain 114 mg of a colorless oily product.

The obtained oily product was a mixture of (2R,3S,4S)-4-bromo-3,5-bis((tert-butyldiphenylsilyl)oxy)-2-fluoropentanal and a water adduct thereof.

$^1$H-NMR (CDCl$_3$) δ value:

9.59 (1H, d, J=7.9 Hz), 7.66-7.57 (8H, m), 7.44-7.27 (12H, m), 4.93 (1H, dd, J=46.9, 4.0 Hz), 4.42 (1H, ddd, J=18.5, 4.0, 2.6 Hz), 4.16-4.09 (2H, m), 3.88 (1H, ddd, J=12.9, 8.9, 2.6 Hz), 1.03 (9H, s), 1.01 (9H, s)

(7)

[Formula 305]

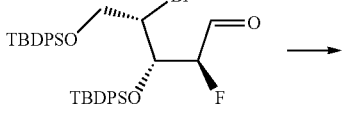

and water adduct thereof

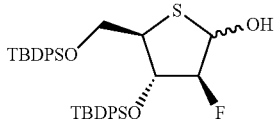

87 mg of a 15%-18% sodium hydrogen sulfide aqueous solution 87 mg was added to a solution of 114 mg of the colorless oily product obtained in Example 31(6) in 0.5 mL of N,N-dimethylformamide at a temperature of 0° C. to 10° C., and the obtained mixture was then stirred at the same temperature as described above for 30 minutes. Thereafter, ethyl acetate was added to the reaction mixture, and the thus obtained mixture was then washed with a 10% sodium chloride aqueous solution three times. The solvent was distilled away under reduced pressure, so as to obtain a light yellow oily product containing (3S,4S,5R)-4-((tert-butyldiphenylsilyl)oxy)5-(((tert-butyldiphenylsilyl)oxy)methyl)-3-fluorotetrahydrothiophen-2-ol.

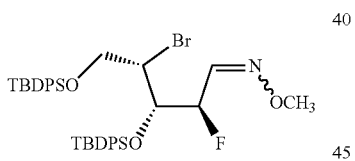

The light yellow oily product was directly used in the subsequent reaction.

¹H-NMR (CDCl₃) δ value:
7.74-7.22 (20H, m), 5.43-5.28 (1H, m), 4.96 (0.5H, d, J=48.2 Hz), 4.86 (0.5H, ddd, J=51.5, 5.9, 4.0 Hz), 4.60-4.53 (1H, m), 3.93 (0.5H, t, J=7.9 Hz), 3.48-3.32 (2H, m), 3.26 (0.5H, dd, J=9.2, 5.3 Hz), 1.08 (4.5H, s), 1.07 (4.5H, s), 0.92 (4.5H, s), 0.91 (4.5H, s)

(8)

[Formula 306]

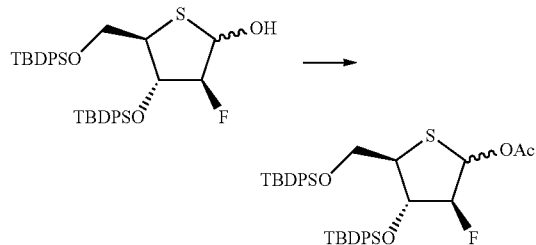

0.1 mg of dimethylaminopyridine and 0.1 mL of acetic anhydride were added to a solution of the light yellow oily product obtained in Example 31(7) in 1.0 mL of tetrahydrofuran. The obtained mixture was stirred at room temperature for 1 hour, and it was then left at room temperature overnight. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/0 to 9/1), so as to obtain 67 mg of (3S,4S,5R)-4-((tert-butyldiphenylsilyl)oxy)-5-(((tert-butyldiphenylsilyl)oxy)methyl)-3-fluorotetrahydrothiophen-2-yl=acetate in the form of a colorless oily product.

¹H-NMR (CDCl₃) δ value:
7.60-7.48 (8H, m), 7.44-7.23 (12H, m), 6.02 (0.5H, dd, J=4.6, 1.3 Hz), 5.96 (0.5H, dd, J=16.2, 3.0 Hz), 5.06 (0.5H, ddd, J=48.9, 5.0, 3.0 Hz), 4.99 (0.5H, ddd, J=50.9, 8.6, 4.6 Hz), 4.34-4.18 (1H, m), 3.84-3.77 (0.5H, m), 3.66-3.60 (1H, m), 3.41 (0.5H, td, J=7.6, 3.3 Hz), 3.31-3.18 (1H, m), 2.12 (1.5H, s), 1.89 (1.5H, s), 1.03 (4.5H, s), 0.99 (4.5H, s), 0.95 (9H, s)

(9)

[Formula 307]

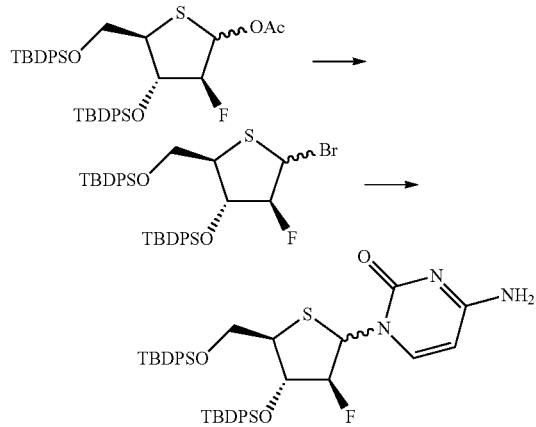

0.03 mL of a 30% hydrogen bromide/acetic acid solution was added to a solution of 59 mg of (3S,4S,5R)-4-((tert-butyldiphenylsilyl)oxy)-5-(((tert-butyldiphenylsilyl)oxy)methyl)-3-fluorotetrahydrothiophen-2-yl=acetate in 1.0 mL of methylene chloride, and the obtained mixture was then stirred at room temperature for 2 hours. Thereafter, methylene chloride and water were added to the reaction mixture. The organic layer was fractionated, and it was washed with a 5% sodium hydrogen carbonate aqueous solution, and was then dried over anhydrous magnesium sulfate. After that, the solvent was distilled away under reduced pressure, so as to obtain a light brown oily product containing (3S,4S,5R)-2-bromo-4-((tert-butyldiphenylsilyl)oxy)-5-(((tert-butyidiphenylsilyl)oxy)methyl)-3-fluorotetrahydrothiophene.

24 mg of cytosine and 0.2 mL of N,O-bis(trimethylsilyl) acetamide were added to the obtained light brown oily product, and the obtained mixture was then stirred 80° C. for 2 hours. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/1 to 0/1), so as to obtain 43 mg of ((3S,4S,5R)-4-((tert-butyldiphenylsilyl)oxy)-5-(((tert-butyldiphenylsilyl)oxy)methyl)-3-fluorotetrahydrothiophen-2-yl)cytosine in the form of a colorless oily product.

As a result of the measurement of ¹H-NMR, the α/β ratio was found to be 15/85.

¹H-NMR (CDCl₃+D₂O) δ value:
8.12 (0.15H, d, J=7.3 Hz), 7.69-7.25 (20.85H, m), 6.89 (0.85H, dd, J=23.1, 4.0 Hz), 6.26 (0.15H, dd, J=16.2, 2.3 Hz), 5.71 (0.15H, d, J=7.3 Hz), 5.55 (0.85H, d, J=7.3 Hz), 5.02 (0.15H, dt, J=48.2, 2.6 Hz), 4.85 (0.85H, dt, J=51.1, 3.3 Hz), 4.42 (0.85H, d, J=7.3 Hz), 4.30 (0.15H, dt, J=11.7, 3.0 Hz), 3.88 (0.15H, t, J=6.6 Hz), 3.65-3.48 (2.7H, m), 3.34 (0.15H, t, J=9.2 Hz), 0.07 (7.65H, s), 0.99 (1.35H, s), 0.91 (9H, s)

(10)

[Formula 308]

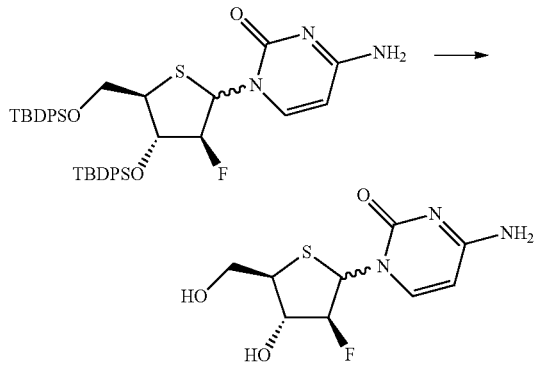

0.24 mL of 0.1 mol/L tetrabutyl ammonium fluoride/tetrahydrofuran solution was added to a solution of 43 mg of ((3S,4S,5R)-4-((tert-butyldiphenylsilyl)oxy)-5-(((tert-butyldiphenylsilyl)oxy)methyl)-3-fluorotetrahydrothiophen-2-yl)cytosine in 1.0 mL of tetrahydrofuran. The obtained mixture was stirred at room temperature for 2 hours, and was then left overnight. Thereafter, the solvent was distilled away under reduced pressure, and the obtained residue was then purified by silica gel column chromatography (ethyl acetate/methanol=1/0 to 2/1), so as to obtain 14 mg of 1-(2-deoxy-2-fluoro-4-thio-D-arabinofuranosyl)cytosine in the form of a white solid.

As a result of the measurement of $^1$H-NMR, the α/β ratio was found to be 16/84.

$^1$H-NMR (DMSO-$d_6$) δ value:

8.01-7.96 (1H, m), 7.30-7.22 (2H, br), 6.46 (0.84H, dd, J=14.5, 5.3 Hz), 6.15 (0.16H, dd, J=17.2, 5.9 Hz), 5.93 (0.16H, d, J=5.3 Hz), 5.87 (0.84H, d, J=4.0 Hz), 5.80-5.76 (1H, m), 5.25 (0.84H, t, J=5.3 Hz), 5.17-4.82 (1.16H, m), 4.29-4.20 (0.84H, m), 4.15-4.06 (0.16H, m), 3.80-3.55 (2H, m), 3.25-3.16 (1H, m)

Example 32

(1)

[Formula 309]

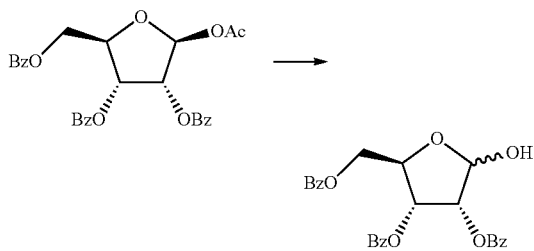

2.9 mL of 30% hydrogen bromide/acetic acid was added dropwise to a suspension of 5.0 g of 1-O-acetyl-2,3,5-tri-O-benzoyl-D-ribofuranose in 1.3 mL of acetic acid at room temperature, and the obtained mixture was then stirred at room temperature for 3 hours. Thereafter, 20 mL of toluene and 20 mL of water were added to the reaction mixture, and the obtained mixture was then stirred for 5 minutes. Thereafter, the water layer was removed. The obtained organic layer was washed with 20 mL of a 10% sodium hydrogen carbonate aqueous solution, and the solvent was then distilled away under reduced pressure. 10 mL of acetonitrile and 10 mL of a 10% sodium hydrogen carbonate aqueous solution were added to the obtained oily product, and the obtained mixture was then stirred at room temperature for 1 hour and was then left overnight. Thereafter, 20 mL of toluene and 10 mL of water were added to the reaction mixture, and the obtained mixture was then stirred for 5 minutes. After that, the water layer was removed, and the solvent was then distilled away under reduced pressure, so as to obtain a colorless oily product containing 2,3,5-tri-O-benzoyl-D-ribofuranose.

The colorless oily product was directly used in the subsequent reaction.

(2)

[Formula 310]

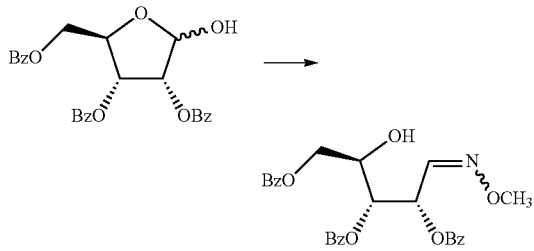

1.3 g of O-methylhydroxylamine hydrochloride and 5.0 mL of methanol were added to the colorless oily product obtained in Example 32(1), and thereafter, 1.8 mL of triethylamine was added dropwise to the mixture under cooling on ice. The obtained mixture was stirred at room temperature for 3 hours. Thereafter, 10 mL of toluene and 10 mL of a 10% sodium chloride aqueous solution were added to the reaction mixture. The water layer was removed, and the solvent was then distilled away under reduced pressure. The obtained residue was purified by silica gel column chromatography (hexane/ethyl acetate=1/0 to 2/1), so as to obtain 2.7 g of (2R,3R,4S)-2-hydroxy-5-(methoxyimino)pentane-1,3,4-triyl=tribenzoate in the form of a colorless oily product.

$^1$H-NMR was measured. As a result, the syn-anti ratio was found to be 4:1.

$^1$H-NMR (CDCl$_3$) δ value:

8.05-8.01 (4H, m), 7.99-7.94 (2H, m), 7.62-7.35 (9.8H, m), 6.92 (0.2H, d, J=5.9 Hz), 6.57 (0.2H, dd, J=5.9, 2.6 Hz), 6.16 (0.8H, dd, J=6.6, 3.3 Hz), 5.87 (0.2H, dd, J=8.9, 3.0 Hz), 5.81 (0.8H, dd, J=7.9, 3.3 Hz), 4.68-4.62 (1H, m), 4.46-4.31 (2H, m), 4.03 (0.6H, s), 3.92 (2.4H, s), 3.24 (0.2H, brs), 3.06 (0.8H, brs)

(3)

[Formula 311]

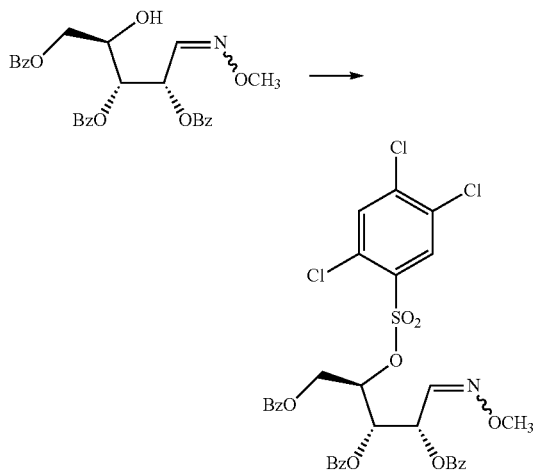

A mixture of 2.7 g of (2R,3R,4S)-2-hydroxy-5-(methoxyimino)pentane-1,3,4-triyl=tribenzoate, 5 mL of acetonitrile, 0.5 mL of N-methylimidazole and 1.7 g of 2,4,5-trichlorobenzenesulfonyl chloride was stirred at room temperature for 8 hours, and it was then left at room temperature for 3 days. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/0 to 3/1), so as to obtain 3.0 g of (2R,3R,4S)-5-(methoxyimino)-2-(((2,4,5-trichlorobenzene)sulfonyl)oxy)pentane-1,3,4-triyl=tribenzoate in the form of a colorless oily product.

$^1$H-NMR (CDCl$_3$) δ value:

8.08-7.96 (5H, m), 7.91-7.88 (2H, m), 7.64-7.33 (10.75H, m), 6.91 (0.25H, d, J=5.9 Hz), 6.55 (0.25H, t, J=5.3 Hz), 6.06-5.95 (1.75H, m), 5.55-5.49 (0.75H, m), 5.48-5.42 (0.25H, m), 4.91-4.84 (1H, m), 4.69-4.62 (1H, m), 3.97 (0.75H, s), 3.85 (2.25H, s)

(4)

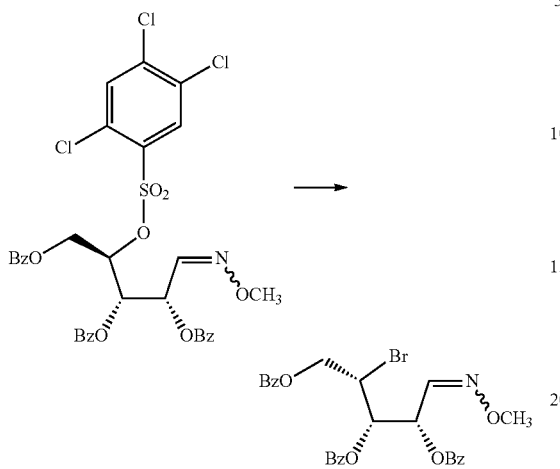

[Formula 312]

1.8 g of anhydrous lithium bromide and 4.0 mL of 1,3-dimethyl-2-imidazolidinone were added to a solution of 3.0 g of the (2R,3R,4S)-5-(methoxyimino)-2-(((2,4,5-trichlorobenzene)sulfonyl)oxy)pentane-1,3,4-triyl=tribenzoate in 4.0 mL of tetrahydrofuran, and the obtained mixture was then stirred at 50° C. for 2 hours. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/0 to 4/1), so as to obtain 1.5 g of (2S,3S,4S)-2-bromo-5-(methoxyimino)pentane-1,3,4-triyl=tribenzoate in the form of a colorless oily product.

$^1$H-NMR (CDCl$_3$) δ value:
8.12-7.93 (6H, m), 7.65-7.36 (9.87H, m), 6.82 (0.13H, d, J=5.9 Hz), 6.53 (0.13H, t, J=6.6 Hz), 6.14-6.06 (0.13mH, m), 6.04-5.95 (1.74H, m), 4.84-4.54 (3H, m), 3.80 (0.39H, s), 3.70 (2.61H, s)

(5)

[Formula 313]

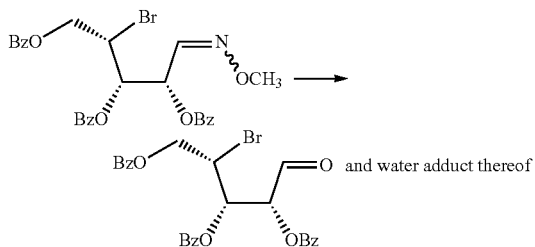

2.8 mL of a 50% glyoxylic acid aqueous solution was added to a solution of 1.5 g of the (2S,3S,4S)-2-bromo-5-(methoxyimino)pentane-1,3,4-triyl=tribenzoate in 5.0 mL of acetonitrile, and the obtained mixture was then stirred at 70° C. for 16 hours. Thereafter, the reaction mixture was cooled to room temperature, ethyl acetate and water were then added to the mixture, and the water layer was then removed. The organic layer was successively washed with a 10% sodium hydrogen carbonate aqueous solution and water, and the solvent was then distilled away under reduced pressure to obtain 1.4 g of an oily product.

The obtained oily product was a mixture of (2S,3S,4S)-2-bromo-5-oxopentane-1,3,4-triyl=tribenzoate and a water adduct thereof.

$^1$H-NMR (CDCl$_3$) δ value:
9.73 (1H, d, J=9.2 Hz), 8.13-7.98 (6H, m), 7.66-7.39 (9H, m), 6.03 (1H, dd, J=7.3, 3.3 Hz), 5.68 (1H, d, J=7.3 Hz), 4.85-1.74 (2H, m), 6.03 (1H, dd, J=10.6, 6.6 Hz)

(6)

[Formula 314]

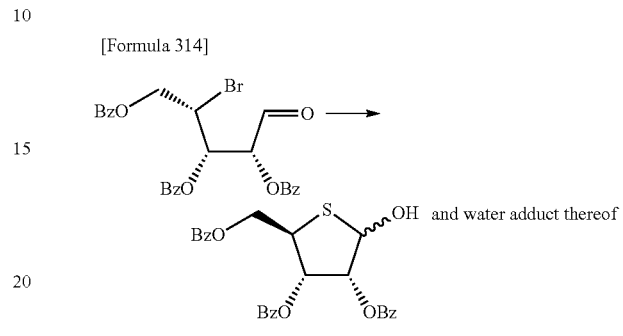

1.2 g of a 15%-18% sodium hydrogen sulfide aqueous solution was added to a solution of 1.4 g of the oily product obtained in Example 32(5) in 4.0 mL of N,N-dimethylformamide at a temperature of 0° C. to 10° C., and the obtained mixture was then stirred at the same temperature as described above for 30 minutes. Thereafter, 15 mL of ethyl acetate and 15 mL of a 10% sodium chloride aqueous solution were added to the reaction mixture, and the water layer was then removed. The organic layer was washed with 15 mL of a 10% sodium chloride aqueous solution twice to obtain an ethyl acetate solution of 2,3,5-tri-O-benzoyl-4-thio-D-ribofuranose.

The ethyl acetate solution was directly used in the subsequent reaction.

$^1$H-NMR (CDCl$_3$) δ value:
8.12-7.88 (6H, m), 7.63-7.29 (9H, m), 6.03 (1H, dd, J=7.9, 3.3 Hz), 5.88 (1H, dd, J=4.0, 2.0 Hz), 5.50 (1H, dd, J=4.6, 2.0 Hz), 4.74 (1H, dd, J=1.6, 6.3 Hz), 4.61 (1H, dd, J=11.9, 5.9 Hz), 4.23 (1H, td, J=7.3, 5.5 Hz), 2.64 (1H, d, J=4.6 Hz)

(7)

[Formula 315]

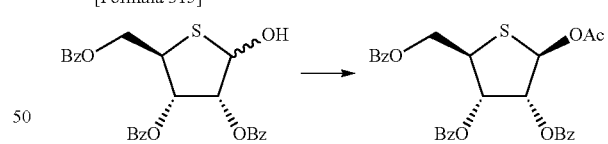

1.6 mg of dimethylaminopyridine and 0.28 mL of acetic anhydride were added to the ethyl acetate solution obtained in Example 32(6), and the obtained mixture was then stirred at room temperature for 1 hour and was then left at room temperature for 3 days. Thereafter, water was added to the reaction mixture. The water layer was removed, and the organic layer was then washed with water. After that, the solvent was distilled away under reduced pressure. The obtained residue was recrystallized from methanol, so as to obtain 402 mg of 1-O-acetyl-2,3,5-tri-O-benzoyl-4-thio-β-D-ribofuranose in the form of a white solid.

$^1$H-NMR (CDCl$_3$) δ value:
8.08-8.02 (2H, m), 7.98-7.95 (2H, m), 7.91-7.88 (2H, m), 7.64-7.58 (1H, m), 7.55-7.44 (4H, m), 7.36-7.29 (4H, m), 6.06 (1H, d, J=2.0 Hz), 5.99 (1H, dd, J=4.0, 2.0 Hz), 5.91 (1H, dd, J=8.6, 4.0 Hz), 4.73 (1H, dd, J=11.2, 5.9 Hz), 4.53 (1H, dd, J=11.2, 5.9 Hz), 4.25 (1H, dt, J=8.6, 5.9 Hz), 2.12 (3H, s)

(8)

[Formula 316]

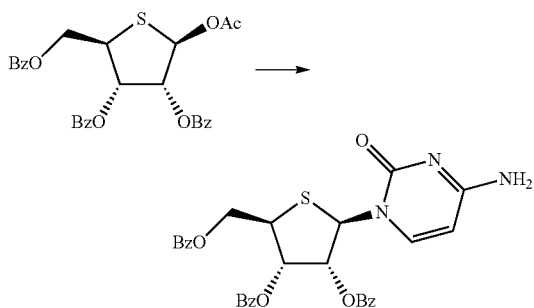

0.44 mL of N,O-bis(trimethylsilyl)acetamide was added to a suspension of 208 mg of 1-O-acetyl-2,3,5-tri-O-benzoyl-4-thio-β-D-ribofuranose and 67 mg of cytosine in 2.0 mL of acetonitrile, and the obtained mixture was then stirred at 60° C. for 1 hour. Thereafter, 0.22 mL of trimethylsilyl trifluoromethanesulfonate was added to the reaction mixture, and the obtained mixture was then stirred at 80° C. for 4 hours. Thereafter, ethyl acetate was added to the reaction mixture, and the thus obtained mixture was then washed with a saturated sodium hydrogen carbonate aqueous solution. After that, the solvent was distilled away under reduced pressure. The obtained residue was purified by silica gel column chromatography (ethyl acetate/methanol=1/0 to 4/1), so as to obtain 70 mg of 1-(2,3,5-tri-O-benzoyl-4-thio-β-D-ribofuranosyl)cytosine in the form of a white solid.

$^1$H-NMR (CDCl$_3$) δ value:
8.14-7.95 (6H, m), 7.89 (1H, d, J=7.3 Hz), 7.63-7.36 (9H, m), 6.90 (1H, d, J=5.9 Hz), 5.94-5.89 (2H, m), 5.59 (1H, d, J=7.9 Hz), 4.79 (1H, dd, J=1.9, 5.9 Hz), 4.66 (1H, dd, J=11.6, 5.0 Hz), 4.10-4.05 (1H, m)

(9)

[Formula 317]

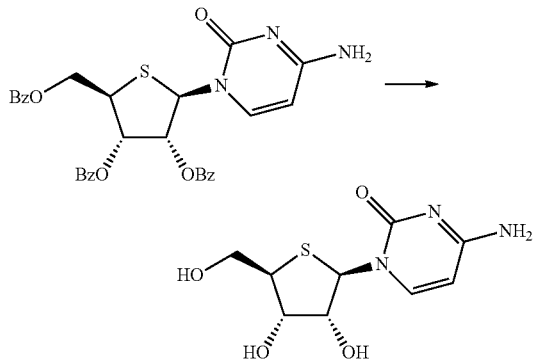

0.1 mL of a 28% sodium methoxide/methanol solution was added to a suspension of 70 mg of 1-(2,3,5-tri-O-benzoyl-4-thio-β-D-ribofuranosyl)cytosine in 2.0 mL of methanol, and the obtained mixture was then stirred at room temperature for 1 hour and was then left overnight. Thereafter, 0.2 mL of acetic acid was added to the reaction mixture, and the solvent was then distilled away under reduced pressure. The obtained residue was purified by silica gel column chromatography (ethyl acetate/methanol=1/0 to 2/1), so as to obtain 18 mg of 1-(4-thio-β-D-ribofuranosyl)cytosine in the form of a white solid.

$^1$H-NMR (DMSO-d$_6$) δ value:
7.97 (1H, d, J=7.3 Hz), 7.14 (2H, brd), 5.94 (1H, d, J=6.6 Hz), 5.76 (1H, d, J=7.3 Hz), 5.42 (1H, brs), 5.29 (1H, brs), 5.14 (1H, brs), 4.08-3.98 (2H, m), 3.69-3.5 (2H, m), 3.20 (1H, dd, J=9.2, 5.9 Hz)

Example 33

(1)

[Formula 318]

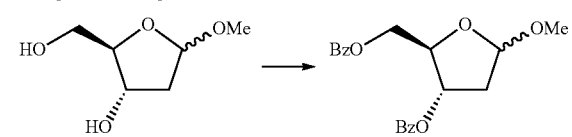

22 mL of a 20% sodium hydroxide aqueous solution and 617 mg of tetrabutylammonium chloride were added to a solution of 6.58 g of 2-deoxy-1-O-methyl-D-ribofuranoside in 44 mL of toluene, and thereafter, 10.8 mL of benzoyl chloride was added to the mixture at a temperature of 10° C. to 25° C. The obtained mixture was stirred at room temperature for 1 hour. Thereafter, ethyl acetate and water were added to the reaction mixture. The organic layer was fractionated, and was then dried over anhydrous sodium sulfate. After that, the solvent was distilled away under reduced pressure. The obtained residue was purified by silica gel column chromatography (hexane/ethyl acetate=100/0 to 70/30), so as to obtain 11.8 g of 2-deoxy-3,5-O-dibenzoyl-1-O-methyl-D-ribofuranoside in the form of a colorless oily product.

As a result of the measurement of $^1$H-NMR, the anomeric ratio was found to be 1:1.

RT(min): 1.73, 1.76.

$^1$H-NMR (CDCl$_3$) δ value:
8.13-7.99 (4H, m), 7.63-7.51 (2H, m), 7.49-7.38 (4H, m), 5.67-5.59 (0.5H, m), 5.49-5.40 (0.5H, m), 5.24 (0.5H, dd, J=5.6, 2.3 Hz), 5.20 (0.5H, d, J=4.6 Hz), 4.70-4.45 (3H, m), 3.43 (1.5H, s), 3.37 (1.5H, s), 2.64-2.50 (1H, m), 2.36 (0.5H, td, J=9.6, 4.6 Hz), 2.21 (0.5H, dd, J=14.5, 1.3 Hz)

(2)

[Formula 319]

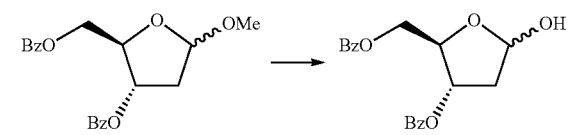

32.4 mL of 1 mol/L hydrochloric acid was added to a solution of 6.49 g of 2-deoxy-3,5-O-dibenzoyl-1-O-methyl-D-ribofuranoside in 32.4 mL of acetic acid, and the obtained mixture was then stirred at 55° C. for 2.58 hours. Thereafter, 20 mL of acetic acid and 20 mL of 1 mol/L hydrochloric acid were added to the reaction mixture, and the thus obtained mixture was then stirred at the same temperature as described above for 2.58 hours. Thereafter, toluene and water were added to the reaction mixture. The organic layer was fractionated, and it was washed with water and a saturated sodium hydrogen carbonate aqueous solution and was then dried over anhydrous magnesium sulfate, so as to obtain 6.23 g of 2-deoxy-3,5-O-dibenzoyl-D-ribofuranoside in the form of a colorless oily product.

As a result of the measurement of ¹H-NMR, the anomeric ratio was found to be 6:4.

RT(min): 1.41, 1.44.

¹H-NMR (CDCl₃) δ value:

8.11-7.99 (4H, m), 7.63-7.51 (2H, m), 7.51-7.37 (4H, m), 5.80-5.69 (1H, m), 5.67-5.60 (0.4H, m), 5.54-5.48 (0.6H, m), 4.76-4.47 (3H, m), 3.11-3.03 (0.4H, m), 2.86 (0.6H, t, J=5.3 Hz), 2.62-2.48 (1H, m), 2.45-2.25 (1H, m)

(3)

[Formula 320]

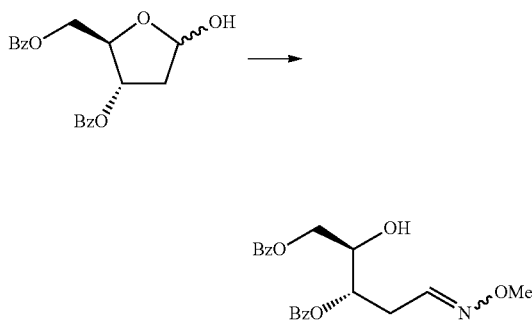

1.98 g of O-methylhydroxylammonium chloride, 3.78 mL of triethylamine and 3 mL of a 5%-10% hydrochloric acid/methanol solution were added to a solution of 6.23 g of 2-deoxy-3,5-O-dibenzoyl-D-ribofuranoside in 62 mL of methanol, and the obtained mixture was then stirred at room temperature for 11.7 hours. Thereafter, the solvent was distilled away under reduced pressure, and ethyl acetate and water were then added to the obtained residue. The organic layer was fractionated, and was then dried over anhydrous sodium sulfate. The solvent was distilled away under reduced pressure, so as to obtain 6.65 g of (2R,3S)-2-hydroxy-5-(methoxyimino)pentane-1,3-diyl dibenzoate in the form of a light yellow oily product.

¹H-NMR was measured. As a result, the syn-anti ratio was found to be 64:36.

RT(min): 1.50.

¹H-NMR (CDCl₃) δ value:

8.04 (4H, d, J=7.9 Hz), 7.62-7.54 (2H, m), 7.51-7.30 (4.64H, m), 6.85 (0.36H, t, J=5.9 Hz), 5.47-5.37 (1H, m), 4.61 (1H, d, J=3.3 Hz), 4.57 (1H, d, J=3.3 Hz), 4.44 (0.64H, dd, J=5.9, 2.6 Hz), 4.40 (0.36H, dd, J=5.9, 2.6 Hz), 4.29-4.17 (1H, m), 3.87 (1.08, s), 3.78 (1.92H, s), 3.07-2.85 (1H, m), 2.82 (1H, t, J=5.9 Hz)

(4)

[Formula 321]

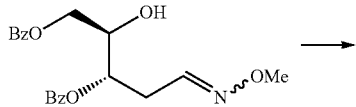

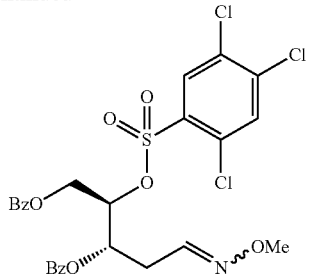

5.51 g of 2,4,5-trichlorobenzenesulfonyl chloride and 2.14 mL of 1-methylimidazole were added to a solution of 6.65 g of (2R,3S)-2-hydroxy-5-(methoxyimino)pentane-1,3-diyl dibenzoate in 67 mL of acetonitrile at room temperature, and the obtained mixture was then stirred at room temperature for 2 hours. Thereafter, ethyl acetate and water were added to the reaction mixture. The organic layer was fractionated, and was then dried over anhydrous sodium sulfate. The solvent was distilled away under reduced pressure. 20 mL of ethyl acetate and 30 mL of hexane were added to the obtained residue, and a solid was then removed by filtration. After that, the solvent was distilled away under reduced pressure, so as to obtain 8.97 g of (2R,3S)-5-(methoxyimino)-2-(((2,4,5-trichlorophenyl)sulfonyl)oxy)pentane-1,3-diyl dibenzoate in the form of a colorless oily product.

¹H-NMR was measured. As a result, the syn-anti ratio was found to be 54:46.

RT(min): 2.06.

¹H-NMR (CDCl₃) δ value:

8.00-8.00 (1H, each s), 7.93 (4H, t, J=7.6 Hz), 7.64-7.54 (2H, m), 7.34 (0.54H, d, J=4.0 Hz), 6.80 (0.46H, t, J=5.6 Hz), 5.56-5.49 (1H, m), 5.42-5.30 (1H, m), 4.63 (1H, brs), 4.61 (1H, s), 3.86 (1.38H, s), 3.77 (1.62H, s), 2.99-2.91 (1H, m), 2.90-2.83 (0.46H, m), 2.82-2.71 (0.54H, m)

(5)

[Formula 322]

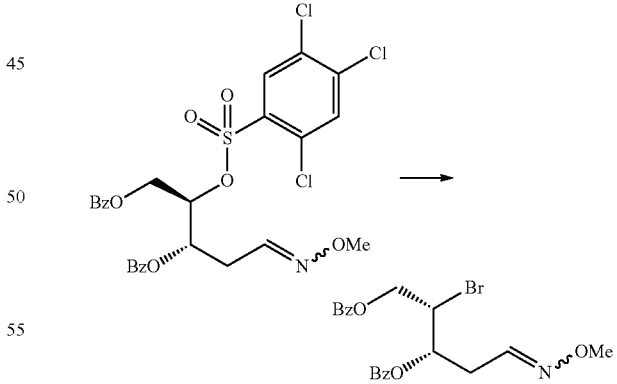

1.52 g of lithium bromide was added to a solution of 8.97 g of (2R,3S)-5-(methoxyimino)-2-(((2,4,5-trichlorophenyl)sulfonyl)oxy)pentane-1,3-diyl dibenzoate in 17.9 mL of tetrahydrofuran and 16.1 mL of 1,3-dimethyl-2-imidazolidinone, and the obtained mixture was then stirred at 50° C. for 3 hours. Thereafter, ethyl acetate and a 25% lithium bromide aqueous solution were added to the reaction mixture. The organic layer was fractionated, and it was washed with a 13% lithium bromide aqueous solution and was then dried over anhydrous sodium sulfate. After that, the solvent was distilled away under reduced pressure. The obtained residue was purified by silica gel column chromatography (hexane/ethyl acetate=100/0 to 75/25), so as to obtain 4.84 g of (2R,3S)-2-bromo-5-(methoxyimino)pentane-1,3-diyl dibenzoate in the form of a colorless oily product.

$^1$H-NMR was measured. As a result, the syn-anti ratio was found to be 55:45.

RT(min): 1.87.

$^1$H-NMR (CDCl$_3$) δ value:

8.11-8.01 (4H, m), 7.64-7.54 (2H, m), 7.51-7.37 (4.55H, m), 6.78 (0.45H, t, J=5.3 Hz), 5.73-5.60 (1H, m), 4.77-4.67 (1H, m), 4.64-4.43 (2H, m), 3.86 (1.35H, s), 3.75 (1.65H, s), 3.09-2.87 (1H, m), 2.84 (1H, t, J=6.3)

(6)

[Formula 323]

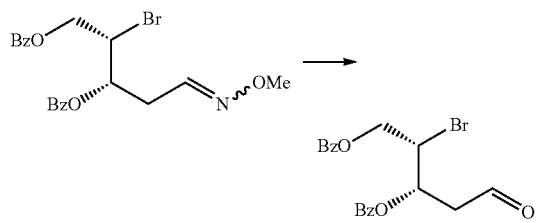

7.1 mL of a 35% formaldehyde aqueous solution, 4.3 mL of water and 1.4 mL of concentrated hydrochloric acid Were added to a solution of 3.54 g of (2R,3S)-2-bromo-5-(methoxyimino)pentane-1,3-diyl dibenzoate in 35 mL of acetone at room temperature, and the obtained mixture was then stirred at 30° C. for 1.5 hours. Thereafter, ethyl acetate and water were added to the reaction mixture. The organic layer was fractionated, and was then dried over anhydrous sodium sulfate. The solvent was distilled away under reduced pressure, so as to obtain 3.75 g of a colorless oily product.

The obtained colorless oily product was a mixture of (2R,3S)-2-bromo-5-oxopentane-1,3-diyldibenzoate and a water adduct thereof.

RT(min): 1.71, 1.81.

(7)

[Formula 324]

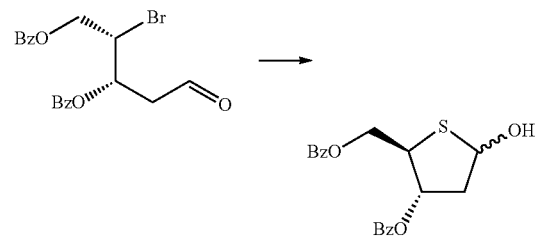

A solution of 720 mg of sodium monohydrogen sulfide n-hydrate in 5 mL of 1-methylpyrrolidone was added to a solution of 3.75 g of the colorless oily product obtained in Example 33(6) in 33 mL of 1-methylpyrrolidone under cooling on ice, and the obtained mixture was then stirred at the same temperature as described above for 1.42 hours. Thereafter, 249 mg of a sodium monohydrogen sulfide n-hydrate was added to the reaction mixture, and the thus obtained mixture was then stirred at the same temperature as described above for 0.58 hours. Thereafter, ethyl acetate and a saline were added to the reaction mixture. The organic layer was fractionated, and was then dried over anhydrous sodium sulfate. The solvent was distilled away under reduced pressure, so as to obtain a 1-methylpyrrolidone solution of 2-deoxy-3,5-O-dibenzoyl-4-thio-D-ribofuranoside.

RT(min): 1.56.

m/z (ESI-positive): 341.1 [M+H–H2O]$^+$ (8)

[Formula 325]

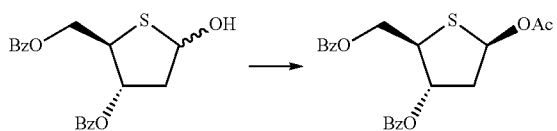

29.2 mL of tetrahydrofuran, 0.916 mL of acetic anhydride and 10 mg of 4-dimethylaminopyridine were added to the 1-methylpyrrolidone solution of 2-deoxy-3,5-O-dibenzoyl-4-thio-D-ribofuranoside obtained in Example 33(7), and the obtained mixture was then stirred at room temperature for 1 hour. Thereafter, ethyl acetate and water were added to the reaction mixture. The organic layer was fractionated, and was then dried over anhydrous sodium sulfate. After that, the solvent was distilled away under reduced pressure. The obtained residue was purified by silica gel column chromatography (hexane/ethyl acetate=100/0 to 75/25). 4 mL of methanol was added to the obtained solid, and the solid was then collected by filtration, so as to obtain 0.942 g of 1-O-acetyl-2-deoxy-3,5-O-dibenzoyl-4-thio-β-D-ribofuranoside in the form of a white solid.

RT(min): 1.77.

$^1$H-NMR (DMSO-d$_6$) δ value:

7.96 (4H, dt, J=7.9, 1.3 Hz), 7.71-7.61 (2H, m), 7.56-7.44 (4H, m), 6.11 (1H, dd, J=5.9, 3.3 Hz), 5.77-5.69 (1H, m), 4.55-4.40 (2H, m), 3.99 (1H, qd, J=5.9, 1.3 Hz), 2.76-2.54 (2H, m), 2.01 (3H, s)

(9)

[Formula 326]

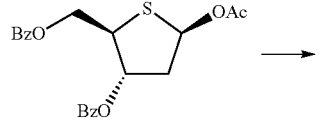

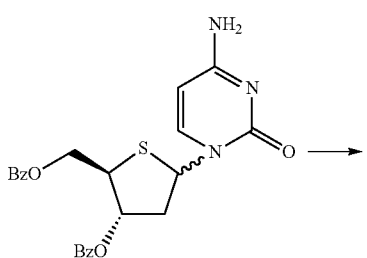

-continued (10)

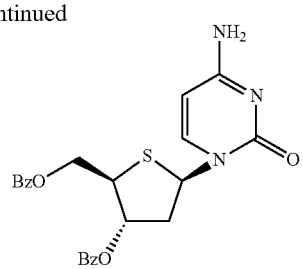

0.700 mL of N,O-bistrimethylsilyl acetamide was added to a solution of 111 mg of cytosine and 200 mg of 1-O-acetyl-2-deoxy-3,5-O-dibenzoyl-4-thio-β-D-ribofuranoside in 2 mL of acetonitrile at room temperature, and the obtained mixture was then stirred in a nitrogen atmosphere at 60° C. for 70 minutes. Thereafter, 0.361 mL of trimethylsilyl trifluoromethanesulfonate was added to the reaction mixture, and the thus obtained mixture was then stirred at the same temperature as described above for 2.5 hours, and then at 80° C. for 2 hours. Thereafter, dichloromethane and water were added to the reaction mixture. The organic layer was fractionated, and it was washed with a saturated sodium chloride aqueous solution and was then dried over anhydrous sodium sulfate. After that, the solvent was distilled away under reduced pressure. The obtained residue was purified by silica gel column chromatography (ethyl acetate/methanol=100/0 to 40/60), and then by HPLC, so as to obtain 1-(2-deoxy-3,5-bis-O-benzoyl-4-thio-D-ribofuranosyl)cytosine in the form of a brown oily product.

As a result of the measurement of $^1$H-NMR, the α/β ratio was found to be 53:47.

The obtained brown oily product was separated by high performance liquid chromatography, so as to obtain 13.6 mg of 1-(2-deoxy-3,5-bis-O-benzoyl-4-thio-1-D-ribofuranosyl)cytosine.

Conditions for high performance liquid chromatography

Column: Sunfire prep C18 OBD 10 μm, 19 mm×0.150 mm (Waters)

Mobile phase: 0.1% formic acid-water/0.1% formic acid-acetonitrile (volume ratio: 70/30 to 55/45)

Flow rate: 17 mL/min

Detection: UV (254 nm)

Temperature: room temperature

Retention time: α form: 7.34 min; β form: 8.50 min

β form

RT(min): 1.25.

$^1$H-NMR (CDCl$_3$) δ value:

8.09-8.02 (4H, m), 7.95 (1H, d, J=7.3 Hz), 7.63-7.54 (2H, m), 7.45 (4H, d, J=7.9 Hz), 6.71 (1H, t, J=7.3 Hz), 5.80 (1H, d, J=7.3 Hz), 5.75 (1H, q, J=3.7 Hz), 4.59 (2H, d, 6.6 Hz), 4.00 (1H, td, 6.6, 3.3 Hz), 2.99-2.13 (2H, brs), 2.82 (1H, dq, 13.9, 3.5 Hz), 2.44-2.33 (1H, m)

α form

RT(min): 1.19.

$^1$H-NMR (CDCl$_3$) δ value:

8.22 (1H, d, J=7.3 Hz), 8.08 (2H, dd, J=7.9, 1.3 Hz), 7.85 (2H, dd, J=7.9, 1.3 Hz), 7.62-7.52 (2H, m), 7.50-7.36 (4H, m), 6.45 (1H, dd, J=7.3, 2.0 Hz), 5.80 (1H, d, J=7.3 Hz), 5.73-5.67 (1H, m), 4.56-4.38 (2H, m), 4.24 (1H, dt, J=6.9, 2.0 Hz), 2.95-2.82 (1H, m), 2.66 (1H, dt, J=15.2, 2.6 Hz)

[Formula 327]

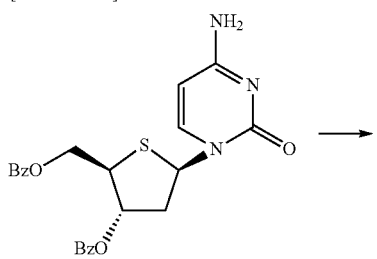

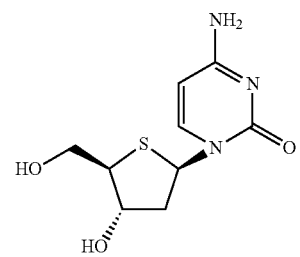

1 mL of a 7 mol/L ammonia/methanol solution was added to a solution of 9.6 mg of 1-(2-deoxy-3,5-bis-O-benzoyl-4-thio-β-D-ribofuranosyl)cytosine in 1 mL of methanol, and the obtained mixture was then stirred at room temperature for 3 hours. Thereafter, the solvent was distilled away under reduced pressure, and the obtained residue was then purified by silica gel column chromatography (ethyl acetate/methanol=95/5 to 30/70), so as to obtain 4.7 mg of 1-(2-deoxy-4-thio-β-D-ribofuranosyl)cytosine in the form of a white solid.

RT(min): 0.27.

$^1$H-NMR (DMSO-d$_6$) δ value:

7.931H, d, J=7.3 Hz), 7.19 (1H, brs), 7.12 (1H, brs), 6.35 (1H, dd, J=8.6, 6.6 Hz), 5.78 (1H, d, J=7.3 Hz), 5.23 (1H, d, J=3.3 Hz), 5.12 (1H, t, J=5.3 Hz), 4.36-4.29 (1H, m), 3.64-3.22 (3H, m), 2.28-2.01 (2H, m), 1.83 (1H, s)

Example 34

(1)

[Formula 328]

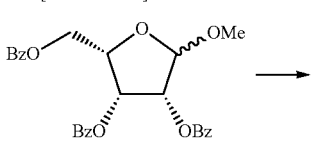 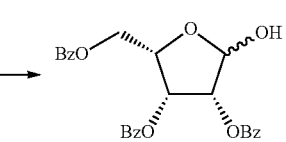

0.2 mL of 30% hydrogen bromide/acetic acid was added dropwise to a solution of 238 mg of 1-O-methyl-2,3,5-tri-O-benzoyl-L-lyxose in 1.0 mL of acetic acid at room temperature, and the obtained mixture was then stirred at room temperature for 2 hours. Thereafter, methylene chloride and water were added to the reaction mixture, and the thus obtained mixture was then stirred for 5 minutes. Thereafter, the water layer was removed. The obtained organic layer was washed with a 10% sodium hydrogen carbonate aqueous solution, and the solvent was then distilled away under reduced pressure, to obtain a brown oily product.

Separately, 0.2 mL of 30% hydrogen bromide/acetic acid was added dropwise to a solution of 238 mg of 1-O-methyl-2,3,5-tri-O-benzoyl-L-lyxose in 1.0 mL of methylene chloride at room temperature, and the obtained mixture was then stirred at room temperature for 2 hours. Thereafter, methylene chloride and water were added to the reaction mixture, and the thus obtained mixture was then stirred for 5 minutes. After that, the water layer was removed. The obtained organic layer was washed with a 10% sodium hydrogen carbonate aqueous solution, and the solvent was then distilled away under reduced pressure. 2.0 mL of acetone and 2.0 mL of water were added to the obtained oily product, and the obtained mixture was then stirred at room temperature for 2 hours. Thereafter, ethyl acetate and water were added to the reaction mixture. The organic layer was fractionated, and the solvent was then distilled away under reduced pressure, so as to obtain a brown oily product.

Brown oily products obtained in the above-described two operations were combined with each other, and the thus combined product was then purified by silica gel column chromatography (hexane/ethyl acetate=1/0 to 3/1), so as to obtain 462 mg of a colorless oily product containing 2,3,5-tri-O-benzoyl-L-lyxose.

(2)

[Formula 329]

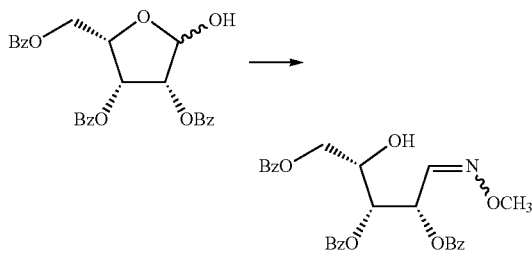

125 mg of O-methylhydroxylamine hydrochloride and 1.0 mL of methanol were added to 462 mg of a mixture comprising 2,3,5-tri-O-benzoyl-L-lyxose, and thereafter, 0.18 mL of triethylamine was added dropwise to the mixture under cooling on ice. The obtained mixture was stirred at room temperature for 1 hour. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/0 to 3/1), so as to obtain 201 mg of (2S,3R,4S)-2-hydroxy-5-(methoxyimino)pentane-1,3,4-triyl=tribenzoate in the form of a colorless oily product.

$^1$H-NMR was measured. As a result, the syn-anti ratio was found to be 4:1.

$^1$H-NMR (CDCl$_3$) δ value:
8.08-7.98 (6H, m), 7.62-7.32 (9.8H, m), 6.91 (0.2H, d, J=5.9 Hz), 6.56 (0.2H, t, J=6.3 Hz), 6.06 (0.8H, t, J=6.9 Hz), 5.83-5.76 (1H, m), 4.58-4.44 (2H, m), 4.39-4.35 (1H, m), 3.88 (0.6H, s), 3.74 (2.4H, s)

(3)

[Formula 330]

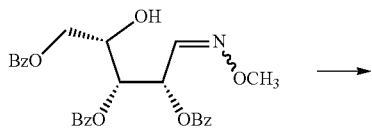

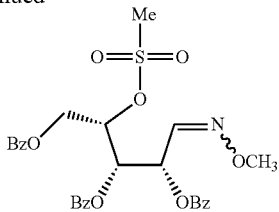

2.0 mL of ethyl acetate and 0.08 mL of triethylamine were added to 201 mg of (2S,3R,4S)-2-hydroxy-5-(methoxyimino)pentane-1,3,4-triyl=tribenzoate, and thereafter, 0.04 mL of methanesulfonyl chloride was added dropwise to the mixture under cooling on ice. The obtained mixture was stirred at room temperature for 1 hour, and was then left at room temperature overnight. Thereafter, 0.2 mL of triethylamine and 0.1 mL of methanesulfonyl chloride were added to the reaction mixture, and the thus obtained mixture was then stirred at room temperature for 1 hour. Thereafter, ethyl acetate and water were added to the reaction mixture. The organic layer was fractionated, and the solvent was then distilled away under reduced pressure. The obtained residue was purified by silica gel column chromatography (hexane/ethyl acetate=1/0 to 3/1), so as to obtain 197 mg of (2S,3S,4S)-5-(methoxyimino)-2-((methylsulfonyl)oxy)pentane-1,3,4-triyl=tribenzoate in the form of a colorless oily product.

$^1$H-NMR (CDCl$_3$) δ value:
8.10-8.00 (6H, m), 7.62-7.41 (9.8H, m), 6.87 (0.2H, d, J=5.9 Hz), 6.47 (0.2H, dd, J=5.9, 4.6 Hz), 6.07-6.03 (1H, m), 5.95 (0.8H, t, J=6.3 Hz), 5.47 (0.8H, dt, J=7.5, 3.3 Hz), 5.39 (0.2H, td, J=6.3, 3.3 Hz), 4.85-4.75 (1H, m), 4.69-4.60 (1H, m), 4.39-4.35 (1H, m), 3.91 (0.6H, s), 3.77 (2.4H, s), 3.05 (2.4H, s), 3.01 (0.6H, s)

(4)

[Formula 331]

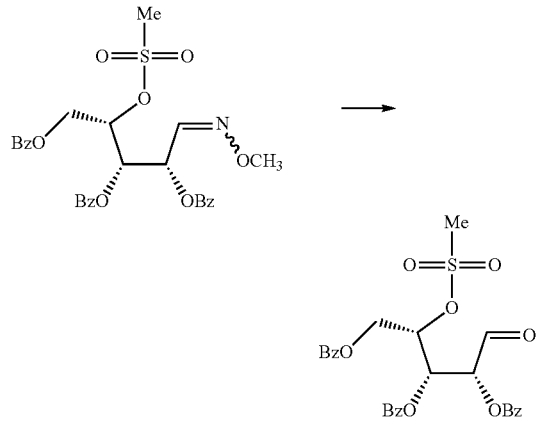

0.35 mL of a 50% glyoxylic acid aqueous solution was added to a solution of 197 mg of (2S,3S,4S)-5-(methoxyimino)-2-((methylsulfonyl)oxy)pentane-1,3,4-triyl=tribenzoate in 1.0 mL of acetonitrile. The obtained mixture was stirred at 70° C. for 9 hours, and was then left at room temperature overnight. Thereafter, ethyl acetate and water were added to the reaction mixture, and the water layer was then removed. The obtained residue was purified by silica gel column chromatography (hexane/ethyl acetate=1/0 to 1/1), so as to obtain 130 mg of (2S,3S,4R)-2-((methylsulfonyl)

oxy)-5-oxopentane-1,3,4-triyl=tribenzoate in the form of a colorless oily product.

¹H-NMR (CDCl₃) δ value:

9.73 (1H, s), 8.11-8.04 (6H, m), 7.66-7.42 (9H, m), 6.09 (1H, t, J=5.3 Hz), 5.68 (1H, d, J=5.9 Hz), 5.61-5.56 (1H, m), 4.81 (1H, dd, J=12.6, 4.0 Hz), 4.66 (1H, dd, J=12.6, 6.6 Hz), 3.05 (3H, s)

(5)

[Formula 332]

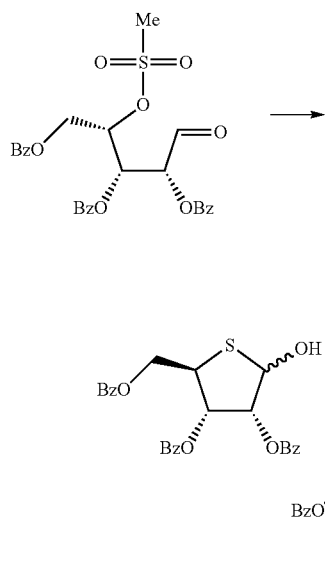

0.11 mL of a 15%-18% sodium hydrogen sulfide aqueous solution was added to a solution of 130 mg of (2S,3S,4R)-2-((methylsulfonyl)oxy)-5-oxopentane-1,3,4-triyl=tribenzoate in 0.5 mL of N,N-dimethylformamide at a temperature of 0° C. to 10° C., and the obtained mixture was then stirred at the same temperature as described above for 1 hour. Thereafter, 10 mL of ethyl acetate was added to the reaction mixture, and the thus obtained mixture was then washed with a 10% sodium chloride aqueous solution three times, so as to obtain an ethyl acetate solution of 2,3,5-tri-O-benzoyl-4-thio-D-ribofuranose.

0.1 mg of dimethylaminopyridine and 0.025 mL of acetic anhydride were added to the obtained ethyl acetate solution. The obtained mixture was stirred at room temperature for 1 hour, and was then left at room temperature for 4 days. Thereafter, the reaction mixture was washed with water, and the solvent was then distilled away under reduced pressure. The obtained residue was recrystallized from mL of methanol, so as to obtain 28 mg of 1-O-acetyl-2,3,5-tri-O-benzoyl-4-thio-β-D-ribofuranose in the form of a white solid.

¹H-NMR (CDCl₃) δ value:

8.06-8.02 (2H, m), 7.98-7.95 (2H, m), 7.91-7.88 (2H, m), 7.64-7.58 (1H, m), 7.55-7.44 (4H, m), 7.36-7.29 (4H, m), 6.06 (1H, d, J=1.3 Hz), 5.99 (1H, dd, J=3.6, 1.7 Hz), 5.91 (1H, dd, J=8.6, 4.0 Hz), 4.74 (1H, dd, J=11.2, 5.9 Hz), 4.53 (1H, dd, J=11.2, 5.9 Hz), 4.25 (1H, dt, J=8.6, 5.9 Hz), 2.12 (3H, s)

Example 35

(1)

[Formula 333]

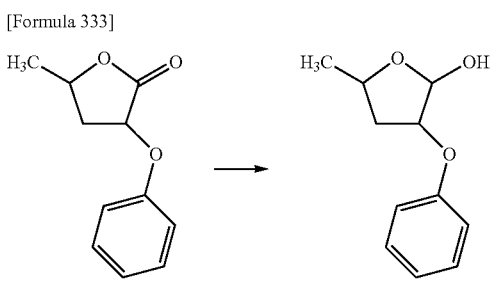

13.5 mL of a 1.5 mol/L diisobutylaluminum hydride/toluene solution was added dropwise to a solution of 3.8 g of 5-methyl-3-phenoxyoxolane-2-one in 40 mL of toluene at −78° C., and the obtained mixture was then stirred for 15 minutes. Thereafter, 1 mL of methanol was added to the reaction mixture, and thereafter, 50 mL of a 20% potassium sodium tartrate aqueous solution was added to the mixture at room temperature. The thus obtained mixture was stirred for 1 hour, and the water layer was then removed. The water layer was extracted with 100 mL of ethyl acetate, and the combined organic layer was then dried over anhydrous sodium sulfate. After that, the solvent was distilled away under reduced pressure, so as to obtain 3.9 g of 5-methyl-3-phenoxyoxolan-2-ol in the form of a colorless oily product.

¹H-NMR (CDCl₃) δ value:

6.85-7.30 (5H, m), 5.40-5.55 (1H, m), 4.70-4.80 (1H, m), 4.45-4.55 (1H, m), 3.15-3.40 (2H, m), 1.65-2.60 (2H, m), 1.35-1.40 (3H, m)

(2)

[Formula 334]

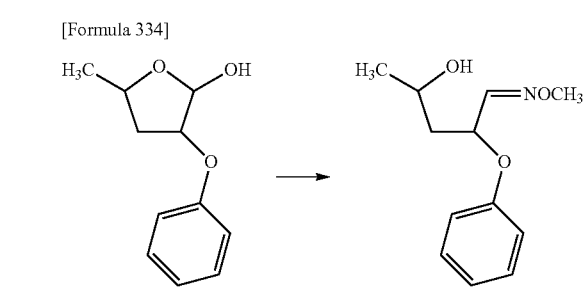

20 mL of methanol and 1.8 g of O-methylhydroxylamine hydrochloride were added to 3.6 g of 5-methyl-3-phenoxyoxolan-2-ol that was a colorless oily product, and thereafter, 2.79 mL of triethylamine was added dropwise to the mixture. The thus obtained mixture was stirred at room temperature for 5.5 hours. Thereafter, methanol was distilled away under reduced pressure, 100 mL of ethyl acetate and 100 mL of water were then added to the residue, and the water layer was then removed. The organic layer was dried over anhydrous magnesium sulfate, and the solvent was then distilled away under reduced pressure, so as to obtain 3.65 g of 5-(methoxyimino)-4-phenoxypentan-2-ol in the form of a colorless oily product.

¹H-NMR (CDCl₃) δ value:
6.65-7.40 (6H, m), 4.90-5.60 (1H, m), 4.00-4.20 (1H, m), 3.70-4.00 (3H, m), 1.50-2.50 (3H, m), 1.20-1.30 (3H, m)
(3)

[Formula 335]

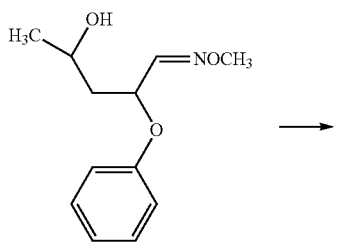

3.3 mL of triethylamine was added to a solution of 3.6 g of 5-(methoxyimino)-4-phenoxypentan-2-ol in 36 mL of tetrahydrofuran, and thereafter, 1.2 mL of methanesulfonyl chloride was added to the mixture at a temperature of 0° C. to 10° C. The obtained mixture was stirred at 15° C. or lower for 1 hour. Thereafter, 200 mL of ethyl acetate and 200 mL of water were added to the reaction mixture, and the water layer was then removed. The organic layer was dried over anhydrous magnesium sulfate, and the solvent was then distilled away under reduced pressure. The obtained residue was purified by silica gel column chromatography (hexane/ethyl acetate=4/1), so as to obtain 4.4 g of 5-(methoxyimino)-4-phenoxypentan-2-yl methanesulfonate in the form of a light yellow oily product.

¹H-NMR (CDCl₃) δ value:
6.60-7.40 (6H, m), 4.90-5.40 (2H, m), 3.80-4.00 (3H, m), 2.70-3.10 (3H, m), 1.90-2.40 (2H, m), 1.45-1.55 (3H, m)
(4)

[Formula 336]

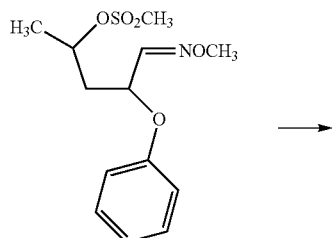 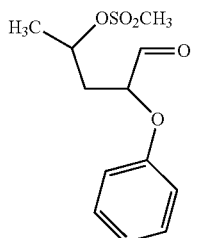

and water adduct thereof 15 mL of 2 mol/L hydrochloric acid was added to a mixture of 2.0 g of 5-(methoxyimino)-4-phenoxypentan-2-yl methanesulfonate, 4.8 mL of a 36% formalin aqueous solution and 60 mL of acetone, and the obtained mixture was then stirred at room temperature for 4 hours. Thereafter, the solvent was distilled away under reduced pressure, and 30 mL of ethyl acetate and 30 mL of water were then added to the residue.

After that, the water layer was removed. The organic layer was washed with a saturated sodium chloride aqueous solution, and was then dried over anhydrous sodium sulfate. Thereafter, the solvent was distilled away under reduced pressure. The obtained residue was purified by silica gel column chromatography (hexane/ethyl acetate=4/1), so as to obtain 0.66 g of a mixture of colorless oily 5-oxo-4-phenoxypentan-2-yl methanesulfonate and a water adduct thereof.

¹H-NMR (CDCl₃) δ value:
9.71-9.76 (1H, m), 7.26-7.33 (2H, m), 7.0-7.04 (1H, m), 6.88-6.92 (2H, m), 5.05-5.15 (1H, m), 4.67-4.77 (1H, m), 3.00 (1.4H, s), 2.83 (1.6H, s), 2.0-2.4 (2H, m), 1.48-1.55 (3H, m)
(5)

[Formula 337]

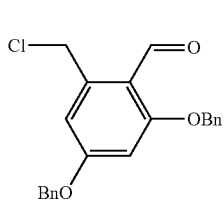  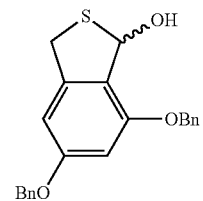

and water adduct thereof 0.53 g of a sodium hydrogen sulfide x-hydrate (Wako Pure Chemical Industries, Ltd.) was added to a solution of 0.62 g of 5-oxo-4-phenoxypentan-2-yl methanesulfonate in 6 mL of N,N-dimethylformamide at a temperature of 0° C. to 10° C., and the obtained mixture was then stirred at the same temperature as described above for 1 hour. Thereafter, 30 mL of ethyl acetate and 30 mL of water were added to the reaction mixture, and the water layer was then removed. The organic layer was washed with 30 mL of water, and was then dried over anhydrous magnesium sulfate. After that, the solvent was distilled away under reduced pressure. The obtained residue was purified by silica gel column chromatography (hexane/ethyl acetate=4/1), so as to obtain 0.34 g of 5-methyl-3-phenoxythiolan-2-ol in the form of a colorless oily product.

¹H-NMR (CDCl₃) δ value:
7.25-7.35 (2H, m), 6.90-7.00 (3H, m), 5.40-5.55 (1H, m), 4.90 (1H, m), 3.75-3.90 (1H, m), 2.40-2.70 (1H, m), 1.90-2.20 (2H, m), 1.42-1.46 (3H, m)

Example 36

[Formula 338]

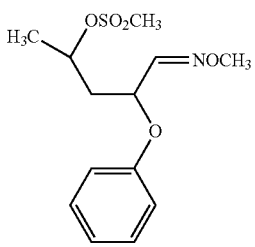 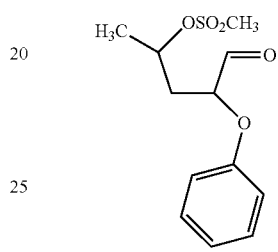  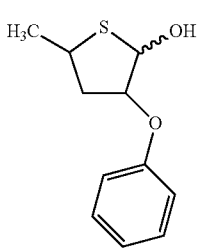

1.83 g of a 15% sodium hydrogen sulfide aqueous solution was added to a solution of 400 mg of 2-chloromethyl-4,6-dibenzyloxybenzaldehyde in 4.5 mL of N,N-dimethylformamide at a temperature of 0° C. to 10° C., and the obtained mixture was then stirred at 15° C. for 1 hour. Thereafter, 40 mL of ethyl acetate and 20 mL of a 10% sodium chloride aqueous solution were added to the reaction mixture, and the water layer was then removed. The organic layer was washed with a saturated sodium hydrogen carbonate aqueous solution, and 30 mL of hexane was then added thereto. A solid was collected by filtration, so as to obtain 206 mg of 5,7-bis (benzyloxy)-1,3-dihydrobenzothiophen-1-ol in the form of a white solid.

$^1$H-NMR (CDCl$_3$) δ value:
7.30-7.45 (1 OH, m), 6.68 (1H, dd, J=2.1, 6.9 Hz), 6.48 (1H, d, J=8.4 Hz), 6.47 (1H, d, J=8.4 Hz), 5.14 (H, d, J=12.3 Hz), 5.09 (1H, d, J=12.3 Hz), 5.03 (2H, s), 4.49 (1H, dd, J=2.1, 14.7 Hz), 4.02 (1H, d, J=14.7 Hz), 2.45 (1H, d=6.9 Hz)

Example 37

(1)

[Formula 339]

2.1 mL of trifluoromethanesulfonic acid was added to a solution of 13.8 g of 5-(hydroxymethyl)oxolane-2-one and 19.0 g of 2,4,6-tris(benzyloxy)-1,3,5-triazine in 150 mL of dioxane at a temperature of 5° C. to 10° C., and the obtained mixture was then stirred at room temperature for 5 hours. Thereafter, the reaction mixture was added to a mixture of 400 mL of ethyl acetate and 300 mL of a saturated sodium hydrogen carbonate aqueous solution. The organic layer was fractionated, and it was successively washed with 300 mL of water and 300 mL of a saturated sodium chloride aqueous solution, and was then dried over anhydrous sodium sulfate. The solvent was distilled away under reduced pressure, and the obtained residue was then purified by silica gel column chromatography (ethyl acetate/hexane=2/3 to 1/1), so as to obtain 22.4 g of 5-((benzyloxy)methyl)oxolane-2-one in the form of a colorless oily product.

$^1$H-NMR (CDCl$_3$) δ value:
7.33-7.28 (5H, m), 4.68-4.61 (1H, m), 4.572 (1H, s), 4.566 (1H, s), 3.68 (1H, dd, J=10.8, 4.5 Hz), 3.58 (1H, dd, J=10.8, 4.2 Hz), 2.57-2.42 (2H, m), 2.35-2.06 (2H, m)

(2)

[Formula 340]

2.3 g of sodium tetrahydroborate was added to a solution of 9.9 g of 5-((benzyloxy)methyl)oxolane-2-one in 12 mL of ethanol and 48 mL of tetrahydrofuran in a nitrogen atmosphere at a temperature of 5° C. to 10° C., and thereafter, a solution of 7.0 g of calcium chloride in 25 mL of ethanol was then added dropwise to the mixture over 20 minutes. Thereafter, 25 mL of tetrahydrofuran was added to the reaction mixture, and the obtained mixture was then stirred at room temperature for 200 minutes. Thereafter, 200 mL of ethyl acetate was added to the reaction mixture, and 1 mol/L hydrochloric acid was then added dropwise to the mixture. The organic layer was fractionated. The obtained organic layer was washed with 100 mL of a saturated sodium hydrogen carbonate aqueous solution, and then with 100 mL of a saturated sodium chloride aqueous solution twice, and it was then dried over anhydrous sodium sulfate. The solvent was distilled away under reduced pressure, so as to obtain 9.4 g of 5-(benzyloxy)pentane-1,4-diol in the form of a colorless oily product.

$^1$H-NMR (CDCl$_3$) δ value:
7.35-7.31 (5H, m), 4.55 (2H, s), 3.89-3.81 (1H, m), 3.71-3.58 (2H, m), 3.49 (1H, dd, J=9.3, 3.3 Hz), 3.36 (1H, dd, J=9.3, 7.8 Hz), 2.92 (1H, brs), 2.55 (1H, brs), 1.67-1.41 (4H, m)

(3)

[Formula 341]

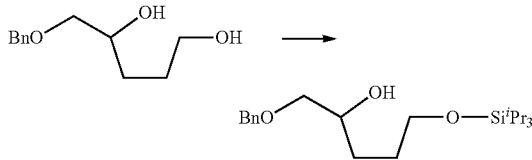

0.96 g of sodium hydride (60 wt % in oil) was added to a solution of 5.0 g of 5-(benzyloxy)pentane-1,4-diol in 50 mL of tetrahydrofuran in a nitrogen atmosphere at a temperature of 5° C. to 10° C., and the obtained mixture was then stirred at room temperature for 30 minutes. Thereafter, 5.3 mL of triisopropylsilyl chloride was added dropwise to the reaction mixture at a temperature of 5° C. to 10° C. The reaction mixture was stirred at room temperature for 1 hour, and it was then added to a mixture of 100 mL of ethyl acetate and 100 mL of water. The organic layer was fractionated. The obtained organic layer was successively washed with 100 mL of a saturated sodium hydrogen carbonate aqueous solution, 100 mL of water and 100 mL of a saturated sodium chloride aqueous solution, and it was then dried over anhydrous sodium sulfate. The solvent was distilled away under reduced pressure, and the obtained residue was then purified by silica gel column chromatography (ethyl acetate/hexane=1/5 to 1/5), so as to obtain 5.4 g of 1-benzyloxy-5-((triisopropyl) silyloxy)pentan-2-ol in the form of a colorless oily product.

$^1$H-NMR (CDCl$_3$) δ value:
7.35-7.26 (5H, m), 4.56 (2H, s), 3.85-3.79 (1H, m), 3.72 (2H, t, J=5.9 Hz), 3.49 (1H, dd, J=9.3, 3.9 Hz), 3.38 (1H, dd, J=9.3, 7.2 Hz), 2.86 (1H, d, J=3.3 Hz), 1.76-1.45 (4H, m), 1.15-1.00 (21H, m)

(4)

[Formula 342]

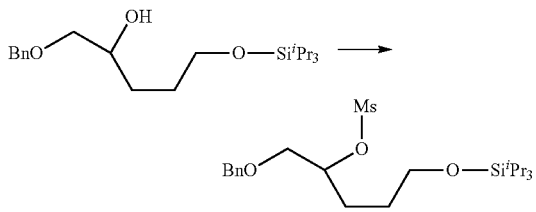

0.35 mL of methanesulfonyl chloride was added dropwise to a solution of 1.5 g of 1-benzyloxy-5-((triisopropyl)silyloxy)pentan-2-ol and 0.7 mL of triethylamine in 15 mL of ethyl acetate at a temperature of 5° C. to 10° C., and the obtained mixture was then stirred at room temperature for 1 hour. Thereafter, the reaction mixture was added to a mixture of 100 mL of ethyl acetate and 50 mL of 1 mol/L hydrochloric acid. The organic layer was fractionated. The obtained organic layer was successively washed with 50 mL of a saturated sodium hydrogen carbonate aqueous solution, 50 mL of water and 50 mL of a saturated sodium chloride aqueous solution, and it was then dried over anhydrous sodium sulfate. The solvent was distilled away under reduced pressure, so as to obtain 1.8 g of 1-benzyloxy-5-((triisopropyl)silyloxy)pentan-2-yl methanesulfonate in the form of a colorless oily product.

$^1$H-NMR (CDCl$_3$) δ value:
7.36-7.26 (5H, m), 4.92-4.83 (1H, m), 4.58 (1H, d, J=17.6 Hz), 4.54 (1H, d, J=17.6 Hz), 3.77-3.58 (4H, m), 3.02 (3H, s), 1.90-1.52 (4H, m), 1.15-1.00 (21H, m)

(5)

[Formula 343]

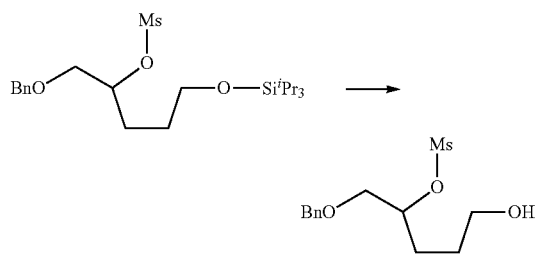

0.33 g of p-toluenesulfonic acid was added to a solution of 1.53 g of I-benzyloxy-5-((triisopropyl)silyloxy)pentan-2-yl methanesulfonate in 20 mL of methanol, and the obtained mixture was then stirred at room temperature for 1 hour. Thereafter, the reaction mixture was added to a mixture of 50 mL of ethyl acetate and 30 mL of a saturated sodium hydrogen carbonate aqueous solution. The organic layer was fractionated, and it was successively washed with 10 mL of water and 30 mL of a saturated sodium chloride aqueous solution, and was then dried over anhydrous sodium sulfate. The solvent was distilled away under reduced pressure, and the obtained residue was then purified by silica gel column chromatography (ethyl acetate/hexane=2/3 to 3/2), so as to obtain 0.8 g of 1-benzyloxy-5-hydroxypentan-2-yl methanesulfonate in the form of a colorless oily product.

$^1$H-NMR (CDCl$_3$) δ value:
7.36-7.26 (5H, m), 4.93-4.84 (1H, m), 4.58 (1H, d, J=12.0 Hz), 4.53 (1H, d, J=12.0 Hz), 3.74-3.57 (4H, m), 3.02 (3H, s), 1.84-1.64 (4H, m)

(6)

[Formula 344]

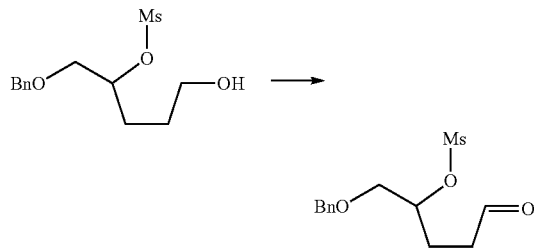

440 mg of 1,1,1-triacetoxy-1,1-dihydro-1,2-benziodoxol-3(1H)-one (Dess-Martin Periodinane) was added to a solution of 200 mg of 1-benzyloxy-5-hydroxypentan-2-yl methanesulfonate in 2 mL of dichloromethane, and the obtained mixture was then stirred at room temperature for 1 hour. Thereafter, 100 mg of Dess-Martin Periodinane was added to the reaction mixture, and the thus obtained mixture was then stirred at room temperature for 1 hour. Thereafter, the reaction mixture was added to a mixture of 50 mL of ethyl acetate and 30 mL of a saturated sodium hydrogen carbonate aqueous solution, and the obtained mixture was then filtrated with Celite. The organic layer was fractionated. The obtained organic layer was washed with 30 mL of a sodium thiosulfate aqueous solution twice, and then with 30 mL of a saturated sodium chloride aqueous solution, and it was then dried over anhydrous sodium sulfate. The solvent was distilled away under reduced pressure, and the obtained residue was then purified by silica gel column chromatography (ethyl acetate/hexane=1/2 to 1/1), so as to obtain 141 mg of 1-benzyloxy-5-oxopentan-2-yl methanesulfonate in the form of a colorless oily product.

$^1$H-NMR (CDCl$_3$) δ value:
9.79 (1H, s), 7.36-7.26 (5H, m), 4.89-4.80 (1H, m), 4.57 (1H, d, J=13.5 Hz), 4.52 (1H, d, J=13.5 Hz), 3.67-3.57 (2H, m), 3.01 (3H, s), 2.79-2.61 (2H, m), 2.10-1.83 (2H, m)

(7)

[Formula 345]

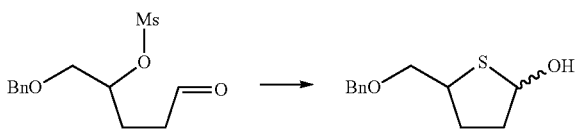

58 mg of a sodium hydrogen sulfide n-hydrate was added to a solution of 103 mg of 1-benzyloxy-5-oxopentan-2-yl methanesulfonate in 3 mL of N,N-dimethylformamide at room temperature, and the obtained mixture was then stirred at room temperature for 2 hours. Thereafter, the reaction mixture was added to a mixture of 30 mL of ethyl acetate and 20 mL of a saturated sodium hydrogen carbonate aqueous solution. The organic layer was fractionated, and it was washed with 20 mL of a saturated sodium chloride aqueous solution, and was then dried over anhydrous sodium sulfate. The solvent was distilled away under reduced pressure, and the obtained residue was then purified by silica gel column chromatography (ethyl acetate/hexane=1/3 to 1/2), so as to obtain 49 mg of 5-((benzyloxy)methyl)thiolan-2-ol in the form of a colorless oily product.

As a result of the measurement of $^1$H-NMR, the cis/trans ratio was found to be 50:50.

Moreover, 3, 30, 60, 90 and 120 minutes after initiation of the reaction, approximately 20 mg of the reaction mixture was precisely weighed with a precision balance, and the remaining amount of the 1-benzyloxy-5-oxopentan-2-yl methanesulfonate used as a raw material was measured by HPLC. As a result, it was found that the remaining amount of the substance was 53% three minutes after initiation of the reaction, and that the substance was completely consumed from 30 minutes after initiation of the reaction.

$^1$H-NMR (CDCl$_3$) δ value:
7.38-7.26 (5H, m), 5.55-5.45 (1H, m), 4.59 (1H, s), 4.56 (0.5H, d, J=2.0 Hz), 4.45 (0.5H, d, J=12.0 Hz), 3.85-3.57 (2H, m), 3.42-3.31 (1H, m), 2.72 (0.5H, d, J=6.90 Hz), 2.29-1.87 (4.5H, m)

Example 38

(1)

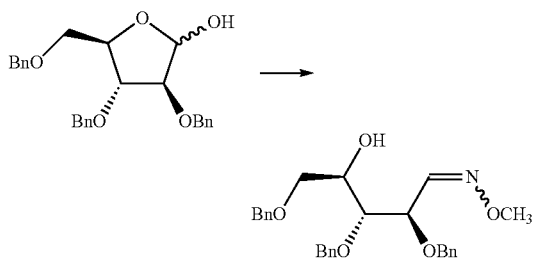

[Formula 346]

3.35 g of O-methylhydroxylamine hydrochloride was added to a mixture of 8.02 g of 2,3,5-tris(O-benzyl)-D-arabinofuranose, 48 mL of acetonitrile and 24 mL of water, and thereafter, 3.45 mL of triethylamine was added dropwise to the mixture. The thus obtained mixture was stirred at room temperature for 4 hours. Thereafter, 80 mL of ethyl acetate and 50 mL of a 8% sodium hydrogen carbonate aqueous solution were added to the reaction mixture. The organic layer was fractionated, and the water layer was then extracted with ethyl acetate twice. The organic layer was combined with the extract, and the obtained mixture was then dried over anhydrous magnesium sulfate. The solvent was distilled away under reduced pressure, so as to obtain 8.48 g of (2R,3R,4R)-1,3,4-tris(benzyloxy)-5-(methoxyimino)pentan-2-ol in the form of a colorless oily product.

$^1$H-NMR was measured. As a result, the syn-anti ratio was found to be 78:22.

$^1$H-NMR (CDCl$_3$) δ value:
2.60 (0.22H, d, J=1.5 Hz), 2.68 (0.78H, d, J=1.5 Hz), 3.56-3.60 (2.22H, m), 3.67 (0.78H, dd, J=7.1, 3.6 Hz), 3.79 (0.22H, dd, J=7.5, 3.0 Hz), 3.85 (0.66H, s), 3.86 (2.34H, s), 3.97-4.04 (1H, m), 4.27 (0.78H, dd, J=7.8, 3.9 Hz), 4.38-4.65 (6H, m), 4.93 (0.22H, dd, J=6.0, 3.0 Hz), 6.90 (0.22H, d, J=6.3 Hz), 7.23-7.35 (15H, m), 7.43 (0.78H, dd, J=8, 1, 0.6 Hz)

(2)

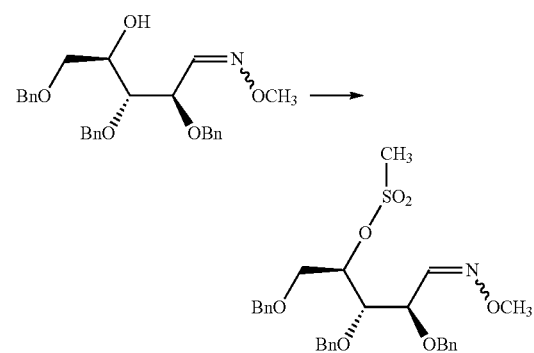

[Formula 347]

1.54 mL of triethylamine and 0.89 mL of N-methylimidazole were added to a solution of 3.33 g of (2R,3R,4R)-2,3,5-tris(benzyloxy)-4-hydroxypentanal=O-methyloxime in 33 mL of acetonitrile, and thereafter, 0.86 mL of methanesulfonyl chloride was added dropwise to the mixture. The obtained mixture was stirred at room temperature for 1 hour. Thereafter, 40 mL of water and 80 mL of ethyl acetate were added to the reaction mixture. The organic layer was fractionated. The obtained organic layer was successively washed with a mixed solution of 20 mL of 1 mol/L hydrochloric acid and 20 mL of a 10% sodium chloride aqueous solution, and with a mixed solution of 20 mL of a 5% sodium hydrogen carbonate aqueous solution and 20 mL of a 10% sodium chloride aqueous solution, and it was then dried over anhydrous magnesium sulfate. The solvent was distilled away under reduced pressure, and the obtained residue was then purified by silica gel column chromatography, so as to obtain 3.16 g of (2R,3S,4R)-1,3,4-tris(benzyloxy)-5-(methoxyimino)pentan-2-yl=methanesulfonate in the form of a colorless oily product.

$^1$H-NMR was measured. As a result, the syn-anti ratio was found to be 75:25.

$^1$H-NMR (CDCl$_3$) δ value:
2.93 (2.25H, s), 2.95 (0.75H, s), 3.80 (1H, dd, J=11.4, 6.9 Hz), 3.85 (0.75H, s), 3.86 (2.25H, s), 3.90 (1H, dd, J=11.4, 2.1 Hz), 3.98 (0.75H, t, J=4.5 Hz), 4.16 (0.75H, ddd, J=7.7, 4.5, 0.6 Hz), 4.41-4.62 (4.25H, m), 4.67 (2H, dd, J=20.4, 11.1 Hz), 4.80 (0.25H, dd, J=7.5, 4.5 Hz), 4.99 (1H, m), 6.81 (0.25H, d, J=6.3 Hz), 7.24-7.37 (15.75H, m)

(3)

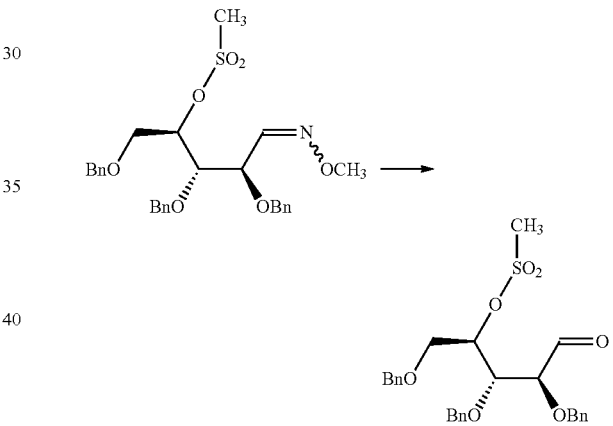

[Formula 348]

10 mL of 2 mol/L hydrochloric acid and 3.10 mL of a 35% formaldehyde aqueous solution were added to a solution of 2.06 g of (2R,3S,4R)-1,3,4-tris(benzyloxy)-5-(methoxyimino)pentan-2-yl=methanesulfonate in 40 mL of acetone in a nitrogen atmosphere, and the obtained mixture was then stirred at room temperature for 5 hours. Thereafter, 40 mL of a 10% sodium chloride aqueous solution and 40 mL of ethyl acetate were added to the reaction mixture. The organic layer was fractionated, and it was washed with a mixed solution of 20 mL of a 5% sodium hydrogen carbonate aqueous solution and 20 mL of a 10% sodium chloride aqueous solution, and was then dried over anhydrous magnesium sulfate. After that, the solvent was distilled away under reduced pressure. The obtained residue was purified by silica gel column chromatography, so as to obtain 1.50 g of (2R,3S,4S)-1,3,4-tris(benzyloxy)-5-oxopentan-2-yl=methanesulfonate in the form of a colorless oily product.

$^1$H-NMR (CDCl$_3$) δ value:
2.97 (1H, s), 3.76 (1H, dd, J=11.4, 6.6 Hz), 3.89 (1H, dd, J=11.4, 3.0 Hz), 4.04 (1H, dd, J=3.3, 0.9 Hz), 4.18 (1H, dd, J=5.3, 3.3 Hz), 4.47-4.60 (4H, m), 4.67 (2H, dd, J=22.2, 110.4 Hz), 5.97 (1H, m), 7.20-7.25 (2H, m), 7.27-7.36 (13H, m)

(4)

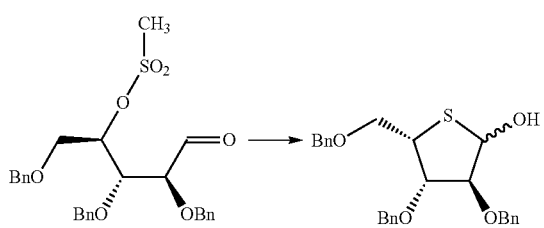
[Formula 349]

0.06 g of a sodium hydrogen sulfide x-hydrate was added to a solution of 0.10 g of (2R,3S,4S)-1,3,4-tris(benzyloxy)-5-oxopentan-2-yl=methanesulfonate in 2 mL of N,N-dimethylformamide, and the obtained mixture was then stirred at room temperature for 12 hours. Thereafter, 2 mL of water and 5 mL of ethyl acetate were added to the reaction mixture. The organic layer was fractionated, and it was washed with 5 mL of a 10% sodium chloride aqueous solution and was then dried over anhydrous magnesium sulfate. After that, the solvent was distilled away under reduced pressure. The obtained residue was purified by silica gel column chromatography, so as to obtain 0.02 g of (3S,4S,5S)-3,4-bis(benzyloxy)-5-((benzyloxy)methyl)thiolan-2-ol in the form of a colorless oily product.

$^1$H-NMR (CDCl$_3$) δ value:
3.69 (1H, d, J=12.6 Hz), 3.77-3.82 (3H, m), 4.19 (2H, m), 4.51-4.67 (6H, m), 5.26 (1H, d, J=12.6 Hz), 7.22-7.37 (15H, m)

Example 39

(1)

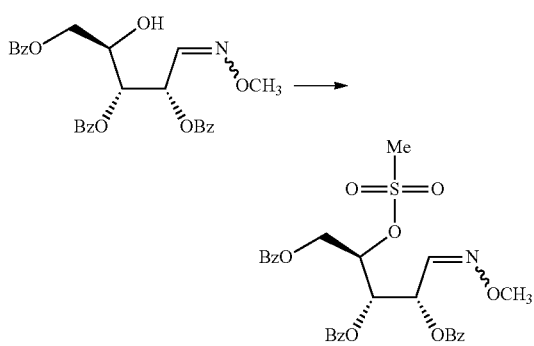
[Formula 350]

10 mL of ethyl acetate and 0.19 mL of methanesulfonyl chloride were added to 0.99 g of (2R,3R,4S)-2-hydroxy-5-(methoxyimino)pentane-1,3,4-triyl=tribenzoate, and thereafter, 0.39 mL of triethylamine was added dropwise to the mixture under cooling on ice. The obtained mixture was stirred at room temperature for 1 hour. Thereafter, 0.19 mL of triethylamine and 0.39 mL of methanesulfonyl chloride were added to the reaction mixture. The thus obtained mixture was stirred at room temperature for 2 hours, and was then left at room temperature for 2 days. Thereafter, ethyl acetate and water were added to the reaction mixture, the organic layer was then fractionated, and the solvent was then distilled away under reduced pressure. The obtained residue was purified by silica gel column chromatography (hexane/ethyl acetate=1/0 to 3/1), so as to obtain 1.02 g of (2R,3S,4S)-5-(methoxyimino)-2-((methylsulfonyl)oxy)pentane-1,3,4-triyl=tribenzoate in the form of a colorless oily product.

$^1$H-NMR (CDCl$_3$) δ value:
8.11-8.00 (6H, m), 7.64-7.41 (9.75H, m), 6.92 (0.25H, d, J=5.9 Hz), 6.55 (0.25H, dd, J=5.3, 4.0 Hz), 6.1 (0.25H, dd, J=5.9, 4.0 Hz), 6.08-6.02 (1.5H, m), 5.53-5.46 (1H, m), 5.01-4.91 (1H, m), 4.59-4.47 (1H, m), 3.97 (0.75H, s), 3.88 (2.25H, s), 3.17 (2.25H, s), 3.13 (0.75H, s)

(2)

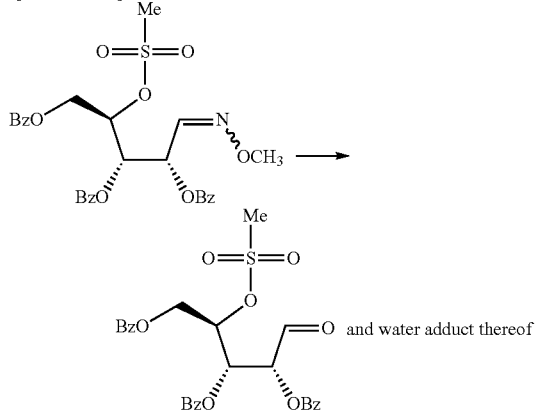
[Formula 351]

1.8 mL of a 50% glyoxylic acid aqueous solution was added to a solution of 1.02 g of (2R,3S,4S)-5-(methoxyimino)-2-((methylsulfonyl)oxy)pentane-1,3,4-triyl=tribenzoate in 3.0 mL of acetonitrile, and the obtained mixture was then stirred at 80° C. for 4 hours. Thereafter, the reaction mixture was cooled to room temperature, ethyl acetate and water were then added to the mixture, and the water layer was then removed. The organic layer was successively washed with a 10% sodium hydrogen carbonate aqueous solution and water, and the solvent was then distilled away under reduced pressure. The obtained residue was purified by silica gel column chromatography (hexane/ethyl acetate=1/0 to 1/1), so as to obtain 317 mg of a colorless oily product.

The obtained oily product was a mixture of (2R,3S,4R)-2-((methylsulfonyl)oxy)-5-oxopentane-1,3,4-triyl=tribenzoate and a water adduct thereof.

$^1$H-NMR (CDCl$_3$) δ value:
9.74 (1H, s), 8.20-7.96 (6H, m), 7.66-7.42 (9H, m), 6.12 (1H, dd, J=7.9, 2.6 Hz), 5.87 (1H, d, J=2.6 Hz), 5.64-5.58 (1H, m), 4.96 (1H, dd, J=13.2, 2.6 Hz), 4.49 (1H, dd, J=13.2, 5.3 Hz), 3.13 (3H, s)

(3)

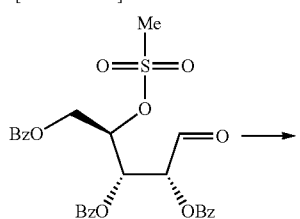
[Formula 352]

-continued

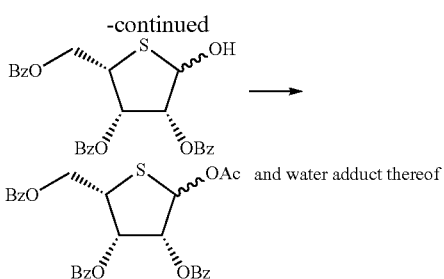

and water adduct thereof 0.27 mL of a 15%-18% sodium hydrogen sulfide aqueous solution was added to a solution of 317 mg of the colorless oily product obtained in Example 39(2) in 1.5 mL of N,N-dimethylformamide at a temperature of 0° C. to 10° C., and the obtained mixture was then stirred at the same temperature as described above for 1 hour. Thereafter, 10 mL of ethyl acetate was added to the reaction mixture, and the thus obtained mixture was washed with 10 mL of a 10% sodium chloride aqueous solution three times, to obtain an ethyl acetate solution of 2,3,5-tri-O-benzoyl-4-thio-L-lyxose.

0.4 mg of 4-dimethylaminopyridine and 0.061 mL of acetic anhydride were added to the obtained ethyl acetate solution. The obtained mixture was stirred at room temperature for 1 hour, and was then left at room temperature overnight. Thereafter, the reaction mixture was washed with water, and the solvent was then distilled away under reduced pressure. The obtained residue was purified by silica gel column chromatography (hexane/ethyl acetate=1/0 to 3/1), so as to obtain 107 mg of 1-O-acetyl-2,3,5-tri-O-benzoyl-4-thio-L-lyxose in the form of a colorless oily product. The obtained compound was a single anomer.

$^1$H-NMR (CDCl$_3$) δ value:
8.05-8.01 (2H, m), 7.96-7.92 (2H, m), 7.90-7.87 (2H, m), 7.64-7.3 (9H, m), 6.20 (1H, d, J=4.0 Hz), 6.09 (1H, dd, J=5.9, 4.0 Hz), 5.94 (1H, t, J=3.6 Hz), 4.77 (1H, dd, J=11.2, 7.3 Hz), 4.61 (1H, dd, J=11.2, 7.3 Hz), 4.37 (1H, q, J=6.8 Hz), 2.15 (3H, s)

Example 40

(1)

[Formula 353]

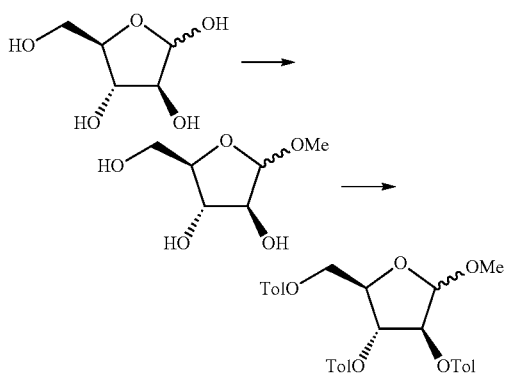

720 mL of acetyl chloride was added dropwise to 1200 mL of a methanol solution of 12.0 kg of (2R,3R,4S)-3,4,5-trihydroxy-2-hydroxymethyloxolane at a temperature of 15° C. or lower over 30 minutes, and the obtained mixture was then stirred at a temperature of 20° C. to 30° C. for 1 hour. Thereafter, 2100 mL of a 28% sodium methoxide/methanol solution and 1000 mL of toluene were added to the reaction mixture, and methanol was then distilled away under reduced pressure, to obtain 4500 mL of a toluene solution of (2R,3R,4S)-3,4-dihydroxy-2-hydroxymethyl-5-methoxyoxolane.

2400 mL of a 50% sodium hydroxide aqueous solution, 6000 mL of toluene and 72.0 g of tetrabutylammonium chloride were added to 4500 mL of the obtained toluene solution at a temperature of 30° C. or lower, and thereafter, 3290 mL of 4-methylbenzoyl chloride was added dropwise to the mixture at a temperature of 15° C. or lower over 1 hour. The thus obtained mixture was stirred at 30° C. for 3 hours. Thereafter, the water layer was removed, and the organic layer was successively washed with 3000 mL of water and 3000 mL of a 10% sodium chloride aqueous solution, and was then dried over anhydrous sodium sulfate. The solvent was distilled away under reduced pressure, so as to obtain 3.94 kg of ((2R,3S,4S)-3,4-di((4-methylphenyl)carbonyloxy)-5-methoxyoxiran-2-yl)methyl=4-methylbenzoate in the form of a white solid.

$^1$H-NMR (CDCl$_3$) δ value:
2.33-2.45 (9H, m), 3.49 (3H, s), 4.53-4.57 (1H, m), 4.60-4.76 (1H, m), 4.82 (1H, dd, J=3.2, 12.0 Hz), 5.16 (1H, s), 5.44-5.48 (1H, m), 5.55 (1H, d, J=5.6 Hz), 7.08-7.26 (6H, m), 7.86-7.97 (6H, m)

(2)

[Formula 354]

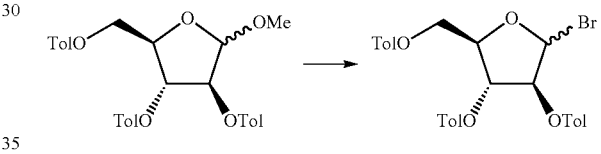

50 mL of a 30% hydrogen bromide/acetic acid solution was added to a mixed solution of 50.0 g of ((2R,3S,4S)-3,4-di((4-methylphenyl)carbonyloxy)-5-methoxyoxiran-2-yl)methyl=4-methylbenzoate in 50 mL of acetic acid and 25 mL of toluene at 25° C., and the obtained mixture was then stirred at the same temperature as described above for 2 hours. Thereafter, 100 mL of hexane was added to the reaction mixture, and a solid was then collected by filtration, so as to obtain 37.7 g of ((2R,3S,4S)-5-bromo-3,4-di((4-methylphenyl)carbonyloxy)oxiran-2-yl)methyl=4-methylbenzoate in the form of a white solid.

$^1$H-NMR (CDCl$_3$) δ value:
2.44 (3H, s), 2.42 (3H, s), 2.37 (3H, s), 4.72-4.92 (3H, m), 5.59 (1H, d, J=4.4 Hz), 5.92 (1H, s), 6.19 (1H, s), 7.08-7.30 (6H, m), 7.82-8.03 (6H, m)

(3)

[Formula 355]

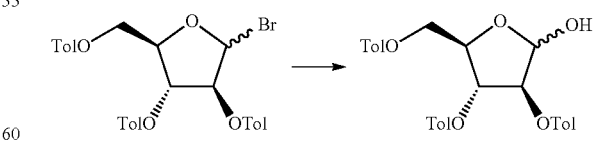

71.0 g of sodium hydrogen carbonate was added to a mixed solution of 400 g of ((2R,3S,4S)-5-bromo-3,4-di((4-methylphenyl)carbonyloxy)oxiran-2-yl)methyl=4-methylbenzoate in 950 mL of toluene, 480 mL of water and 600 mL of acetonitrile at 25° C., and the obtained mixture was then stirred at 55° C. for 6 hours 30 minutes. Thereafter, 500 mL of a 10% sodium hydrogen carbonate aqueous solution was added to the reaction mixture, and the water layer was then removed. The organic layer was washed with 3 L of a 10% sodium chloride aqueous solution, and was then dried over anhydrous magnesium sulfate. After that, the solvent was distilled away under reduced pressure, so as to obtain 361 g of ((2R,3S,4S)-3,4-di((4-methylphenyl)carbonyloxy)-5-hydroxyoxiran-2-yl)methyl=4-methylbenzoate in the form of a white solid.

$^1$H-NMR (CDCl$_3$) δ value:
2.37-2.45 (9H, m), 4.73-4.92 (3H, m), 5.59 (1H, d, J=4.4 Hz), 5.92 (1H, s), 6.59 (1H, s), 7.04-7.26 (6H, m), 7.83-8.03 (6H, m)
(4)

[Formula 356]

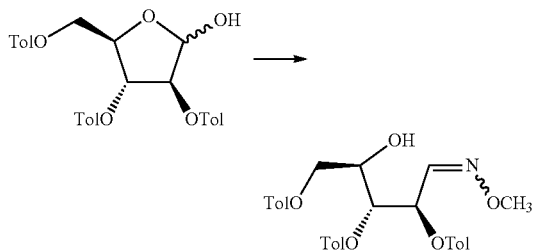

360 mL of pyridine, 180 g of p-toluenesulfonic acid dihydrate and 106 g of O-methylhydroxylamine hydrochloride were added to a solution of 361 g of ((2R,3S,4S)-3,4-di((4-methylphenyl)carbonyloxy)-5-hydroxyoxiran-2-yl)methyl=4-methylbenzoate in 1080 mL of methanol, and thereafter, 176 mL of triethylamine was added dropwise to the mixture at 25° C. The obtained mixture was stirred at the same temperature as described above for 8 hours. Thereafter, ethyl acetate and water were added to the reaction mixture, and the water layer was then removed. The organic layer was successively washed with a 10% sodium chloride aqueous solution twice, hydrochloric acid twice, a sodium hydrogen carbonate aqueous solution once and a saturated sodium chloride aqueous solution once, and it was then dried over anhydrous magnesium sulfate. After that, the solvent was distilled away under reduced pressure, so as to obtain 394 g of (2R,3R,4R)-1,3-di((4-methylphenyl)carbonyloxy)-2-hydroxy-5-(methoxyimino)pentan-4-yl=4-methylbenzoate in the form of a colorless oily product.

$^1$H-NMR was measured. As a result, the syn-anti ratio was found to be 75:25.

$^1$H-NMR (CDCl$_3$) δ value:
2.37-2.43 (9H, m), 3.40 (1H, d, J=8.4 Hz), 3.79 (2.25H, s), 4.11 (0.75H, s), 4.36-4.40 (1H, m), 4.53-4.59 (1H, m), 5.66 (0.75H, dd, J=3.2, 8.4 Hz), 5.84 (0.25H, dd, J=2.8, 8.4 Hz), 6.17 (0.75H, dd, J=3.2, 6.0 Hz) 6.57 (0.25H, dd, J=2.8, 5.2 Hz), 6.76 (0.25H, d, J=5.2 Hz), 7.06-7.29 (6H, m), 7.45 (0.75H, d, J=6.0 Hz), 7.89-8.03 (6H, m)
(5)

[Formula 357]

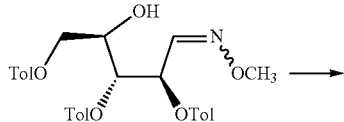

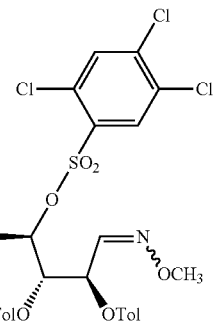

195 g of (2,4,5-trichlorobenzene)sulfonyl chloride was added to a solution of 338 g of (2R,3R,4R)-1,3-di((4-methylphenyl)carbonyloxy)-2-hydroxy-5-(methoxyimino)pentan-4-yl=4-methylbenzoate in 1200 mL of acetonitrile at 25° C., and thereafter, 130 mL of N-methylimidazole was added dropwise to the mixture at a temperature of 0° C. to 10° C. over 40 minutes. The obtained mixture was stirred at 10° C. for 5 hours. Thereafter, 1500 mL of ethyl acetate and 1000 mL of water were added to the reaction mixture, and the water layer was then removed. The organic layer was successively washed with a 10% sodium chloride aqueous solution twice, hydrochloric acid once, a sodium hydrogen carbonate aqueous solution once and a saturated sodium chloride aqueous solution once, and it was then dried over anhydrous magnesium sulfate. After that, the solvent was distilled away under reduced pressure, so as to obtain (2R,3R,4R)-1-(methoxyimino)-2,5-di((4-methylphenyl)carbonyloxy)-4-(((2,4,5-trichlorobenzene)sulfonyl)oxy)pentan-3-yl=4-methylbenzoate in the form of a colorless oily product.

$^1$H-NMR was measured. As a result, the syn-anti ratio was found to be 75:25.

$^1$H-NMR (CDCl$_3$) δ value:
2.37-2.49 (9H, m), 3.82 (2.25H, s), 3.96 (0.75H, s), 4.62-4.80 (2H, m), 5.35-5.51 (1H, m), 5.90-6.05 (1.75H, m), 6.30-6.38 (0.25H, m), 6.74-6.76 (0.25H, m), 7.15-7.35 (7H, m), 7.44-7.49 (0.75H, m), 7.75-7.99 (7H, m)
(6)

[Formula 358]

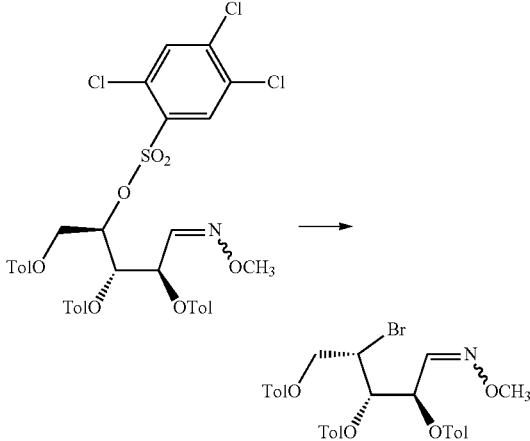

110 g of lithium bromide was added to a mixed solution of (2R,3R,4R)-1-(methoxyimino)-2,5-di((4-methylphenyl)carbonyloxy)-4-(((2,4,5-trichlorobenzene)sulfonyl)oxy)pentan-3-yl=4-methylbenzoate in 450 mL of tetrahydrofuran and 370 mL of 1,2-dimethylimidazole at a temperature of 10° C. or lower, and the obtained mixture was then stirred at 25° C. for 6 hours. Thereafter, 800 mL of ethyl acetate and 800 mL of water were added to the reaction mixture, and the water layer was then removed. The organic layer was dried over anhydrous magnesium sulfate, and the solvent was then distilled away under reduced pressure, so as to obtain (2S,3S,4R)-2-bromo-1,4-di((4-methylphenyl)carbonyloxy)-5-(methoxyimino)pentan-3-yl=4-methylbenzoate in the form of a colorless oily product.

$^1$H-NMR was measured. As a result, the syn-anti ratio was found to be 79:21.

$^1$H-NMR (CDCl$_3$) δ value:
2.34-2.41 (9H, m), 3.38 (2.37H, s), 3.88 (0.63H, s), 4.44-4.75 (3H, m), 6.04-6.11 (1.79H, m), 6.41-6.44 (0.21H, m), 6.75 (0.21H, d, J=5.6 Hz), 7.11-7.26 (6H, m), 7.53 (0.79H, d, J=5.2 Hz), 7.78-7.96 (6H, m)

(7)

[Formula 359]

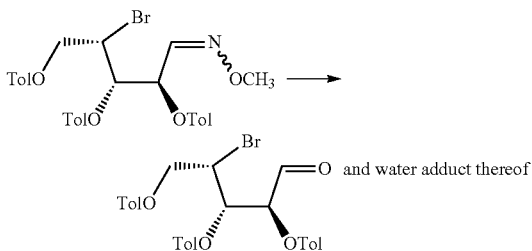

420 mL of a 50% glyoxylic acid aqueous solution was added to a solution of (2S,3S,4R)-2-bromo-1,4-di((4-methylphenyl)carbonyloxy)-5-(methoxyimino)pentan-3-yl=4-methylbenzoate in 900 mL of acetonitrile, and the obtained mixture was then stirred at 75° C. for 12 hours. Thereafter, the reaction mixture was cooled to room temperature, and 600 mL of ethyl acetate and 200 mL of water were then added to the mixture. After that, the water layer was removed. The organic layer was successively washed with a 10% sodium chloride aqueous solution and with a mixed solution of a sodium hydrogen carbonate aqueous solution and a saturated sodium chloride aqueous solution, and it was then dried over anhydrous magnesium sulfate. After that, the solvent was distilled away under reduced pressure to obtain 337 g of a brown oily product.

The obtained oily product was a mixture of (2S,3S,4S)-2-bromo-1,4-di((4-methylphenyl)carbonyloxy)-5-oxopentan-3-yl=4-methylbenzoate and a water adduct thereof.

$^1$H-NMR (CDCl$_3$) δ value:
2.34-2.45 (9H, m), 4.55-4.85 (3H, m), 5.78-5.80 (1H, m), 5.95-6.00 (1H, m), 7.18-7.26 (6H, m), 7.89-7.96 (6H, m), 9.72 (1H, s)

(8)

[Formula 360]

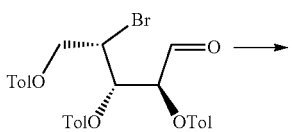

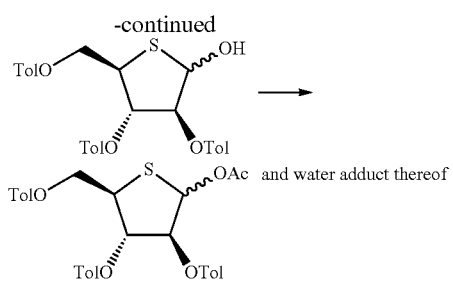

584 mL of a 25% sodium hydrogen sulfide aqueous solution was added dropwise to a solution of 337 g of the oily product obtained in Example 40(7) in 1000 mL of N,N-dimethylformamide at −10° C. over 30 minutes, and the obtained mixture was then stirred at 15° C. for 2 hours. Thereafter, 1000 mL of ethyl acetate and a saturated sodium chloride aqueous solution were added to the reaction mixture, and the water layer was then removed. The organic layer was washed with a sodium hydrogen carbonate aqueous solution three times, and was then dried over anhydrous magnesium sulfate, so as to obtain an ethyl acetate solution of ((2R,3S,4S)-3,4-di((4-methylphenyl)carbonyloxy)-5-hydroxythiolan-2-yl)methyl=4-methylbenzoate.

15.0 g of N,N-dimethyl-4-aminopyridine was added to the obtained ethyl acetate solution, and 180 mL of acetic anhydride was then added thereto dividedly over four times at 0° C. The obtained mixture was left at rest at room temperature for 16 hours. Thereafter, 400 mL of water was added to the reaction mixture, and the water layer was then removed. The organic layer was washed with a sodium hydrogen carbonate aqueous solution four times, and was then dried over anhydrous magnesium sulfate. After that, the solvent was distilled away under reduced pressure. The obtained residue was recrystallized from methanol, so as to obtain 167 g of ((2R,3S,4S)-5-(acetyloxy)-3,4-di((4-methylphenyl)carbonyloxy)thiolan-2-yl)methyl=4-methylbenzoate in the form of a white solid.

$^1$H-NMR (DMSO-d$_6$) δ value:
1.99 (1.50H, s), 2.04 (1.50H, s), 2.31-2.45 (9H, m), 3.78-3.87 (1H, m), 4.46-4.53 (1H, m), 4.64-4.71 (1H, m), 5.66-5.73 (1H, m), 6.08-6.21 (1H, m), 6.31 (0.50H, d, J=4.4 Hz), 6.40 (0.50H, d, J=4.4 Hz), 6.96-7.28 (6H, m), 7.76-7.96 (6H, m)

(9)

[Formula 361]

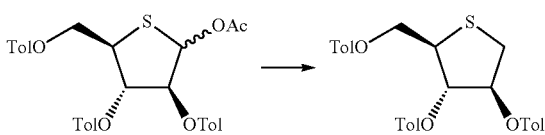

25 mL of triethylsilane was added to a solution of 25 g of ((2R,3S,4S)-5-(acetyloxy)-3,4-di((4-methylphenyl)carbonyloxy)thiolan-2-yl)methyl=4-methylbenzoate in 75 mL of trifluoroacetic acid, and the obtained mixture was then stirred at room temperature for 8 hours 30 minutes. Thereafter, the solvent was distilled away under reduced pressure, and the obtained residue was then recrystallized from methanol, so as to obtain 167 g of ((2R,3S,4S)-5-(acetyloxy)-3,4-di((4-methylphenyl)carbonyloxy)thiolan-2-yl)methyl=4-methylbenzoate in the form of a white solid.

¹H-NMR (DMSO-d₆) δ value:
2.31-2.45 (9H, m), 3.18 (1H, dd, J=5.6, 16.0 Hz), 3.52 (1H, d, J=4.8, 16.0 Hz), 3.92 (1H, ddd, J=4.8, 9.2, 10.8 Hz), 4.57 (1H, dd, J=9.2, 14.8 Hz), 4.67 (1H, dd, J=10.8, 14.8), 5.72-5.77 (1H, m), 5.85-5.88 (1H, m), 7.15-7.26 (6H, m), 7.88-7.96 (6H, m)

Example 41

(1)

[Formula 362]

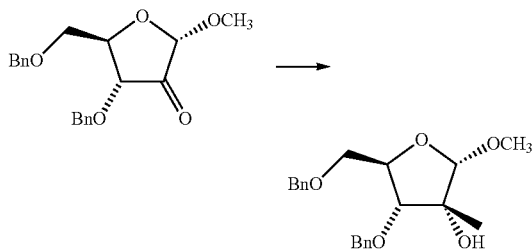

92 mL of a 1 mol/L methyl magnesium bromide/tetrahydrofuran solution and 23 mL of a 3 mol/L methyl magnesium bromide/diethyl ether solution were added dropwise to a solution of 23.2 g of (2S,4R,5R)-4-(benzyloxy)-5-((benzyloxy)methyl)-2-methoxyoxolane-3-one in 100 mL of tetrahydrofuran at −40° C., and the obtained mixture was then stirred at the same temperature as described above for 30 minutes. Thereafter, the temperature of the reaction mixture was increased to 0° C. over 1 hour, and 500 mL of a saturated ammonium chloride aqueous solution and 500 mL of ethyl acetate were then added to the mixture. The organic layer was fractionated, and it was washed with 300 mL of a saturated sodium chloride aqueous solution and was then dried over anhydrous magnesium sulfate. The solvent was distilled away under reduced pressure, and the obtained residue was then purified by silica gel column chromatography, so as to obtain 12.0 g of (2S,3R,4R,5R)-4-(benzyloxy)-5-((benzyloxy)methyl)-2-methoxy-3-methyloxolan-3-ol in the form of a colorless oily product.

¹H-NMR (CDCl₃) δ value:
7.37-7.24 (10H, m), 4.80-4.48 (5H, m), 4.12 (1H, m), 3.53-3.42 (2H, m), 3.44 (3H, s), 3.38 (1H, d, J=0.6 Hz), 3.34 (1H, d, J=4.2 Hz), 1.31 (3H, s).

(2)

[Formula 363]

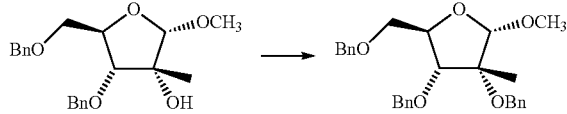

1.2 g of sodium hydride was added to an N,N-dimethylformamide solution of 7.2 g of (2S,3R,4R,5R)-4-(benzyloxy)-5-((benzyloxy)methyl)-2-methoxy-3-methyloxolan-3-ol, and thereafter, 5.1 g of benzyl bromide was added dropwise to the mixture at a temperature of 15° C. or lower. The obtained mixture was stirred at room temperature for 1.5 hours. Thereafter, 200 mL of water and 200 mL of ethyl acetate were added to the reaction mixture. The organic layer was fractionated, and it was successively washed with 200 mL of 1 mol/L hydrochloric acid and 200 mL of a saturated sodium chloride aqueous solution. The solvent was distilled away under reduced pressure, so as to obtain 9.0 g of (2S,3R,4R,5R)-3,4-bis(benzyloxy)-5-((benzyloxy)methyl)-2-methoxy-3-methyloxolane in the form of a colorless oily product.

¹H-NMR (CDCl₃) δ value:
7.44-7.22 (15H, m), 4.82-4.46 (6H, m), 4.70 (1H, s), 4.27 (1H, q, J=3.9 Hz), 3.59-3.43 (3H, m), 3.46 (3H, s), 1.34 (3H, s).

(3)

[Formula 364]

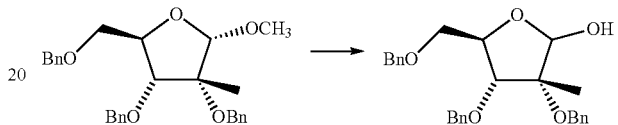

4.9 g of concentrated sulfuric acid was added dropwise to a solution of 9.0 g of (2S,3R,4R,5R)-3,4-bis(benzyloxy)-5-((benzyloxy)methyl)-2-methoxy-3-methyloxolane in 80 mL of acetic acid and 20 mL of water at room temperature, and the obtained mixture was then stirred at 70° C. for 3 hours. Thereafter, the reaction mixture was cooled to 30° C., and 200 mL of water and 200 mL of ethyl acetate were then added to the mixture. The organic layer was fractionated, and it was successively washed with 200 mL of 1 mol/L hydrochloric acid and 200 mL of a saturated sodium chloride aqueous solution. The solvent was distilled away under reduced pressure. The obtained residue was purified by silica gel column chromatography, so as to obtain 5.5 g of (2S,3R,4R,5R)-3,4-bis(benzyloxy)-5-((benzyloxy)methyl)-3-methyloxolan-2-ol in the form of a colorless oily product.

¹H-NMR (dmso-d₆) δ value:
7.38-7.24 (15H, m), 6.56 (0.64H, d, J=4.8 Hz), 5.84 (0.36H, d, J=6.9 Hz), 5.01 (0.64H, d, J=4.8 Hz), 4.99 (0.36H, d, J=6.9), 4.75-4.47 (6H, m), 4.17 (0.36H, m), 4.03 (0.64H, m), 3.79 (0.64H, d, J=7.5 Hz), 3.66 (0.36H, d, J=6.0 Hz), 3.61-3.49 (2H, m), 1.34 (1.92H, s), 1.33 (1.08H, s).

(4)

[Formula 365]

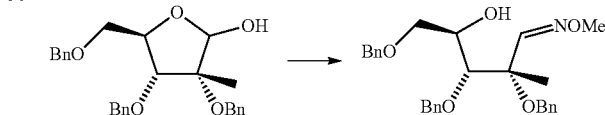

0.69 g of O-methylhydroxylamine hydrochloride was added to a mixture of 2.0 g of (2S,3R,4R,5R)-3,4-bis(benzyloxy)-5-((benzyloxy)methyl)-3-methyloxolan-2-ol and 10 mL of methanol, and thereafter, 0.56 g of triethylamine was added dropwise to the mixture. The obtained mixture was stirred at room temperature for 6 hours. Thereafter, the solvent was distilled away under reduced pressure, and 20 mL of ethyl acetate and 20 mL of water were then added to the obtained residue. The organic layer was fractionated, and was then washed with water twice. The solvent was distilled away under reduced pressure, so as to obtain 2.0 g of (2R,3R,4S)-

1,3,4-tris(benzyloxy)-4-((methoxyimino)methyl)pentan-2-ol in the form of a colorless oily product.

¹H-NMR (CDCl₃) δ value:

7.42 (s(1H), 7.35-18 (15H, m), 4.64-4.39 (6H, m), 4.06 (1H, m), 3.87 (3H, s), 3.76-3.68 (4H, m), 1.58 (3H, s).

(5)

[Formula 366]

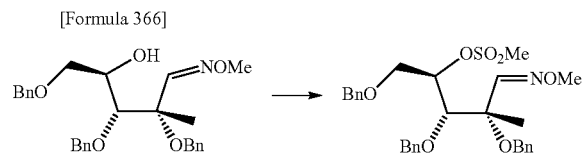

0.66 g of triethylamine and 0.53 g of N-methylimidazole were added to a solution of 2.0 g of (2R,3R,4S)-1,3,4-tris(benzyloxy)-4-((methoxyimino)methyl)pentan-2-ol in 1.0 mL of acetonitrile, and thereafter, 0.75 g of methanesulfonyl chloride was added dropwise to the mixture. The obtained mixture was stirred at room temperature for 1 hour. Thereafter, 30 mL of water and 50 mL of ethyl acetate were added to the reaction mixture. The organic layer was fractionated. The obtained organic layer was washed with 20 mL of 1 mol/L hydrochloric acid twice, and then, it was successively washed with 20 mL of a saturated sodium hydrogen carbonate aqueous solution and 20 mL of a saturated sodium chloride aqueous solution. The solvent was distilled away under reduced pressure. The obtained residue was purified by silica gel column chromatography, so as to obtain 1.7 g of (2R,3R,4S)-1,3,4-tris(benzyloxy)-5-(methoxyimino)-4-methylpentan-2-yl=methanesulfonate in the form of a colorless oily product.

¹H-NMR (CDCl₃) δ value:

7.35 (1H, s), 7.34-7.22 (15H, m), 5.23 (1H, m), 4.81-3.39 (6H, m), 3.96 (1H, d, J=1.8 Hz), 3.89-3.79 (2H, m), 3.87 (3H, s), 2.96 (3H, s), 1.48 (3H, s).

(6)

[Formula 367]

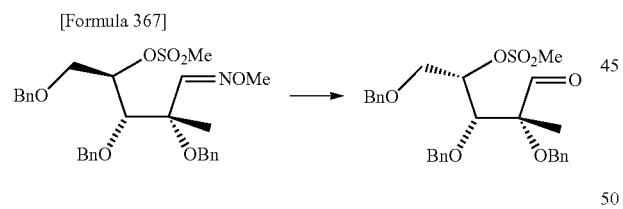

3.5 mL of 2 mol/L hydrochloric acid and 1.12 g of a 35% formaldehyde aqueous solution were added to a solution of 0.7 g of (2R,3R,4S)-1,3,4-tris(benzyloxy)-5-(methoxyimino)-4-methylpentan-2-yl=methanesulfonate in 14 mL of acetone in a nitrogen atmosphere, and the obtained mixture was then stirred at room temperature for 22 hours. Thereafter, 1.2 g of a 35% formaldehyde aqueous solution and 2 mL of acetone were added to the reaction mixture, and the thus obtained mixture was then stirred at 40° C. for 5 hours. Thereafter, 15 mL of water and 20 mL of ethyl acetate were added to the reaction mixture. The organic layer was fractionated, and it was successively washed with 20 mL of a saturated sodium hydrogen carbonate aqueous solution and 20 mL of a saturated sodium chloride aqueous solution. The solvent was distilled away under reduced pressure. The obtained residue was purified by silica gel column chromatography, so as to obtain 0.31 g of (2R,3R,4R)-1,3,4-tris(benzyloxy)-4-methyl-5-oxopentan-2-yl=methanesulfonate in the form of a colorless oily product.

¹H-NMR (CDCl₃) δ value:

9.51 (1H, s), 7.38-7.24 (15H, m), 5.09 (1H, m), 4.77-4.43 (6H, m), 4.09 (1H, d, J=4.5 Hz), 3.96-3.77 (2H, m), 2.93 (3H, s), 1.43 (3H, s).

(7)

[Formula 368]

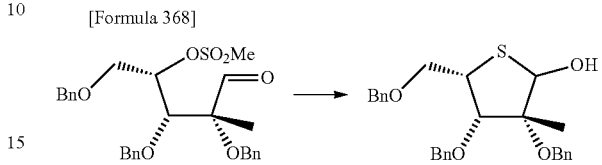

0.035 g of a sodium hydrogen sulfide x-hydrate was added to an N,N-dimethylformamide solution of 0.12 g of (2R,3R,4R)-1,3,4-tris(benzyloxy)-4-methyl-5-oxopentan-2-yl=methanesulfonate, and the obtained mixture was then stirred at room temperature for 2 hours. Thereafter, water and 5 mL of ethyl acetate were added to the reaction mixture. The organic layer was fractionated, and it was then washed with 5 mL of a saturated sodium chloride aqueous solution. The solvent was distilled away under reduced pressure. The obtained residue was purified by silica gel column chromatography, so as to obtain 0.05 g of (3R,4S,5R)-3,4-bis(benzyloxy)-5-((benzyloxy)methyl)-3-methylthiolan-2-ol in the form of a colorless oily product.

¹H-NMR (CDCl₃) δ value:

7.37-7.22 (15H, m), 5.29 (1H, d, J=6.0 Hz), 4.75-4.37 (6H, m), 4.02 (1H, d, J=6.3 Hz), 3.94 (1H, dd, J=9.3, 4.8 Hz), 3.80 (1H, m), 3.70 (1H, dd, J=9.3, 8.1 Hz), 1.95 (1H, d, J=6.3 Hz), 1.48 (3H, s).

Example 42

(1)

[Formula 369]

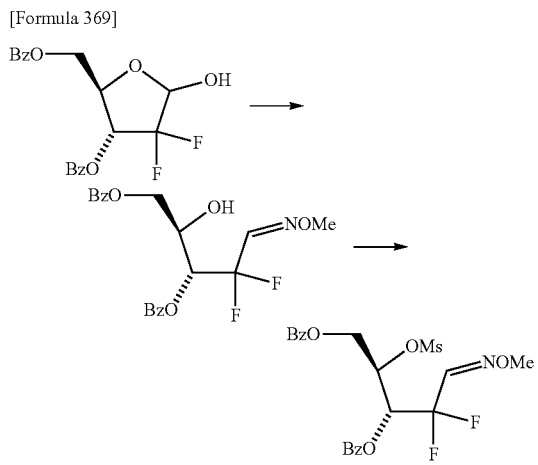

190 mg of (2R,3R)-2-((benzoyloxy)methyl)-4,4-difluoro-5-hydroxyoxolan-3-yl benzoate was dissolved in 4 mL of a mixed solvent of acetonitrile/water (3/1), and thereafter, 83.5 mg of O-methylhydroxylamine hydrochloride and 0.09 mL of triethylamine were added to the obtained solution. The thus obtained mixture was then stirred for 2 hours. Thereafter, 82 mg of pyridinium p-toluenesulfonate was added to the reaction mixture, and the thus obtained mixture was then stirred for 69 hours. Thereafter, a saturated sodium hydrogen carbonate aqueous solution was added to the reaction mixture, and the water layer was then removed. The water layer was extracted with ethyl acetate, and the organic layer was then combined with the extract. The thus obtained mixture was washed with a saturated sodium chloride aqueous solution, and was then dried over anhydrous sodium sulfate. The solvent was distilled away under reduced pressure to obtain a colorless oily product. 0.42 mL of triethylamine was added to a solution of this oily product in 3 mL of tetrahydrofuran, and 0.12 mL of methanesulfonyl chloride was then added to the mixture at 0° C. The obtained mixture was stirred for 30 minutes. Thereafter, a saturated sodium hydrogen carbonate aqueous solution was added to the reaction mixture, and the water layer was then removed. The water layer was extracted with ethyl acetate, and the organic layer was then combined with the extract. The thus obtained mixture was washed with a saturated sodium chloride aqueous solution, and was then dried over anhydrous sodium sulfate. After that, the solvent was distilled away under reduced pressure, so as to obtain 202 mg of (2R,3R,5E)-3-benzoyloxy-4,4-difluoro-2-(methylsulfonyloxy)-5-(methoxyimino)pentyl benzoate in the form of a colorless oily product.

$^1$H-NMR (CDCl$_3$) δ value:

8.10-8.05 (4H, m), 7.67-7.40 (7H, m), 6.17 (1H, ddd, 12.9 Hz, 10.8 Hz, 3.0 Hz), 5.62 (1H, ddd, 8.4 Hz, 3.0 Hz, 2.7 Hz), 4.89 (1H, dd, 12.6 Hz, 2.7 Hz), 4.60 (1H, dd, 12.6 Hz, 8.4 Hz), 3.90 (3H, s), 3.06 (3H, s) ppm.

(2)

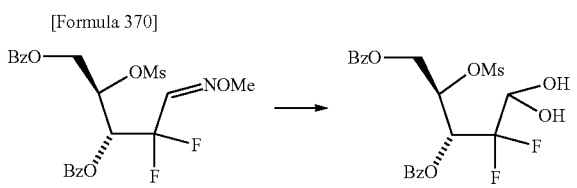

[Formula 370]

1 mol/L hydrochloric acid and a 35% formaldehyde aqueous solution were added to a solution of 202 mg of (2R,3R,5E)-3-benzoyloxy-4,4-difluoro-2-(methylsulfonyloxy)-5-(methoxyimino)pentyl benzoate in 4 mL of acetone, and the obtained mixture was then stirred at room temperature for 72 hours. Thereafter, ethyl acetate and water were added to the reaction mixture, and the water layer was then removed. The solvent was distilled away under reduced pressure, and the obtained residue was then purified by silica gel column chromatography (hexane/ethyl acetate=2/3 to 1/4), so as to obtain 70.5 mg of (3R,4R)-5-benzoyloxy-2,2-difluoro-1,1-dihydroxy-4-(methylsulfonyloxy)pentan-3-yl benzoate in the form of a colorless oily product.

$^1$H-NMR (CDCl$_3$) δ value:

8.08-8.02 (4H, m), 7.64-7.36 (6H, m), 6.19 (1H, ddd, 12.9 Hz, 12.9 Hz, 2.7 Hz), 5.70 (1H, ddd, 8.7 Hz, 2.4 Hz, 2.4 Hz), 5.30 (1H, br), 4.93 (1H, br), 4.92 (1H, dd, 12.6 Hz, 2.4 Hz), 4.59 (1H, dd, 12.6 Hz, 8.7 Hz), 3.10 (1H, br), 3.08 (3H, s) ppm.

(3)

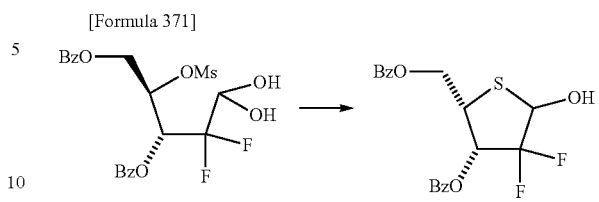

[Formula 371]

17 mg of a sodium hydrogen sulfide n-hydrate was added to a solution of 70.5 mg of (3R,4R)-5-benzoyloxy-2,2-difluoro-1,1-dihydroxy-4-(methylsulfonyloxy)pentan-3-yl benzoate in 1 mL of N,N-dimethylformamide, and the obtained mixture was then stirred at room temperature for 5 minutes. Thereafter, ethyl acetate and water were added to the reaction mixture, and the water layer was then removed. The solvent was distilled away under reduced pressure, and the obtained residue was then purified by silica gel column chromatography (hexane/ethyl acetate=5/1 to 0/1), so as to obtain 26.5 mg of (2R,3R)-2-((benzoyloxy)methyl)-4,4-difluoro-5-hydroxythiolan-3-yl benzoate in the form of a colorless oily product.

$^1$H-NMR (CDCl$_3$) δ value:

8.04 (2H, d, J=7.2 Hz), 7.90 (0.6H, d, J=7.2 Hz), 7.82 (1.4H, d, J=7.2 Hz), 7.27-7.65 (6H, m), 5.98 (1H, m), 5.36-5.54, (1H, m), 4.62 (0.6H, d, J=7.5 Hz), 4.55 (0.7H, dd, J=1.4, 8.1 Hz), 4.44 (0.7 H, d, J=11.4, 6.1 Hz). 4.28 (0.7H, ddd, J=8.1 Hz, 6.1 Hz, 6.6 Hz), 2.80-3.15 (1H, br).

Example 43

(1)

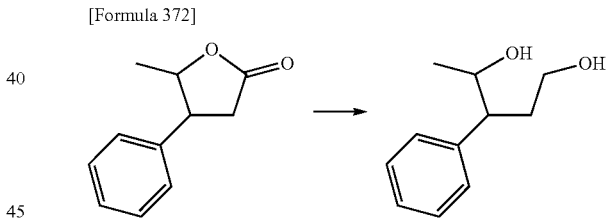

[Formula 372]

0.64 g of sodium tetrahydroborate was added to a solution of 1.2 g of 5-methyl-4-phenyloxolane-2-one in 2 mL of ethanol and 20 mL of tetrahydrofuran in a nitrogen atmosphere at a temperature of 5° C. to 10° C., and thereafter, a solution of 2.0 g of calcium chloride in 8 mL of ethanol was added dropwise to the mixture. The obtained mixture was stirred at room temperature for 200 minutes. Thereafter, 30 mL of ethyl acetate was added to the reaction mixture, and thereafter, 20 mL of 3 mol/L hydrochloric acid was added dropwise to the mixture. The organic layer was fractionated, and it was washed with a saturated sodium hydrogen carbonate aqueous solution and was then dried over anhydrous magnesium sulfate. The solvent was distilled away under reduced pressure, so as to obtain 1.05 g of 3-phenylpentane-1,4-diol in the form of a colorless oily product.

$^1$H-NMR (CDCl$_3$) δ value:

7.35-7.15 (5H, m), 3.95 (1H, dqb, J=6.9 Hz, 6.3H), 3.70-3.61 (1H, m), 3.57-3.46 (1H, m), 2.69 (1H, ddd, J=8.3 Hz, 8.3 Hz, 5.1 Hz), 2.28-2.15 (1H, m), 2.00-1.80 (1H, m), 1.04 (3H, d, J=6.3 Hz).

(2)

[Formula 373]

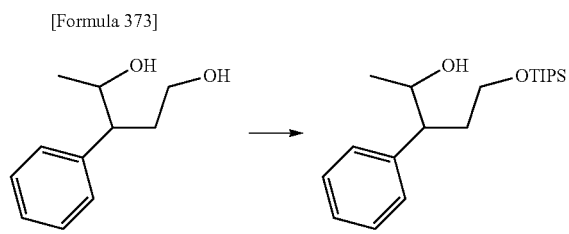

1.25 mL of triisopropylsilyl chloride was added dropwise to a solution of 1.0 g of 3-phenylpentane-1,4-diol and 0.45 g of imidazole in 20 mL of N,N-dimethylformamide in a nitrogen atmosphere at a temperature of 5° C. to 10° C., and the obtained mixture was then stirred at room temperature for 19 hours. Thereafter, ethyl acetate and water were added to the reaction mixture. The organic layer was fractionated, and it was washed with a saturated sodium chloride aqueous solution and was then dried over anhydrous magnesium sulfate. The solvent was distilled away under reduced pressure. The obtained residue was purified by silica gel column chromatography (ethyl acetate/hexane=1/19 to 1/10), so as to obtain 1.2 g of 3-phenyl-5-((tris(propan-2-yl)silyl)oxy)pentan-2-ol in the form of a colorless oily product.

$^1$H-NMR (CDCl$_3$) δ value:

7.33-7.12 (5H, m), 4.00-3.89 (1H, m), 3.76-3.68 (1H, m), 3.63-3.53 (1H, m), 2.81-2.78 (1H, m), 2.75-2.67 (1H, m), 2.20-2.08 (1H, m), 1.99-1.88 (1, m), 1.15-1.00 (24H, m).

(3)

[Formula 374]

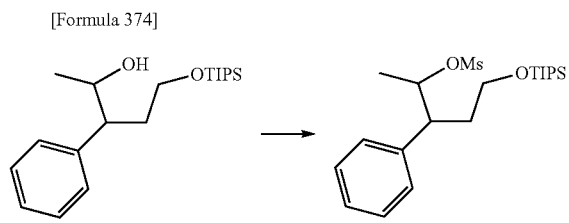

0.46 mL of methanesulfonyl chloride was added dropwise to a solution of 1.0 g of 3-phenyl-5-((tris(propan-2-yl)silyl)oxy)pentan-2-ol and 1.67 mL of triethylamine in 10 mL of an ethyl acetate at a temperature of 5° C. to 10° C., and the obtained mixture was then stirred at room temperature for 5.5 hours. Thereafter, ethyl acetate and water were added to the reaction mixture. The organic layer was fractionated, and it was washed with a saturated sodium chloride aqueous solution and was then dried over anhydrous magnesium sulfate. The solvent was distilled away under reduced pressure, so as to obtain 1.2 g of 3-phenyl-5-((tris(propan-2-yl)silyl)oxy) pentan-2-yl methanesulfonate in the form of a yellow oily product.

$^1$H-NMR (CDCl$_3$) δ value:

7.35-7.15 (5H, m), 4.90 (1H, dq, J=6.3 Hz, 6.8 Hz), 3.66-3.58 (1H, m), 3.46-3.35 (1H, m), 3.10-3.02 (1H, m), 2.85 (3H, s), 2.27-2.14 (1H, m), 1.94-1.81 (1H, m), 1.31 (3H, d, J=6.3 Hz), 1.09-0.95 (21H, m).

(4)

[Formula 375]

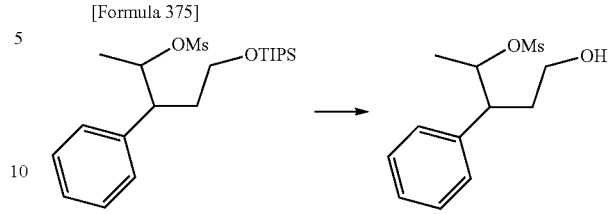

0.24 g of p-toluenesulfonic acid monohydrate was added to a solution of 1.05 g of 3-phenyl-5-((tris(propan-2-yl)silyl)oxy)pentan-2-yl methanesulfonate in 15 mL of methanol, and the obtained mixture was then stirred at room temperature for 1 hour. Thereafter, ethyl acetate and a saturated sodium hydrogen carbonate aqueous solution were added to the reaction mixture. The organic layer was fractionated, and it was successively washed with water and a saturated sodium chloride aqueous solution, and was then dried over anhydrous magnesium sulfate. The solvent was distilled away under reduced pressure, and the obtained residue was then purified by silica gel column chromatography (ethyl acetate/hexane=1/4 to 1/1), so as to obtain 0.56 g of 5-hydroxy-3-phenylpentan-2-yl methanesulfonate in the form of a colorless oily product.

$^1$H-NMR (CDCl$_3$) δ value:

7.38-7.16 (5H, m), 4.92 (1H, dq, J=7.8 Hz, 6.3 Hz), 3.62-3.53 (1H, m), 3.44-3.34 (1H, m), 3.05-2.95 (1H, m), 2.92 (3H, s), 2.29-2.16 (1H, m), 1.99-1.85 (1H, m), 1.28 (3H, d, J=6.3 Hz).

(5)

[Formula 376]

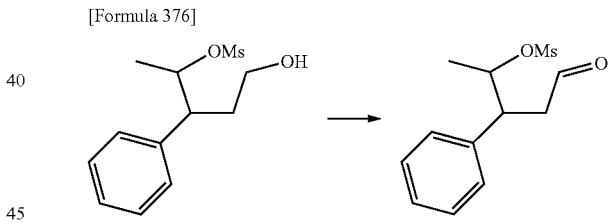

1.2 g of 1,1,1-triacetoxy-1,1-dihydro-1,2-benziodoxol-3 (H)-one (Dess-Martin Periodinane) was added to a solution of 490 mg of 5-hydroxy-3-phenylpentan-2-yl methanesulfonate in 5 mL of dichloromethane, and the obtained mixture was then stirred at room temperature for 2 hours. Thereafter, ethyl acetate and a saturated sodium hydrogen carbonate aqueous solution were added to the reaction mixture. The organic layer was fractionated, and it was successively washed with a sodium thiosulfate aqueous solution and a saturated sodium chloride aqueous solution, and was then dried over anhydrous magnesium sulfate. The solvent was distilled away under reduced pressure, and the obtained residue was then purified by silica gel column chromatography (ethyl acetate/hexane=1/10 to 1/1), so as to obtain 414 mg of 5-oxo-3-phenylpentan-2-yl methanesulfonate in the form of a colorless oily product.

$^1$H-NMR (CDCl$_3$) δ value:

9.69 (1H, m), 7.38-7.18 (5H, m), 4.93-4.85 (1H, m), 3.50-3.43 (1H, m), 3.15-3.04 (1H, m), 2.93-2.80 (4H, m), 1.31 (3H, d, J=4.5 Hz).

(6)

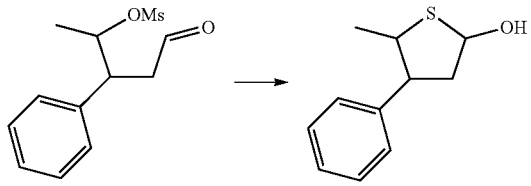

[Formula 377]

240 mg of a sodium hydrogen sulfide n-hydrate was added to a solution of 256 mg of 5-oxo-3-phenylpentan-2-yl methanesulfonate in 3 mL of N,N-dimethylformamide at room temperature, and the obtained mixture was then stirred at room temperature for 2 hours. Thereafter, ethyl acetate and water were added to the reaction mixture. The organic layer was fractionated, and it was washed with a saturated sodium chloride aqueous solution twice and was then dried over anhydrous magnesium sulfate. The solvent was distilled away under reduced pressure, and the obtained residue was then purified by silica gel column chromatography (ethyl acetate/hexane=1/19 to 1/9), so as to obtain 80 mg of 5-methyl-4-phenylthiolan-2-ol in the form of a colorless oily product.

$^1$H-NMR (CDCl$_3$) δ value:
7.38-7.17 (5H, m), 5.82-5.72 (0.17H, m), 5.63-5.58 (0.83H, m), 3.99-3.90 (0.83H, m), 3.82-3.51 (0.83H, m), 3.66-3.47 (0.34H, m), 2.75-2.68 (0.17H, m), 2.56-2.31 (1.83H, m), 1.10 (0.51H, d, J=6.9 Hz), 0.84 (2.49H, d, J=6.9 Hz).

Example 44

(1)

[Formula 378]

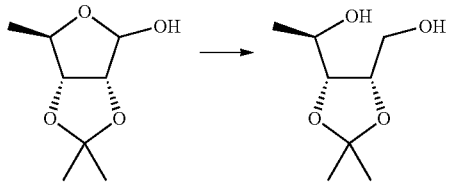

4.0 g of sodium tetrahydroborate was added to a solution of 12.2 g of (3aR,6R,6aR)-2,2,6-trimethyltetrahydro-2H-furo(3,4-d)(1,3)dioxol-4-ol in 10 mL of ethanol and 120 mL of tetrahydrofuran in a nitrogen atmosphere at a temperature of 5° C. to 10° C., and thereafter, a solution of 10.3 g of calcium chloride in 50 mL of ethanol was added dropwise to the mixture. The obtained mixture was stirred at room temperature for 4 hours. Thereafter, 200 mL of ethyl acetate and 300 mL of water were added to the reaction mixture. The organic layer was fractionated, and the water layer was then extracted with 200 mL of ethyl acetate six times. The organic layer was combined with the extract, and the obtained mixture was washed with a saturated sodium chloride aqueous solution and was then dried over anhydrous magnesium sulfate. The solvent was distilled away under reduced pressure, and the obtained residue was then purified by silica gel column chromatography (ethyl acetate/hexane=1/4 to 1/1), so as to obtain 7.4 g of (1R)-1-((4R,5S)-5-(hydroxymethyl)-2,2-dimethyl-1,3-dioxolane-4-yl)ethan-1-ol in the form of a colorless oily product.

$^1$H-NMR (CDCl$_3$) δ value:
4.34-4.27 (1H, m), 4.03-3.71 (4H, m), 2.73-2.62 (2H, m), 1.41 (3H, s), 0.36 (3H, s), 1.33 (3H, d, J=6.0 Hz).

(2)

[Formula 379]

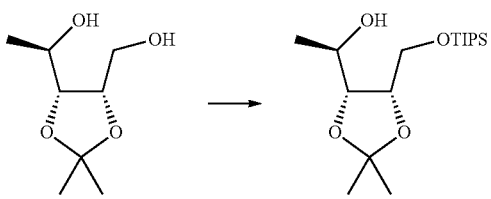

4.46 mL of triisopropylsilyl chloride was added dropwise to a solution of 3.5 g of (1R)-1-((4R,5S)-5-(hydroxymethyl)-2,2-dimethyl-1,3-dioxolane-4-yl)ethan-1-ol and 1.63 g of imidazole in 50 mL of N,N-dimethylformamide in a nitrogen atmosphere at a temperature of 5° C. to 10° C., and the obtained mixture was then stirred at room temperature for 23 hours. Thereafter, ethyl acetate and water were added to the reaction mixture. The organic layer was fractionated, and it was washed with a saturated sodium chloride aqueous solution and was then dried over anhydrous magnesium sulfate. The solvent was distilled away under reduced pressure, so as to obtain 7.1 g of (1R)-1-((4R,5S)-2,2-dimethyl-5-(((tris(propan-2-yl)silyl)oxy)methyl)-1,3-dioxolane-4-yl)ethan-1-ol in the form of a colorless oily product.

$^1$H-NMR (CDCl$_3$) δ value:
4.29 (1H, ddd, J=3.6, 5.1, 10.2 Hz), 4.12 (1H, br), 4.02-3.94 (2H, m), 3.88 (1H, dd, J=10.2, 10.2 Hz), 3.67 (1H, dd, J=3.6, 10.2 Hz), 1.40-1.03 (30H, m).

(3)

[Formula 380]

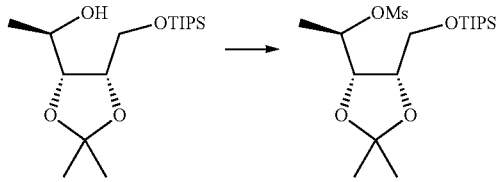

0.75 mL of methanesulfonyl chloride was added dropwise to a solution of 1.6 g of (1R)-1-((4R,5S)-2,2-dimethyl-5-(((tris(propan-2-yl)silyl)oxy)methyl)-1,3-dioxolane-4-yl)ethan-1-ol and 2.7 mL of triethylamine in 16 mL of ethyl acetate at a temperature of 5° C. to 10° C., and the obtained mixture was then stirred at room temperature for 10 minutes. Thereafter, ethyl acetate and water were added to the reaction mixture. The organic layer was fractionated, and it was washed with a saturated sodium chloride aqueous solution and was then dried over anhydrous magnesium sulfate. The solvent was distilled away under reduced pressure, so as to obtain 1.98 g of (1R)-1-((4R,5S)-2,2-dimethyl-5-(((tris(propan-2-yl)silyl)oxy)methyl)-1,3-dioxolane-4-yl)ethyl methanesulfonate in the form of a colorless oily product.

$^1$H-NMR (CDCl$_3$) δ value:
5.17 (1H, dq, J=3.3, 6.6 Hz), 4.35-4.27 (2H, m), 3.94-3.82 (2H, m), 3.02 (3H, s), 1.51 (3H, d, J=6.6 Hz), 1.47 (3H, s), 1.37 (3H, s), 1.17-1.03 (21H, m).

(4)

[Formula 381]

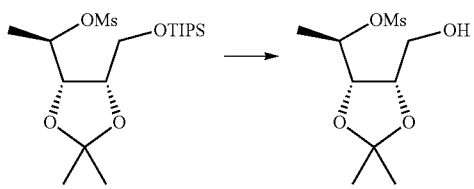

5.8 mL of a 1 mol/L tetrabutyl ammonium fluoride/tetrahydrofuran solution was added to a solution of 1.98 g of (1R)-1-((4R,5S)-2,2-dimethyl-5-(((tris(propan-2-yl)silyl)oxy)methy)-1,3-dioxolane-4-yl)ethyl methanesulfonate in 24 mL of tetrahydrofuran at a temperature of 5° C. to 10° C., and the obtained mixture was then stirred at room temperature for 20 minutes. Thereafter, a saturated ammonium chloride aqueous solution, a saturated sodium hydrogen carbonate aqueous solution and ethyl acetate were added to the reaction mixture. The organic layer was fractionated, and it was washed with a saturated sodium chloride aqueous solution and was then dried over anhydrous magnesium sulfate. The solvent was distilled away under reduced pressure, so as to obtain 1.8 g of (1R)-1-((4S,5S)-5-(hydroxymethyl)-2,2-dimethyl-1,3-dioxolane-4-yl)ethyl methanesulfonate in the form of a colorless oily product.

The obtained oily product contained fluorotris(propan-2-yl)silane. However, the oily product was directly used in the subsequent reaction.

¹H-NMR (CDCl₃) δ value:
4.96 (1H, dq, J=6.3, 6.3 Hz), 4.32 (1H, dt, J=4.5, 6.3 Hz), 4.17-4.11 (1H, m), 3.90-3.79 (2H, m), 3.75 (1H, br), 3.06 (3H, s), 10.53 (3H, d, J=6.3 Hz), 1.47 (3H, s), 1.38 (3H, s).

(5)

[Formula 382]

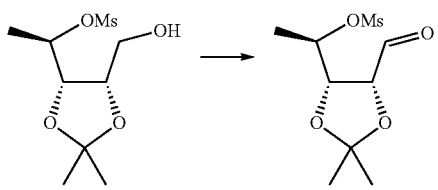

3 g of 1,1,1-triacetoxy-1,1-dihydro-1,2-benziodoxol-3 (1H)-one (Dess-Martin Periodinane) was added to a solution of 1.8 g of (1R)-1-((4S,5S)-5-(hydroxymethyl)-2,2-dimethyl-1,3-dioxolane-4-yl)ethyl methanesulfonate (which contained fluorotris(propan-2-yl)silane) and 1.16 mL of pyridine in 20 mL of dichloromethane at a temperature of 5° C. to 10° C., and the obtained mixture was then stirred at room temperature for 2 hours. Thereafter, ethyl acetate, a saturated sodium hydrogen carbonate aqueous solution and a sodium thiosulfate aqueous solution were added to the reaction mixture. The organic layer was fractionated, and it was successively washed with water and a saturated sodium chloride aqueous solution and was then dried over anhydrous magnesium sulfate. The solvent was distilled away under reduced pressure, so as to obtain 1.7 g of (1R)-1-((4S,5R)-5-formyl-2,2-dimethyl-1,3-dioxolane-4-yl)ethyl methanesulfonate in the form of a yellow oily product.

The obtained oily product contained fluorotris(propan-2-yl)silane. However, the oily product was directly used in the subsequent reaction.

¹H-NMR (CDCl₃) δ value:
9.69 (1H, d, J=3.0 Hz), 4.99 (1H, dq, J=5.1, 6.6 Hz), 4.50-4.39 (2H, m), 3.02 (3H, s), 1.60 (3H, s), 1.50 (3H, d, J=6.6 Hz), 1.42 (3H, s).

(6)

[Formula 383]

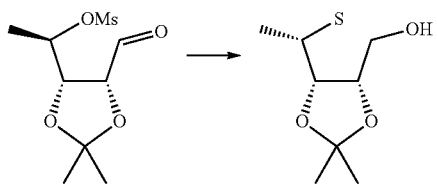

0.38 g of a sodium hydrogen sulfide n-hydrate was added to a solution of 0.85 g of (1R)-1-((4S,5R)-5-formyl-2,2-dimethyl-1,3-dioxolane-4-yl)ethyl methanesulfonate (which contained fluorotris(propan-2-yl)silane) in 8 mL of N,N-dimethylformamide at a temperature of 5° C. to 10° C., and the obtained mixture was then stirred at room temperature for 1.5 hours. Thereafter, ethyl acetate and water were added to the reaction mixture. The organic layer was fractionated, and it was washed with a saturated sodium chloride aqueous solution twice and was then dried over anhydrous magnesium sulfate. The solvent was distilled away under reduced pressure, and the obtained residue was then purified by silica gel column chromatography (ethyl acetate/hexane=1/19 to 1/4), so as to obtain 0.11 g of (3aR,6S,6aS)-2,2,6-trimethyltetrahydro-2H-thieno(3,4-d)(1,3)dioxol-4-ol in the form of a white solid.

¹H-NMR (CDCl₃) δ value:
5.21 (1H, s), 4.77-4.70 (2H, m), 3.82 (1H, dq, J=3.3, 6.9 Hz), 1.76 (1H, br), 1.49 (3H, s), 1.38 (3H, d, J=6.9 Hz), 1.33 (3H, s).

Example 45

(1)

[Formula 384]

4.1 mL of a 1.5 mol/L diisobutylaluminum hydride/toluene solution was added dropwise to a solution of 1.0 g of 5-phenyloxolane-2-one in 12 mL of toluene at −60° C., and the obtained mixture was then stirred for 30 minutes. Thereafter, 1 mL of methanol was added to the reaction mixture, and thereafter, 40 mL of a 20% potassium sodium tartrate aqueous solution was then added to the mixture at room temperature. The thus obtained mixture was stirred for 1 hour. Thereafter, the water layer was removed, and the solvent was then distilled away under reduced pressure, so as to obtain 0.98 g of 5-phenyloxolan-2-ol in the form of a colorless oily product.

As a result of the measurement of $^1$H-NMR, it was found that the obtained oily product was a mixture of isomer A and isomer B, and that the ratio of A:B=56:54.

$^1$H-NMR (CDCl$_3$) δ value:

7.46-7.23 (5H+5H, m, A+B), 5.77-5.75 (1H, m, A), 5.64-5.62 (1H, m, B), 5.25 (1H, t, J=6.9 Hz, A), 5.04-4.98 (1H, m, B), 2.98-2.92 (1H, m, B), 2.90-2.83 (1H, m, B), 2.59-2.42 (1H, m, A), 2.36-2.02 (1H+4H, m, A+B), 2.21-1.91 (1H, m, A), 1.86-1.75 (1H, m, A).

(2)

[Formula 385]

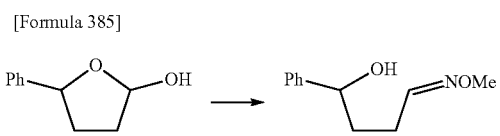

12 mL of acetonitrile, 6 mL of water and 1.0 g of O-methylhydroxylamine hydrochloride were added to 0.98 g of the 5-phenyloxolan-2-ol, and thereafter, 1.08 mL of triethylamine was added dropwise to the mixture. The thus obtained mixture was stirred at room temperature for 0.5 hours. Thereafter, hexane, ethyl acetate and water were added to the reaction mixture, and the water layer was then removed. The organic layer was dried over anhydrous sodium sulfate. After that, the solvent was distilled away under reduced pressure, so as to obtain 1.10 g of 4-(methoxyimino)-1-phenylbutan-1-ol in the form of a colorless oily product.

As a result of the measurement of $^1$H-NMR, it was found that the obtained oily product was a mixture of isomer A and isomer B, and that the ratio of A:B=60:40.

$^1$H-NMR (CDCl$_3$) δ value:

7.41 (1H, t, J=5.9 Hz, A), 7.38-7.25 (5H+5H, m, A+B), 6.68 (1H, t, J=5.7 Hz, A), 4.77-4.71 (1H, m, A), 4.70-4.64 (1H, m, B), 3.87 (3H, s, B), 3.81 (3H, s, A), 2.54-2.25 (2H+2H, m, A+B), 2.20 (1H, d, J=3.6 Hz, A), 2.17 (1H, d, J=3.6 Hz, B), 2.06-1.80 (2H+2H, m, A+B).

(3)

[Formula 386]

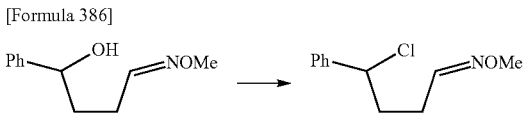

0.24 mL of N-methylimidazole was added to a solution of 0.39 g of 4-(methoxyimino)-1-phenylbutan-1-ol in 4 mL of acetonitrile. Thereafter, 0.19 mL of methanesulfonyl chloride was added to the mixture at a temperature of 0° C. to 10° C., and the thus obtained mixture was then stirred at a temperature of 5° C. or lower for 1.5 hours. Thereafter, 0.24 mL of methanesulfonyl chloride was added to the reaction mixture, ethyl acetate and water were then added thereto, and the water layer was then removed. The organic layer was washed with a saturated sodium chloride aqueous solution, and was then dried over anhydrous sodium sulfate. After that, the solvent was distilled away under reduced pressure. The obtained product was purified by silica gel column chromatography (hexane/ethyl acetate=90/10 to 59/41), so as to obtain 0.07 g of (4-chloro-4-phenylbutylidene)(methoxy)amine in the form of a light yellow oily product.

As a result of the measurement of $^1$H-NMR, it was found that the obtained oily product was a mixture of isomer A and isomer B, and that the ratio of A:B=58:42.

$^1$H-NMR (CDCl$_3$) δ value:

7.41-7.30 (6H+5H, m, A+B), 6.63 (1H, t, J=5.4 Hz, B), 4.92 (1H, t, J=6.8 Hz, A), 4.84 (1H, dd, J=6.2, 8.0 Hz, B), 3.86 (3H, s, B), 3.82 (3H, s, A), 2.53-2.20 (4H+4H, m, A+B).

(4)

[Formula 387]

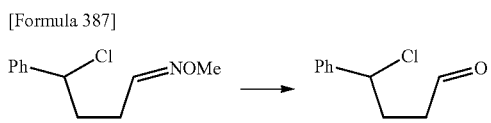

0.1 mL of 2 mol/L hydrochloric acid was added to a mixture of 82 mg of (4-chloro-4-phenylbutylidene)(methoxy)amine, 0.32 mL of a 36% formalin aqueous solution and 4 mL of acetone, and the obtained mixture was then stirred at room temperature for 0.5 hours. Thereafter, hexane and water were added to the reaction mixture, and the water layer was then removed. The solvent was distilled away under reduced pressure, so as to obtain 61 mg of 4-chloro-4-phenylbutanal in the form of a colorless oily product.

$^1$H-NMR (CDCl$_3$) δ value:

9.78 (1H, t, J=0.9 Hz), 7.41-7.28 (5H, m), 4.94 (1H, dd, J=6.6, 7.5 Hz), 2.66 (2H, t, J=6.9 Hz), 2.39 (2H, dd, J=6.6, 7.4 Hz), 3.86 (3H, s, B), 3.82 (3H, s, A), 2.53-2.20 (4H+4H, m, A+B).

(5)

[Formula 388]

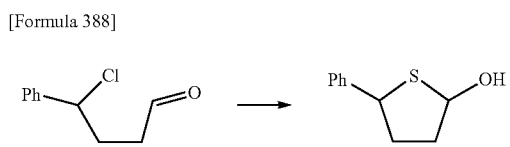 [SMILES: O=CCCC(Cl)c1ccccc1 ; OC1CCC(c2ccccc2)S1]

32 mg of anhydrous sodium hydrogen sulfide was added to a solution of 61 mg of 4-chloro-4-phenylbutanal in 1 mL of N,N-dimethylformamide at a temperature of 0° C. to 10° ° C. and the obtained mixture was then stirred at the same temperature as described above for 1 hour. Thereafter, ethyl acetate and water were added to the reaction mixture, and the water layer was then removed. The organic layer was washed with water, and was then dried over anhydrous sodium sulfate. After that, the solvent was distilled away under reduced pressure. The obtained residue was purified by silica gel column chromatography (hexane/ethyl acetate=85/15 to 60/40), so as to obtain 37 mg of 5-phenylthiolan-2-ol in the form of a colorless oily product.

As a result of the measurement of $^1$H-NMR, it was found that the obtained oily product was a mixture of isomer A and isomer B, and that the ratio of A:B=68:32.

$^1$H-NMR (CDCl$_3$) δ value:

7.45 (2H, brd, J=7.8 Hz, A), 7.39-7.20 (3H+5H, m, A+B), 5.80 (1H, m, B), 5.64 (1H, t, J=4.2 Hz, A), 4.80 (1H, dd, J=5.0, 7.1 Hz, B), 4.56 (1H, dd, J=6.1, 10.5 Hz, A), 2.65-2.00 (4H+4H, m, A+B)

Example 46

[Formula 389]

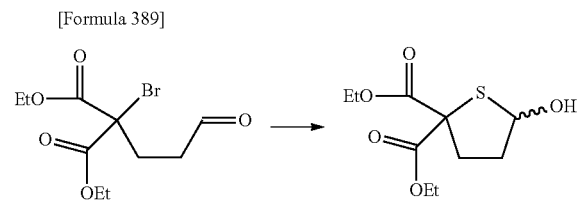

80 mg of a sodium hydrogen sulfide x-hydrate was added to a solution of 295 mg of diethyl 2-bromo-2-(3-oxopropyl) malonate in 3 mL of N,N-dimethylformamide at a temperature of 0° C. to 10° C., and the obtained mixture was then stirred at the same temperature as described above for 15 minutes, and then at room temperature for 15 minutes. Thereafter, 10 mL of ethyl acetate and 10 mL of water were added to the reaction mixture. The organic layer was fractionated. The obtained organic layer was successively washed with 10 mL of 1 mol/L hydrochloric acid, 10 mL of a saturated sodium hydrogen carbonate aqueous solution and 10 mL of a saturated sodium chloride aqueous solution, and it was then dried over anhydrous sodium sulfate. The solvent was distilled away under reduced pressure, and the obtained residue was then purified by silica gel column chromatography (ethyl acetate/hexane=5/1), so as to obtain 29 mg of diethyl 5-hydroxydihydrothiophene-2,2(3H)-dicarboxylate in the form of a colorless oily product.

$^1$H-NMR (CDCl$_3$) δ value:
1.23-1.31 (6H, m), 2.30 (2H, m), 2.58 (1H, m), 2.67 (1H, d, J=6.9 Hz), 2.77 (1H, m), 4.15-4.30 (4H, m), 5.62 (1H, dt, J=6.9 Hz, 3.3 Hz).

Example 47

(1)

[Formula 390]

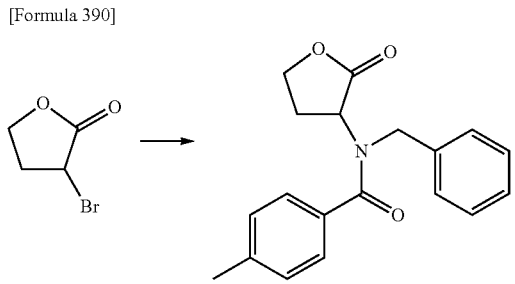

A mixture of 10 g of 3-bromo-2-oxooxolane, 6.6 g of benzylamine, 21 g of potassium carbonate and 200 mL of acetonitrile was stirred at 70° C. for 1 hour 30 minutes. Thereafter, 7.9 mL of 4-methylbenzoyl chloride was added dropwise to the reaction mixture at a temperature of 5° C. to 10° C., and the obtained mixture was then stirred at room temperature for 2 hours. Thereafter, 400 mL of ethyl acetate and 200 mL of water were added to the reaction mixture. The organic layer was fractionated. The obtained organic layer was successively washed with 100 mL of water and 100 mL of a saturated sodium chloride aqueous solution, and it was then dried over anhydrous sodium sulfate. The solvent was distilled away under reduced pressure, and the obtained residue was then dissolved in 100 mL of ethyl acetate under heating. After that, 100 mL of hexane was added dropwise to the reaction mixture at 50° C. A solid was collected by filtration, so as to obtain 11.2 g of N-benzyl-4-methyl-N-(2-oxooxolan-3-yl)benzamide.

$^1$H-NMR (CDCl$_3$) δ value:
7.47-7.15 (9H, m), 4.85-4.50 (3H, m), 4.27-4.14 (1H, m), 4.06-3.89 (1H, m), 2.71-2.50 (1H, m), 2.34 (3H, s), 2.36-2.20 (1H, m)

(2)

[Formula 391]

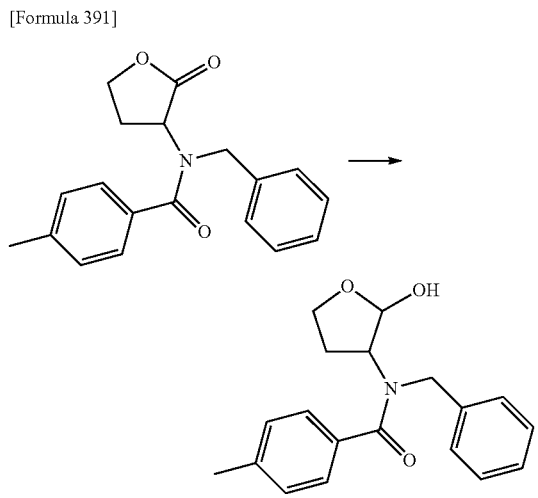

4.4 mL of a 1.5 mol/L diisobutylaluminum hydride/toluene solution was added dropwise to a solution of 2.0 g of N-benzyl-4-methyl-N-(2-oxooxolan-3-yl)benzamide in 30 mL of toluene and 10 mL of methylene chloride at −60° C., and the obtained mixture was then stirred for 30 minutes. Thereafter, the reaction mixture was heated to 15° C., and 6.6 mL of a 1.5 mol/L diisobutylaluminum hydride/toluene solution was added dropwise to the mixture at −60° C. The obtained mixture was stirred for 25 minutes. Thereafter, 1 mL of methanol was added to the reaction mixture, and 80 mL of a 20% potassium sodium tartrate aqueous solution was then added thereto at room temperature. The water layer was removed, and the solvent was then distilled away under reduced pressure. The obtained residue was purified by silica gel column chromatography (hexane/ethyl acetate=−60/40 to 35/65), so as to obtain 0.89 g of N-benzyl-N-(2-hydroxyoxolan-3-yl)benzamide in the form of a colorless oily product.

As a result of the measurement of $^1$H-NMR, it was found that the obtained oily product was a mixture of isomer A and isomer B, and that the ratio of A:B=61:39.

$^1$H-NMR (CDCl$_3$) δ value:
7.40-7.10 (9H+9H, m, A+B), 5.47 (1H, brs, A), 5.24 (1H, dd, J=5.1, 7.8 Hz, B), 4.90-4.48 (2H+2H, m, A+B), 4.25-3.50 (3H+3H, m, A+B), 2.35 (3H, s, A), 2.32 (3H, s, B), 2.22-1.92 (2H+2H, m, A+B).

(3)

[Formula 392]

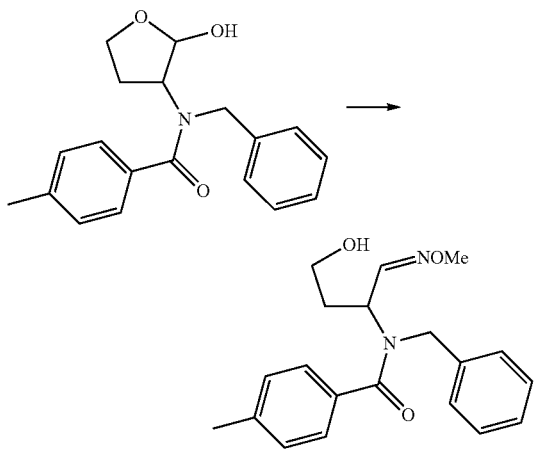

1.2 mL of acetonitrile, 0.6 mL of water and 0.1 g of O-methylhydroxylamine hydrochloride were added to 0.2 g of N-benzyl-N-(2-hydroxyoxolan-3-yl)benzamide, and the obtained mixture was then stirred at room temperature for 0.5 hours. The reaction mixture was then left at rest for 11 hours. Thereafter, hexane, ethyl acetate and water were added to the reaction mixture, and the water layer was then removed. The organic layer was successively washed with water and a saturated sodium chloride aqueous solution, and was then dried over anhydrous sodium sulfate. After that, the solvent was distilled away under reduced pressure. The obtained residue was purified by silica gel column chromatography (hexane/ethyl acetate=60/40 to 30/70), so as to obtain 99 mg of N-benzyl-N-(4-hydroxy-1-(methoxyimino)butan-2-yl)-4-methylbenzamide in the form of a colorless oily product.

As a result of the measurement of $^1$H-NMR, it was found that the obtained oily product was a mixture of isomer A and isomer B, and that the ratio of A:B=80:20.

$^1$H-NMR (CDCl$_3$) δ value:

7.38-7.15 (10H+10H, m, A+B), 5.14 (1H, q, J=7.2 Hz, B), 4.86 (1H, q, J=6.3 Hz, A), 4.70-4.50 (2H+2H, m, A+B), 3.85 (3H, s, B), 3.79 (3H, s, A), 3.58 (2H+2H, brs, A+B), 3.36 (3H, s, B), 3.35 (3H, s, A), 2.22-1.88 (2H+2H, m, A+B).

(4)

[Formula 393]

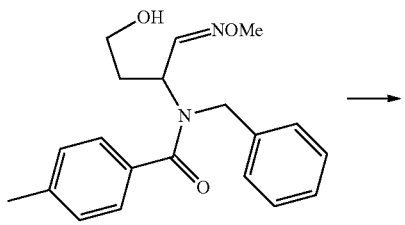

-continued

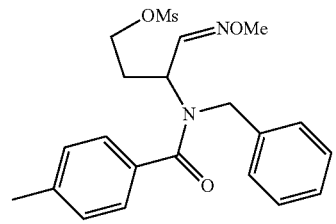

0.083 mL of triethylamine was added to a solution of 99 mg of N-benzyl-N-(4-hydroxy-1-(methoxyimino)butan-2-yl)-4-methylbenzamide in 3 mL of tetrahydrofuran, and thereafter, 0.028 mL of methanesulfonyl chloride was added to the mixture at a temperature of 0° C. to 10° C. The obtained mixture was stirred at a temperature of 5° C. or lower for 105 minutes. Thereafter, 0.028 mL of methanesulfonyl chloride was added to the reaction mixture. After that, ethyl acetate and water were added to the mixture, and the water layer was then removed. The organic layer was successively washed with water and a saturated sodium chloride aqueous solution, and the solvent was then distilled away under reduced pressure, so as to obtain 3-(N-benzyl-1-(4-methylphenyl)formamide)-4-(methoxyimino)butyl methanesulfonate.

As a result of the measurement of $^1$H-NMR, signals of methanesulfonate were observed at 2.90 ppm and 2.93 ppm.

(5)

[Formula 394]

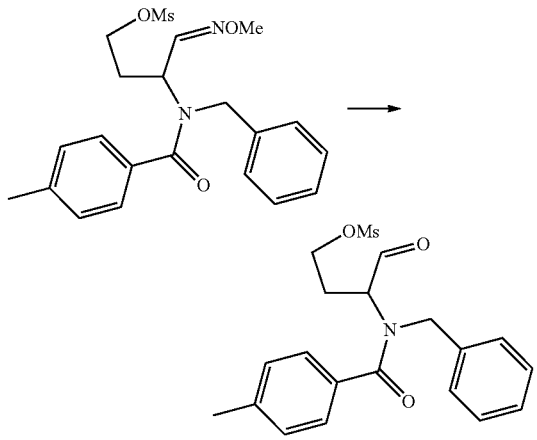

0.05 mL of 2 mol/L hydrochloric acid was added to a mixture of the obtained 3-(N-benzyl-1-(4-methylphenyl)formamide)-4-(methoxyimino)butyl methanesulfonate, 0.23 mL of a 36% formalin aqueous solution and 3 mL of acetone, and the obtained mixture was then stirred at room temperature for 75 minutes. Thereafter, hexane, ethyl acetate and water were added to the reaction mixture, and the water layer was then removed. The organic layer was washed with a saturated sodium chloride aqueous solution, and was then dried over anhydrous sodium sulfate. After that, the solvent was distilled away under reduced pressure, so as to obtain 3-(N-benzyl-1-(4-methylphenyl)formamide)-4-oxobutyl methanesulfonate.

As a result of the measurement of $^1$H-NMR, a signal of aldehyde was observed at 9.42 ppm.

(6)

[Formula 395]

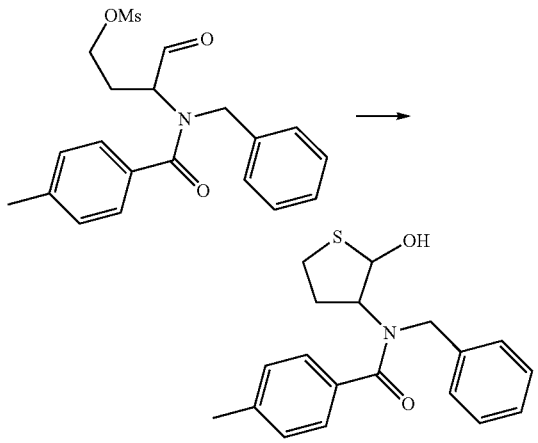

29 mg of anhydrous sodium hydrogen sulfide was added to a solution of 3-(N-benzyl-1-(4-methylphenyl)formamide)-4-oxobutyl methanesulfonate in 3 mL of N,N-dimethylformamide at a temperature of 0° C. to 10° C., and the obtained mixture was then stirred at the same temperature as described above for 1 hour. Thereafter, ethyl acetate and water were added to the reaction mixture, and the water layer was then removed. The organic layer was washed with water, and was then dried over anhydrous sodium sulfate. After that, the solvent was distilled away under reduced pressure. The obtained residue was purified by silica gel column chromatography (hexane/ethyl acetate=70/30 to 50/50), so as to obtain 46 mg of N-benzyl-N-(2-hydroxythiolan-3-yl)-4-methylbenzamide in the form of a colorless oily product.

As a result of the measurement of $^1$H-NMR, it was found that the obtained oily product was a mixture of isomer A and isomer B, and that the ratio of A:B=57:43.

$^1$H-NMR (CDCl$_3$) δ value:
7.40-7.14 (9H+9H, m, A+B), 5.56 (1H, brs, B), 5.42 (1H, brs, A), 4.95-4.80 (1H, m, B), 4.80-4.54 (2H+2H, m, A+B), 4.16-4.07 (1H, m, A), 3.10-2.95 (1H+1H, m, A+B), 2.77-2.64 (1H, m, A), 2.36 (3H, s, B), 2.34 (3H, s, A), 2.28-2.04 (2H+2H, m, A+B).

Example 48

(1)

[Formula 396]

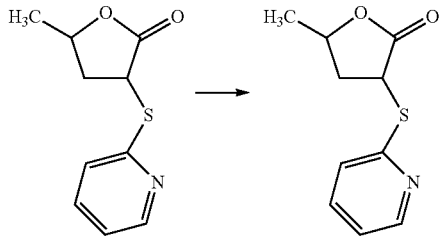

16.4 mL of a 1.5 mol/L diisobutylaluminum hydride/toluene solution was added dropwise to a solution of 4.3 g of 5-methyl-3-(pyridin-2-ylsulfanyl)oxolane-2-one in 100 mL of tetrahydrofuran at −78° C., and the obtained mixture was then stirred for 7.5 hours. Thereafter, 15 mL of methanol was added to the reaction mixture, and 100 mL of a saturated potassium sodium tartrate aqueous solution was then added to the mixture at room temperature. The thus obtained mixture was stirred for 30 minutes, and the water layer was then removed. The water layer was extracted with 100 mL of ethyl acetate. The organic layer was combined with the extract, and the obtained mixture was then washed with a saturated sodium chloride aqueous solution and was then dried over anhydrous magnesium sulfate. After that, the solvent was distilled away under reduced pressure. The obtained residue was purified by silica gel column chromatography (hexane/ethyl acetate=4/1), so as to obtain 2.8 g of 5-methyl-3-(pyridin-2-ylsulfanyl)oxolan-2-ol in the form of a colorless oily product.

$^1$H-NMR (CDCl$_3$) δ value:
8.36-8.43 (1H, m), 7.47-7.57 (1H, m), 7.20-7.32 (1H, m), 6.99-7.09 (1H, m), 5.61 (0.18H, t, J=5.1 Hz), 5.43-5.55 (0.73H, m), 5.35 (0.28H, s), 5.16 (0.27H, d, J=2.1 Hz), 5.04 (0.39H, s), 4.86 (0.15H, d, J=5.7 Hz), 4.31-4.58 (1H, m), 4.01-4.28 (1H, m), 2.49-2.60 (0.40H, m), 2.37-2.47 (0.16H, m), 1.74-2.27 (1.02H, m), 1.49-1.62 (0.42H, m), 1.23-1.42 (3H, m)

(2)

[Formula 397]

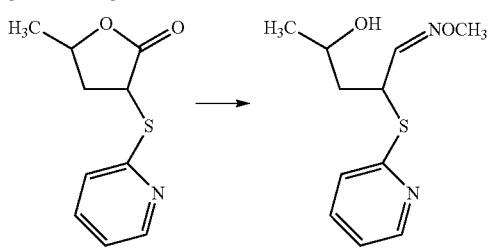

8.0 mL of methanol and 712 mg of O-methylhydroxylamine hydrochloride were added to 1.5 g of 5-methyl-3-(pyridin-2-ylsulfanyl)oxolan-2-ol, and thereafter, 1.1 mL of triethylamine was added dropwise to the mixture. The thus obtained mixture was stirred at room temperature for 2 hours. Thereafter, the solvent was distilled away under reduced pressure, 50 mL of ethyl acetate and 50 mL of water were then added to the residue, and the water layer was then removed. The organic layer was washed with a saturated sodium chloride aqueous solution, and was then dried over anhydrous magnesium sulfate. After that, the solvent was distilled away under reduced pressure. The obtained residue was purified by silica gel column chromatography (hexane/acetone=4/1), so as to obtain 1.74 g of 5-(methoxyimino)-4-(pyridin-2-ylsulfanyl)pentan-2-ol in the form of a colorless oily product.

$^1$H-NMR (CDCl$_3$) δ value:
8.37-8.45 (1H, m), 7.48-7.58 (1.76H, m), 7.14-7.30 (1H, m), 6.99-7.10 (1H, m), 6.76-6.82 (0.24H, m), 5.06-5.19 (0.88H, m), 4.69-4.79 (0.79H, m), 3.97-4.12 (1H, m), 3.82-3.87 (3H, m), 2.91-3.05 (0.33H, m), 1.76-2.22 (2H, m), 1.21-1.29 (3H, m)

(3)

[Formula 398]

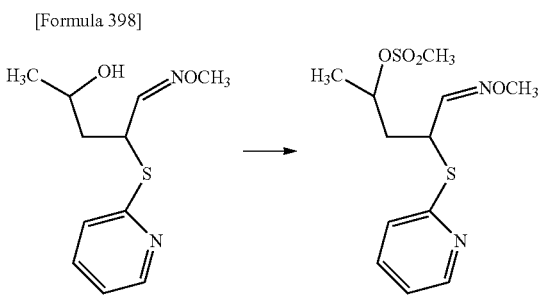

1.2 mL of triethylamine was added to a solution of 1.7 g of 5-(methoxyimino)-4-(pyridin-2-ylsulfanyl)pentan-2-ol in 7.0 mL of tetrahydrofuran, and thereafter, 602 µL of methanesulfonyl chloride was added to the mixture at a temperature of 0° C. to 10° C. The thus obtained mixture was stirred at a temperature of 15° C. or lower for 1.5 hours. Thereafter, 50 mL of ethyl acetate and 50 mL of water were added to the reaction mixture, and the water layer was then removed. The organic layer was washed with a saturated sodium chloride aqueous solution, and was then dried over anhydrous magnesium sulfate. After that, the solvent was distilled away under reduced pressure, so as to obtain 2.12 g of 5-(methoxyimino)-4-(pyridin-2-ylsulfanyl)pentan-2-yl methanesulfonate in the form of a brown oily product.

$^1$H-NMR (CDCl$_3$) δ value:
8.39-8.45 (1H, m), 7.47-7.57 (1.8H, m), 7.16-7.23 (1H, m), 7.00-7.07 (1H, m), 6.89 (0.2H, d, J=7.5 Hz), 4.95-5.16 (1H, m), 4.67-4.78 (1H, m), 3.79-3.91 (3H, m), 3.07 (0.87H, s), 3.01-3.04 (0.59H, m), 2.97 (1.54H, s), 2.39-2.51 (0.54H, m), 2.05-2.35 (0.46H, m), 1.48-1.55 (3H, m)

(4)

[Formula 399]

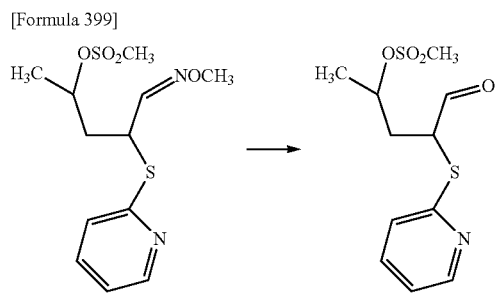

14 mL of 2 mol/L hydrochloric acid was added to a mixture of 2.1 g of 5-(methoxyimino)-4-(pyridin-2-ylsulfanyl)pentan-2-yl methanesulfonate, 4.7 mL of a 36% formalin aqueous solution and 60 mL of acetone, and the obtained mixture was stirred at room temperature for 2 hours, and then at 50° C. for 3 hours. Thereafter, the solvent was distilled away under reduced pressure, 100 mL of ethyl acetate and 100 mL of water were then added to the residue, and the water layer was then removed. The organic layer was washed with a saturated sodium chloride aqueous solution, and was then dried over anhydrous magnesium sulfate. After that, the solvent was distilled away under reduced pressure. The obtained residue was purified by silica gel column chromatography (hexane/acetone=3/1), so as to obtain 0.90 g of 5-oxo-4-(pyridin-2-ylsulfanyl)pentan-2-yl methanesulfonate in the form of a colorless oily product.

(5)

[Formula 400]

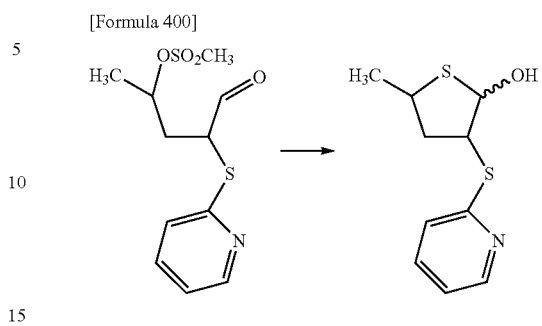

0.74 g of sodium hydrogen sulfide (Wako Pure Chemical Industries, Ltd.) was added to a solution of 0.60 mg of 5-oxo-4-(pyridin-2-ylsulfanyl)pentan-2-yl methanesulfonate in 10 mL of N,N-dimethylformamide at a temperature of 0° C. to 10° C., and the obtained mixture was then stirred at the same temperature as described above for 1.5 hours. Thereafter, 30 mL of ethyl acetate and 30 mL of a saturated sodium hydrogen carbonate aqueous solution were added to the reaction mixture, and the water layer was then removed. The organic layer was successively washed with 30 mL of water and a saturated sodium chloride aqueous solution, and was then dried over anhydrous magnesium sulfate. After that, the solvent was distilled away under reduced pressure. The obtained residue was purified by column chromatography (hexane/ethyl acetate=5/1), so as to obtain 120 mg of 5-methyl-3-(pyridin-2-ylsulfanyl)thiolan-2-ol in the form of a light yellow oily product.

$^1$H-NMR (CDCl$_3$) δ value:
8.33-8.43 (1H, m), 7.48-7.58 (1H, m), 7.20-7.34 (1H, m), 6.99-7.09 (1H, m), 5.62-5.70 (0.37H, m), 5.50-5.59 (0.63H, m), 4.41-4.53 (0.36H, m), 4.22-4.30 (0.24H, m), 4.14-4.21 (0.20H, m), 3.85-3.94 (0.20H, m), 3.54-3.80 (1H, m), 2.45-2.68 (0.80H, m), 2.33-2.42 (0.31H, m), 2.22-2.30 (0.28H, m), 1.99-2.11 (0.42H, m), 1.77-1.88 (0.19H, m), 1.50 (0.97H, d, J=6.8 Hz), 1.44 (0.89H, d, J=6.4 Hz), 1.33-1.40 (1.14H, m)

INDUSTRIAL APPLICABILITY

The compound of the present invention is useful as an intermediate for producing a thionucleoside, and the production method of the present invention is useful as a method for producing a thionucleoside.

The invention claimed is:
1. A production method of 1-(2-deoxy-2-halogeno-4-thio-β-D-arabinofuranosyl)cytosine represented by the following formula [14]:

[14]

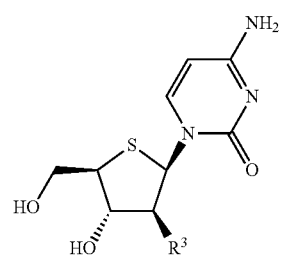

(wherein R$^3$ has the same meanings as those described below) which comprises obtaining a compound represented by the following formula [1e] by a production method of a compound represented by the following formula [1e]:

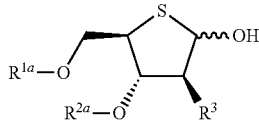
[1e]

(wherein $R^{1a}$, $R^{2a}$ and $R^3$ have the same meanings as those described below)

which comprises allowing a compound represented by the following formula [1d]:

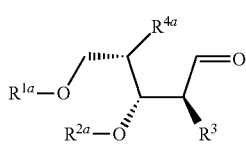
[1d]

wherein $R^{1a}$ represents a hydroxyl-protecting group; $R^{2a}$ represents a hydroxyl-protecting group; or $R^{1a}$ and $R^{2a}$ may together form an optionally substituted $C_{1-3}$ alkylene group; $R^3$ represents a halogen atom; and $R^{4a}$ represents a halogen atom, to react with a hydrogen sulfide or a salt thereof;

then allowing the compound represented by the formula [1e] to react with a compound represented by the following formula [7]:

[7]

(wherein $R^9$ represents an optionally substituted acyl group, an optionally substituted $C_{1-6}$alkylsulfonyl group or an optionally substituted arylsulfonyl group; and $X^2$ represents a halogen atom), or with a compound represented by the following formula [8]:

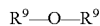
[8]

(wherein $R^9$ has the same meanings as those described above), to obtain a compound represented by the following formula [9]:

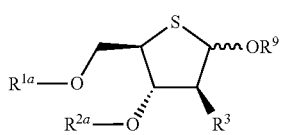
[9]

(wherein $R^{1a}$, $R^{2a}$, $R^3$ and $R^9$ have the same meanings as those described above), then subjecting the compound represented by the formula [9] to any one of the following methods (1) to (4):

"(1) a method of allowing the compound represented by the formula [9] to react with protected cytosine or protected $N^4$-acylcytosine to obtain a compound represented by the following formula [11]:

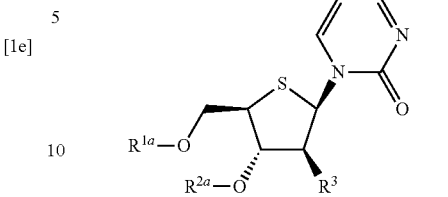
[11]

(wherein $R^{10}$ represents a hydrogen atom or an optionally substituted acyl group; and $R^{1a}$, $R^{2a}$ and $R^3$ have the same meanings as those described above), and then deprotecting the compound represented by the formula [11], (2) a method of allowing the compound represented by the formula [9] to react with protected cytosine to obtain a compound represented by the following formula [11a]:

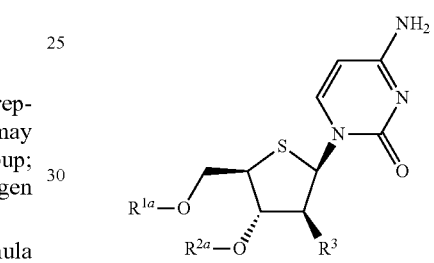
[11a]

(wherein $R^{1a}$, $R^{2a}$ and $R^3$ have the same meanings as those described above), then allowing the compound represented by the formula [11a] to react with a compound represented by the following formula [12]:

[12]

(wherein $R^{10a}$ represents an optionally substituted acyl group; and $X^4$ represents a halogen atom), or with a compound represented by the following formula [13]:

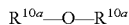
[13]

(wherein $R^{10a}$ has the same meanings as those described above), to obtain a compound represented by the following formula [11b]:

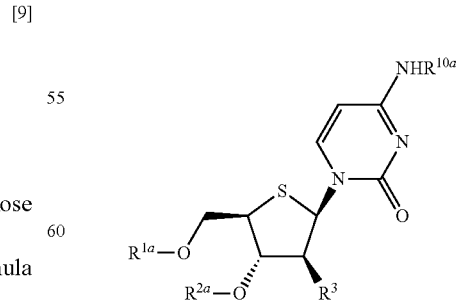
[11b]

(wherein $R^{1a}$, $R^{2a}$, $R^3$ and $R^{10a}$ have the same meanings as those described above), and then deprotecting the compound represented by the formula [11b], (3) a method of halogenating the compound represented by the formula [9] to obtain a compound represented by the following formula [10]:

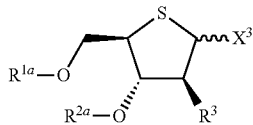

[10]

(wherein $X^3$ represents a halogen atom; and $R^{1a}$, $R^{2a}$ and $R^3$ have the same meanings as those described above), then allowing the compound represented by the formula [10] to react with protected cytosine or protected $N^4$-acylcytosine to obtain a compound represented by the following formula [11]:

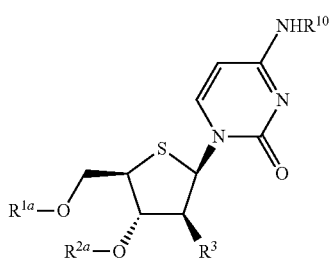

[11]

(wherein $R^{1a}$, $R^{2a}$, $R^3$ and $R^{10}$ have the same meanings as those described above), and then deprotecting the compound represented by the formula [11], and (4) a method of halogenating the compound represented by the formula [9] to obtain a compound represented by the following formula [10]:

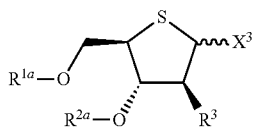

[10]

(wherein $R^{1a}$, $R^{2a}$, $R^3$ and $X^3$ have the same meanings as those described above), then allowing the compound represented by the formula [10] to react with protected cytosine to obtain a compound represented by the following formula [11a]:

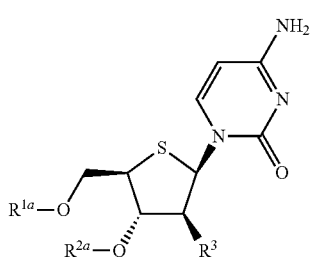

[11a]

(wherein $R^{1a}$, $R^{2a}$ and $R^3$ have the same meanings as those described above), then allowing the compound represented by the formula [11a] to react with a compound represented by the following formula [12]:

$$R^{10a}X^4 \quad [12]$$

(wherein $R^{10a}$ and $X^4$ have the same meanings as those described above)), or with a compound represented by the following formula [13]:

$$R^{10a}-O-R^{10a} \quad [13]$$

(wherein $R^{10a}$ has the same meanings as those described above), to obtain a compound represented by the following formula [11b]:

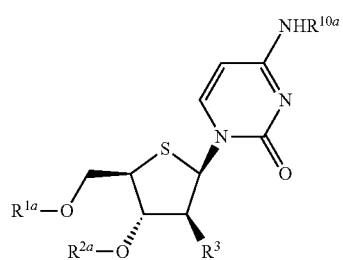

[11b]

wherein $R^{1a}$, $R^{2a}$, $R^3$ and $R^{10a}$ have the same meanings as those described above), and then deprotecting the compound represented by the formula [11b]".

2. A production method of 1-(2-deoxy-2-halogeno-4-thio-β-D-arabinofuranosyl)cytosine represented by the following formula [14]:

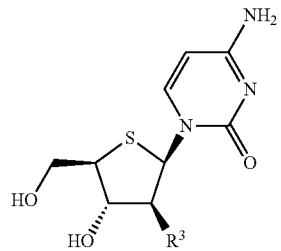

[14]

(wherein $R^3$ has the same meanings as those described below) which comprises allowing a compound represented by the following formula [4]:

[4]

(wherein $R^{1a}$ represents a hydroxyl-protecting group; $R^{2a}$ represents a hydroxyl-protecting group; or $R^{1a}$ and $R^{2a}$ may together form an optionally substituted $C_{1-3}$ alkylene group; and $R^3$ represents a halogen atom), to react with a compound represented by the following formula [5]:

   [5]

(wherein $R^7$ represents a hydrogen atom, an optionally substituted $C_{1-6}$ alkyl group, an optionally substituted aryl group, an optionally substituted heterocyclic group or an optionally substituted silyl group), or a salt thereof, to obtain a compound represented by the following formula [1a]:

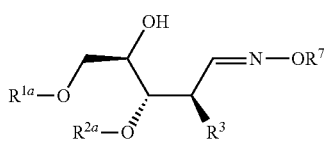   [1a]

(wherein $R^{1a}$, $R^{2a}$, $R^3$ and $R^7$ have the same meanings as those described above),
then subjecting the compound represented by the formula [1a] to the following method (1), or (2):
"(1) a method of allowing the compound represented by the formula [1a] to react with a halogenating agent in the presence of a base, or
(2) a method of allowing the compound represented by the formula [1a] to react, in the presence of a base, with a compound represented by the following formula [6]:

   [6]

(wherein $R^8$ represents an optionally substituted $C_{1-6}$ alkyl group or an optionally substituted aryl group; and $X^1$ represents a halogen atom), to obtain a compound represented by the following formula [1b]:

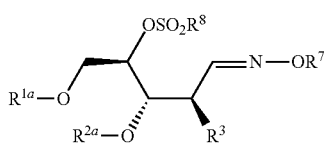   [1b]

(wherein $R^{1a}$, $R^{2a}$, R3, $R^7$ and $R^8$ have the same meanings as those described above), and then allowing the compound represented by the formula [1b] to react with a halide of alkaline metal,"
so as to obtain a compound represented by the following formula [1c]:

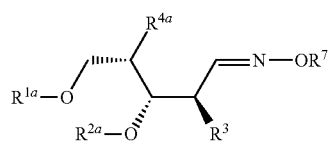   [1c]

(wherein $R^{4a}$ represents a halogen atom; and $R^{1a}$, $R^{2a}$, $R_3$ and $R^7$ have the same meanings as those described above),
then hydrolyzing the compound represented by the formula [1c] to obtain a compound represented by the following formula [1d]:

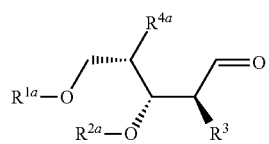   [1d]

(wherein $R^{1a}$, $R^{2a}$, $R^3$ and $R^{4a}$ have the same meanings as those described above),
then subjecting the compound represented by the formula [1d] to the production method of claim 1.

3. The production method according to claim 1, wherein $R^3$ represents a fluorine atom; and $R^{10a}$ represents an acetyl group.

4. The production method according to claim 1, wherein $R^{1a}$ represents an optionally substituted benzoyl group; and $R^{2a}$ represents an optionally substituted benzoyl group.

5. The production method according to claim 1, wherein any one of the methods (1) to (4) is the method (4).

6. The production method according to claim 5, wherein the compound represented by the formula [11b] is isolated in the form of a solid.

* * * * *